(12) United States Patent
Bonvini et al.

(10) Patent No.: US 11,697,684 B2
(45) Date of Patent: *Jul. 11, 2023

(54) TRI-SPECIFIC BINDING MOLECULES THAT SPECIFICALLY BIND TO MULTIPLE CANCER ANTIGENS

(71) Applicant: MACROGENICS, INC., Rockville, MD (US)

(72) Inventors: Ezio Bonvini, Rockville, MD (US); Paul A. Moore, Rockville, MD (US); Jonathan C. Li, Rockville, MD (US); Leslie S. Johnson, Rockville, MD (US); Kalpana Shah, Rockville, MD (US)

(73) Assignee: MACROGENICS, INC., Rockville, MD (US)

( * ) Notice: Subject to any disclaimer, the term of this patent is extended or adjusted under 35 U.S.C. 154(b) by 562 days.

This patent is subject to a terminal disclaimer.

(21) Appl. No.: 16/805,105

(22) Filed: Feb. 28, 2020

(65) Prior Publication Data

US 2020/0199223 A1 Jun. 25, 2020

Related U.S. Application Data

(62) Division of application No. 15/313,765, filed as application No. PCT/US2015/033081 on May 29, 2015, now Pat. No. 10,633,440.

(60) Provisional application No. 62/107,824, filed on Jan. 26, 2015, provisional application No. 62/008,229, filed on Jun. 5, 2014, provisional application No. 62/004,571, filed on May 29, 2014.

(51) Int. Cl.
*C07K 16/28* (2006.01)
*C07K 16/30* (2006.01)

(52) U.S. Cl.
CPC .......... *C07K 16/28* (2013.01); *C07K 16/2803* (2013.01); *C07K 16/283* (2013.01); *C07K 16/2809* (2013.01); *C07K 16/2815* (2013.01); *C07K 16/2827* (2013.01); *C07K 16/2878* (2013.01); *C07K 16/30* (2013.01); *C07K 2317/31* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/73* (2013.01); *C07K 2317/92* (2013.01); *C07K 2318/20* (2013.01); *C07K 2319/00* (2013.01)

(58) Field of Classification Search
CPC ........ C07K 2317/626; C07K 2317/522; C07K 2317/31; C07K 16/28
USPC .......................................... 424/133.1, 136.1
See application file for complete search history.

(56) References Cited

U.S. PATENT DOCUMENTS

| | | |
|---|---|---|
| 3,842,067 A | 10/1974 | Sarantakis |
| 3,862,925 A | 1/1975 | Sarantakis et al. |
| 3,972,859 A | 8/1976 | Fujino et al. |
| 4,105,603 A | 8/1978 | Vale et al. |
| 4,526,938 A | 7/1985 | Churchill et al. |
| 4,816,567 A | 3/1989 | Cabilly et al. |
| 4,880,078 A | 11/1989 | Inoue et al. |
| 4,980,286 A | 12/1990 | Morgan et al. |
| 5,128,326 A | 7/1992 | Balazs et al. |
| 5,290,540 A | 3/1994 | Prince et al. |
| 5,565,332 A | 10/1996 | Hoogenboom et al. |
| 5,580,717 A | 12/1996 | Dower et al. |
| 5,601,819 A | 2/1997 | Wong et al. |
| 5,624,821 A | 4/1997 | Winter et al. |
| 5,679,377 A | 10/1997 | Bernstein et al. |
| 5,733,743 A | 3/1998 | Johnson et al. |
| 5,807,715 A | 9/1998 | Morrison et al. |
| 5,843,749 A | 12/1998 | Maisonpierre et al. |
| 5,855,913 A | 1/1999 | Hanes et al. |
| 5,866,692 A | 2/1999 | Shitara et al. |
| 5,874,064 A | 2/1999 | Edwards et al. |
| 5,885,573 A | 3/1999 | Bluestone et al. |
| 5,888,533 A | 3/1999 | Dunn |
| 5,912,015 A | 6/1999 | Bernstein et al. |
| 5,916,597 A | 6/1999 | Lee et al. |

(Continued)

FOREIGN PATENT DOCUMENTS

| | | |
|---|---|---|
| CN | 101802010 A | 8/2010 |
| CN | 102448985 A | 5/2012 |

(Continued)

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*

(Continued)

*Primary Examiner* — Lynn A Bristol
(74) *Attorney, Agent, or Firm* — Medler Ferro Woodhouse & Mills

(57) ABSTRACT

The present invention relates to Tri-Specific Binding Molecules, which are multi-chain polypeptide molecules that possess three Binding Domains and are thus capable of mediating coordinated binding to three epitopes. The Tri-Specific Binding Molecule is preferably characterized in possessing binding domains that permit it to immunospecifically bind to: (1) an epitope of a first Cancer Antigen, (2) an epitope of a second Cancer Antigen, and (3) an epitope of a molecule that is expressed on the surface of an immune system effector cell, and are thus capable of localizing an immune system effector cell to a cell that expresses a Cancer Antigen, so as to thereby facilitate the killing of such cancer cell.

13 Claims, 23 Drawing Sheets

Specification includes a Sequence Listing.

(56) References Cited

U.S. PATENT DOCUMENTS

| | | |
|---|---|---|
| 5,934,272 A | 8/1999 | Lloyd et al. |
| 5,945,155 A | 8/1999 | Grill et al. |
| 5,985,309 A | 11/1999 | Edwards et al. |
| 5,985,320 A | 11/1999 | Edwards et al. |
| 5,989,463 A | 11/1999 | Tracy et al. |
| 5,997,867 A | 12/1999 | Waldmann et al. |
| 6,019,968 A | 2/2000 | Platz et al. |
| 6,054,297 A | 4/2000 | Carter et al. |
| 6,171,586 B1 | 1/2001 | Lam et al. |
| 6,180,377 B1 | 1/2001 | Morgan et al. |
| 6,194,551 B1 | 2/2001 | Idusogie et al. |
| 6,218,149 B1 | 4/2001 | Morrison et al. |
| 6,265,150 B1 | 7/2001 | Terstappen et al. |
| 6,331,415 B1 | 12/2001 | Cabilly et al. |
| 6,472,511 B1 | 10/2002 | Leung et al. |
| 6,551,592 B2 | 4/2003 | Lindhofer et al. |
| 6,994,853 B1 | 2/2006 | Lindhofer et al. |
| 7,148,038 B2 | 12/2006 | Mather |
| 7,276,586 B2 | 10/2007 | Goddard et al. |
| 7,317,091 B2 | 1/2008 | Lazar et al. |
| 7,351,803 B2 | 4/2008 | Johnson et al. |
| 7,405,061 B2 | 7/2008 | Mather et al. |
| 7,569,672 B2 | 8/2009 | Mather et al. |
| 7,572,895 B2 | 8/2009 | Mather et al. |
| 7,572,896 B2 | 8/2009 | Mather et al. |
| 7,585,952 B2 | 9/2009 | D et al. |
| 7,695,936 B2 | 4/2010 | Carter et al. |
| 8,044,178 B2 | 10/2011 | Boghaert et al. |
| 8,277,806 B2 | 10/2012 | Lindhofer |
| 8,394,374 B2 | 3/2013 | Bernett et al. |
| 8,586,713 B2 | 11/2013 | Davis et al. |
| 8,834,876 B2 | 9/2014 | Kosaka et al. |
| 10,633,440 B2 | 4/2020 | Bonvini et al. |
| 10,647,768 B2 | 5/2020 | Johnson |
| 2002/0028486 A1 | 3/2002 | Morrison et al. |
| 2003/0115614 A1 | 6/2003 | Kanda et al. |
| 2004/0058400 A1 | 3/2004 | Holliger et al. |
| 2004/0220388 A1 | 11/2004 | Mertens et al. |
| 2005/0079170 A1 | 4/2005 | Le et al. |
| 2005/0175606 A1 | 8/2005 | Huang et al. |
| 2005/0175618 A1 | 8/2005 | Carroll et al. |
| 2005/0255110 A1 | 11/2005 | Lindhofer et al. |
| 2006/0166291 A1 | 7/2006 | Mather et al. |
| 2006/0172349 A1 | 8/2006 | Mather et al. |
| 2006/0172350 A1 | 8/2006 | Mather et al. |
| 2007/0031436 A1 | 2/2007 | Little et al. |
| 2007/0071675 A1 | 3/2007 | Wu et al. |
| 2007/0196363 A1 | 8/2007 | Arathoon et al. |
| 2008/0057054 A1 | 3/2008 | Annaert et al. |
| 2008/0271208 A1 | 10/2008 | Cnops et al. |
| 2009/0060910 A1 | 3/2009 | Johnson et al. |
| 2009/0117108 A1 | 5/2009 | Wang et al. |
| 2010/0099853 A1 | 4/2010 | Little et al. |
| 2010/0173978 A1 | 7/2010 | D et al. |
| 2010/0174053 A1 | 7/2010 | Johnson et al. |
| 2010/0291112 A1 | 11/2010 | Kellner et al. |
| 2011/0020667 A1 | 1/2011 | Deeman et al. |
| 2011/0206670 A1 | 8/2011 | Golde et al. |
| 2012/0294874 A1 | 11/2012 | Macary et al. |
| 2013/0189263 A1 | 7/2013 | Little et al. |
| 2013/0251642 A1 | 9/2013 | Rader et al. |
| 2013/0281922 A1 | 10/2013 | Teige |
| 2013/0295098 A1 | 11/2013 | Wu et al. |
| 2013/0295121 A1 | 11/2013 | Johnson et al. |
| 2014/0065142 A1 | 3/2014 | Roschke et al. |
| 2014/0099318 A1 | 4/2014 | Huang et al. |
| 2017/0198045 A1 | 7/2017 | Johnson et al. |
| 2017/0204176 A1 | 7/2017 | Bonvini et al. |
| 2018/0016344 A1* | 1/2018 | Moore .................... A61P 35/02 |
| 2019/0002563 A1 | 1/2019 | Johnson et al. |
| 2019/0085075 A1 | 3/2019 | La Motte-mohs et al. |
| 2019/0127467 A1* | 5/2019 | Shah ........................ A61P 35/04 |
| 2020/0062854 A1* | 2/2020 | Liu .................... C07K 16/2878 |
| 2020/0207850 A1* | 7/2020 | Johnson .................. A61P 13/10 |
| 2020/0231675 A1* | 7/2020 | Shah ........................ A61P 1/04 |
| 2021/0155694 A1 | 5/2021 | Bonvini et al. |
| 2021/0171630 A1 | 6/2021 | Diedrich et al. |
| 2021/0246194 A1 | 8/2021 | Lam et al. |

FOREIGN PATENT DOCUMENTS

| | | |
|---|---|---|
| CN | 103154025 A | 6/2013 |
| EP | 0 403 156 A1 | 12/1990 |
| EP | 0 519 596 A1 | 12/1992 |
| EP | 0 359 096 B1 | 11/1997 |
| EP | 1 293 514 B1 | 11/2006 |
| EP | 1 736 484 A1 | 12/2006 |
| EP | 1 820 513 A1 | 8/2007 |
| EP | 1 078 004 B1 | 10/2007 |
| EP | 2 158 221 A2 | 3/2010 |
| EP | 2 186 527 A1 | 5/2010 |
| EP | 2 241 576 A1 | 10/2010 |
| EP | 2 361 936 A1 | 8/2011 |
| EP | 2 371 866 A2 | 10/2011 |
| EP | 2 376 109 A1 | 10/2011 |
| EP | 2 585 476 A2 | 5/2013 |
| EP | 2 601 216 A1 | 6/2013 |
| EP | 2 714 079 A2 | 4/2014 |
| EP | 2 840 091 A1 | 2/2015 |
| EP | 2839842 * | 2/2015 |
| JP | 2007-535915 A | 12/2007 |
| JP | 2008-512485 A | 4/2008 |
| JP | 2009-526823 A | 7/2009 |
| JP | 2009-529578 A | 8/2009 |
| JP | 2010-246546 A | 11/2010 |
| JP | 2011-505792 A | 3/2011 |
| JP | 2011-508592 A | 3/2011 |
| JP | 2012-228248 A | 11/2012 |
| JP | 2012-528092 A | 11/2012 |
| JP | 2013-506654 A | 2/2013 |
| JP | 2013-540696 A | 11/2013 |
| RU | 94028282 A | 7/1996 |
| WO | WO 91/03493 A1 | 3/1991 |
| WO | WO 91/05548 A1 | 5/1991 |
| WO | WO 92/19244 A2 | 11/1992 |
| WO | WO 92/22583 A2 | 12/1992 |
| WO | WO 96/20698 A2 | 7/1996 |
| WO | 96/27011 A1 | 9/1996 |
| WO | WO 97/32572 A2 | 9/1997 |
| WO | WO 97/44013 A1 | 11/1997 |
| WO | WO 98/02463 A1 | 1/1998 |
| WO | WO 98/03670 A1 | 1/1998 |
| WO | WO 98/06749 A2 | 2/1998 |
| WO | WO 98/31346 A1 | 7/1998 |
| WO | WO 99/15154 A1 | 4/1999 |
| WO | WO 99/20253 A1 | 4/1999 |
| WO | WO 99/42597 A1 | 8/1999 |
| WO | WO 99/57150 A2 | 11/1999 |
| WO | WO 99/58572 A1 | 11/1999 |
| WO | WO 99/66903 A2 | 12/1999 |
| WO | WO 00/18806 A1 | 4/2000 |
| WO | WO 00/42072 A2 | 7/2000 |
| WO | WO 02/02781 A1 | 1/2002 |
| WO | WO 02/14870 A2 | 2/2002 |
| WO | WO 02/20039 A2 | 3/2002 |
| WO | WO 02/072141 A2 | 9/2002 |
| WO | WO 03/012069 A2 | 2/2003 |
| WO | WO 03/024191 A2 | 3/2003 |
| WO | WO 03/025018 A2 | 3/2003 |
| WO | WO 03/032814 A2 | 4/2003 |
| WO | WO 03/035835 A2 | 5/2003 |
| WO | WO 03/087340 A2 | 10/2003 |
| WO | 03/094859 A2 | 11/2003 |
| WO | WO 03/093443 A2 | 11/2003 |
| WO | WO 03/100033 A2 | 12/2003 |
| WO | WO 2004/043239 A2 | 5/2004 |
| WO | WO 2004/063351 A2 | 7/2004 |
| WO | WO 2005/028498 A2 | 3/2005 |
| WO | WO 2005/061547 A2 | 7/2005 |
| WO | WO 2005/070966 A2 | 8/2005 |
| WO | WO 2005/121179 A2 | 12/2005 |
| WO | WO 2006/002438 A2 | 1/2006 |
| WO | 200/6031653 A2 | 3/2006 |
| WO | WO 2006/072152 A2 | 7/2006 |

(56) References Cited

FOREIGN PATENT DOCUMENTS

| | | |
|---|---|---|
| WO | WO 2006/076584 A2 | 7/2006 |
| WO | WO 2006/083852 A2 | 8/2006 |
| WO | WO 2006/084075 A2 | 8/2006 |
| WO | WO 2006/084078 A2 | 8/2006 |
| WO | WO 2006/084092 A2 | 8/2006 |
| WO | WO 2006/084226 A2 | 8/2006 |
| WO | WO 2006/088494 A2 | 8/2006 |
| WO | WO 2006/107617 A2 | 10/2006 |
| WO | WO 2006/107786 A2 | 10/2006 |
| WO | WO 2006/113665 A2 | 10/2006 |
| WO | WO 2007/008712 A2 | 1/2007 |
| WO | WO 2007/021841 A2 | 2/2007 |
| WO | 2007/024715 A2 | 3/2007 |
| WO | WO 2007/024249 A2 | 3/2007 |
| WO | WO 2007/046893 A2 | 4/2007 |
| WO | WO 2007/075270 A2 | 7/2007 |
| WO | WO 2007/093630 A1 | 8/2007 |
| WO | WO 2007/095338 A1 | 8/2007 |
| WO | 2007/106744 A2 | 9/2007 |
| WO | WO 2007/106707 A2 | 9/2007 |
| WO | WO 2007/146968 A2 | 12/2007 |
| WO | WO 2008/003103 A2 | 1/2008 |
| WO | WO 2008/003116 A2 | 1/2008 |
| WO | WO 2008/027236 A2 | 3/2008 |
| WO | WO 2008/140603 A2 | 11/2008 |
| WO | WO 2008/145142 A1 | 12/2008 |
| WO | WO 2008/146911 A1 | 12/2008 |
| WO | WO 2008/157379 A2 | 12/2008 |
| WO | 2009/007124 A1 | 1/2009 |
| WO | WO 2009/018386 A1 | 2/2009 |
| WO | 2009/032845 A2 | 3/2009 |
| WO | 2009/081201 A2 | 7/2009 |
| WO | WO 2009/132876 A1 | 11/2009 |
| WO | WO 2010/027797 A1 | 3/2010 |
| WO | WO 2010/028795 A1 | 3/2010 |
| WO | WO 2010/028796 A1 | 3/2010 |
| WO | WO 2010/028797 A1 | 3/2010 |
| WO | WO 2010/080538 A1 | 7/2010 |
| WO | WO 2010/108127 A1 | 9/2010 |
| WO | 2010/119119 A1 | 10/2010 |
| WO | WO 2010/124188 A1 | 10/2010 |
| WO | WO 2010/136172 A1 | 12/2010 |
| WO | WO 2011/032633 A1 | 3/2011 |
| WO | WO 2011/034660 A1 | 3/2011 |
| WO | 2011/039724 A1 | 4/2011 |
| WO | WO 2011/086091 A1 | 7/2011 |
| WO | WO 2011/109400 A2 | 9/2011 |
| WO | WO 2011/133886 A2 | 10/2011 |
| WO | WO 2011/163401 A2 | 12/2011 |
| WO | WO 2012/009544 A2 | 1/2012 |
| WO | WO 2012/018687 A1 | 2/2012 |
| WO | 2012/076066 A1 | 6/2012 |
| WO | WO 2012/075158 A1 | 6/2012 |
| WO | WO 2012/088290 A1 | 6/2012 |
| WO | 2012/131527 A1 | 10/2012 |
| WO | WO 2012/156430 A1 | 11/2012 |
| WO | WO 2012/162067 A2 | 11/2012 |
| WO | WO 2012/162068 A2 | 11/2012 |
| WO | WO 2012/162561 A2 | 11/2012 |
| WO | WO 2012/162583 A1 | 11/2012 |
| WO | 2012/167067 A1 | 12/2012 |
| WO | 2013/004842 A2 | 1/2013 |
| WO | WO 2013/003652 A1 | 1/2013 |
| WO | WO 2013/006544 A1 | 1/2013 |
| WO | WO 2013/013700 A1 | 1/2013 |
| WO | 2013/041687 A1 | 3/2013 |
| WO | 2013/068874 A1 | 5/2013 |
| WO | WO 2013/070565 A1 | 5/2013 |
| WO | WO 2013/119903 A1 | 8/2013 |
| WO | WO 2013/163427 A1 | 10/2013 |
| WO | WO 2013/174873 A1 | 11/2013 |
| WO | WO 2014/022540 A1 | 2/2014 |
| WO | WO 2014/072888 A1 | 5/2014 |
| WO | WO 2014/116846 A2 | 7/2014 |
| WO | 2014/006217 A9 | 2/2015 |
| WO | WO 2015/026894 A2 | 2/2015 |
| WO | WO 2015/158636 A1 | 10/2015 |
| WO | WO 2015/184203 A1 | 12/2015 |
| WO | WO 2015/184207 A1 | 12/2015 |

OTHER PUBLICATIONS

Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021.*
Lo et al., BMC Genomics vol. 22, Article No. 116 (2021).*
Felices, M et al. (Annals of Oncology, (Dec. 2021) vol. 32, Supp. Supplement 7, pp. S1433. Meeting Info: ESMO Immuno-Oncology Congress 2021. Virtual, Online. Dec. 8, 2021-Dec. 11, 2021).*
Kang et al., "Antibody Redesign by Chain Shuffling from Random Combinatorial Immunoglobulin Libraries", Proceedings of the National Academy of Sciences USA, Dec. 1991, 88:11120-11123.
Lamminmaki et al., "Crystal Structure of a Recombinant Anti-estradiol Fab Fragment in Complex with 17β-Estradiol", The Journal of Biological Chemistry, Jul. 12, 2001, 276(39):36687-36694.
Padlan et al., "Structure of an Antibody-Antigen Complex: Crystal Structure of the HyHEL-10 Fab-Lysozyme Complex", Proceedings of the National Academy of Sciences USA, Aug. 1989, 86:5938-5942.
Extended European Search Report dated Dec. 22, 2017 in Europe Patent Application No. 15799237.1, filed on May 29, 2015, 11 pages.
Extended European Search Report dated Jan. 18, 2018 in Europe Patent Application No. 15799187.8, filed on May 29, 2015, 13 pages.
International Preliminary Report on Patentability dated Dec. 8, 2016 in International Patent Application No. PCT/US2015/033076, filed on May 29, 2015, 8 pages.
International Preliminary Report on Patentability dated Dec. 8, 2016 in International Patent Application No. PCT/US2015/033081, filed on May 29, 2015, 7 pages.
International Search Report and Written Opinion dated Oct. 26, 2015 in International Patent Application No. PCT/US2015/033076, filed on May 29, 2015, 12 pages.
International Search Report and Written Opinion dated Sep. 2, 2015 in International Patent Application No. PCT/US2015/033081, filed on May 29, 2015, 10 pages.
Office Action dated Apr. 15, 2019 in U.S. Appl. No. 15/313,741, filed Nov. 23, 2016 and published as US 2017-0198045 on Jul. 13, 2017, 22 pages.
Office Action dated Apr. 15, 2019 in U.S. Appl. No. 15/313,765, filed Nov. 23, 2016 and published as 2017-0204176 on Jul. 20, 2017, 23 pages.
Office Action dated Dec. 2, 2019 in U.S. Appl. No. 15/313,765, filed Nov. 23, 2016 and published as US-2017-0204176-A1 on Jul. 20, 2017, 9 pages.
Office Action dated Dec. 27, 2019 in U.S. Appl. No. 15/313,741, filed Nov. 23, 2016 and published as 2017-0198045 on Jul. 13, 2017, 9 pages.
Office Action dated Sep. 18, 2019 in U.S. Appl. No. 15/313,741, filed Nov. 23, 2016 and published as 2017-0198045 on Jul. 13, 2017, 11 pages.
Office Action dated Sep. 18, 2019 in U.S. Appl. No. 15/313,765, filed Nov. 23, 2016 and published as 2017-0204176 on Jul. 20, 2017, 10 pages.
Abdulghani et al., "TRAIL Receptor Signaling and Therapeutics", Expert Opinion on Therapeutic Targets, Oct. 2010, 14(10):1091-1108.
Adenis et al., "Inhibitors of Epidermal Growth Factor Receptor and Colorectal Cancer", Bull Cancer, 2003, 90:S228-S232.
Adkins et al., "Edrecolomab (Monoclonal Antibody 17-1A)", Drugs, Oct. 1998, 56(4):619-626.
Ahmed et al., "Intercellular Trogocytosis Plays an Important Role in Modulation of Immune Responses", Cellular & Molecular Immunology, Sep. 2008, 5(4):261-269.

(56) References Cited

OTHER PUBLICATIONS

Ahmed et al., "Mechanisms of Cellular Communication through Intercellular Protein Transfer", Journal of Cellular and Molecular Medicine, 2011, 15(7):1458-1473.
Akcakanat et al., "Heterogeneous Expression of GAGE, NY-ESO-1, MAGE-A and SSX Proteins in Esophageal Cancer: Implications for Immunotherapy", International Journal of Cancer, Jan. 1, 2006, 118(1):123-128.
Albrecht, "Recombinant Antibodies: From the Laboratory to the Clinic", Cancer Biotherapy and Radiopharmaceuticals, 2006, 21(4):285-304.
Alegre et al., "A Non-Activating "Humanized" Anti-CD3 Monoclonal Antibody Retains Immunosuppressive Properties In Vivo", Transplantation, 1994, 57:1537-1543.
Almqvist et al., "In Vitro and in Vivo Characterization of 177Lu-Hua33: A Radioimmunoconjugate against Colorectal Cancer", Nuclear Medicine and Biology, 2006, 33(8):991-998.
Alt et al., "Novel Tetravalent and Bispecific IgG-Like Antibody Molecules Combining Single-Chain Diabodies With the Immunoglobin Gamma 1 Fc or CH3 Region", FEBS Letters, 1999, 454(1-2):90-94.
Altschul S., "Amino Acid Substitution Matrices from an Information Theoretic Perspective", Journal of Molecular Biology, 1991, 219(3):555-565.
Andera L., "Signaling Activated by the Death Receptors of the TNFR Family", Biomed Pap Med Fac Univ Palacky Olomouc Czech Repub, 2009, 153(3):173-180.
Apostolovic et al., "pH-Sensitivity of the E3/K3 Heterodimeric Coiled Coil", Biomacromolecules, Nov. 2008, 9(11):3173-3180.
Armour et al., "Recombinant Human IgG Molecules Lacking Fcgamma Receptor I Binding and Monocyte Triggering Activities", European Journal of Immunology, 1999, 29:2613-2624.
Armstrong et al., "Conformational Changes and Flexibility in T-Cell Receptor Recognition of Peptide-MHC Complexes", Biochemical Journal, Oct. 15, 2008, 415(2):183-196.
Arndt et al., "Comparison of in Vivo Selection and Rational Design of Heterodimeric Coiled Coils", Structure, 2002, 10:1235-1248.
Arndt et al., "Helix-stabilized Fv (hsFv) Antibody Fragments: Substituting the Constant Domains of a Fab Fragment for a Heterodimeric Coiled-coil Domain", Journal of Molecular Biology, Oct. 2002, 312(1):221-228.
Aruffo et al., "Molecular Cloning of A CD28 cDNA By A High-Efficiency COS Cell Expression System", Proc. Natl. Acad. Sci. (U.S.A.), 1987, 84:8573-8577.
Asano et al., "A Diabody for Cancer Immunotherapy and its Functional Enhancement by Fusion of Human Fc Domain", Abstract 3P-683, Journal of Biochemistry, 2004, 76(8):992.
Asano et al., "Domain Order of a Bispecific Diabody Dramatically Enhances Its Antitumor Activity Beyond Structural Format Conversion: The Case of the hEx3 Diabody", Protein Engineering, Design & Selection, XP55190198. ISSN: 1741-0126. DOI: 10.1093/proteinjgzt009, Mar. 6, 2013, 26(5):359-367.
Atwell et al., "Stable Heterodimers from Remodeling the Domain Interface of a Homodimer Using a Phage Display Library", Journal of Molecular Biology, 1997, 271(1):26-35.
Bachanova et al., "NK Cells in Therapy of Cancer", Critical Reviews in Oncogenesis, 2014, 19(1-2):133-141.
Baeuerle et al., "Bispecific T-Cell Engaging Antibodies for Cancer Therapy", Cancer Research, 2009, 69(12):4941-4944.
Baeuerle et al., "BiTE: A New Class of Antibodies That Recruit T Cells", Drugs of the Future, 2008, 33:137-147.
Barderas et al., "Affinity Maturation of Antibodies Assisted by In Silico Modeling", Proceedings of the National Academy of Sciences, 2008, 105(26):9029-9034.
Barderas et al., "High Expression of IL-13 Receptor α2 in Colorectal Cancer Is Associated with Invasion, Liver Metastasis, and Poor Prognosis", Cancer Research, Jun. 2012, 72(11):2780-2790.
Bargou et al., "Tumor Regression in Cancer Patients by Very Low Doses of a T Cell-Engaging Antibody", Science, 2008, 321:974-977.
Bast et al., "New Tumor Markers: CA125 and Beyond", International Journal of Gynecological Cancer, Nov.-Dec. 2005, 15(3):274-281.
Bataille et al., "The Phenotype of Normal, Reactive and Malignant Plasma Cells. Identification of "Many and Multiple Myelomas" and of New Targets for Myeloma Therapy", Haematologica, Sep. 2006, 91(9):1234-1240.
Bauer et al., "Activation of NK Cells and T Cells by NKG2D, a Receptor for Stress-Inducible MICA", Science, Jul. 1999, 285(5428):727-729.
Bedzyk et al., "Comparison of Variable Region Primary Structures Within an Anti-Fluorescein Idiotype Family", Journal of Biological Chemistry, 1989, 264(3):1565-1569.
Beier et al., "Master Switches of T-Cell Activation and Differentiation", European Respiratory Journal, Apr. 2007, 29(4):804-812.
Bhattacharya-Chatterjee et al., "Idiotype Vaccines Against Human T Cell Acute Lymphoblastic Leukemia. I. Generation and Characterization of Biologically Active Monoclonal Anti-Idiotopes", The Journal of Immunology, 1987, 139(4):1354-1360.
Bhattacharya-Chatterjee et al., "Idiotype Vaccines Against Human T Cell Leukemia. II. Generation and Characterization of a Monoclonal Idiotype Cascade (Ab1, Ab2, and Ab3)", The Journal of Immunology, Aug. 15, 1988, 141(4):1398-1403.
Bird et al., "Single-Chain Antigen-Binding Proteins", Science, 1988, 242:423-426.
Blank et al., "Absence of Programmed Death Receptor 1 Alters Thymic Development and Enhances Generation of CD4/CD8 Double-Negative TCR-Transgenic T Cells", Journal of Immunology, 2003, 171(9):4574-4581.
Blumenthal et al., "Expression Patterns of CEACAM5 And CEACAM6 In Primary and Metastatic Cancers", BMC Cancer, 2007, 7(2):15 pages.
Bodey B., "Cancer-Testis Antigens: Promising Targets for Antigen Directed Antineoplastic Immunotherapy", Expert Opinion on Biological Therapy, 2002, 2(6):577-584.
Bodhinayake et al., "Targeting a Heterogeneous Tumor: The Promise of the Interleukin-13 Receptor A2", Neurosurgery, Aug. 2014, 75(2):N18-N19.
Boghaert et al., "The Oncofetal Protein, 5T4, Is A Suitable Target for Antibody-Guided Anti-Cancer Chemotherapy with Calicheamicin", International Journal of Oncology, Jan. 2008, 32(1):221-234.
Bostrom et al., "Improving Antibody Binding Affinity and Specificity for Therapeutic Development", Therapeutic Antibodies, 2009, 525:353-376.
Boucher et al., "Protein Detection by Western Blot via Coiled-Coil Interactions", Analytical Biochemistry, Apr. 2010, 399(1):138-140.
Bozinov et al., "Decreasing Expression of the Interleukin-13 Receptor IL-13Rα2 in Treated Recurrent Malignant Gliomas", Neurol Med Chir (Tokyo), 2010, 50(8):617-621.
Brown et al., "Glioma IL13Rα2 Is Associated with Mesenchymal Signature Gene Expression and Poor Patient Prognosis", PLoS One, Oct. 18, 2013, 8(10):e77769.
Brown et al., "Trogocytosis Generates Acquired Regulatory T Cells Adding Further Complexity to the Dysfunctional Immune Response in Multiple Myeloma", Oncolmmunology, 2012, 1:1658-1660.
Brown et al., "Tumor-Specific Genetically Engineered Murine-Human Chimeric Monoclonal Antibody", Cancer Research, 1987, 47(13):3577-3583.
Bruggemann et al., "Comparison of the Effector Functions of Human Immunoglobulins using a Matched Set of Chimeric Antibodies", Journal of Experimental Medicine, Nov. 1987, 166(5):1351-1361.
Buchwald et al., "Long-Term, Continuous Intravenous Heparin Administration by an Implantable Infusion Pump in Ambulatory Patients with Recurrent Venous Thrombosis", Surgery, 1980, 88(4):507-516.
Bujis et al., "SPR-MS in Functional Proteomics", Briefings in Functional Genomics, 2005, 4(1):39-47.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", Journal of Cell Biology, Nov. 1990, 111:2129-2138.

(56) References Cited

OTHER PUBLICATIONS

Cachia et al., "Synthetic Peptide Vaccine Development: Measurement of Polyclonal Antibody Affinity and Cross-Reactivity Using a New Peptide Capture and Release System for Surface Plasmon Resonance Spectroscopy", Journal of Molecular Recognition, 2004, 17(6):540-557.

Cai et al., "Up-Regulation of Bone Marrow Stromal Protein 2 (BST2) In Breast Cancer with Bone Metastasis", BMC Cancer, 2009, 9:102.

Calin et al., "Genomics of Chronic Lymphocytic Leukemia MicroRNAs as New Players with Clinical Significance", Seminars in Oncology, May 2006, 33(2):167-173.

Call et al., "Common Themes in the Assembly and Architecture of Activating Immune Receptors", Nature Reviews Immunology, Nov. 2007, 7(11):841-850.

Cambier et al., "M19 Modulates Skeletal Muscle Differentiation and Insulin Secretion in Pancreatic β-Cells through Modulation of Respiratory Chain Activity", Plos One, Feb. 2012, 7(2):11 pages.

Cambier John C., "New Nomenclature for the Reth Motif (or ARH1/TAM/ARAM/YXXL)", Trends in Immunology, 1995, 16(2):110.

Cameron et al., "Focal Overexpression of CEACAM6 Contributes to Enhanced Tumorigenesis in Head and Neck Cancer via Suppression of Apoptosis", Molecular Cancer, Sep. 2012, 11(74):11 pages.

Canafax et al., "Monoclonal Antilymphocyte Antibody (OKT3) Treatment of Acute Renal Allograft Rejection", Pharmacotherapy, Aug. 1987, 7(4):121-124.

Cang et al., "Novel CD20 Monoclonal Antibodies for Lymphoma Therapy", Journal of Hematology & Oncology, Oct. 11, 2012, 5(64):9 pages.

Cao et al., "Bispecific Antibody Conjugates in Therapeutics", Advanced Drug Delivery Reviews, 2003, 55(2):171-197.

Carlo-Stella et al., "Targeting TRAIL Agonistic Receptors for Cancer Therapy", Clinical Cancer Research, Apr. 2007, 13(8):2313-2317.

Caron et al., "Engineered Humanized Dimeric Forms of IgG Are More Effective Antibodies", Journal of Experimental Medicine, 1992, 176:1191-1195.

Carter et al., "Humanization of an Anti-p185her2 Antibody for Human Cancer Therapy", Proceedings of the National Academy of Sciences, 1992, 89:4285-4289.

Castelli et al., "T-Cell Recognition of Melanoma-Associated Antigens", Journal of Cellular Physiology, Mar. 2000, 182(3):323-331.

Castillo et al., "Newer Monoclonal Antibodies for Hematological Malignancies", Experimental Hematology, 2008, 36(7):755-768.

Castriconi et al., "Identification Of 4Ig-B7-H3 As A Neuroblastoma-Associated Molecule That Exerts A Protective Role from An NK Cell-Mediated Lysis", Proc. Natl. Acad. Sci. (U.S.A.), 2004, 101(34):12640-12645.

Caumartin et al., "Intercellular Exchanges of Membrane Patches (Trogocytosis) Highlight the Next Level of Immune Plasticity", Transplant Immunology, 2006, 17(1):20-22.

Chan et al., "The Use of Antibodies in the Treatment of Infectious Diseases", Singapore Medical Journal, 2009, 50(7):663-666.

Chapin et al., "Distribution and Surfactant Association of Carcinoembryonic Cell Adhesion Molecule 6 In Human Lung", American Journal of Physiology—Lung Cellular and Molecular Physiology, Jan. 15, 2012, 302(2):L216-L225.

Chapoval et al., "B7-H3: A Costimulatory Molecule for T Cell Activation and IFN-γ Production", Nature Immunology, 2001, 2:269-274.

Chappel et al., "Identification of a Secondary FcrRI Binding Site within a Genetically Engineered Human IgG Antibody", Journal of Biological Chemistry, 1993, 268(33):25124-25131.

Chappel et al., "Identification of the Fc Gamma Receptor Class I Binding Site in Human IgG Through the use of Recombinant IgG1/IgG2 Hybrid and Point-Mutated Antibodies", Proc. Natl. Acad. Sci U.S.A., 1991, 88:9036-9040.

Chaudhari et al., "Following the TRAIL to Apoptosis", Immunologic Research, 2006, 35(3):249-262.

Chen et al., "EphA2 Enhances the Proliferation and Invasion Ability of LnCap Prostate Cancer Cells", Oncology Letters, Jul. 2014, 8(1):41-46.

Chen et al., "Targeting B Lymphoma with Nanoparticles Bearing Glycan Ligands of CD22", Leukemia & Lymphoma, 2012, 53(2):208-210.

Chen et al., "The Role and Mechanisms of Double Negative Regulatory T Cells in the Suppression of Immune Responses", Cell Mol Immunol, 2004, 1:328-335.

Cheson et al., "Monoclonal Antibody Therapy for B-Cell Non-Hodgkin's Lymphoma", The New England Journal of Medicine, 2008, 359(6):613-626.

Chetty et al., "CD3: Structure, Function, and Role of Immunostaining in Clinical Practice", The Journal of Pathology, 1994, 173(4):303-307.

Chu et al., "CD79: A Review", Applied Immunohistochemistry & Molecular Morphology, 2001, 9(2):97-106.

Chu et al., "Nonviral Oncogenic Antigens and the Inflammatory Signals Driving Early Cancer Development as Targets for Cancer Immunoprevention", Clinical Cancer Research, Apr. 1, 2015, 21(7):1549-1557.

Cleek et al., "Biodegradable Polymeric Carriers for a bFGF Antibody for Cardiovascular Application", Proc Int Symp Controlled Release Bioact Mater, 1997, 24:853-854.

Clement et al., "Anti-CD8 Antibodies Can Trigger CD8+ T Cell Effector Function in the Absence of TCR Engagement and Improve Peptide-MHCI Tetramer Staining", Journal of Immunology, 2011, 187(2):654-663.

Co et al., "Chimeric and Humanized Antibodies with Specificity for the CD33 Antigen", The Journal of Immunology, 1992, 148(4):1149-1154.

Co et al., "Humanized Antibodies for Antiviral Therapy", Proceedings of the National Academy of Sciences, 1991, 88:2869-2873.

Coleman, "Epratuzumab: targeting B-cell malignancies through CD22", Clinical Cancer Research, 2003, 9(10 Pt 2):3991S-3994S.

Collins et al., "The B7 Family of Immune-Regulatory Ligands", Genome Biology, 2005, 6(6):223.1-223.7.

Comerci et al., "CD2 Promotes Human Natural Killer Cell Membrane Nanotube Formation", PLoS One, Oct. 2012, 7(10):e47664:1-12.

Coudert et al., "Altered NKG2D Function in NK Cells Induced by Chronic Exposure to NKG2D Ligand-expressing Tumor Cells", Blood, Oct. 2005, 106:1711-1717.

Cracco et al., "Immune Response in Prostate Cancer", Minerva Urologica e Nefrologica, Dec. 2005, 57(4):301-311.

Crescenzo et al., "Real-Time Monitoring of the Interactions of Two-Stranded de Novo Designed Coiled-Coils: Effect of Chain Length on the Kinetic and Thermodynamic Constants of Binding", Biochemistry, 2003, 42(6):1754-1763.

D'Acquisto et al., "CD3+CD4-CD8—(Double Negative) T Cells: Saviours or Villains of the Immune Response?", Biochemical Pharmacology, 2011, 82(4):333-340.

Dao et al., "Identification of a Human Cyclin D1-Derived Peptide that Induces Human Cytotoxic CD4 T Cells", PLoS One, Aug. 2009, 4(8):9 pages.

Daugherty et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.

Defranco Al, "The Complexity of Signaling Pathways Activated by the BCR", Current Opinion in Immunology, 1997, 9(3):296-308.

Deng et al., "Expression Profiling of CEACAM6 Associated with the Tumorigenesis and Progression in Gastric Adenocarcinoma", Genetics and Molecular Research, Sep. 26, 2014, 13(3):7686-7697.

Dennis et al., "Glycoprotein Glycosylation and Cancer Progression", Biochimica et Biophysica Acta, 1999, 1473(1):21-34.

Dhainaut et al., "Regulation of Immune Reactivity by Intercellular Transfer", Frontiers in Immunology, Mar. 2014, 5(112):4 pages.

Dimaio et al., "Human Papillomaviruses and Cervical Cancer", Advances in Virus Research, 2006, 66:125-159.

Dong et al., "Immune Regulation by Novel Costimulatory Molecules", Immunologic Research, 2003, 28(1):39-48.

(56) References Cited

OTHER PUBLICATIONS

Duncan et al., "Localization of The Binding Site for The Human High-Affinity Fc Receptor on IgG", Nature, 1988, 332:563-564.
During et al., "Controlled Release of Dopamine from a Polymeric Brain Implant: In Vivo Characterization", Annals of Neurology, 1989, 25(4):351-356.
Durrant et al., "Development of an ELISA to Detect Early Local Relapse of Colorectal Cancer", British Journal of Cancer, Oct. 1, 1989, 60(4):533-537.
Dylke et al., "Role of the Extracellular and Transmembrane Domain of Ig-Alpha/Beta in Assembly of the B Cell Antigen Receptor (BCR)", Immunology Letters, 2007, 112(1):47-57.
Eddy Sean R., "Where did the BLOSUM62 Alignment Score Matrix Come from?", Nature Biotechnology, 2004, 22:1035-1036.
Edelson et al., "Cutaneous T Cell Lymphoma: The Helping Hand of Dendritic Cells", Annals of the New York Academy of Sciences, 2001, 941:1-11.
Edelson, "Cutaneous T-Cell Lymphoma: A Model for Selective Immunotherapy", The cancer journal from Scientific American, Mar.-Apr. 1998, 4(2):62-71.
Egloff et al., "Cyclin B1 and other Cyclins as Tumor Antigens in Immunosurveillance and Immunotherapy of Cancer", Cancer Research, Jan. 1, 2006, 66(1):6-9.
Eisen et al., "Naptumomab Estafenatox: Targeted Immunotherapy with a Novel Immunotoxin", Current Oncology Reports, Feb. 2014, 16(370):6 pages.
Elkabetz et al., "Cysteines in CH1 Underlie Retention of Unassembled Ig Heavy Chains", J. Biol. Chem., 2005, 280:14402-14412.
Emmrich et al., "Synergism in the Activation of Human CD8 T Cells by Cross-Linking the T-cell Receptor Complex with the CD8 Differentiation Antigen", PNAS, Nov. 1, 1986, 83(21):8298-8302.
Estin et al., "Transfected Mouse Melanoma Lines That Express Various Levels of Human Melanoma-Associated Antigen p97", Journal of the National Cancer Institute, Apr. 1989, 81(6):445-458.
Feizi T., "Demonstration by Monoclonal Antibodies that Carbohydrate Structures of Glycoproteins and Glycolipids are Onco-Developmental Antigens", Nature, Mar. 7-13, 1985, 314(6006):53-57.
Fernandez-Rodriquez et al., "Induced Heterodimerization and Purification of Two Target Proteins by a Synthetic Coiled-Coil Tag", Protein Science, 2012, 21:511-519.
Ferran et al., "Cytokine-Related Syndrome following Injection of Anti-CD3 Monoclonal Antibody: Further Evidence for Transient In vivo T Cell Activation", European Journal of Immunology, 1990, 20(3):509-515.
Finck et al., "The Role of T-Cell Subsets in the Response to Anti-CD3 Monoclonal Antibodies", Clinical Immunology and Immunopathology, Dec. 1992, 65(3):234-241.
Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions", Journal of Molecular Biology, 2009, 388(3):541-558.
Fitzgerald et al., "Improved Tumour Targeting by Disulphide Stabilized Diabodies Expressed in Pichia pastoris", Protein Engineering, 1997, 10(10):1221-1225.
Fivash et al., "BIAcore for Macromolecular Interaction", Current Opinions in Biotechnology, 1998, 9(1):97-101.
Flesch et al., "Functions of the Fc Receptors for Immunoglobulin G", Journal of Clinical Laboratory Analysis, 2000, 14:141-156.
Foon et al., "Immune Response to the Carcinoembryonic Antigen in Patients Treated with an Anti-Idiotype Antibody Vaccine", Journal of Clinical Investigation, 1995, 96(1):334-342.
Frangione et al., "Human Lambda Light-Chain Constant Region Gene CMor Lambda: The Primary Structure of Lambda VI Bence Jones Protein Mor", PNAS, 1985, 82(10):3415-3419.
Fujisawa et al., "A Novel Role of Interleukin-13 Receptor α2 in Pancreatic Cancer Invasion and Metastasis", Cancer Research, Nov. 2009, 69(22):8678-8685.

Ganesan A., "Solid-Phase Synthesis in the Twenty-First Century", Mini-Reviews in Medicinal Chemistry, 2006, 6(1):3-10.
Gardnerova et al., "The Use of TNF Family Ligands and Receptors and Agents Which Modify their Interaction as Therapeutic Agents", Current Drug Targets, Dec. 2000, 1(4):327-364.
Garratty G., "Blood Group Antigens as Tumor Markers, Parasitic/Bacterial/Viral Receptors, and Their Association with Immunologically Important Proteins", Immunological Investigations, Jan.-Feb. 1995, 24(1-2):213-232.
Ge et al., "CD36: A Multiligand Molecule", Laboratory Hematology, 2005, 11(1):31-37.
Geraud et al., "Endothelial Transdifferentiation in Hepatocellular Carcinoma: Loss of Stabilin-2 Expression in Peri-Tumourous Liver Correlates with Increased Survival.", Liver international: official journal of the International Association for the Study of the Liver, Jun. 2013, 33(9):1428-1440.
Ghetie et al., "Anti-CD19 Inhibits the Growth of Human B-Cell Tumor Lines in Vitro and of Daudi Cells in SCID Mice by Inducing Cell Cycle Arrest", Blood, Mar. 1994, 83(5):1329-1336.
Ghosh et al., "End-To-End and End-To-Middle Interhelical Interactions: New Classes of Interacting Helix Pairs in Protein Structures", Acta Crystallogr D Biol Crystallogr., 2009, 65(Pt10):1032-1041.
Gil et al., "Regulation of the INK4b-ARF-INK4a Tumour Suppressor Locus: All for one or one for all", Nature Reviews Molecular Cell Biology, Sep. 2006, 7(9):667-677.
Glaser et al., "Antibody Engineering by Codon-Based Mutagenesis in a Filamentous Phage Vector System", The Journal of Immunology, Dec. 15, 1992, 149(12):3903-3913.
Gooi et al., "Monoclonal Antibody Reactive with the Human Epidermal-Growth-Factor Receptor Recognizes the Blood-Group-A Antigen", Bioscience Reports, Nov. 1983, 3(11):1045-1052.
Gorman et al., "Reshaping A Therapeutic CD4 Antibody", Proceedings of the National Academy of Sciences, 1991, 88:4181-4185.
Gorny et al., "Human Monoclonal Antibodies that Neutralize HIV-1", Hiv Immunology and HIV/SIV Vaccine Databases, 2003, 37-51.
Gregoire et al., "Covalent assembly of a soluble T cell receptor-peptide-major histocompatibility class I complex", PNAS, 1996, 93:7184-7189.
Greulich et al., "Functional Analysis of Receptor Tyrosine Kinase Mutations in Lung Cancer Identifies Oncogenic Extracellular Domain Mutations of ERBB2", Proceedings of the National Academy of Sciences, Sep. 4, 2012, 109(36):14476-14481.
Grigoryan et al., "Structural Specificity in Coiled-Coil Interactions", Current Opinion in Structural Biology, Aug. 2008, 18(4):477-483.
Groh et al., "Costimulation of CD8αβ T cells by NKG2D via engagement by MIC induced on virus-infected cells", Nature Immunology, Mar. 2001, 2(3):255-260.
Groneberg et al., "Nanoparticle-Based Diagnosis and Therapy", Current Cancer Drug Targets, 2006, 7(6):643-648.
Gruber et al., "Efficient Tumor Cell Lysis Mediated by a Bispecific Single Chain Antibody Expressed in *Escherichia coli*", Journal of Immunology, 1994, 152(11):5368-5374.
Gustchina et al., "Affinity Maturation by Targeted Diversification of the CDR-H2 Loop of a Monoclonal Fab Derived from a Synthetic Naïve Human Antibody Library and Directed Against the Internal Trimeric Coiled-Coil of Gp41 Yields a Set of Fabs with Improved HIV-1 Neutralization Potency and Breadth", Virology, Oct. 2009, 393(1):112-119.
Guy et al., "Organization of Proximal Signal Initiation at the TCR:CD3 Complex", Immunological Reviews, Nov. 2009, 232(1):7-21.
Hackel et al., "Stability and CDR Composition Biases Enrich Binder Functionality Landscapes", Journal of Molecular Biology, Aug. 2010, 401(1):84-96.
Hakomori S., "Cancer-Associated Glycosphingolipid Antigens: their Structure, Organization, and Function", Acta Anatomica, 1998, 161(1-4):79-90.

(56) References Cited

OTHER PUBLICATIONS

Heath et al., "The Human A33 Antigen is a Transmembrane Glycoprotein and a Novel Member of the Immunoglobulin Superfamily", Proceedings of the National Academy of Sciences, Jan. 21, 1997, 94(2):469-474.

Hellstrom et al., "Monoclonal Antibodies to Cell Surface Antigens Shared by Chemically Induced Mouse Bladder Carcinomas", Cancer Research, May 1985, 45:2210-2218.

Hellstrom et al., "Monoclonal Mouse Antibodies Raised against Human Lung Carcinoma", Cancer Research, Aug. 1986, 46(8):3917-3923.

Henikoff et al., "Amino Acid Substitution Matrices from Protein Blocks", Proceedings of the National Academy of Sciences, Nov. 1992, 89(22):10915-10919.

Henttu et al., "cDNA coding for the entire human prostate specific antigen shows high homologies to the human tissue kallikrein genes", Biochemical and Biophysical Research Communications, Apr. 1989, 160(2):903-910.

Herlyn et al., "Monoclonal Antibody Detection of a Circulating Tumor-Associated Antigen. I. Presence of Antigen in Sera of Patients with Colorectal, Gastric, and Pancreatic Carcinoma", Journal of Clinical Immunology, Apr. 1982, 2(2):135-140.

Hilkens et al., "Cell Membrane-Associated Mucins and Their Adhesion-Modulating Property", Trends in Biochemical Sciences, Sep. 1992, 17(9):359-363.

Hillhouse et al., "A Comprehensive Review of the Phenotype and Function of Antigen-Specific Immunoregulatory Double Negative T Cells", Journal of Autoimmunity, Feb. 2013, 40:58-65.

Hoelzer D., "Targeted Therapy with Monoclonal Antibodies in Acute Lymphoblastic Leukemia", Current Opinion in Oncology, Nov. 2013, 25(6):701-706.

Hofmeyer et al., "The Contrasting Role of B7-H3", Proceedings of the National Academy of Sciences of the United States of America, Jul. 29, 2008, 105(30):10277-10278.

Hogg et al., "A Monoclonal Antibody Exhibiting Reactivity with both X-Hapten- and Lactose-Bearing Glycolipids", Tissue Antigens, Jan. 1991, 37(1):33-38.

Holliger et al., "Carcinoembryonic Antigen (CEA)-specific T-Cell Activation in Colon Carcinoma Induced by Anti-CD3xAnti-CEA Bispecific Diabodies and B7xAnti-CEA Bispecific Fusion Proteins", Cancer Research, 1999, 59(12):2909-2916.

Holliger et al., "'Diabodies': Small Bivalent and Bispecific Antibody Fragments", Proceedings of the National Academy of Sciences, 1993, 90:6444-6448.

Holliger et al., "Specific Killing of Lymphoma Cells by Cytotoxic T-Cells Mediated by a Bispecific Diabody", Protein Engineering, 1996, 9(3):299-305.

Holmberg et al., "Theratope Vaccine (STn-KLH).", Expert Opinion on Biological Therapy, Sep. 2001, 1 (5):881-891.

Hoo et al., "Characterization of a single-chain T-cell receptor expressed in *Escherichia coli*", PNAS USA, 1992, 89:4759-4763.

Hoon et al., "Molecular Cloning of a Human Monoclonal Antibody Reactive to Ganglioside GM3 Antigen on Human Cancers", Cancer Research, Nov. 1993, 53(21):5244-5250.

Houghten et al., "General Method for The Rapid Solid-Phase Synthesis of Large Numbers of Peptides: Specificity of Antigen-Antibody Interaction at The Level of Individual Amino Acids", Proceedings of the National Academy of Sciences, 1985, 82(15):5131-5135.

Howard et al., "Intracerebral Drug Delivery in Rats with Lesion-Induced Memory Deficits", Journal of Neurosurgery, 1989, 71(1):105-112.

Hudrisier et al., "Capture of Target Cell Membrane Components via Trogocytosis Is Triggered by a Selected Set of Surface Molecules on T or B Cells", Journal of Immunology, Mar. 15, 2007, 178(6):3637-3647.

Hutchins et al., "Improved Biodistribution, Tumor Targeting, and Reduced Immunogenicity in Mice with A Gamma 4 Variant of Campath-1H", Proc. Natl. Acad. Sci. (U.S.A.), 1995, 92:11980-11984.

Idusogie et al., "Engineered Antibodies with Increased Activity to Recruit Complement", Journal of Immunology, 2001, 166:2571-2575.

Idusogie et al., "Mapping of The C1q Binding Site on Rituxan, A Chimeric Antibody with A Human IgG1 Fc", Journal of Immunology, 2000, 164: 4178-4184.

Israeli et al., "Molecular cloning of a complementary DNA encoding a prostate-specific membrane antigen", Cancer Research, Jan. 1993, 53(2):227-230.

Jamieson et al., "The Role of the NKG2D Immunoreceptor in Immune Cell Activation and Natural Killing", Immunity, Jul. 2002, 17(1):19-29.

Jason-Moller et al., "Overview of Biacore Systems and Their Applications", Current Protocols in Protein Science, Aug. 2006, 44(1):19.13.1-19.13.14.

Jefferis et al., "Interaction Sites on Human IgG-Fc for FcgammaR: Current Models", Immunology Letters, 2002, 82:57-65.

Jefferis et al., "Modulation of Fc(Gamma)R and Human Complement Activation by IgG3-Core Oligosaccharide Interactions", Immunology Letters, 1996, 54:101-104.

Jefferis et al., "Recognition Sites on Human IgG for Fc Gamma Receptors: The Role of Glycosylation", Immunology Letters, 1995, 44:111-117.

Jennings Veronica M., "Review of Selected Adjuvants Used in Antibody Production", ILAR Journal, 1995, 37(3):119-125.

Johansson et al., "A Unique Population of Extrathymically Derived αβTCR+CD4-CD8-T Cells with Regulatory Functions Dominates the Mouse Female Genital Tract", The Journal of Immunology, Mar. 2003, 170(4):1659-1666.

Johansson et al., "Structure, Specificity, and Mode of Interaction for Bacterial Albumin-binding Modules", Journal of Biological Chemistry, Mar. 2002, 277(10):8114-8120.

Johnson et al., "Effector Cell Recruitment with Novel Fv-Based Dual-Affinity Re-Targeting Protein Leads to Potent Tumor Cytolysis And In vivo B-Cell Depletion", Journal of Molecular Biology, 2010, 399(3):436-449.

Joliot et al., "Antennapedia Homeobox Peptide Regulates Neural Morphogenesis", Proceedings of the National Academy of Sciences, 1991, 88:1864-1868.

Joly et al., "What is Trogocytosis and what is its Purpose?", Nature Immunology, Oct. 2003, 4(9):815.

Jones et al., "Replacing the Complementarity-Determining Regions in a Human Antibody with Those from A Mouse", Nature, 1986, 321:522-525.

Jung et al., "Target Cell-induced T Cell Activation with Bi- and Trispecific Antibody Fragments", European Journal of Immunology, Oct. 1, 1991, 21(10):2431-2435.

Jurcic Joseph G., "Immunotherapy for Acute Myeloid Leukemia", Current Oncology Reports, 2005, 7(5):339-346.

Karlin et al., "Methods for Assessing the Statistical Significance of Molecular Sequence Features by using General Scoring Schemes", Proceedings of the National Academy of Sciences, 1990, 87(6):2264-2268.

Karlsson R., "SPR For Molecular Interaction Analysis: A Review of Emerging Application Areas", Journal of Molecular Recognition, 2004, 17(3):151-161.

Karu et al., "Recombinant Antibody Technology", ILAR Journal, 1995, 37(3):132-141.

Kasaian et al., "IL-13 Antibodies Influence IL-13 Clearance in Humans by Modulating Scavenger Activity of IL-13Rα2", The Journal of Immunology, Jul. 1, 2011, 187(1):561-569.

Kawai et al., "Interferon-α enhances CD317 expression and the antitumor activity of anti-CD317 monoclonal antibody in renal cell carcinoma xenograft models", Cancer Science, Dec. 2008, 99(12):2461-2466.

Kelley et al., "In: Genetic Engineering Principles and Methods", Setlow, J.K. Ed., Plenum Press, N.Y., 1990, 12:1-19.

Kettleborough et al., "Humanization of a Mouse Monoclonal Antibody by CDR-Grafting: The Importance of Framework Residues on Loop Conformation", Protein Engineering, 1991, 4(7):773-783.

Khawli et al., "Cytokine, Chemokine, and Co-Stimulatory Fusion Proteins for the Immunotherapy of Solid Tumors", Handbook of Experimental Pharmacology, 2008, 181:291-328.

(56) References Cited

OTHER PUBLICATIONS

Kim et al., "Signalling Function of the B-cell Antigen Receptors", Immunological Reviews, 1993, 132:125-146.
Klein et al., "Examination of the contributions of size and avidity to the neutralization mechanisms of the anti-HIV antibodies b12 and 4E10", PNAS USA, 2009, 106:7385-7390.
Kohler et al., "Continuous Cultures of Fused Cells Secreting Antibody of Predefined Specificity", Nature, 1975, 256:495-497.
Kontermann Re., "Dual targeting strategies with bispecific antibodies", MAbs., vol. 4, No. 2, 2012, 182-197.
Korman et al., "Checkpoint Blockade in Cancer Immunotherapy", Advances in Immunology, 2007, 90:297-339.
Kounalakis et al., "Tumor Cell and Circulating Markers in Melanoma: Diagnosis, Prognosis, and Management", Current Oncology Reports, Sep. 2005, 7(5):377-382.
Krause et al., "An Insertion Mutation That Distorts Antibody Binding Site Architecture Enhances Function of a Human Antibody", mBio, Jan./Feb. 2011, 2(1):8 pages.
Kreitman, "Immunotoxins for Targeted Cancer Therapy", The AAPS Journal, Sep. 2006, 8(3):E532-E551.
Kuan et al., "Affinity-Matured Anti-Glycoprotein NMB Recombinant Immunotoxins Targeting Malignant Gliomas and Melanomas", International Journal of Cancer, Jul. 2011, 129(1):111-121.
Kügler M, "A recombinant trispecific single-chain Fv derivative directed against CD123 and CD33 mediates effective elimination of acute myeloid leukaemia cells by dual targeting", Br J Haematol. vol. 150, No. 5, (Abstract; Figures 1 and 5) Citation is not enclosed due to copyright restrictions., Jul. 16, 2010, 574-586.
Kuhns et al., "Deconstructing the Form and Function of the TCR/CD3 Complex", Immunity, Feb. 2006, 24(2):133-139.
Kurosaki et al., "Molecular Mechanisms in B Cell Antigen Receptor Signaling", Current Opinion in Immunology, 1997, 9(3):309-318.
Kurrle et al., "BMA 031—A TCR-Specific Monoclonal Antibody for Clinical Application", Transplantation Proceedings, 1989, 21(1 Pt 1):1017-1019.
Kwong et al., "Generation, Affinity Maturation, and Characterization of A Human Anti-Human NKG2D Monoclonal Antibody with Dual Antagonistic and Agonistic Activity", Journal of Molecular Biology, Dec. 2008, 384(5):1143-1156.
Lam et al., "Microencapsulation of Recombinant Humanized Monoclonal Antibody for Local Delivery", Proc Int Symp Controlled Release Bioact Mater, 1997, 24:759-760.
Langer Robert, "New Methods of Drug Delivery", Science, 1990, 249:1527-1533.
Lanier et al., "Up on the tightrope: natural killer cell activation and inhibition", Nat Immunol., 2008, 9(5):495-502.
Lazar et al., "Transforming Growth Factor A: Mutation of Aspartic Acid 47 and Leucine 48 Results in Different Biological Activities", Molec. Cell. Biol., 1988, 8:1247-1252.
Lbragimova et al., "Stability of the beta-sheet of the WW domain: A molecular dynamics simulation study", Biophysical Journal, Oct. 1999, 77(4): 2191-2198.
Lee et al., "Targeting Cyclins and Cyclin-Dependent Kinases in Cancer: Lessons from Mice, Hopes for Therapeutic Applications in Humans", Cell Cycle, Sep. 2006, 5(18):2110-2114.
Lefranc et al., "Gm, Am and Km immunoglobulin allotypes of two populations in Tunisia", Human Genetics, 1979, 50:199-211.
Lefranc et al., "Molecular Genetics of Immunoglobulin Allotype Expression", The Human IgG Subclasses: Molecular Analysis of Structure, Function and Regulation, Pergamon Press, 1990, 43-78.
Legendre et al., "Prognostic Stratification of Dukes B Colon Cancer by a Neoglycoprotein", International Journal of Oncology, Sep. 2004, 25(2):269-276.
Lemaoult et al., "Exchanges of Membrane Patches (Trogocytosis) Split Theoretical and Actual Functions of Immune Cells", Human Immunology, Apr. 2007, 68(4):240-243.
Levy et al., "Inhibition of Calcification of Bioprosthetic Heart Valves by Local Controlled-Release Diphosphonate", Science, 1985, 228(4696):190-192.

Lewis-Wambi et al., "Overexpression of CEACAM6 promotes migration and invasion of oestrogen-deprived breast cancer cells", European Journal of Cancer, Aug. 2008, 44(12):1770-1779.
Liang et al., "Integrin-Beta6-targeted Immunoliposomes 1~fediate Tumor Specific Drug Delivery and Enhance Therapeutic Efficacy in Colon Carcinoma", Clinical Cancer Research, Mar. 2015, 21(5): 14 pages.
Lin et al., "Structure-function relationships in glucagon: properties of highly purified des-His-1-, monoiodo-, and (des-Asn-28, Thr-29)(homoserine lactone-27)-glucagon", Biochemistry, Apr. 22, 1975, 14(8):1559-1563.
Lindley et al., "The Clinical Utility of Inhibiting CD28-Mediated Costimulation", Immunological Reviews, 2009, 229:307-321.
Litowski et al., "Designing Heterodimeric Two-Stranded Alpha-Helical Coiled-Coils. Effects of Hydrophobicity and Alpha-Helical Propensity on Protein Folding, Stability, and Specificity", Journal of Biological Chemistry, Oct. 4, 2002, 277(40):37272-37279.
Livingston et al., "Improved survival in stage III melanoma patients with GM2 antibodies: a randomized trial of adjuvant vaccination with GM2 ganglioside", Journal of Clinical Oncology, May 1994, 12(5):1036-1044.
Livingston et al., "Selection of GM2, Fucosyl GM1, Globo H and Polysialic Acid as Targets on Small Cell Lung Cancers for Antibody Mediated Immunotherapy", Cancer Immunology Immunotherapy, Oct. 2005, 54(10):1018-1025.
Lobuglio et al., "Mouse-Human Chimeric Monoclonal Antibody in Man: Kinetics and Immune Response", Proceedings of the National Academy of Sciences, 1989, 86:4220-4224.
Lonberg et al., "Human Antibodies from Transgenic Mice", International Reviews of Immunology, 1995, 13:65-93.
Lotem et al., "Presentation of Tumor Antigens by Dendritic Cells Genetically Modified with Viral and Nonviral Vectors", Journal of Immunotherapy, Nov.-Dec. 2006, 29(6):616-627.
Loveless et al., "Developmental Patterning of the Carbohydrate Antigen FC10.2 during Early Embryogenesis in the Chick", Development, 1990, 108(1):97-106.
Lu et al., "A Fully Human Recombinant IgG-Like Bispecific Antibody to Both the Epidermal Growth Factor Receptor and The Insulin-Like Growth Factor Receptor for Enhanced Antitumor Activity", Journal of Biological Chemistry, 2005, 280(20):19665-19672.
Lu et al., "The Effect of a Point Mutation on the Stability of IgG4 as Monitored by Analytical Ultracentrifugation", Journal of Pharmaceutical Sciences, Feb. 2008, 97(2):960-969.
Lund et al., "Human Fc Gamma RI and Fc Gamma RII Interact with Distinct but Overlapping Sites on Human IgG", Journal of Immunology, 1991, 147:2657-2662.
Lund et al., "Multiple Binding Sites on The CH2 Domain of IgG for Mouse Fc Gamma R11", Molecular Immunology, 1992, 29:53-59.
Lund et al., "Multiple Interactions of IgG with Its Core Oligosaccharide Can Modulate Recognition by Complement and Human Fc Gamma Receptor I and Influence the Synthesis of Its Oligosaccharide Chains", Journal of Immunology, 1996, 157:4963-4969.
Lund et al., "Oligosaccharide-Protein Interactions in IgG Can Modulate Recognition by Fc Gamma Receptors", The FASEB Journal, 1995, 9:115-119.
Mace et al., "Cell Biological Steps and Checkpoints in Accessing NK Cell Cytotoxicity", Immunology & Cell Biology, Mar. 2014, 92(3):245-255.
Maeda et al., "Construction of Reshaped Human Antibodies With HIV-Neutralizing Activity", Human Antibodies Hybridoma, 1991, 2:124-134.
Malaguarnera et al., "Serum Markers of Hepatocellular Carcinoma", Digestive Diseases and Sciences, 2010, 55(10):2744-2755.
Mallone et al., "Targeting T lymphocytes for immune monitoring and intervention in autoimmune diabetes", American Journal of Therapeutics, 2005, 12(6):534-550.
Malmborg et al., "BIAcore as a Tool in Antibody Engineering", Journal of Immunological Methods, 1995, 183:7-13.
Malmqvist et al., "Biomolecular Interaction Analysis: Affinity Biosensor Technologies for Functional Analysis of Proteins", Current Opinion in Chemical Biology, Oct. 1997, 1(3):378-383.

(56) References Cited

OTHER PUBLICATIONS

Malmqvist Magnus, "Biacore: An Affinity Biosensor System for Characterization of Biomolecular Interactions", Biochemical Society Transactions, Mar. 1999, 27(2):335-340.

Maloney, "Anti-CD20 Antibody Therapy for B-Cell Lymphomas", The New England Journal of Medicine, 2012, 366:2008-2016.

Mariuzza et al., "The Structural Basis of Antigen-Antibody Recognition", Annual Review of Biophysics, 1987, 16:139-159.

Maroun et al., "Distinct Roles for CD4 and CD8 as Co-Receptors in T Cell Receptor Signalling", European Journal of Immunol, 1994, 24:959-966.

Marvin et al., "Recombinant Approaches to IgG-Like Bispecific Antibodies", Acta Pharmacologica Sinica, 2005, 26:649-658.

Masuda et al., "Possible Implication of Fcγ Receptor-Mediated Trogocytosis in Susceptibility to Systemic Autoimmune Disease", Clinical and Developmental Immunology, 2013, 2013:6 pages.

Mathelin et al., "Circulating Proteinic Biomarkers and Breast Cancer", Gynecologie, obstetrique & fertilite, 2006, 34(7-8):638-646.

McIntyre et al., "Consequences of Double Negative Regulatory T Cell and Antigen Presenting Cell Interaction on Immune Response Suppression", International Immunopharmacology, May 2011, 11(5):597-603.

Mei, "Rationale of Anti-CD19 Immunotherapy: An Option to Target Autoreactive Plasma Cells in Autoimmunity", Arthritis Research & Therapy, 2012, 14(Suppl 5): S1:1-16.

Merrifield et al., "Solid Phase Synthesis", Science, 1986, 232(4748):341-347.

Messmer et al., "CD154 Gene Therapy for Human B-Cell Malignancies", Annals of the New York Academy of Sciences, 2005, 1062:51-60.

Miao et al., "EphA2 is a Mediator of Vemurafenib Resistance and a Novel Therapeutic Target in Melanoma", Cancer Discovery, Mar. 2015, 5(3):274-287.

Michalk et al., "Characterization of a Novel Single-Chain Bispecific Antibody for Retargeting of T Cells to Tumor Cells via the TCR Co-Receptor CD8", PLoS One, Apr. 21, 2014, 9(4):1-8.

Miller Jeffreys., "Therapeutic applications: Natural killer cells in the clinic", Hematology, Dec. 2013, 2013(1):247-253.

Mittelman et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies", Journal of Clinical Investigation, Dec. 1990, 86(6):2136-2144.

Moller et al., "Bispecific-Monoclonal-Antibody-Directed Lysis of Ovarian Carcinoma Cells by Activated Human T Lymphocytes", Cancer Immunology, Immunotherapy, 1991, 33(4):210-216.

Montgomery et al., "Affinity Maturation and Characterization of a Human Monoclonal Antibody Against HIV-1 Gp41", mAbs, 2009, 1(5):462-474.

Moore et al., "Application of Dual Affinity Retargeting Molecules to Achieve Optimal Redirected T-Cell Killing Of B-Cell Lymphoma", Blood, 2011, 117(17):4542-4551.

Muramatsu et al., "Carbohydrate Antigens Expressed on Stem Cells and Early Embryonic Cells", Glycoconjugate Journal, 2004, 21(1-2):41-45.

Muta et al., "CD30: from Basic Research to Cancer Therapy", Immunologic Research, Dec. 2013, 57(1-3):151-158.

Nakamura et al., "NK-Cell Fratricide: Dynamic Crosstalk Between NK and Cancer Cells", Oncolmmunology, 2013, 2(11):e26529.

Nashan et al., "Fine Specificity of a Panel of Antibodies Against the TCR/CD3 Complex", Transplantation Proceedings, Oct. 1987, 19(5):4270-4272.

Natali et al., "Immunohistochemical Detection of Antigen in Human Primary and Metastatic Melanomas by the Monoclonal Antibody 140.240 and Its Possible Prognostic Significance", Cancer, 1987, 59(1):55-63.

Ning et al., "Intratumoral Radioimmunotherapy of a Human Colon Cancer Xenograft Using a Sustained-Release Gel", Radiotherapy and Oncology, May 1996, 39(2):179-189.

Norman Douglasj., "Mechanisms of Action and Overview of OKT3", Therapeutic Drug Monitoring, Dec. 1995, 17(6):615-620.

Notley et al., "ANTI-CD3 therapy expands the numbers of CD4+ and CDS+ Treg cells and induces sustained amelioration of collagen-induced arthritis", Arthritis & Rheumatism, 2010, 62:171-178.

O'Dwyer P., "The Present and Future of Angiogenesis-Directed Treatments of Colorectal Cancer", Oncologist, Oct. 2006, 11(9):992-998.

Olafsen et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.

Pal et al., "Targeting HER2 Epitopes", Seminars in Oncology, Aug. 2006, 33(4):386-391.

Palma et al., "Plasmacytoids Dendritic Cells are a Therapeutic Target in Anticancer Immunity", Biochimica et Biophysica Acta (BBA)—Reviews on Cancer, Dec. 2012, 1826(2):407-414.

Peeters et al., "Production of Antibodies and Antibody Fragments in Plants", Vaccine, 2001, 19:2756-2761.

Peggs et al., "Principles and Use of Anti-CTLA4 Antibody in Human Cancer Immunotherapy", Current Opinion in Immunology, 2006, 18(2):206-213.

Peipp et al., "Bispecific Antibodies Targeting Cancer Cells", Biochemical Society Transactions, 2002, 30(4):507-511.

Peltz et al., "Human FcγRIII: Cloning, expression, and identification of the chromosomal locus of two Fc receptors for IgG", Proc. Natl. Acad. Sci. (U.S.A.), Feb. 1989, 86(3):1013-1017.

Perez et al., "Isolation and Characterization of a Cdna Encoding the KS1/4 Epithelial Carcinoma Marker", Journal of Immunology, May 15, 1989, 142(10):3662-3667.

Peters et al., "Engineering an Improved IgG4 Molecule with Reduced Disulfide Bond Heterogeneity and Increased Fab Domain Thermal Stability", Journal of Biological Chemistry, Jul. 13, 2012, 287(29):24525-24533.

Poe et al., "CD22 And Siglec-G in B Cell Function and Tolerance", Trends in Immunology, 2012, 33(8):413-420.

Pollock et al., "Transgenic Milk as a Method for The Production of Recombinant Antibodies", Journal of Immunological Methods, 1999, 231:147-157.

Ponomarenko et al., "Role of K—+A light-chain constant-domain switch in the structure and functionality of A 17 reactibody", Acta Crystallographica Section D, 2014, D70:708-719.

Portoles et al., "The TCR/CD3 Complex: Opening the Gate to Successful Vaccination", Current Pharmaceutical Design, 2009, 15(28):3290-3300.

Prange et al., "Beta-Catenin Accumulation in the Progression of Human Hepatocarcinogenesis Correlates with loss of E-Cadherin and Accumulation of P53, but not with Expression of Conventional WNT-1 Target Genes", The Journal of Pathology, 2003, 201(2):250-259.

Presta et al., "Engineering Therapeutic Antibodies for Improved Function", Biochemical Society Transactions, 2002, 30(4):487-490.

Pui et al., "Characterization of Childhood Acute Leukemia with Multiple Myeloid and Lymphoid Markers at Diagnosis and at Relapse", Blood, Sep. 1991, 78(5):1327-1337.

Rabbani et al., "Expression of ROR1 in Patients with Renal Cancer—A Potential Diagnostic Marker", Iranian Biomedical Journal, Jul. 2010, 14(3):77-82.

Ragnhammar et al., "Effect of monoclonal antibody 17-1A and gm-CSF in patients with advanced colorectal carcinoma—long-lasting, complete remissions can be induced", International Journal of Cancer, Mar. 1993, 53(5):751-758.

Ragupathi et al., "Antibody Inducing Polyvalent Cancer Vaccines", Cancer Treatment and Research, Feb. 2005, 123:157-180.

Raufi et al., "Targeting CD19 in B-Cell Lymphoma: Emerging Role of SAR3419", Cancer Management and Research, 2013, 5:225-233.

Raulet Davidh., "Roles of The NKG2D Immunoreceptor and Its Ligands", Nature Reviews Immunology, Oct. 2003, 3:781-790.

Ravoet et al., "Molecular profiling of CD3-CD4+ T cells from patients with the lymphocytic variant of hypereosinophilic syndrome reveals targeting of growth control pathways", Blood, 2009, 114:2969-2983.

(56) References Cited

OTHER PUBLICATIONS

Reddy et al., "Elimination of Fc Receptor-Dependent Effector Functions of a Modified IgG4 Monoclonal Antibody to Human CD4", Journal of Immunology, 2000, 164:1925-1933.
Reff et al., "Depletion of B Cells In vivo By A Chimeric Mouse Human Monoclonal Antibody to CD20", Blood, Jan. 15, 1994, 83(2):435-445.
Renders et al., "Engineered CD3 Antibodies for Immunosuppression", Clinical & Experimental Immunology, 2003, 133(3):307-309.
Ridgway et al., "'Knobs-Into-Holes' Engineering of Antibody CH3 Domains for Heavy Chain Heterodimerization", Protein Engineering, 1996, 9(7):617-621.
Riechmann et al., "Reshaping Human Antibodies for Therapy", Nature, 1988, 332:323-327.
Riley et al., "Design and Activity of a Murine and Humanized anti-CEACAM6 scFv in the Treatment of Pancreatic Cancer", Cancer research, Mar. 2009, 69(5):1933-1940.
Rimon et al., "Gonadotropin-Induced Gene Regulation in Human Granulosa Cells Obtained from IVF Patients: Modulation of Genes Coding for Growth Factors and their Receptors and Genes Involved in Cancer and other Diseases", International Journal of Oncology, May 2004, 24(5):1325-1338.
Ritter et al., "Characterization of Posttranslational Modifications of Human A33 Antigen, a Novel Palmitoylated Surface Glycoprotein of Human Gastrointestinal Epithelium", Biochemical and Biophysical Research Communications, Jul. 30, 1997, 236(3):682-686.
Robak et al., "Anti-CD37 Antibodies for Chronic Lymphocytic Leukemia", Expert Opinion on Biological Therapy, Feb. 2014, 14(5):651-661.
Rodriquez et al., "Influence of Interleukin-15 in CD8+ Natural Killer Cells in Human Immunodeficiency Virus Type 1-Infected Chimpanzees", Journal of General Virology, Mar. 2007, 88(Pt 2):641-651.
Rosati et al., "Chronic Lymphocytic Leukaemia: A Review of the Immuno-Architecture", Current Topics in Microbiology and Immunology, 2005, 294:91-107.
Rudikoff et al., "Single Amino Acid Substitution Altering Antigen-Binding Specificity", Proceedings of the National Academy of Sciences, 1982, 79:1979-1983.
Russell S., "CD46: A Complement Regulator and Pathogen Receptor that Mediates Links Between Innate and Acquired Immune Function", Tissue Antigens, Aug. 2004, 64(2):111-118.
Saalmuller et al., "Discrimination between two subsets of porcine CDS+ cytolytic T lymphocytes by the expression of CDS antigen", Immunology, 1994, 81:578-583.
Saatian et al., "Expression of Genes for B7-H3 and Other T Cell Ligands by Nasal Epithelial Cells During Differentiation and Activation", AJP Lung Cellular and Molecular Physiology, Aug. 2004, 287(1):L217-225.
Saito et al., "Complete primary structure of a heterodimeric T-cell receptor deduced from cDNA sequences", Nature, 1984, 309:757-762.
Saleh et al., "Generation of a human anti-idiotypic antibody that mimics the GD2 antigen", The Journal of Immunology, Sep. 15, 1993, 151(6):3390-3398.
Sato et al., "Reshaping a Human Antibody to Inhibit the Interleukin 6-dependent Tumor Cell Growth", Cancer Research, 1993, 53:851-856.
Saudek et al., "A Preliminary Trial of the Programmable Implantable Medication System for Insulin Delivery", New England Journal of Medicine, Sep. 1989, 321(9):574-579.
Sayeed et al., "Aberrant Regulation of the BST2 (Tetherin) Promoter Enhances Cell Proliferation and Apoptosis Evasion in High Grade Breast Cancer Cells", PLoS ONE, Jun. 2013, 8(6):e67191, 10 pages.
Schier et al., "Isolation of Picomolar Affinity Anti-C-Erbb-2 Single-Chain Fv by Molecular Evolution of the Complementarity Determining Regions in the Center of the Antibody Binding Site", Journal of Molecular Biology, 1996, 263(4):551-567.
Schoonjians et al., "Fab chains as an efficient heterodimerization scaffold for the production of recombinant bispecific and trispecific antibody derivatives", Journal of Immunology, 2000, 165(12):7050-7057.
Schwartz et al., "A superactive insulin: [B10-aspartic acid]insulin(human)", PNAS, 1987, 84(18):6408-6411.
Sefton et al., "Implantable Pumps", Critical Reviews in Biomedical Engineering, 1980, 14:201-240.
Sgouros et al., "Modeling and Dosimetry of Monoclonal Antibody M195 (Anti-CD33) in Acute Myelogenous Leukemia", The Journal of Nuclear Medicine, Mar. 1, 1993, 34:422-430.
Shahani et al., "Human liver sinusoidal endothelial cells but not hepatocytes contain factor VII", Journal of Thrombosis and Haemostasis, Jan. 2014, 12(1):36-42.
Shaw et al., "Characterization of A Mouse-Human Chimeric Monoclonal Antibody (17-1A) To A Colon Cancer Tumor-Associated Antigen", Journal of Immunology, 1987, 138(12):4534-4538.
Shearman et al., "Construction, expression and characterization of humanized antibodies directed against the human $\alpha/\beta$ T cell receptor", The Journal of Immunology, Dec. 1991, 147(12):4366-4373.
Shearman et al., "Construction, expression, and biologic activity of murine/human chimeric antibodies with specificity for the human $\alpha/\beta$ T cell receptor", The Journal of Immunology, Feb. 1991, 146(3):928-935.
Shields et al., "High Resolution Mapping of the Binding Site on Human Igg1 for Fc Gamma RI, Fc Gamma RII, Fc Gamma RIII, and Fcrn and Design of Igg1 Variants with Improved Binding to the Fc Gamma R", Journal of Biological Chemistry, 2001, 276:6591-6604.
Shitara et al., "A mouse/human chimeric anti-(ganglioside GD3) antibody with enhanced antitumor activities", Cancer Immunology, Immunotherapy, Nov. 1993, 36:373-380.
Shopes Bob, "A Genetically Engineered Human IgG Mutant with Enhanced Cytolytic Activity", J. Immunol., 1992, 148:2918-2922.
Silverberg et al., "Cancer statistics, 1989", CA:A Cancer Journal for Clinicians, Jan./Feb. 1989, 39(1):3-20.
Smith-Garvin et al., "T Cell Activation", Annual Review of Immunology, 2009, 27:591-619.
Sondermann et al., "The 3.2-A Crystal Structure of The Human Igg1 Fc Fragment-Fc GammaRIII Complex", Nature, 2000, 406:267-273.
Song et al., "Antibody Mediated Lung Targeting of Long-Circulating Emulsions", PDA Journal of Pharmaceutical Science & Technology, 1996, 50(6):372-377.
St. Clair Ew., "Novel Targeted Therapies for Autoimmunity", Current Opinion in Immunology, Dec. 2009, 21(6):648-657.
Staerz et al., "Hybrid Antibodies Can Target Sites for Attack by T Cells", Nature, 1985, 314:628-631.
Staudinger et al., "The Novel Immunotoxin HM1.24-ETA' Induces Apoptosis in Multiple Myeloma Cells", Blood Cancer Journal, 2014, 13;4:e219.
Stavenhagen et al., "Fc Optimization of Therapeutic Antibodies Enhances Their Ability to Kill Tumor Cells In Vitro And Controls Tumor Expansion In Vivo Via Low-Affinity Activating Fcgamma Receptors", Cancer Research, 2007, 67(18):8882-8890.
Steidl et al., "In Vitro Affinity Maturation of Human GM-CSF Antibodies by Targeted CDR-Diversification", Molecular Immunology, Nov. 2008, 46(1):135-144.
Steinkruger et al., "The d'—d—d' Vertical Triad is Less Discriminating Than the a'—a—a' Vertical Triad in the Antiparallel Coiled-coil Dimer Motif", Journal of the American Chemical Society, Feb. 2012, 134(5):2626-2633.
Stephan et al., "Selective Cloning of Cell Surface Proteins Involved in Organ Development: Epithelial Glycoprotein Is Involved in Normal Epithelial Differentiation", Endocrinology, 1999, 140:5841-5854.
Stevenson et al., "A Chimeric Antibody with Dual Fc Regions (bisFabFc) Prepared by Manipulations at the IgG Hinge", Anti-Cancer Drug Design, 1989, 3(4):219-230.
Stievano et al., "CDS+ alpha beta+ T cells that lack surface CDS antigen expression are a major lymphotactin (XCL 1) source in peripheral blood lymphocytes", Journal of Immunology, 2003, 171:4528-4538.

(56) References Cited

OTHER PUBLICATIONS

Straussman et al., "Kinking the Coiled Coil—Negatively Charged Residues at the Coiled-coil Interface", Journal of Molecular Biology, 2007, 366(4):1232-1242.
Sun et al., "Characterization of Mouse and Human B7-H3 Genes", Journal of Immunology, 2002, 168:6294-6297.
Sun et al., "Mechanisms Contributing to T Cell Receptor Signaling and Assembly Revealed by The Solution Structure of An Ectodomain Fragment of The CD3ε:γ Heterodimer", Cell, Jun. 29, 2001, 105(7):913-923.
Swanson Sj, "Characterization of an Immune Response", Dev Biol (Basel), 2005, 122:95-101.
Swinnen et al., "OKT3 monoclonal antibodies induce interleukin-6 and interleukin-10: a possible cause of lymphoproliferative disorders associated with transplantation", Current Opinion in Nephrology and Hypertension, Jul. 1993, 2(4):670-678.
Tailor et al., "Nucleotide Sequence of Human Prostatic Acid Phosphatase Determined from a Full-Length CDNA Clone", Nucleic Acids Research, 1990, 18(16):1 page.
Takabe et al., "Immunomagnetic exclusion of E-cadherin-positive hepatoblasts in fetal mouse liver cell cultures impairs morphogenesis and gene expression of sinusoidal endothelial cells", Journal of Anatomy, Jun. 2012, 221(3):229-239.
Takahashi M., "A Study on Clinical Significance of Oncofetal Antigen-1 in Gynecologic Tumors", Nihon Sanka Fujinka Gakkai Zasshi, Dec. 1984, 36(12):2613-2618.
Takemura et al., "Construction of A Diabody (Small Recombinant Bispecific Antibody) Using A Refolding System", Protein Engineering, 2000, 13(8):583-588.
Tanner et al., "Characterization of A Novel Cell Line Established from A Patient with Herceptin-Resistant Breast Cancer", Molecular Cancer Therapeutics, Dec. 2004, 3(12):1585-1592.
Tellez-Avila et al., "The Carcinoembryonic Antigen: about an Old Acquaintance", Journal of Clinical Research, 2005, 57(6):814-819.
Tempest et al., "Reshaping A Human Monoclonal Antibody to Inhibit Human Respiratory Syncytial Virus Infection in Vivo", Bio-Technology, 1991, 9:266-271.
Thomas et al., "Molecular Immunology Lessons from Therapeutic T-Cell Receptor Gene Transfer", Immunology, 2010, 129(2):170-177.
Thomas et al., "Monoclonal Antibody Therapy for Hairy Cell Leukemia", Hematology/Oncology Clinics of North America, Oct. 2006, 20(5):1125-1136.
Thompson et al., "Carcinoembryonic Antigen Gene Family: Molecular Biology and Clinical Perspectives", Journal of Clinical Laboratory Analysis, 1991, 5(5):344-366.
Trauth et al., "Monoclonal antibody-mediated tumor regression by induction of apoptosis", Science, Jul. 21, 1989, 245(4915):301-305.
Tripet et al., "Kinetic Analysis of the Interactions between Troponin C and the C-terminal Troponin I Regulatory Region and Validation of a New Peptide Delivery/Capture System used for Surface Plasmon Resonance", Journal of Molecular Biology, 2002, 323(2):345-362.
Troussard et al., "Hairy Cell Leukemia. What is New Forty Years after the First Description?", Hematology and Cell Therapy, Aug. 1998, 40(4):139-148.
Tutt et al., "Trispecific F(ab')3 Derivatives That Use Cooperative Signaling via the TCR/CD3 Complex and CD2 to Activate and Redirect Resting Cytotoxic T Cells", The Journal of Immunology, Jul. 1, 1991, 147(1):60-69.
Van Der Merwe et al., "Mechanisms for T Cell Receptor Triggering", Nature Reviews Immunology, Jan. 2011, 11(1):47-55.
Van Horsen et al., "TNF-α in Cancer Treatment: Molecular Insights, Antitumor Effects, and Clinical Utility", Oncologist, 2006, 11(4):397-408.
Van Regenmortel, "Improving the Quality of BIACORE-Based Affinity Measurements", Developments in Biologicals, Feb. 2003, 112:141-151.
Velázquez-Márquez et al., "Sialyl Lewis X Expression in Cervical Scrapes of Premalignant Lesions", Journal of Biosciences, Dec. 2012, 37(6):999-1004.

Verhoeyen et al., "Reshaping Human Antibodies: Grafting an Antilysozyme Activity", Science, 1988, 239:1534-1536.
Veri et al., "Monoclonal Antibodies Capable of Discriminating the Human Inhibitory Fcgamma-Receptor IIB (CD32B) From the Activating Fcgamma-Receptor IIA (CD32A): Biochemical, Biological and Functional Characterization", Immunology, 2007, 121(3):392-404.
Veri et al., "Therapeutic Control of B Cell Activation Via Recruitment of Fcgamma Receptor IIb (CD32B) Inhibitory Function with A Novel Bispecific Antibody Scaffold", Arthritis & Rheumatology, 2010, 62(7):1933-1943.
Viglietta et al., "Modulating Co-Stimulation", Neurotherapeutics, 2007, 4:666-675.
Vijayasardahl et al., "The Melanoma Antigen Gp75 is the Human Homologue of the Mouse B (Brown) Locus Gene Product", Journal of Experimental Medicine, Apr. 1, 1990, 171(4):1375-1380.
Walker et al., "Activation of T Cells by Cross-Linking an Anti-CD3 Antibody with a Second Anti-T Cell Antibody: Mechanism and Subset-Specific Activation", European Journal of Immunology, Jun. 1, 1987, 17(6):873-880.
Walker, "CD22: An Inhibitory Enigma", Immunology, 2008, 123(3):314-325.
Walter et al., "Acute Myeloid Leukemia Stem Cells and CD33-Targeted Immunotherapy", Blood, Jun. 28, 2012, 119(26):6198-6208.
Wang et al., "Chimeric and humanized anti-HM1.24 antibodies mediate antibody-dependent cellular cytotoxicity against lung cancer cells", Lung Cancer, Jan. 2009, 63(1):23-31.
Wang et al., "HM1.24 (CD317) is a novel target against lung cancer for immunotherapy using anti-HM1.24 antibody", Cancer Immunology Immunotherapy, Jun. 2009, 58(6):967-976.
Watanabe et al., "The quantity of TCR signal determines positive selection and lineage commitment of T cells", Journal of Immunology, 2000, 165:6252-6261.
Weidle et al., "The Intriguing Options of Multispecific Antibody Formats for Treatment of Cancer", Cancer Genomics Proteomics, Feb. 2, 2013, 10(1):1-18.
Weinacker et al., "Role of the integrin alpha v beta 6 in cell attachment to fibronectin. Heterologous expression of intact and secreted forms of the receptor", Journal of Biological Chemistry, 1994, 269:6940-6948.
Weiss Arthur, "T Cell Antigen Receptor Signal Transduction: A Tale of Tails and Cytoplasmic Protein-Tyrosine Kinases", Cell, Apr. 23, 1993, 73(2):209-212.
Who Drug Information, "International Nonproprietary Names for Pharmaceutical Substances (INN)", Recommended INN: List 44, 2000, 14(3):27 pages.
Who Drug Information, "International Nonproprietary Names for Pharmaceutical Substances (INN)", Recommended INN: List 60, 2008, 22(3):30 pages.
Who Drug Information, "International Nonproprietary Names for Pharmaceutical Substances (INN)", Recommended INN: List 61, 2009, 23(1):35 pages.
Who Drug Information, "International Nonproprietary Names for Pharmaceutical Substances (INN)", Recommended INN: List 65, 2011, 25(1):50 pages.
Willemsen et al., "Selection of human antibody fragments directed against tumor T-cell epitopes for adoptive T-cell therapy", Cytometry A., Nov. 2008, 73(11):1093-1099.
Williams et al., "Biochemical and Genetic Analysis of the Oka Blood Group Antigen", Immunogenetics, 1988, 27(5):322-329.
Winter et al., "Making Antibodies by Phage Display Technology", Annual Review of Immunology, 1994, 12.433-455.
Winter et al., "Man-made Antibodies", Nature, 1991, 349:293-299.
Wolff et al., "Monoclonal Antibody Homodimers: Enhanced Antitumor Activity in Nude Mice", Cancer Research, 1993, 53:2560-2565.
Wong et al., "EpCAM and gpA33 are markers of Barrett's metaplasia", Journal of Clinical Pathology, Mar. 2006, 59(3):260-263.
Wong et al., "Rheumatoid Arthritis T Cells Produce Th1 Cytokines in Response to Stimulation with a Novel Trispecific Antibody Directed Against CD2, CD3, and CD28", Scandinavian Journal of Rheumatology, 2000, 29(5):282-287.

(56) References Cited

OTHER PUBLICATIONS

Woolfson et al., "The Design of Coiled-Coil Structures and Assemblies", Advances in Protein Chemistry, 2005, 70:79-112.
Wu et al., "Multimerization of a Chimeric Anti-CD20 Single Chain Fv-Fv Fusion Protein Is Mediated Through Variable Domain Exchange", Protein Engineering, 2001, 14(12):1025-1033.
Wu et al., "Receptor-Mediated In Vitro Gene Transformation by A Soluble DNA Carrier System", Journal of Biological Chemistry, 1987, 262(10):4429-4432.
Wu et al., "Stepwise In Vitro Affinity Maturation of Vitaxin, an Avβ3-Specific Humanized Mab", Proceedings of the National Academy of Sciences, May 26, 1998, 95(11):6037-6042.
Wucherpfennig et al., "Structural Biology of the T-cell Receptor: Insights into Receptor Assembly, Ligand Recognition, and Initiation of Signaling", Cold Spring Harbor Perspectives in Biology, Apr. 2010, 2(4):14 pages.
Xie et al., "A New Format of Bispecific Antibody: Highly Efficient Heterodimerization, Expression and Tumor Cell Lysis", Journal of Immunological Methods, 2005, 296:95-101.
Xu et al., "High EphA2 Protein Expression in Renal Cell Carcinoma Is Associated with A Poor Disease Outcome", Oncology Letters, Aug. 2014, 8(2):687-692.
Xu et al., "In Vitro Characterization of Five Humanized OKT3 Effector Function Variant Antibodies", Cellular Immunology, 2000, 200:16-26.
Yang et al., "Therapeutic potential and challenges of targeting receptor tyrosine kinase ROR 1 with monoclonal antibodies in B-cell malignancies", PLoS One, 2011, 6(6):e21018.
Yelton et al., "Affinity Maturation of the BR96 Anti-Carcinoma Antibody by Codon-Based Mutagenesis", Journal of Immunology, Aug. 15, 1995, 155(4):1994-2004.
Yi et al., "BST-2 Is A Potential Activator of Invasion and Migration in Tamoxifen-Resistant Breast Cancer Cells", Biochemical and Biophysical Research Communications, 2013, 435(4):685-690.
Yokota et al., "Rapid Tumor Penetration of a Single-Chain Fv and Comparison with Other Immunoglobulin Forms", Cancer Research, Jul. 1992, 52(12):3402-3408.
Youinou et al., "Pathogenic Effects of Anti-Fc Gamma Receptor IIIb (Cd16) on Polymorphonuclear Neutrophils in Non-Organ-Specific Autoimmune Diseases", Autoimmunity Reviews, Feb. 2002, 1(1-2):13-19.
Yu et al., "Coexpression of different antigenic markers on moieties that bear CA 125 determinants", Cancer Research, Jan. 15, 1991, 51(2):468-475.
Zeng et al., "A Ligand-Pseudo receptor System Based on De Novo Designed Peptides for the Generation of Adenoviral Vectors with Altered Tropism", Journal of Gene Medicine, 2008, 10(4):355-367.
Zheng et al., "A Novel Anti-CEACAM5 Monoclonal Antibody, CC4, Suppresses Colorectal Tumor Growth and Enhances NK Cells-Mediated Tumor Immunity", Plos One, e21146, Jun. 2011, 6(6):11 pages.
Zhou et al., "Constitutive Overexpression of a Novel 21 Kda Protein by Hodgkin Lymphoma and Aggressive Non-Hodgkin Lymphomas", Molecular Cancer, 2008, 7(12):11 pages.
Zhou et al., "Lung Tumorigenesis Associated with Erb-B-2 and Erb-B-3 Overexpression in Human Erb-B-3 Transgenic Mice is Enhanced by Methylnitrosourea", Oncogene, 2002, 21(57):8732-8740.
Al-Taei et al., "Overexpression and Potential Targeting of the Oncofoetal Antigen 5T4 in Malignant Pleural Mesothelioma", Lung Cancer, 2012, 77:312-318.
Office Action dated Jul. 21, 2022 in U.S. Appl. No. 16/818,893, filed Mar. 13, 2020 and published as US-2020-0207850-A1 on Jul. 2, 2020, 47 pages.

* cited by examiner

SEQUENCE LISTING

```
<160> NUMBER OF SEQ ID NOS: 322

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human Wild-Type IgG CH2-CH3 Domain

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140
```

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
210                 215

<210> SEQ ID NO 2
<211> LENGTH: 440
<212> TYPE: PRT
<213> ORGANISM: Homo sapiens
<220> FEATURE:
<221> NAME/KEY: MISC_FEATURE
<222> LOCATION: (1)..(440)
<223> OTHER INFORMATION: Human DR5 Precursor (NCBI Sequence NP_003833.4)

<400> SEQUENCE: 2

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
            85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270
```

-continued

```
Asn Glu Ile Val Ser Ile Leu Gln Pro Thr Gln Val Pro Glu Gln Glu
            275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440

<210> SEQ ID NO 3
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Murine Anti-Human DR5 Antibody ("DR5 mAb 1")
      Light Chain Variable Domain

<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys
            100                 105                 110

<210> SEQ ID NO 4
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: Murine Anti-Human DR5 Antibody ("DR5 mAb 1")
      Light Chain Variable Domain CDRL1

<400> SEQUENCE: 4
```

Arg Ala Ser Lys Ser Val Ser Ser Gly Tyr Ser Tyr Met His
1               5                   10                  15

<210> SEQ ID NO 5
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human DR5 Antibody ("DR5 mAb 1")
      Light Chain Variable Domain CDRL2

<400> SEQUENCE: 5

Leu Ser Ser Asn Leu Asp Ser
1               5

<210> SEQ ID NO 6
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody ("DR5 mAb 1")
      Light Chain Variable Domain CDRL3

<400> SEQUENCE: 6

Gln His Ser Arg Asp Leu Pro Pro Thr
1               5

<210> SEQ ID NO 7
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding Murine Anti-Human DR5
      Antibody ("DR5 mAb 1") Light Chain Variable Domain

<400> SEQUENCE: 7
gacattgtgc tgacacagtc tcctgcttcc ttagctgtat ctctcgggca gagggccacc      60
atctcatgca gggccagcaa aagtgtcagt tcctctggct atagttatat gcactggtac     120
caacagaaac aggacagcc acccaaagtc ctcatctttc tttcatccaa cctagattct     180
ggggtccctg ccaggttcag tggcagtggg tctgggacag acttcaccct caacatccat     240
cctgtggagg atggggatgc tgcaacctat tactgtcagc acagtaggga tcttcctccg     300
acgttcggtg gaggcaccaa gctggaaatc aaa                                  333

<210> SEQ ID NO 8
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Murine Anti-Human DR5 Antibody ("DR5 mAb 1")
      Heavy Chain Variable Domain

<400> SEQUENCE: 8

Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Asn Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

Gln Gly Thr Leu Val Thr Val Ser Ser
        115                 120

<210> SEQ ID NO 9
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody ("DR5 mAb 1")
      Heavy Chain Variable Domain CDRH1

<400> SEQUENCE: 9

Gly Phe Asp Phe Ser Arg Tyr Trp Met Ser
1               5                   10

<210> SEQ ID NO 10
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody ("DR5 mAb 1")
      Heavy Chain Variable Domain CDRH2

<400> SEQUENCE: 10

Glu Ile Asn Pro Asp Ser Asn Thr Ile Asn Tyr Thr Pro Ser Leu Lys
1               5                   10                  15

Asp

<210> SEQ ID NO 11
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: Murine Anti-Human DR5 Antibody ("DR5 mAb 1")
      Heavy Chain Variable Domain CDRH3

<400> SEQUENCE: 11

Arg Ala Tyr Tyr Gly Asn Pro Ala Trp Phe Ala Tyr
1               5                   10

<210> SEQ ID NO 12
<211> LENGTH: 363
<212> TYPE: DNA
<213> ORGANISM: Mus musculus
<220> FEATURE:
<221> NAME/KEY: misc_feature
<222> LOCATION: (1)..(363)
<223> OTHER INFORMATION: Polynucleotide Encoding Murine Anti-Human DR5
      Antibody ("DR5 mAb 1") Heavy Chain Variable Domain

<400> SEQUENCE: 12

```
gaggtgaagt tctcgagtc tggaggtggc ctggtgcagc ctggaggatc cctgaaactc    60
tcctgtgtag cctcaggatt cgatttagt agatactgga tgagttgggt ccggcaggct   120
ccagggaaag gctagaatg gattggagaa attaatccag atagcaatac gataaactat   180
acgccatctc taaaggataa attcatcatc tccagagaca acgccaaaaa tacgctgtat   240
ctgcaaatga ccaaagtgag atctgaggac acagcccttt attattgtac aagaagggcc   300
tactatggta acccggcctg gtttgcttac tggggccaag ggactctggt cactgtctct   360
tcc                                                                  363
```

<210> SEQ ID NO 13
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human DR5 Antibody ("DR5 mAb 2")
      Light Chain Variable Domain

<400> SEQUENCE: 13

```
Asp Ile Val Met Thr Gln Ser His Lys Phe Met Ser Thr Ser Val Gly
1               5                   10                  15
Asp Arg Val Ser Ile Thr Cys Lys Ala Ser Gln Asp Val Asn Thr Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Asp Arg Phe Thr Gly
    50                  55                  60
Ser Gly Ser Gly Thr Asp Tyr Thr Leu Thr Ile Lys Ser Val Gln Ala
65                  70                  75                  80
Glu Asp Leu Thr Leu Tyr Tyr Cys Gln Gln His Tyr Ile Thr Pro Trp
                85                  90                  95
Thr Phe Gly Gly Gly Thr Lys Leu Glu Ile Lys
            100                 105
```

<210> SEQ ID NO 14
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Murine Anti-Human DR5 Antibody ("DR5 mAb 2")
      Light Chain Variable Domain CDRL1

<400> SEQUENCE: 14

```
Lys Ala Ser Gln Asp Val Asn Thr Ala Val Ala
1               5                   10
```

<210> SEQ ID NO 15
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human DR5 Antibody ("DR5 mAb 2")
      Light Chain Variable Domain CDRL2

<400> SEQUENCE: 15

-continued

```
Trp Ala Ser Thr Arg His Thr
1               5

<210> SEQ ID NO 16
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody ("DR5 mAb 2")
      Light Chain Variable Domain CDRL3

<400> SEQUENCE: 16

Gln Gln His Tyr Ile Thr Pro Trp Thr
1               5

<210> SEQ ID NO 17
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding Murine Anti-Human DR5
      Antibody ("DR5 mAb 2") Light Chain Variable Domain

<400> SEQUENCE: 17
gacattgtga tgacccagtc tcacaaattc atgtccactt cagtaggaga cagggtcagc      60
atcacctgca aggccagtca ggatgtgaat actgctgtag cctggtatca acaaaaacca     120
gggcaatctc ctaaactact gatttactgg gcatccaccc ggcacactgg agtccctgat     180
cgcttcacag gcagtggatc tgggacagat tatacactca ccatcaaaag tgtgcaggct     240
gaagacctga cactttatta ctgtcagcaa cactatatca ctccgtggac gttcggtgga     300
ggcaccaagc tggaaatcaa a                                               321

<210> SEQ ID NO 18
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Murine Anti-Human DR5 Antibody ("DR5 mAb 2")
      Heavy Chain Variable Domain

<400> SEQUENCE: 18

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Glu Tyr
            20                  25                  30

Ile Leu His Trp Val Lys Gln Lys Ser Gly Gln Gly Leu Glu Trp Ile
        35                  40                  45

Gly Trp Phe Tyr Pro Gly Asn Asn Asn Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Gln Gly Pro Gly Tyr Phe Asp Tyr Trp Gly Gln Gly
            100                 105                 110
```

Thr Thr Leu Thr Val Ser Ser
    115

<210> SEQ ID NO 19
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody ("DR5 mAb 2")
      Heavy Chain Variable Domain CDRH1

<400> SEQUENCE: 19

Gly Tyr Thr Phe Thr Glu Tyr Ile Leu His
1               5                   10

<210> SEQ ID NO 20
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody ("DR5 mAb 2")
      Heavy Chain Variable Domain CDRH2

<400> SEQUENCE: 20

Trp Phe Tyr Pro Gly Asn Asn Asn Ile Lys Tyr Asn Glu Lys Phe Lys
1               5                   10                  15

Asp

<210> SEQ ID NO 21
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody ("DR5 mAb 2")
      Heavy Chain Variable Domain CDRH3

<400> SEQUENCE: 21

His Glu Gln Gly Pro Gly Tyr Phe Asp Tyr
1               5                   10

<210> SEQ ID NO 22
<211> LENGTH: 357
<212> TYPE: DNA
<213> ORGANISM: Mus musculus
<220> FEATURE:
<221> NAME/KEY: misc_feature
<222> LOCATION: (1)..(357)
<223> OTHER INFORMATION: Polynucleotide Encoding Murine Anti-Human DR5
      Antibody ("DR5 mAb 2") Heavy Chain Variable Domain

<400> SEQUENCE: 22
aaggtccagc tgcagcagtc tggagctgaa ctggtgaaac cgggggcatc agtgaagctg      60
tcctgcaagg cttctgggta caccttcact gagtatattt tacactgggt aaagcagaag     120
tctggacagg gtcttgagtg gattgggtgg ttttatcctg gaaataataa tataaagtac     180
aatgagaaat tcaaggacaa ggccacactg actgcggaca atcctccag cacagtctat      240 atggaactta gtagattgac atctgaagac tctgcggtct atttctgtgc aagacacgaa     300
caaggaccag gttactttga ctactggggc caaggcacca ctctcacagt ctcctcc       357

```
<210> SEQ ID NO 23
<211> LENGTH: 107
<212> TYPE: PRT
<213> ORGANISM: Artificial Sequence
<220> FEATURE:
<223> OTHER INFORMATION: Humanized Anti-Human DR5 Antibody ("hDR5 mAb 2
      VL-2") Light Chain Variable Domain

<400> SEQUENCE: 23

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 24
<211> LENGTH: 321
<212> TYPE: DNA
<213> ORGANISM: Artificial Sequence
<220> FEATURE:
<223> OTHER INFORMATION: Polynucleotide Encoding Humanized Anti-Human
      DR5 Antibody ("hDR5 mAb 2 VL-2") Light Chain Variable Domain

<400> SEQUENCE: 24
gatattcaga tgacccagag tccctcattt ctgtccgcct ccgtcggtga ccgcgtgact      60
attacttgta aagcttctca ggatgtcaac accgccgtgg cttggtacca gcagaagccc     120
ggtaaagcac ctaagctgct gatctattgg gccagcactc ggcacaccgg agtcccatct     180
aggttctctg gcagtggatc agggacagac tttacccctga caattagctc cctgcagccc    240
gaggatgtgg ctacttacta ttgtcagcag cactacatca ctccttggac cttcggcggg    300
ggcacaaaac tggaaatcaa a                                               321

<210> SEQ ID NO 25
<211> LENGTH: 107
<212> TYPE: PRT
<213> ORGANISM: Artificial Sequence
<220> FEATURE:
<223> OTHER INFORMATION: Humanized Anti-Human DR5 Antibody ("hDR5 mAb 2
      VL-3") Light Chain Variable Domain

<400> SEQUENCE: 25

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80
```

```
Glu Asp Val Ala Thr Tyr Tyr Cys Gln Gln His Tyr Ile Thr Pro Trp
            85                  90                  95

Thr Phe Gly Gly Gly Thr Lys Leu Glu Ile Lys
            100                 105
```

<210> SEQ ID NO 26
<211> LENGTH: 321
<212> TYPE: DNA
<213> ORGANISM: Artificial Sequence
<220> FEATURE:
<223> OTHER INFORMATION: Polynucleotide Encoding Humanized Anti-Human
      DR5 Antibody ("hDR5 mAb 2 VL-3") Light Chain Variable Domain

<400> SEQUENCE: 26

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccagat   180
aggttctctg gcagtggatc agggacagac tttacccctg caattagctc cctgcagccc   240
gaggatgtgg ctacttacta ttgtcagcag cactacatca ctccttggac cttcggcggg   300
ggcacaaaac tggaaatcaa a                                              321
```

<210> SEQ ID NO 27
<211> LENGTH: 107
<212> TYPE: PRT
<213> ORGANISM: Artificial Sequence
<220> FEATURE:
<223> OTHER INFORMATION: Murine Anti-Human DR5 Antibody ("DR5 mAb 4")
      Light Chain Variable Domain

<400> SEQUENCE: 27

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
            85                  90                  95

Thr Phe Gly Gly Gly Thr Lys Leu Glu Ile Lys
            100                 105
```

<210> SEQ ID NO 28
<211> LENGTH: 321
<212> TYPE: DNA
<213> ORGANISM: Artificial Sequence
<220> FEATURE:
<223> OTHER INFORMATION: Polynucleotide Encoding Humanized Anti-Human
      DR5 Antibody ("hDR5 mAb 2 VL-4") Light Chain Variable Domain

<400> SEQUENCE: 28

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccatct   180
```

```
aggttctctg gcagtggatc agggacagac tttaccctga caattagctc cctgcagcca    240
gaggatatcg ctacatacta ttgtcagcag cactacatca ctccttggac cttcggcggg    300
ggcacaaaac tggaaatcaa a                                              321
```

<210> SEQ ID NO 29
<211> LENGTH: 107
<212> TYPE: PRT
<213> ORGANISM: Artificial Sequence
<220> FEATURE:
<223> OTHER INFORMATION: Humanized Anti-Human DR5 Antibody ("hDR5 mAb 2 VL-5") Light Chain Variable Domain

<400> SEQUENCE: 29

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

<210> SEQ ID NO 30
<211> LENGTH: 321
<212> TYPE: DNA
<213> ORGANISM: Artificial Sequence
<220> FEATURE:
<223> OTHER INFORMATION: Polynucleotide Encoding Humanized Anti-Human DR5 Antibody ("hDR5 mAb 2 VL-5") Light Chain Variable Domain

<400> SEQUENCE: 30

```
gatattcaga tgacccagag tccctcattt ctgtccgcct ccgtcggtga ccgcgtgact    60
attacttgtc gggcttctca ggatgtcaac accgccgtgg cttggtacca gcagaagccc    120
ggtaaagcac ctaagctgct gatctattgg gccagcactc ggcacaccgg agtcccagat    180
aggttctctg gcagtggatc agggacagac tttaccctga caattagctc cctgcagccc    240
gaggatatcg ctacttacta ttgtcagcag cactacatca ctccttggac cttcggcggg    300
ggcacaaaac tggaaatcaa a                                              321
```

<210> SEQ ID NO 31
<211> LENGTH: 119
<212> TYPE: PRT
<213> ORGANISM: Artificial Sequence
<220> FEATURE:
<223> OTHER INFORMATION: Humanized Anti-Human DR5 Antibody ("hDR5 mAb 2 VH-2") Heavy Chain Variable Domain

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ile Leu His Trp Val Arg Gln Ala Pro Gly Gln Gly Leu Glu Trp Met
```

```
                35                  40                  45
Gly Trp Phe Tyr Pro Gly Asn Asn Ile Lys Tyr Asn Glu Lys Phe
     50                  55                  60
Lys Asp Arg Val Thr Ile Thr Ala Asp Lys Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg His Glu Gln Gly Pro Gly Tyr Phe Asp Tyr Trp Gly Gln Gly
             100                 105                 110
Thr Leu Val Thr Val Ser Ser
        115

<210> SEQ ID NO 32
<211> LENGTH: 357
<212> TYPE: DNA
<213> ORGANISM: Artificial Sequence
<220> FEATURE:
<223> OTHER INFORMATION: Polynucleotide Encoding Humanized Anti-Human
      DR5 Antibody ("hDR5 mAb 2 VH-2") Heavy Chain Variable Domain

<400> SEQUENCE: 32
caggtccagc tggtgcagag tggggcagag gtgaaaaagc caggggcatc agtgaaagtg      60
tcttgtaaag catcaggtta tacatttact gagtacatcc tgcactgggt gcgacaggca     120
ccaggacagg gactggaatg gatggggtgg ttctaccctg gcaacaacaa cattaagtac     180
aacgagaagt ttaaagaccg ggtgaccatc acagcggata gtctaccag tacagtctat      240 atggagctga gctccctgag aagcgaagac accgccgtct actattgcgc tcgccacgaa     300
cagggtccag gttactttga ttattggggg cagggaactc tggtcacagt cagctcc        357

<210> SEQ ID NO 33
<211> LENGTH: 8
<212> TYPE: PRT
<213> ORGANISM: Artificial Sequence
<220> FEATURE:
<223> OTHER INFORMATION: Linker 1

<400> SEQUENCE: 33

Gly Gly Gly Ser Gly Gly Gly Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Cysteine-Containing Spacer Peptide ("Linker 2")

<400> SEQUENCE: 34

Gly Gly Cys Gly Gly Gly
1               5

<210> SEQ ID NO 35
<211> LENGTH: 7
<212> TYPE: PRT
<213> ORGANISM: Artificial Sequence
<220> FEATURE:
<223> OTHER INFORMATION: Cysteine-Containing Peptide Variant of Human
      IgG Hinge Domain

<400> SEQUENCE: 35

Gly Val Glu Pro Lys Ser Cys
1               5
```

```
<210> SEQ ID NO 36
<211> LENGTH: 6
<212> TYPE: PRT
<213> ORGANISM: Artificial Sequence
<220> FEATURE:
<223> OTHER INFORMATION: Cysteine-Containing Peptide Variant of Human
      IgG Hinge Domain

<400> SEQUENCE: 36

Val Glu Pro Lys Ser Cys
1               5

<210> SEQ ID NO 37
<211> LENGTH: 7
<212> TYPE: PRT
<213> ORGANISM: Artificial Sequence
<220> FEATURE:
<223> OTHER INFORMATION: Cysteine-Containing Peptide Variant of Human
      IgG CL Domain

<400> SEQUENCE: 37

Gly Phe Asn Arg Gly Glu Cys
1               5

<210> SEQ ID NO 38
<211> LENGTH: 6
<212> TYPE: PRT
<213> ORGANISM: Artificial Sequence
<220> FEATURE:
<223> OTHER INFORMATION: Cysteine-Containing Peptide Variant of Human
      IgG CL Domain

<400> SEQUENCE: 38

Phe Asn Arg Gly Glu Cys
1               5

<210> SEQ ID NO 39
<211> LENGTH: 28
<212> TYPE: PRT
<213> ORGANISM: Artificial Sequence
<220> FEATURE:
<223> OTHER INFORMATION: Heterodimer-Promoting "E-coil" Domain

<400> SEQUENCE: 39

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 40
<211> LENGTH: 28
<212> TYPE: PRT
<213> ORGANISM: Artificial Sequence
<220> FEATURE:
<223> OTHER INFORMATION: Heterodimer-Promoting "K-coil" Domain

<400> SEQUENCE: 40

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 41
<211> LENGTH: 28
<212> TYPE: PRT
```

```
<213> ORGANISM: Artificial Sequence
<220> FEATURE:
<223> OTHER INFORMATION: Cysteine-Containing Heterodimer-Promoting
      "E-coil" Domain

<400> SEQUENCE: 41

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 42
<211> LENGTH: 28
<212> TYPE: PRT
<213> ORGANISM: Artificial Sequence
<220> FEATURE:
<223> OTHER INFORMATION: Cysteine-Containing Heterodimer-Promoting
      "K-coil" Domain

<400> SEQUENCE: 42

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 43
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus Strain G148

<400> SEQUENCE: 43

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
            35                  40                  45

<210> SEQ ID NO 44
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148

<400> SEQUENCE: 44

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Ala Lys Thr Val Glu
            20                  25                  30

Gly Val Lys Ala Leu Ile Ala Glu Ile Leu Ala Ala Leu Pro
            35                  40                  45

<210> SEQ ID NO 45
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
```

(ABD3) of Protein G of Streptococcus Strain G148

<400> SEQUENCE: 45

Leu Ala Glu Ala Lys Val Leu Ala Asn Arg Glu Leu Asp Lys Tyr Gly
1               5                   10                  15
Val Ser Asp Tyr Tyr Lys Asn Leu Ile Ser Asn Ala Lys Ser Val Glu
            20                  25                  30
Gly Val Lys Ala Leu Ile Ala Glu Ile Leu Ala Ala Leu Pro
        35                  40                  45

<210> SEQ ID NO 46
<211> LENGTH: 4
<212> TYPE: PRT
<213> ORGANISM: Artificial Sequence
<220> FEATURE:
<223> OTHER INFORMATION: Peptide Linker ("Linker 3")

<400> SEQUENCE: 46

Gly Gly Gly Ser
1

<210> SEQ ID NO 47
<211> LENGTH: 5
<212> TYPE: PRT
<213> ORGANISM: Artificial Sequence
<220> FEATURE:
<223> OTHER INFORMATION: Peptide Linker

<400> SEQUENCE: 47

Ala Ser Thr Lys Gly
1               5

<210> SEQ ID NO 48
<211> LENGTH: 10
<212> TYPE: PRT
<213> ORGANISM: Artificial Sequence
<220> FEATURE:
<223> OTHER INFORMATION: Peptide Linker

<400> SEQUENCE: 48

Asp Lys Thr His Thr Cys Pro Pro Cys Pro
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Peptide Linker

<400> SEQUENCE: 49

Leu Glu Pro Lys Ser Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Peptide Linker

<400> SEQUENCE: 50

Ala Pro Ser Ser Ser Pro Met Glu
1               5

<210> SEQ ID NO 51
<211> LENGTH: 16
<212> TYPE: PRT
<213> ORGANISM: Artificial Sequence
<220> FEATURE:
<223> OTHER INFORMATION: Peptide Linker

<400> SEQUENCE: 51

```
Leu Glu Pro Lys Ser Ser Asp Lys Thr His Thr Cys Pro Pro Cys Pro
1               5                   10                  15
```

<210> SEQ ID NO 52
<211> LENGTH: 217
<212> TYPE: PRT
<213> ORGANISM: Artificial Sequence
<220> FEATURE:
<223> OTHER INFORMATION: "Knob-Bearing" Variant Human IgG Fc Domain

<400> SEQUENCE: 52

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 53
<211> LENGTH: 217
<212> TYPE: PRT
<213> ORGANISM: Artificial Sequence
<220> FEATURE:
<223> OTHER INFORMATION: "Hole-Bearing" Variant Human IgG Fc Domain

<400> SEQUENCE: 53

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215

<210> SEQ ID NO 54
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: human Anti-Human DR5 Antibody (Drozitumab; "DR5
      mAb 3") Light Chain Variable Domain

<400> SEQUENCE: 54

Ser Glu Leu Thr Gln Asp Pro Ala Val Ser Val Ala Leu Gly Gln Thr
1               5                  10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ala Asp Ser Ser Gly Asn His Val
                 85                  90                  95

Val Phe Gly Gly Gly Thr Lys Leu Thr Val Leu Gly
            100                 105

<210> SEQ ID NO 55
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
```

```
<223> OTHER INFORMATION: Human Anti-Human DR5 Antibody (Drozitumab; "DR5
      mAb 3") Light Chain Variable Domain CDRL1

<400> SEQUENCE: 55

Ser Gly Asp Ser Leu Arg Ser Tyr Tyr Ala Ser
1               5                   10

<210> SEQ ID NO 56
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Human Anti-Human DR5 Antibody (Drozitumab; "DR5
      mAb 3") Light Chain Variable Domain CDRL2

<400> SEQUENCE: 56

Gly Ala Asn Asn Arg Pro Ser
1               5

<210> SEQ ID NO 57
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Human Anti-Human DR5 Antibody (Drozitumab; "DR5
      mAb 3") Light Chain Variable Domain CDRL3

<400> SEQUENCE: 57

Asn Ser Ala Asp Ser Ser Gly Asn His Val Val
1               5                   10

<210> SEQ ID NO 58
<211> LENGTH: 121
<212> TYPE: PRT
<213> ORGANISM: Homo sapiens
<220> FEATURE:
<221> NAME/KEY: MISC_FEATURE
<222> LOCATION: (1)..(121)
<223> OTHER INFORMATION: Human Anti-Human DR5 Antibody (Drozitumab; "DR5
      mAb 3") Heavy Chain Variable Domain

<400> SEQUENCE: 58

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser
        115                 120

<210> SEQ ID NO 59
```

```
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Human Anti-Human DR5 Antibody (Drozitumab; "DR5
      mAb 3") Heavy Chain Variable Domain CDRH1

<400> SEQUENCE: 59

Gly Phe Thr Phe Asp Asp Tyr Ala Met Ser
1               5                   10

<210> SEQ ID NO 60
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Human Anti-Human DR5 Antibody (Drozitumab; "DR5
      mAb 3") Heavy Chain Variable Domain CDRH2

<400> SEQUENCE: 60

Ile Asn Trp Gln Gly Gly Ser Thr Gly Tyr Ala Asp Ser Val Lys Gly
1               5                   10                  15

<210> SEQ ID NO 61
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human Anti-Human DR5 Antibody (Drozitumab; "DR5
      mAb 3") Heavy Chain Variable Domain CDRH2

<400> SEQUENCE: 61

Ile Leu Gly Ala Gly Arg Gly Trp Tyr Phe Asp Tyr
1               5                   10

<210> SEQ ID NO 62
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: Human Anti-Human DR5 Antibody (Conatumumab;
      "DR5 mAb 4") Light Chain Variable Domain

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105
```

```
<210> SEQ ID NO 63
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human Anti-Human DR5 Antibody (Conatumumab;
      "DR5 mAb 4") Light Chain Variable Domain CDRL1

<400> SEQUENCE: 63

Arg Ala Ser Gln Gly Ile Ser Arg Ser Tyr Leu Ala
1               5                   10

<210> SEQ ID NO 64
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Huamn Anti-Human DR5 Antibody (Conatumumab;
      "DR5 mAb 4") Light Chain Variable Domain CDRL2

<400> SEQUENCE: 64

Gly Ala Ser Ser Arg Ala Thr
1               5

<210> SEQ ID NO 65
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Human Anti-Human DR5 Antibody (Conatumumab;
      "DR5 mAb 4") Light Chain Variable Domain CDRL3

<400> SEQUENCE: 65

Gln Gln Phe Gly Ser Ser Pro Trp Thr
1               5

<210> SEQ ID NO 66
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: Human Anti-Human DR5 Antibody (Conatumumab;
      "DR5 mAb 4") Heavy Chain Variable Domain

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95
```

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120

<210> SEQ ID NO 67
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human Anti-Human DR5 Antibody (Conatumumab;
      "DR5 mAb 4") Heavy Chain Variable Domain CDRH1

<400> SEQUENCE: 67

Gly Gly Ser Ile Ser Ser Gly Asp Tyr Phe Trp Ser
1               5                   10

<210> SEQ ID NO 68
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Human Anti-Human DR5 Antibody (Conatumumab;
      "DR5 mAb 4") Heavy Chain Variable Domain CDRH2

<400> SEQUENCE: 68

His Ile His Asn Ser Gly Thr Thr Tyr Tyr Asn Pro Ser Leu Lys Ser
1               5                   10                  15

<210> SEQ ID NO 69
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human Anti-Human DR5 Antibody (Conatumumab;
      "DR5 mAb 4") Heavy Chain Variable Domain CDRH3

<400> SEQUENCE: 69

Asp Arg Gly Gly Asp Tyr Tyr Tyr Gly Met Asp Val
1               5                   10

<210> SEQ ID NO 70
<211> LENGTH: 106
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Light Chain Variable Domain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro

```
              65                  70                  75                  80
Glu Asp Phe Ala Thr Tyr Tyr Cys Gln Gln Tyr Ser Ser Tyr Arg Thr
                    85                  90                  95

Phe Gly Gln Gly Thr Lys Val Glu Ile Lys
                100                 105

<210> SEQ ID NO 71
<211> LENGTH: 11
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Light Chain Variable Domain CDRL1

<400> SEQUENCE: 71

Lys Ala Ser Gln Asp Val Gly Thr Ala Val Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Light Chain Variable Domain CDRL2

<400> SEQUENCE: 72

Trp Ala Ser Thr Arg His Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Light Chain Variable Domain CDRL3

<400> SEQUENCE: 73

Gln Gln Tyr Ser Ser Tyr Arg Thr
1               5

<210> SEQ ID NO 74
<211> LENGTH: 119
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Heavy Chain Variable Domain

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Val Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Arg Gly Asp Ser Met Ile Thr Thr Asp Tyr Trp Gly Gln Gly
                100                 105                 110

Thr Leu Val Thr Val Ser Ser
        115

<210> SEQ ID NO 75
<211> LENGTH: 10
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Heavy Chain Variable Domain CDRH1

<400> SEQUENCE: 75

Gly Phe Thr Phe Ser Ser Tyr Val Met Ser
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Heavy Chain Variable Domain CDRH2

<400> SEQUENCE: 76

Thr Ile Ser Ser Gly Gly Ser Tyr Thr Tyr Tyr Pro Asp Ser Val Lys
1               5                   10                  15

Gly

<210> SEQ ID NO 77
<211> LENGTH: 10
<212> TYPE: PRT
<213> ORGANISM: Artificial Sequence
<220> FEATURE:
<223> OTHER INFORMATION: Humanized Anti-Human DR5 Antibody (Tigatuzumab;
      "DR5 mAb 5") Heavy Chain Variable Domain CDRH3

<400> SEQUENCE: 77

Arg Gly Asp Ser Met Ile Thr Thr Asp Tyr
1               5                   10

<210> SEQ ID NO 78
<211> LENGTH: 109
<212> TYPE: PRT
<213> ORGANISM: Mus musculus
<220> FEATURE:
<221> NAME/KEY: MISC_FEATURE
<222> LOCATION: (1)..(109)
<223> OTHER INFORMATION: Murine Anti-Human DR5 Antibody (LBY135-1; "DR5
      mAb 6") Light Chain Variable Domain

<400> SEQUENCE: 78

Asp Ile Ala Met Thr Gln Ser His Lys Phe Met Ser Thr Leu Val Gly
1               5                   10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Tyr Gly
    50                  55                  60

Ser Gly Ser Gly Thr Asp Tyr Thr Leu Thr Ile Ser Ser Met Glu Ala
65                  70                  75                  80

Glu Asp Ala Ala Thr Tyr Tyr Cys Gln Gln Trp Ser Ser Asn Pro Leu
```

```
                    85                  90                  95

Thr Phe Gly Ala Gly Thr Lys Leu Glu Leu Lys Arg Ala
                100                 105

<210> SEQ ID NO 79
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Murine Anti-Human DR5 Antibody (LBY135-1; "DR5
      mAb 6") Light Chain Variable Domain CDRL1

<400> SEQUENCE: 79

Gln Asp Val Asn Thr Ala Ile Ala
1               5

<210> SEQ ID NO 80
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human DR5 Antibody (LBY135-1; "DR5
      mAb 6") Light Chain Variable Domain CDRL2

<400> SEQUENCE: 80

Trp Ala Ser Thr Arg His Thr
1               5

<210> SEQ ID NO 81
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody (LBY135-1; "DR5
      mAb 6") Light Chain Variable Domain CDRL3

<400> SEQUENCE: 81

Gln Gln Trp Ser Ser Asn Pro Leu Thr
1               5

<210> SEQ ID NO 82
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human DR5 Antibody (LBY135-1; "DR5
      mAb 6") Heavy Chain Variable Domain

<400> SEQUENCE: 82

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Gly Gly Tyr Ile Lys Tyr Asn Glu Lys Phe
    50                  55                  60

Lys Asp Arg Ala Thr Leu Thr Ala Asp Lys Ser Ser Asn Thr Val Tyr
```

```
                65                  70                  75                  80
Met Glu Leu Ser Arg Leu Thr Ser Glu Gly Ser Ala Val Tyr Phe Cys
                    85                  90                  95

Ala Arg His Glu Glu Gly Ile Tyr Phe Asp Tyr Trp Gly Gln Gly Thr
            100                 105                 110

Thr Leu Thr Val Ser Ser
        115

<210> SEQ ID NO 83
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody (LBY135-1; "DR5
      mAb 6") Heavy Chain Variable Domain CDRH1

<400> SEQUENCE: 83

Gly Tyr Thr Phe Thr Asp Tyr Thr Ile His
1               5                   10

<210> SEQ ID NO 84
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody (LBY135-1; "DR5
      mAb 6") Heavy Chain Variable Domain CDRH2

<400> SEQUENCE: 84

Trp Phe Tyr Pro Gly Gly Gly Tyr Ile Lys Tyr Asn Glu Lys Phe Lys
1               5                   10                  15

Asp

<210> SEQ ID NO 85
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody (LBY135-1; "DR5
      mAb 6") Heavy Chain Variable Domain CDRH3

<400> SEQUENCE: 85

His Glu Glu Gly Ile Tyr Phe Asp Tyr
1               5

<210> SEQ ID NO 86
<211> LENGTH: 104
<212> TYPE: PRT
<213> ORGANISM: Mus musculus
<220> FEATURE:
<221> NAME/KEY: MISC_FEATURE
<222> LOCATION: (1)..(104)
<223> OTHER INFORMATION: Murine Anti-Human DR5 Antibody (LBY135-2; "DR5
      mAb 7") Light Chain Variable Domain

<400> SEQUENCE: 86

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30
```

```
Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Phe
                85                  90                  95

Thr Phe Gly Ser Gly Thr Lys Leu
            100

<210> SEQ ID NO 87
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Murine Anti-Human DR5 Antibody (LBY135-2; "DR5
      mAb 7") Light Chain Variable Domain CDRL1

<400> SEQUENCE: 87

Lys Ala Ser Gln Asp Val Asn Thr Ala Ile Ala
1               5                   10

<210> SEQ ID NO 88
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human DR5 Antibody (LBY135-2; "DR5
      mAb 7") Light Chain Variable Domain CDRL2

<400> SEQUENCE: 88

Trp Ala Ser Thr Arg His Thr
1               5

<210> SEQ ID NO 89
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody (LBY135-2; "DR5
      mAb 7") Light Chain Variable Domain CDRL3

<400> SEQUENCE: 89

Gln Gln His Tyr Thr Thr Pro Phe Thr
1               5

<210> SEQ ID NO 90
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human DR5 Antibody (LBY135-2; "DR5
      mAb 7") Heavy Chain Variable Domain

<400> SEQUENCE: 90

Lys Val Gln Leu Gln Gln Ser Gly Ala Glu Leu Val Lys Pro Gly Ala
1               5                   10                  15
```

```
Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
            35                  40                  45

Gly Trp Phe Tyr Pro Gly Gly Gly Tyr Ile Lys Tyr Asn Glu Lys Phe
            50                  55                  60

Lys Asp Arg Ala Thr Leu Thr Ala Asp Lys Ser Ser Asn Thr Val Tyr
65              70                  75                  80

Met Glu Leu Ser Arg Leu Thr Ser Glu Asp Ser Ala Val Tyr Phe Cys
                85                  90                  95

Ala Arg His Glu Glu Gly Ile Tyr Phe Asp Tyr Trp Gly Gln Gly Thr
            100                 105                 110

Thr Leu Thr Val Ser Ser
        115

<210> SEQ ID NO 91
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody (LBY135-2; "DR5
      mAb 7") Heavy Chain Variable Domain CDRH1

<400> SEQUENCE: 91

Gly Tyr Thr Phe Thr Asp Tyr Thr Ile His
1               5                   10

<210> SEQ ID NO 92
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody (LBY135-2; "DR5
      mAb 7") Heavy Chain Variable Domain CDRH2

<400> SEQUENCE: 92

Trp Phe Tyr Pro Gly Gly Gly Tyr Ile Lys Tyr Asn Glu Lys Phe Lys
1               5                   10                  15

Asp

<210> SEQ ID NO 93
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody (LBY135-2; "DR5
      mAb 7") Heavy Chain Variable Domain CDRH3

<400> SEQUENCE: 93

His Glu Glu Gly Ile Tyr Phe Asp Tyr
1               5

<210> SEQ ID NO 94
<211> LENGTH: 108
<212> TYPE: PRT
<213> ORGANISM: Mus musculus
<220> FEATURE:
<221> NAME/KEY: MISC_FEATURE
```

<222> LOCATION: (1)..(108)
<223> OTHER INFORMATION: Murine Anti-Human DR5 Antibody (KMTR2; "DR5 mAb 8") Light Chain Variable Domain

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg
            100                 105

<210> SEQ ID NO 95
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Murine Anti-Human DR5 Antibody (KMTR2; "DR5 mAb 8") Light Chain Variable Domain CDRL1

<400> SEQUENCE: 95

Arg Ala Ser Gln Ser Val Ser Ser Tyr Leu Ala
1               5                   10

<210> SEQ ID NO 96
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human DR5 Antibody (KMTR2; "DR5 mAb 8") Light Chain Variable Domain CDRL2

<400> SEQUENCE: 96

Asp Ala Ser Asn Arg Ala Thr
1               5

<210> SEQ ID NO 97
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human DR5 Antibody (KMTR2; "DR5 mAb 8") Light Chain Variable Domain CDRL3

<400> SEQUENCE: 97

Gln Gln Arg Ser Asn Trp Pro Leu Thr
1               5

<210> SEQ ID NO 98
<211> LENGTH: 126
<212> TYPE: PRT

-continued

```
<213> ORGANISM: Mus musculus
<220> FEATURE:
<221> NAME/KEY: MISC_FEATURE
<222> LOCATION: (1)..(126)
<223> OTHER INFORMATION: Murine Anti-Human DR5 Antibody (KMTR2; "DR5 mAb
      8") Heavy Chain Variable Domain

<400> SEQUENCE: 98

Gln Val Gln Leu Val Gln Ser Gly Ala Glu Met Lys Lys Pro Gly Ala
1               5                   10                  15

Ser Val Lys Val Ser Cys Lys Thr Ser Gly Tyr Thr Phe Thr Asn Tyr
            20                  25                  30

Lys Ile Asn Trp Val Arg Gln Ala Pro Gly Gln Gly Leu Glu Trp Met
        35                  40                  45

Gly Trp Met Asn Pro Asp Thr Asp Ser Thr Gly Tyr Pro Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Ser Gly Ser Tyr Tyr Arg Asp Tyr Tyr Tyr Gly
            100                 105                 110

Met Asp Val Trp Gly Gln Gly Thr Thr Val Thr Val Ser Ser
        115                 120                 125

<210> SEQ ID NO 99
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human DR5 Antibody (KMTR2; "DR5 mAb
      8") Heavy Chain Variable Domain CDRH1

<400> SEQUENCE: 99

Gly Tyr Thr Phe Thr Asn Tyr Lys Ile Asn
1               5                   10

<210> SEQ ID NO 100
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody (KMTR2; "DR5 mAb
      8") Heavy Chain Variable Domain CDRH2

<400> SEQUENCE: 100

Trp Met Asn Pro Asp Thr Asp Ser Thr Gly Tyr Pro Gln Lys Phe Gln
1               5                   10                  15

Gly

<210> SEQ ID NO 101
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human DR5 Antibody (KMTR2; "DR5 mAb
      8") Heavy Chain Variable Domain CDRH3

<400> SEQUENCE: 101
```

Ser Tyr Gly Ser Gly Ser Tyr Tyr Arg Asp Tyr Tyr Gly Met Asp
1               5                   10                  15

Val

<210> SEQ ID NO 102
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Murine Anti-Human CD2 Antibody (Lo-CD2A mAb )
      Light Chain Variable Domain

<400> SEQUENCE: 102

Asp Val Val Leu Thr Gln Thr Pro Pro Thr Leu Leu Ala Thr Ile Gly
1               5                   10                  15

Gln Ser Val Ser Ile Ser Cys Arg Ser Ser Gln Ser Leu Leu His Ser
                20                  25                  30

Ser Gly Asn Thr Tyr Leu Asn Trp Leu Leu Gln Arg Thr Gly Gln Ser
            35                  40                  45

Pro Gln Pro Leu Ile Tyr Leu Val Ser Lys Leu Glu Ser Gly Val Pro
        50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
                100                 105                 110

<210> SEQ ID NO 103
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human CD2 Antibody (Lo-CD2A mAb )
      Heavy Chain Variable Domain

<400> SEQUENCE: 103

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
                20                  25                  30

Tyr Met Tyr Trp Val Lys Gln Arg Pro Lys Gln Gly Leu Glu Leu Val
            35                  40                  45

Gly Arg Ile Asp Pro Glu Asp Gly Ser Ile Asp Tyr Val Glu Lys Phe
        50                  55                  60

Lys Lys Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
                100                 105                 110

Leu Val Thr Val Ser Ser
        115

<210> SEQ ID NO 104

```
<211> LENGTH: 110
<212> TYPE: PRT
<213> ORGANISM: Artificial Sequence
<220> FEATURE:
<223> OTHER INFORMATION: Humanized Anti-Human CD3 Antibody ("CD3 mAb 2")
      Light Chain Variable Domain

<400> SEQUENCE: 104

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 105
<211> LENGTH: 14
<212> TYPE: PRT
<213> ORGANISM: Artificial Sequence
<220> FEATURE:
<223> OTHER INFORMATION: Humanized Anti-Human CD3 Antibody ("CD3 mAb 2")
      Light Chain Variable Domain CDRL1

<400> SEQUENCE: 105

Arg Ser Ser Thr Gly Ala Val Thr Thr Ser Asn Tyr Ala Asn
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Humanized Anti-Human CD3 Antibody ("CD3 mAb 2")
      Light Chain Variable Domain CDRL2

<400> SEQUENCE: 106

Gly Thr Asn Lys Arg Ala Pro
1               5

<210> SEQ ID NO 107
<211> LENGTH: 9
<212> TYPE: PRT
<213> ORGANISM: Artificial Sequence
<220> FEATURE:
<223> OTHER INFORMATION: Humanized Anti-Human CD3 Antibody ("CD3 mAb 2")
      Light Chain Variable Domain CDRL3

<400> SEQUENCE: 107

Ala Leu Trp Tyr Ser Asn Leu Trp Val
1               5

<210> SEQ ID NO 108
<211> LENGTH: 125
<212> TYPE: PRT
<213> ORGANISM: Artificial Sequence
<220> FEATURE:
<223> OTHER INFORMATION: Humanized Anti-Human CD3 Antibody ("CD3 mAb 2")
```

Heavy Chain Variable Domain

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 109
<211> LENGTH: 5
<212> TYPE: PRT
<213> ORGANISM: Artificial Sequence
<220> FEATURE:
<223> OTHER INFORMATION: Humanized Anti-Human CD3 Antibody ("CD3 mAb 2")
      Heavy Chain Variable Domain CDRH1

<400> SEQUENCE: 109

Thr Tyr Ala Met Asn
1               5

<210> SEQ ID NO 110
<211> LENGTH: 19
<212> TYPE: PRT
<213> ORGANISM: Artificial Sequence
<220> FEATURE:
<223> OTHER INFORMATION: Humanized Anti-Human CD3 Antibody ("CD3 mAb 2")
      Heavy Chain Variable Domain CDRH2

<400> SEQUENCE: 110

Arg Ile Arg Ser Lys Tyr Asn Asn Tyr Ala Thr Tyr Tyr Ala Asp Ser
1               5                   10                  15

Val Lys Asp

<210> SEQ ID NO 111
<211> LENGTH: 14
<212> TYPE: PRT
<213> ORGANISM: Artificial Sequence
<220> FEATURE:
<223> OTHER INFORMATION: Humanized Anti-Human CD3 Antibody ("CD3 mAb 2")
      Heavy Chain Variable Domain CDRH3

<400> SEQUENCE: 111

His Gly Asn Phe Gly Asn Ser Tyr Val Ser Trp Phe Ala Tyr
1               5                   10

<210> SEQ ID NO 112
<211> LENGTH: 125
<212> TYPE: PRT
<213> ORGANISM: Artificial Sequence
<220> FEATURE:
<223> OTHER INFORMATION: Humanize Anti-Human CD3 Antibody ("CD3 mAb 2")

Variant Heavy Chain Variable Domain Containing a D65G (Kabat Numbering; D68G in Sequence Relative to SEQ ID NO:108)

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 113
<211> LENGTH: 19
<212> TYPE: PRT
<213> ORGANISM: Artificial Sequence
<220> FEATURE:
<223> OTHER INFORMATION: CDRH2 of Humanized Anti-Human CD3 Antibody
      ("CD3 mAb 2") Variant Heavy Chain Variable Domain Containing a
      D65G (Kabat Numbering; D68G in Sequence Relative to SEQ ID NO:108)

<400> SEQUENCE: 113

Arg Ile Arg Ser Lys Tyr Asn Asn Tyr Ala Thr Tyr Tyr Ala Asp Ser
1               5                   10                  15

Val Lys Gly

<210> SEQ ID NO 114
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human CD3 Antibody (OKT3) Light
      Chain Variable Domain

<400> SEQUENCE: 114

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 115
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Murine Anti-Human CD3 Antibody (OKT3) Heavy
      Chain Variable Domain

<400> SEQUENCE: 115

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 116
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Murine Anti-Human CD16 Antibody (3G8) Light
      Chain Variable Domain

<400> SEQUENCE: 116

Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 117
<211> LENGTH: 118
<212> TYPE: PRT
<213> ORGANISM: Mus musculus
<220> FEATURE:
<221> NAME/KEY: MISC_FEATURE

```
<222> LOCATION: (1)..(118)
<223> OTHER INFORMATION: Murine Anti-Human CD16 Antibody (3G8) Heavy
      Chain Variable Domain

<400> SEQUENCE: 117

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ala
        115

<210> SEQ ID NO 118
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Murine Anti-Human CD16 Antibody (A9) Light
      Chain Variable Domain

<400> SEQUENCE: 118

Asp Ile Gln Ala Val Val Thr Gln Glu Ser Ala Leu Thr Thr Ser Pro
1               5                   10                  15

Gly Glu Thr Val Thr Leu Thr Cys Arg Ser Asn Thr Gly Thr Val Thr
            20                  25                  30

Thr Ser Asn Tyr Ala Asn Trp Val Gln Glu Lys Pro Asp His Leu Phe
        35                  40                  45

Thr Gly Leu Ile Gly His Thr Asn Asn Arg Ala Pro Gly Val Pro Ala
    50                  55                  60

Arg Phe Ser Gly Ser Leu Ile Gly Asp Lys Ala Ala Leu Thr Ile Thr
65                  70                  75                  80

Gly Ala Gln Thr Glu Asp Glu Ala Ile Tyr Phe Cys Ala Leu Trp Tyr
                85                  90                  95

Asn Asn His Trp Val Phe Gly Gly Gly Thr Lys Leu Thr Val Leu
            100                 105                 110

<210> SEQ ID NO 119
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: Murine Anti-Human CD16 Antibody (A9) Heavy
      Chain Variable Domain

<400> SEQUENCE: 119

Gln Val Gln Leu Gln Gln Ser Gly Ala Glu Leu Val Arg Pro Gly Thr
1               5                   10                  15
```

-continued

```
Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Tyr Thr Asn Tyr Asn Glu Lys Phe
50                  55                  60

Lys Gly Lys Ala Thr Val Thr Ala Asp Thr Ser Ser Arg Thr Ala Tyr
65                  70                  75                  80

Val Gln Val Arg Ser Leu Thr Ser Glu Asp Ser Ala Val Tyr Phe Cys
                85                  90                  95

Ala Arg Ser Ala Ser Trp Tyr Phe Asp Val Trp Gly Ala Arg Thr Thr
            100                 105                 110

Val Thr Val Ser Ser
            115

<210> SEQ ID NO 120
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Murine Anti-Human CD19 Antibody (HD37) Light
      Chain Variable Domain

<400> SEQUENCE: 120

Asp Ile Leu Ile Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 121
<211> LENGTH: 124
<212> TYPE: PRT
<213> ORGANISM: Mus musculus
<220> FEATURE:
<221> NAME/KEY: MISC_FEATURE
<222> LOCATION: (1)..(124)
<223> OTHER INFORMATION: Murine Anti-Human CD19 Antibody (HD37) Heavy
      Chain Variable Domain

<400> SEQUENCE: 121

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
```

```
                50                  55                  60
Lys Gly Lys Ala Thr Leu Thr Ala Asp Glu Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
                100                 105                 110

Tyr Trp Gly Gln Gly Thr Ser Val Thr Val Ser Ser
            115                 120
```

<210> SEQ ID NO 122
<211> LENGTH: 107
<212> TYPE: PRT
<213> ORGANISM: Artificial Sequence
<220> FEATURE:
<223> OTHER INFORMATION: Chimeric Anti-Human CD20 Antibody (Rituximab)
      Light Chain Variable Domain

<400> SEQUENCE: 122

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
             35                  40                  45

Ala Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg
                100                 105
```

<210> SEQ ID NO 123
<211> LENGTH: 121
<212> TYPE: PRT
<213> ORGANISM: Artificial Sequence
<220> FEATURE:
<223> OTHER INFORMATION: Chimeric Anti-Human CD20 Antibody (Rituximab)
      Heavy Chain Variable Domain

<400> SEQUENCE: 123

```
Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
             35                  40                  45

Gly Ala Ile Tyr Pro Gly Asn Gly Asp Thr Ser Tyr Asn Gln Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala
```

<210> SEQ ID NO 124
<211> LENGTH: 113
<212> TYPE: PRT
<213> ORGANISM: Artificial Sequence
<220> FEATURE:
<223> OTHER INFORMATION: Humanized Anti-Human CD22 Antibody
(Epratuzumab) Light Chain Variable Domain

<400> SEQUENCE: 124

Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Val Gln Ile Lys
            100                 105                 110

Arg

<210> SEQ ID NO 125
<211> LENGTH: 116
<212> TYPE: PRT
<213> ORGANISM: Artificial Sequence
<220> FEATURE:
<223> OTHER INFORMATION: Humanized Anti-Human CD22 Antibody
(Epratuzumab) Heavy Chain Variable Domain

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Murine Anti-Human CD32B Antibody ("CD32B mAb
1") Light Chain Variable Domain

<400> SEQUENCE: 126

Asp Ile Gln Met Thr Gln Ser Pro Ser Ser Leu Leu Ala Ala Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
50                  55                  60

Ser Glu Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Phe Ser Tyr Pro Leu
                85                  90                  95

Thr Phe Gly Ala Gly Thr Lys Leu Glu Leu Lys
            100                 105

<210> SEQ ID NO 127
<211> LENGTH: 116
<212> TYPE: PRT
<213> ORGANISM: Artificial Sequence
<220> FEATURE:
<223> OTHER INFORMATION: Murine Anti-Human CD32B Antibody ("CD32B mAb
      1") Heavy Chain Variable Domain

<400> SEQUENCE: 127

Glu Val Lys Leu Glu Glu Ser Gly Gly Gly Leu Val Gln Pro Gly Gly
1               5                   10                  15

Ser Met Lys Leu Ser Cys Glu Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Lys Asn His Ala Thr Tyr Tyr Ala Glu
50                  55                  60

Ser Val Ile Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Gly Ala Leu Gly Leu Asp Tyr Trp Gly Gln Gly Thr Thr Leu
            100                 105                 110

Thr Val Ser Ser
        115

<210> SEQ ID NO 128
<211> LENGTH: 109
<212> TYPE: PRT
<213> ORGANISM: Mus musculus
<220> FEATURE:
<221> NAME/KEY: MISC_FEATURE
<222> LOCATION: (1)..(109)
<223> OTHER INFORMATION: Murine Anti-Human CD64 Antibody ("CD64 mAb 1")
      Light Chain Variable Domain

<400> SEQUENCE: 128

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                35                  40                  45
Tyr Asp Ala Ser Ser Arg Ala Thr Gly Ile Pro Ala Arg Phe Gly Gly
 50                  55                  60

Ser Gly Ser Gly Gly Thr Asp Phe Thr Leu Thr Ile Ser Ser Leu Glu
 65                  70                  75                  80

Pro Glu Asp Phe Ala Val Tyr Tyr Cys Gln Leu Arg Ser Asn Trp Pro
                 85                  90                  95

Pro Tyr Thr Phe Gly Gln Gly Thr Lys Leu Glu Ile Lys
            100                 105
```

<210> SEQ ID NO 129
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human CD64 Antibody ("CD64 mAb 1")
      Heavy Chain Variable Domain

<400> SEQUENCE: 129

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Ile Phe Ser Gly Tyr
                20                  25                  30

Gly Met His Trp Val Arg Gln Ala Pro Gly Lys Gly Leu Glu Trp Val
            35                  40                  45

Thr Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Gly Asp Arg Phe Phe Asp Tyr Trp Gly Gln Gly Thr
            100                 105                 110

Leu Val Thr Val Ser Ser
        115
```

<210> SEQ ID NO 130
<211> LENGTH: 112
<212> TYPE: PRT
<213> ORGANISM: Artificial Sequence
<220> FEATURE:
<223> OTHER INFORMATION: Chimeric Anti-Human CD79 Antibody ("CD79 mAb
      1") Light Chain Variable Domain

<400> SEQUENCE: 130

```
Asp Val Val Met Thr Gln Thr Pro Leu Thr Leu Ser Val Asn Ile Gly
 1               5                  10                  15

Gln Pro Ala Ser Ile Ser Cys Lys Ser Ser Gln Ser Leu Leu Asp Thr
                20                  25                  30

Asp Gly Lys Thr Tyr Leu Asn Trp Leu Leu Gln Arg Pro Gln Gly Ser
            35                  40                  45

Pro Asn Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Trp Gln Gly
                 85                  90                  95
```

-continued

Thr His Phe Pro Leu Thr Phe Gly Ala Gly Thr Lys Leu Glu Leu Lys
                100                 105                 110

<210> SEQ ID NO 131
<211> LENGTH: 113
<212> TYPE: PRT
<213> ORGANISM: Artificial Sequence
<220> FEATURE:
<223> OTHER INFORMATION: Chimeric Anti-Human CD79 Antibody ("CD79 mAb
      1") Heavy Chain Variable Domain

<400> SEQUENCE: 131

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Met Asn Trp Val Lys Gln Arg Pro Gly Gln Gly Leu Glu Trp Ile
            35                  40                  45

Gly Met Val Asp Pro Ser Asp Ser Glu Thr His Tyr Asn Gln Met Phe
        50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Met Gly Tyr Trp Gly Gln Gly Thr Ser Val Thr Val Ser
                100                 105                 110

Ser

<210> SEQ ID NO 132
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: Murine Anti-Human TCR Antibody (BMA 031) Light
      Chain Variable Domain

<400> SEQUENCE: 132

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys
                100                 105

<210> SEQ ID NO 133
<211> LENGTH: 120
<212> TYPE: PRT
<213> ORGANISM: Mus musculus
<220> FEATURE:
<221> NAME/KEY: MISC_FEATURE

```
<222> LOCATION: (1)..(120)
<223> OTHER INFORMATION: Murine Anti-Human TCR Antibody (BMA 031) Heavy
      Chain Variable Domain

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Leu Gln Met Asn Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 134
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Murine Anti-Human NKG2D Antibody (KYK-1.0)
      Light Chain Variable Domain

<400> SEQUENCE: 134

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asn Asn Asp Glu
                85                  90                  95

Trp Val Phe Gly Gly Gly Thr Gln Leu Thr Val Leu
            100                 105

<210> SEQ ID NO 135
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human NKG2D Antibody (KYK-1.0)
      Heavy Chain Variable Domain

<400> SEQUENCE: 135

Glu Val Gln Leu Val Glu Ser Gly Gly Gly Val Val Gln Pro Gly Gly
1               5                   10                  15
```

-continued

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Lys Tyr
 65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
            100                 105                 110

Leu Val Thr Val Ser Ser
            115
```

<210> SEQ ID NO 136
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: Murine Anti-Human NKG2D Antibody (KYK-2.0)
      Light Chain Variable Domain

<400> SEQUENCE: 136

```
Gln Ser Ala Leu Thr Gln Pro Ala Ser Val Ser Gly Ser Pro Gly Gln
 1               5                  10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60

Gly Ser Lys Ser Gly Thr Ser Ala Phe Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 137
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Murine Anti-Human NKG2D Antibody (KYK-2.0)
      Heavy Chain Variable Domain

<400> SEQUENCE: 137

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 138
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Murine Anti-Fluorescein Antibody 4-4-20 Light
      Chain Variable Domain

<400> SEQUENCE: 138

Asp Val Val Met Thr Gln Thr Pro Phe Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu Arg Trp Tyr Leu Gln Lys Pro Gly Gln Ser
             35                  40                  45

Pro Lys Val Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

<210> SEQ ID NO 139
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Fluorescein Antibody 4-4-20 Heavy
      Chain Variable Domain

<400> SEQUENCE: 139

Glu Val Lys Leu Asp Glu Thr Gly Gly Gly Leu Val Gln Pro Gly Arg
 1               5                  10                  15

Pro Met Lys Leu Ser Cys Val Ala Ser Gly Phe Thr Phe Ser Asp Tyr
                 20                  25                  30

Trp Met Asn Trp Val Arg Gln Ser Pro Glu Lys Gly Leu Glu Trp Val
             35                  40                  45

Ala Gln Ile Arg Asn Lys Pro Tyr Asn Tyr Glu Thr Tyr Tyr Ser Asp
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95
```

Tyr Cys Thr Gly Ser Tyr Gly Met Asp Tyr Trp Gly Gln Gly Thr
            100                 105                 110

Ser Val Thr Val Ser Ser
            115

<210> SEQ ID NO 140
<211> LENGTH: 277
<212> TYPE: PRT
<213> ORGANISM: Artificial Sequence
<220> FEATURE:
<223> OTHER INFORMATION: First Polypeptide Chain of "DR5 mAb 1 x CD3 mAb
      2 Diabody"

<400> SEQUENCE: 140

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
225                 230                 235                 240

Thr Val Ser Ser Ala Ser Thr Lys Gly Glu Val Ala Ala Cys Glu Lys
                245                 250                 255

Glu Val Ala Ala Leu Glu Lys Glu Val Ala Ala Leu Glu Lys Glu Val
            260                 265                 270

Ala Ala Leu Glu Lys
            275

<210> SEQ ID NO 141
<211> LENGTH: 831
<212> TYPE: DNA
<213> ORGANISM: Artificial Sequence
<220> FEATURE:
<223> OTHER INFORMATION: Polynucleotide Encoding First Polypeptide Chain
      of "DR5 mAb 1 x CD3 mAb 2 Diabody"

<400> SEQUENCE: 141

```
gacattgtgc tgacacagtc tcctgcttcc ttagctgtat ctctcgggca gagggccacc    60
atctcatgca gggccagcaa agtgtcagt tcctctggct atagttatat gcactggtac   120
caacagaaac caggacagcc acccaaagtc ctcatctttc tttcatccaa cctagattct   180
ggggtccctg ccaggttcag tggcagtggg tctgggacag acttcaccct caacatccat   240
cctgtggagg atgggatgc tgcaacctat tactgtcagc acagtaggga tcttcctccg   300
acgttcggtg gaggcaccaa gctggaaatc aaaggaggcg gatccggcgg cggaggcgag   360
gtgcagctgg tggagtctgg gggaggcttg gtccagcctg agggtccct gagactctcc   420
tgtgcagcct ctggattcac cttcagcaca tacgctatga attgggtccg ccaggctcca   480
gggaaggggc tggagtgggt tggaaggatc aggtccaagt acaacaatta tgcaacctac   540
tatgccgact ctgtgaaggg tagattcacc atctcaagag atgattcaaa gaactcactg   600
tatctgcaaa tgaacagcct gaaaaccgag gacacggccg tgtattactg tgtgagacac   660
ggtaacttcg gcaattctta cgtgtcttgg tttgcttatt ggggacaggg gacactggtg   720
actgtgtctt ccgcctccac caagggcgaa gtggccgcat gtgagaaaga ggttgctgct   780
ttggagaagg aggtcgctgc acttgaaaag gaggtcgcag ccctggagaa a            831
```

<210> SEQ ID NO 142
<211> LENGTH: 272
<212> TYPE: PRT
<213> ORGANISM: Artificial Sequence
<220> FEATURE:
<223> OTHER INFORMATION: Second Polypeptide Chain of "DR5 mAb 1 x CD3 mAb 2 Diabody"

<400> SEQUENCE: 142

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Phe Leu Glu Ser Gly Gly Gly
        115                 120                 125

Leu Val Gln Pro Gly Gly Ser Leu Lys Leu Ser Cys Val Ala Ser Gly
    130                 135                 140

Phe Asp Phe Ser Arg Tyr Trp Met Ser Trp Val Arg Gln Ala Pro Gly
145                 150                 155                 160

Lys Gly Leu Glu Trp Ile Gly Glu Ile Asn Pro Asp Ser Asn Thr Ile
                165                 170                 175

Asn Tyr Thr Pro Ser Leu Lys Asp Lys Phe Ile Ile Ser Arg Asp Asn
            180                 185                 190

Ala Lys Asn Thr Leu Tyr Leu Gln Met Thr Lys Val Arg Ser Glu Asp
```

```
              195                 200                 205
Thr Ala Leu Tyr Tyr Cys Thr Arg Arg Ala Tyr Tyr Gly Asn Pro Ala
        210                 215                 220

Trp Phe Ala Tyr Trp Gly Gln Gly Thr Leu Val Thr Val Ser Ala Ala
225                 230                 235                 240

Ser Thr Lys Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
            260                 265                 270
```

<210> SEQ ID NO 143
<211> LENGTH: 816
<212> TYPE: DNA
<213> ORGANISM: Artificial Sequence
<220> FEATURE:
<223> OTHER INFORMATION: Polynucleotide Encoding Second Polypeptide
      Chain of "DR5 mAb 1 x CD3 mAb 2 Diabody"

<400> SEQUENCE: 143

```
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc gggggtacaa acaaagggc tccctggacc    180 cctgcacggt tttctggaag tctgctgggc ggaaaggccg ctctgactat taccggggca   240
caggccgagg acgaagccga ttactattgt gctctgtggt atagcaatct gtgggtgttc   300
gggggtggca aaaactgac tgtgctggga ggtggtggat ccggcggcgg aggcgaggtg    360
aagtttctcg agtctggagg tggcctggtg cagcctggag atcctgaa actctcctgt     420 gtagcctcag gattcgattt tagtagatac tggatgagtt gggtccggca ggctccaggg   480
aaagggctag aatggattgg agaaattaat ccagatagca atacgataaa ctatacgcca   540
tctctaaagg ataaattcat catctccaga gacaacgcca aaatacgct gtatctgcaa    600 atgaccaaag tgagatctga ggacacagcc ctttattatt gtacaagaag ggcctactat   660
ggtaacccgg cctggtttgc ttactggggc caagggactc tggtcactgt ctctgcagcc   720
tccaccaagg gcaaagtggc cgcatgtaag gagaaagttg ctgctttgaa agagaaggtc   780
gccgcactta aggaaaaggt cgcagccctg aaagag                             816
```

<210> SEQ ID NO 144
<211> LENGTH: 273
<212> TYPE: PRT
<213> ORGANISM: Artificial Sequence
<220> FEATURE:
<223> OTHER INFORMATION: First Polypeptide Chain of "DR5 mAb 2 x CD3 mAb
      2 Diabody"

<400> SEQUENCE: 144

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80
```

Glu Asp Leu Thr Leu Tyr Tyr Cys Gln Gln His Tyr Ile Thr Pro Trp
            85                  90                  95

Thr Phe Gly Gly Gly Thr Lys Leu Glu Ile Lys Gly Gly Gly Ser Gly
        100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240

Ala Ser Thr Lys Gly Glu Val Ala Ala Cys Glu Lys Glu Val Ala Ala
                245                 250                 255

Leu Glu Lys Glu Val Ala Ala Leu Glu Lys Glu Val Ala Ala Leu Glu
            260                 265                 270

Lys

<210> SEQ ID NO 145
<211> LENGTH: 819
<212> TYPE: DNA
<213> ORGANISM: Artificial Sequence
<220> FEATURE:
<223> OTHER INFORMATION: Polynucleotide Encoding First Polypeptide Chain
      of "DR5 mAb 2 x CD3 mAb 2 Diabody"

<400> SEQUENCE: 145
gacattgtga tgacccagtc tcacaaattc atgtccactt cagtaggaga cagggtcagc      60
atcacctgca aggccagtca ggatgtgaat actgctgtag cctggtatca acaaaaacca     120
gggcaatctc ctaaactact gatttactgg gcatccaccc ggcacactgg agtccctgat     180
cgcttcacag gcagtggatc tgggacagat tatacactca ccatcaaaag tgtgcaggct     240
gaagacctga cactttatta ctgtcagcaa cactatatca ctccgtggac gttcggtgga     300
ggcaccaagc tggaaatcaa aggaggcgga tccggcggcg gaggcgaggt gcagctggtg     360
gagtctgggg gaggcttggt ccagcctgga gggtccctga gactctcctg tgcagcctct     420
ggattcacct tcagcacata cgctatgaat tgggtccgcc aggctccagg aaggggctg      480 gagtgggttg gaaggatcag gtccaagtac aacaattatg caacctacta tgccgactct     540
gtgaagggta gattcaccat ctcaagagat gattcaaaga actcactgta tctgcaaatg     600
aacagcctga aaaccgagga cacggccgtg tattactgtg tgagacacgg taacttcggc     660
aattcttacg tgtcttggtt tgcttattgg ggacagggga cactggtgac tgtgtcttcc     720
gcctccacca agggcgaagt ggccgcatgt gagaaagagg ttgctgcttt ggagaaggag     780
gtcgctgcac ttgaaaagga ggtcgcagcc ctggagaaa                            819

<210> SEQ ID NO 146

<211> LENGTH: 270
<212> TYPE: PRT
<213> ORGANISM: Artificial Sequence
<220> FEATURE:
<223> OTHER INFORMATION: Second Polypeptide Chain of "DR5 mAb 2 x CD3 mAb 2 Diabody"

<400> SEQUENCE: 146

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Lys Val Gln Leu Gln Gln Ser Gly Ala Glu
        115                 120                 125

Leu Val Lys Pro Gly Ala Ser Val Lys Leu Ser Cys Lys Ala Ser Gly
    130                 135                 140

Tyr Thr Phe Thr Glu Tyr Ile Leu His Trp Val Lys Gln Lys Ser Gly
145                 150                 155                 160

Gln Gly Leu Glu Trp Ile Gly Trp Phe Tyr Pro Gly Asn Asn Asn Ile
                165                 170                 175

Lys Tyr Asn Glu Lys Phe Lys Asp Lys Ala Thr Leu Thr Ala Asp Lys
            180                 185                 190

Ser Ser Ser Thr Val Tyr Met Glu Leu Ser Arg Leu Thr Ser Glu Asp
        195                 200                 205

Ser Ala Val Tyr Phe Cys Ala Arg His Glu Gln Gly Pro Gly Tyr Phe
    210                 215                 220

Asp Tyr Trp Gly Gln Gly Thr Thr Leu Thr Val Ser Ser Ala Ser Thr
225                 230                 235                 240

Lys Gly Lys Val Ala Ala Cys Lys Glu Lys Val Ala Ala Leu Lys Glu
                245                 250                 255

Lys Val Ala Ala Leu Lys Glu Lys Val Ala Ala Leu Lys Glu
            260                 265                 270
```

<210> SEQ ID NO 147
<211> LENGTH: 810
<212> TYPE: DNA
<213> ORGANISM: Artificial Sequence
<220> FEATURE:
<223> OTHER INFORMATION: Polynucleotide Encoding Second Polypeptide Chain of "DR5 mAb 2 x CD3 mAb 2 Diabody"

<400> SEQUENCE: 147

```
caggctgtgg tgactcagga gccttcactg accgtgtccc caggcggaac tgtgaccctg     60
acatgcagat ccagcacagg cgcagtgacc acatctaact acgccaattg ggtgcagcag    120
aagccaggac aggcaccaag ggggcctgatc gggggtacaa acaaaagggc tccctggacc    180
cctgcacggt tttctggaag tctgctgggc ggaaaggccg ctctgactat taccggggca    240
```

```
caggccgagg acgaagccga ttactattgt gctctgtggt atagcaatct gtgggtgttc      300
gggggtggca caaaactgac tgtgctggga gggggtggat ccggcggcgg aggcaaggtc      360
cagctgcagc agtctggagc tgaactggtg aaacccgggg catcagtgaa gctgtcctgc      420
aaggcttctg gtacaccctt cactgagtat attttacact gggtaaagca gaagtctgga      480
cagggtcttg agtggattgg gtggttttat cctggaaata ataatataaa gtacaatgag      540
aaattcaagg acaaggccac actgactgcg gacaaatcct ccagcacagt ctatatggaa      600
cttagtagat tgacatctga agactctgcg gtctatttct gtgcaagaca cgaacaagga      660
ccaggttact ttgactactg gggccaaggc accactctca cagtctcctc cgcctccacc      720
aagggcaaag tggccgcatg taaggagaaa gttgctgctt gaaagagaaa ggtcgccgca      780
cttaaggaaa aggtcgcagc cctgaaagag                                       810
```

<210> SEQ ID NO 148
<211> LENGTH: 274
<212> TYPE: PRT
<213> ORGANISM: Artificial Sequence
<220> FEATURE:
<223> OTHER INFORMATION: First Polypeptide Chain of "DR5 mAb 3 x CD3 mAb 2 Diabody"

<400> SEQUENCE: 148

```
Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly Gly Gly Gly Ser
            100                 105                 110

Gly Gly Gly Gly Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Ser Thr Tyr Ala Met Asn Trp Val Arg Gln Ala Pro Gly Lys Gly
145                 150                 155                 160

Leu Glu Trp Val Gly Arg Ile Arg Ser Lys Tyr Asn Asn Tyr Ala Thr
                165                 170                 175

Tyr Tyr Ala Asp Ser Val Lys Gly Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Val Arg His Gly Asn Phe Gly Asn Ser Tyr
    210                 215                 220

Val Ser Trp Phe Ala Tyr Trp Gly Gln Gly Thr Leu Val Thr Val Ser
225                 230                 235                 240

Ser Ala Ser Thr Lys Gly Glu Val Ala Ala Cys Glu Lys Glu Val Ala
                245                 250                 255
```

```
Ala Leu Glu Lys Glu Val Ala Ala Leu Lys Glu Val Ala Ala Leu
            260                 265                 270

Glu Lys

<210> SEQ ID NO 149
<211> LENGTH: 272
<212> TYPE: PRT
<213> ORGANISM: Artificial Sequence
<220> FEATURE:
<223> OTHER INFORMATION: Second Polypeptide Chain of "DR5 mAb 3 x CD3
      mAb 2 Diabody"

<400> SEQUENCE: 149

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Gly Gly
            115                 120                 125

Val Glu Arg Pro Gly Gly Ser Leu Arg Leu Ser Cys Ala Ala Ser Gly
        130                 135                 140

Phe Thr Phe Asp Asp Tyr Ala Met Ser Trp Val Arg Gln Ala Pro Gly
145                 150                 155                 160

Lys Gly Leu Glu Trp Val Ser Gly Ile Asn Trp Gln Gly Gly Ser Thr
                165                 170                 175

Gly Tyr Ala Asp Ser Val Lys Gly Arg Val Thr Ile Ser Arg Asp Asn
            180                 185                 190

Ala Lys Asn Ser Leu Tyr Leu Gln Met Asn Ser Leu Arg Ala Glu Asp
        195                 200                 205

Thr Ala Val Tyr Tyr Cys Ala Lys Ile Leu Gly Ala Gly Arg Gly Trp
    210                 215                 220

Tyr Phe Asp Tyr Trp Gly Lys Gly Thr Thr Val Thr Val Ser Ser Ala
225                 230                 235                 240

Ser Thr Lys Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 150
<211> LENGTH: 274
<212> TYPE: PRT
<213> ORGANISM: Artificial Sequence
<220> FEATURE:
<223> OTHER INFORMATION: First Polypeptide Chain of "DR5 mAb 4 x CD3 mAb
      2 Diabody"

<400> SEQUENCE: 150

Glu Ile Val Leu Thr Gln Ser Pro Gly Thr Leu Ser Leu Ser Pro Gly
```

```
  1               5                  10                 15
Glu Arg Ala Thr Leu Ser Cys Arg Ala Ser Gln Gly Ile Ser Arg Ser
            20                  25                 30

Tyr Leu Ala Trp Tyr Gln Gln Lys Pro Gly Gln Ala Pro Ser Leu Leu
            35                  40                 45

Ile Tyr Gly Ala Ser Ser Arg Ala Thr Gly Ile Pro Asp Arg Phe Ser
        50                  55                 60

Gly Ser Gly Ser Gly Thr Asp Phe Thr Leu Thr Ile Ser Arg Leu Glu
 65                 70                  75                 80

Pro Glu Asp Phe Ala Val Tyr Tyr Cys Gln Gln Phe Gly Ser Ser Pro
                85                  90                 95

Trp Thr Phe Gly Gln Gly Thr Lys Val Glu Ile Lys Gly Gly Gly Ser
            100                 105                110

Gly Gly Gly Gly Glu Val Gln Leu Val Glu Ser Gly Gly Gly Leu Val
            115                 120                125

Gln Pro Gly Gly Ser Leu Arg Leu Ser Cys Ala Ala Ser Gly Phe Thr
        130                 135                140

Phe Ser Thr Tyr Ala Met Asn Trp Val Arg Gln Ala Pro Gly Lys Gly
145                 150                 155                160

Leu Glu Trp Val Gly Arg Ile Arg Ser Lys Tyr Asn Asn Tyr Ala Thr
                165                 170                175

Tyr Tyr Ala Asp Ser Val Lys Gly Arg Phe Thr Ile Ser Arg Asp Asp
            180                 185                190

Ser Lys Asn Ser Leu Tyr Leu Gln Met Asn Ser Leu Lys Thr Glu Asp
        195                 200                205

Thr Ala Val Tyr Tyr Cys Val Arg His Gly Asn Phe Gly Asn Ser Tyr
 210                215                 220

Val Ser Trp Phe Ala Tyr Trp Gly Gln Gly Thr Leu Val Thr Val Ser
225                 230                 235                240

Ser Ala Ser Thr Lys Gly Glu Val Ala Ala Cys Glu Lys Glu Val Ala
                245                 250                255

Ala Leu Glu Lys Glu Val Ala Ala Leu Glu Lys Glu Val Ala Ala Leu
            260                 265                270

Glu Lys
```

<210> SEQ ID NO 151
<211> LENGTH: 273
<212> TYPE: PRT
<213> ORGANISM: Artificial Sequence
<220> FEATURE:
<223> OTHER INFORMATION: Second Polypeptide Chain of "DR5 mAb 4 x CD3
      mAb 2 Diabody"

<400> SEQUENCE: 151

```
  1               5                  10                 15
Gln Ala Val Val Thr Gln Glu Pro Ser Leu Thr Val Ser Pro Gly Gly

Thr Val Thr Leu Thr Cys Arg Ser Ser Thr Gly Ala Val Thr Thr Ser
            20                  25                 30

Asn Tyr Ala Asn Trp Val Gln Gln Lys Pro Gly Gln Ala Pro Arg Gly
            35                  40                 45

Leu Ile Gly Gly Thr Asn Lys Arg Ala Pro Trp Thr Pro Ala Arg Phe
        50                  55                 60

Ser Gly Ser Leu Leu Gly Gly Lys Ala Ala Leu Thr Ile Thr Gly Ala
 65                 70                  75                 80

Gln Ala Glu Asp Glu Ala Asp Tyr Tyr Cys Ala Leu Trp Tyr Ser Asn
```

```
                     85                  90                  95
Leu Trp Val Phe Gly Gly Gly Thr Lys Leu Thr Val Leu Gly Gly Gly
                100                 105                 110

Gly Ser Gly Gly Gly Gln Val Gln Leu Gln Glu Ser Gly Pro Gly
            115                 120                 125

Leu Val Lys Pro Ser Gln Thr Leu Ser Leu Thr Cys Thr Val Ser Gly
        130                 135                 140

Gly Ser Ile Ser Ser Gly Asp Tyr Phe Trp Ser Trp Ile Arg Gln Leu
145                 150                 155                 160

Pro Gly Lys Gly Leu Glu Trp Ile Gly His Ile His Asn Ser Gly Thr
                165                 170                 175

Thr Tyr Tyr Asn Pro Ser Leu Lys Ser Arg Val Thr Ile Ser Val Asp
            180                 185                 190

Thr Ser Lys Lys Gln Phe Ser Leu Arg Leu Ser Ser Val Thr Ala Ala
        195                 200                 205

Asp Thr Ala Val Tyr Tyr Cys Ala Arg Asp Arg Gly Gly Asp Tyr Tyr
    210                 215                 220

Tyr Gly Met Asp Val Trp Gly Gln Gly Thr Thr Val Thr Val Ser Ser
225                 230                 235                 240

Ala Ser Thr Lys Gly Lys Val Ala Ala Cys Lys Glu Lys Val Ala Ala
                245                 250                 255

Leu Lys Glu Lys Val Ala Ala Leu Lys Glu Lys Val Ala Ala Leu Lys
            260                 265                 270

Glu

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Ala Pro Ser Ser Ser
1               5

<210> SEQ ID NO 153
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: Murine Anti-Human EphA2 Antibody EphA2 mAb 1")
      Light Chain Variable Domain

<400> SEQUENCE: 153

Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
```

```
                    85                  90                  95

Phe Gly Gly Gly Thr Lys Leu Glu Ile Lys
            100                 105

<210> SEQ ID NO 154
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Murine Anti-Human EphA2 Antibody ("EphA2 mAb
      1") Light Chain Variable Domain CDRL1

<400> SEQUENCE: 154

Arg Ala Ser Gln Asp Ile Ser Asn Tyr Leu Asn
1               5                   10

<210> SEQ ID NO 155
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human EphA2 Antibody ("EphA2 mAb
      1") Light Chain Variable Domain CDRL2

<400> SEQUENCE: 155

Tyr Thr Ser Arg Leu His Ser
1               5

<210> SEQ ID NO 156
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Murine Anti-Human EphA2 Antibody ("EphA2 mAb
      1") Light Chain Variable Domain CDRL3

<400> SEQUENCE: 156

Gln Gln Gly Tyr Thr Leu Tyr Thr
1               5

<210> SEQ ID NO 157
<211> LENGTH: 318
<212> TYPE: DNA
<213> ORGANISM: Mus musculus
<220> FEATURE:
<221> NAME/KEY: misc_feature
<222> LOCATION: (1)..(318)
<223> OTHER INFORMATION: Polynucleotide Encoding Murine Anti-Human EphA2
      Antibody ("EphA2 mAb 1") Light Chain Variable Domain CDRL1

<400> SEQUENCE: 157
gatatccaga tgacacagac tacatcctcc ctgtctgcct ctctgggaga cagaatcacc      60
atcagttgca gggcaagtca ggacattagc aattatttaa actggtatca gcagaaacca     120
gatggaactg ttaaactcct gatctactac acatcaagat acactcagg agtcccatca      180 aggttcagtg gcagtgggtc tggaacagat tattctctca ccattagcaa cctggagcaa     240
gaagatattg ccacttactt ttgccaacag ggttatacgc tgtacacgtt cggagggggg     300
accaagctgg aaataaaa                                                   318
```

-continued

```
<210> SEQ ID NO 158
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human EphA2 Antibody ("EphA2 mAb
      1") Heavy Chain Variable Domain

<400> SEQUENCE: 158

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Lys His Gly Asn Tyr Tyr Thr Met Asp Tyr Trp Gly Gln Gly Thr
            100                 105                 110

Ser Val Thr Val Ser Ser
        115

<210> SEQ ID NO 159
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human EphA2 Antibody ("EphA2 mAb
      1") Heavy Chain Variable Domain CDRH1

<400> SEQUENCE: 159

Gly Phe Ser Leu Ser Arg Tyr Ser Val His
1               5                   10

<210> SEQ ID NO 160
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Murine Anti-Human EphA2 Antibody ("EphA2 mAb
      1") Heavy Chain Variable Domain CDRH2

<400> SEQUENCE: 160

Met Ile Trp Gly Gly Gly Ser Thr Asp Tyr Asn Ser Ala Leu Lys Ser
1               5                   10                  15

<210> SEQ ID NO 161
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human EphA2 Antibody ("EphA2 mAb
      1") Heavy Chain Variable Domain CDRH3
```

<400> SEQUENCE: 161

Lys His Gly Asn Tyr Tyr Thr Met Asp Tyr
1               5                   10

<210> SEQ ID NO 162
<211> LENGTH: 354
<212> TYPE: DNA
<213> ORGANISM: Mus musculus
<220> FEATURE:
<221> NAME/KEY: misc_feature
<222> LOCATION: (1)..(354)
<223> OTHER INFORMATION: Polynucleotide Encoding Murine Anti-Human EphA2
      Antibody ("EphA2 mAb 1") Heavy Chain Variable Domain

<400> SEQUENCE: 162
caggtgcagc tgaaggagtc aggacctggc ctggtggcac cctcacagag cctgtccatc     60
acatgcactg tctctgggtt ctcattatcc agatatagtg tacactgggt tcgccagcct    120
ccaggaaagg gtctggagtg gctgggaatg atatggggtg gtggaagcac agactataat    180
tcagctctca aatccagact gagtatcagc aaggacaact ccaagagcca agttttctta    240
aaaatgaaca gtctgcaaac tgatgacaca gccatgtact actgtgccag aaaacatggt    300
aactactata ctatggacta ctggggtcaa ggaacctcag tcaccgtctc ctcc          354

<210> SEQ ID NO 163
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Murine Anti-Human EphA2 Antibody ("EphA2 mAb
      2") Light Chain Variable Domain

<400> SEQUENCE: 163

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys
            100                 105                 110

<210> SEQ ID NO 164
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Murine Anti-Human EphA2 Antibody ("EphA2 mAb
      2") Light Chain Variable Domain CDRL1

<400> SEQUENCE: 164

Arg Ser Ser Gln Ser Leu Val His Ser Ser Gly Asn Thr Tyr Leu His
1               5                   10                  15

```
<210> SEQ ID NO 165
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human EphA2 Antibody ("EphA2 mAb
      2") Light Chain Variable Domain CDRL2

<400> SEQUENCE: 165

Lys Val Ser Asn Arg Phe Ser
1               5

<210> SEQ ID NO 166
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Murine Anti-Human EphA2 Antibody ("EphA2 mAb
      2") Light Chain Variable Domain CDRL3

<400> SEQUENCE: 166

Ser Gln Ser Thr His Val Pro Thr
1               5

<210> SEQ ID NO 167
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human EphA2 Antibody ("EphA2 mAb
      2") Heavy Chain Variable Domain

<400> SEQUENCE: 167

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ile Gly Glu Pro Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Leu Gly Pro Tyr Tyr Phe Asp Tyr Trp Gly Gln Gly Thr
            100                 105                 110

Thr Leu Thr Val Ser Ser
        115

<210> SEQ ID NO 168
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human EphA2 Antibody ("EphA2 mAb
```

2") Heavy Chain Variable Domain CDRH1

<400> SEQUENCE: 168

Gly Phe Thr Phe Thr Asn Tyr Gly Met Asn
1               5                   10

<210> SEQ ID NO 169
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human EphA2 Antibody ("EphA2 mAb
      2") Heavy Chain Variable Domain CDRH2

<400> SEQUENCE: 169

Trp Ile Asn Thr Tyr Ile Gly Glu Pro Thr Tyr Ala Asp Asp Phe Lys
1               5                   10                  15

Gly

<210> SEQ ID NO 170
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human EphA2 Antibody ("EphA2 mAb
      2") Heavy Chain Variable Domain CDRH3

<400> SEQUENCE: 170

Glu Leu Gly Pro Tyr Tyr Phe Asp Tyr
1               5

<210> SEQ ID NO 171
<211> LENGTH: 354
<212> TYPE: DNA
<213> ORGANISM: Mus musculus
<220> FEATURE:
<221> NAME/KEY: misc_feature
<222> LOCATION: (1)..(354)
<223> OTHER INFORMATION: Polynucleotide Encoding Murine Anti-Human EphA2
      Antibody ("EphA2 mAb 2") Heavy Chain Variable Domain

<400> SEQUENCE: 171
cagatccagt tggtgcagtc tggacctgag ctgaagaagc ctggagagac agtcaagatc      60
tcctgcaagg cttctgggtt taccttcaca aactatggaa tgaactgggt gaagcaggct     120
ccaggaaagg gtttaaagtg gatgggctgg ataaacacct atattggaga gccgacatat     180
gctgatgact caagggacg gtttgtcttc tctttggaaa cctctgccag cactgcctat     240
ttgcagatca acaacctcaa aaatgaggac atggccacat atttctgtgc aagagaactg     300
ggaccatact actttgacta ctggggccaa ggcaccactc tcacagtctc ctcc           354

<210> SEQ ID NO 172
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human EphA2 Antibody ("EphA2 mAb
      3") Light Chain Variable Domain

<400> SEQUENCE: 172

Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Gly Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 173
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Murine Anti-Human EphA2 Antibody ("EphA2 mAb
      3") Light Chain Variable Domain CDRL1

<400> SEQUENCE: 173

Lys Ala Ser Gln Asp Val Thr Thr Ala Val Ala
1               5                   10

<210> SEQ ID NO 174
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Murine Anti-Human EphA2 Antibody ("EphA2 mAb
      3") Light Chain Variable Domain CDRL2

<400> SEQUENCE: 174

Trp Ala Ser Thr Arg His Ala
1               5

<210> SEQ ID NO 175
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human EphA2 Antibody ("EphA2 mAb
      3") Light Chain Variable Domain CDRL3

<400> SEQUENCE: 175

Gln Gln His Tyr Ser Thr Pro Tyr Thr
1               5

<210> SEQ ID NO 176
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding Murine Anti-Human EphA2
      Antibody ("EphA2 mAb 3") Light Chain Variable Domain

<400> SEQUENCE: 176

```
gacattgtgc tgacccagtc tcacagatcc atgtccacat cagtaggaga cagggtcaac      60
atcacctgca aggccagtca ggatgtgact actgctgtag cctggtatca acaaaaacca     120
gggcaatctc ctaaattact gattttctgg gcatccaccc ggcacgctgg agtccctgat     180
cgcttcacag gcagtggatc tgggacagat tttactctca ccatcagcag tgtgcaggct     240
ggagacctgg cactttatta ctgtcaacaa cattatagca caccgtacac attcggaggg     300
gggaccaagc tggaaataaa a                                                321
```

<210> SEQ ID NO 177
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human EphA2 Antibody ("EphA2 mAb
   3") Heavy Chain Variable Domain

<400> SEQUENCE: 177

Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Thr Asp His
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Phe Thr Ser Tyr Pro Asp Ser Val
    50                  55                  60

Lys Gly Arg Phe Thr Ile Ser Arg Asp Ile Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Asp Glu Ser Asp Arg Pro Phe Pro Tyr Trp Gly Gln Gly Thr
            100                 105                 110

Leu Val Thr Val Ser Ser
        115

<210> SEQ ID NO 178
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Murine Anti-Human EphA2 Antibody ("EphA2 mAb
   3") Heavy Chain Variable Domain CDRH1

<400> SEQUENCE: 178

Gly Phe Thr Phe Thr Asp His Tyr Met Tyr
1               5                   10

<210> SEQ ID NO 179
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Murine Anti-Human EphA2 Antibody ("EphA2 mAb
   3") Heavy Chain Variable Domain CDRH2

-continued

<400> SEQUENCE: 179

Thr Ile Ser Asp Gly Gly Ser Phe Thr Ser Tyr Pro Asp Ser Val Lys
1               5                   10                  15

Gly

<210> SEQ ID NO 180
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Murine Anti-Human EphA2 Antibody ("EphA2 mAb
      3") Heavy Chain Variable Domain CDRH3

<400> SEQUENCE: 180

Asp Glu Ser Asp Arg Pro Phe Pro Tyr
1               5

<210> SEQ ID NO 181
<211> LENGTH: 106
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Light Chain Variable Domain

<400> SEQUENCE: 181

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105

<210> SEQ ID NO 182
<211> LENGTH: 10
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Light Chain Variable Domain CDRL1

<400> SEQUENCE: 182

Ser Ala Arg Ser Ser Ile Ser Phe Met Tyr
1               5                   10

<210> SEQ ID NO 183
<211> LENGTH: 7
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Light Chain Variable Domain CDRL2

<400> SEQUENCE: 183

Asp Thr Ser Asn Leu Ala Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Light Chain Variable Domain CDRL3

<400> SEQUENCE: 184

Gln Gln Trp Ser Ser Tyr Pro Leu Thr
1               5

<210> SEQ ID NO 185
<211> LENGTH: 318
<212> TYPE: DNA
<213> ORGANISM: Artificial Sequence
<220> FEATURE:
<223> OTHER INFORMATION: Polynucleotide Encoding Humanized Anti-Human
      gpA33 Antibody ("gpA33 mAb 1") Light Chain Variable Domain

<400> SEQUENCE: 185
gacattcagc tgactcagtc cccctctttt ctgtccgcat ccgtcggaga tcgagtgact      60
attacttgct ctgctaggtc ctcaatcagc ttcatgtact ggtatcagca gaagcccggc    120
aaagcaccta agctgctgat ctacgacaca agcaacctgg cctccggggt gccatctcgg    180
ttctctggca gtgggtcagg aactgagttt accctgacaa ttagctccct ggaggctgaa    240
gatgccgcta cctactattg ccagcagtgg agcagctatc ctctgacctt cggacagggg    300
actaaactgg aaatcaag                                                  318

<210> SEQ ID NO 186
<211> LENGTH: 119
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Heavy Chain Variable Domain

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser
        115

<210> SEQ ID NO 187
<211> LENGTH: 10

```
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Heavy Chain Variable Domain CDRH1

<400> SEQUENCE: 187

Gly Tyr Thr Phe Thr Gly Ser Trp Met Asn
1               5                   10

<210> SEQ ID NO 188
<211> LENGTH: 17
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Heavy Chain Variable Domain CDRH2

<400> SEQUENCE: 188

Arg Ile Tyr Pro Gly Asp Gly Glu Thr Asn Tyr Asn Gly Lys Phe Lys
1               5                   10                  15

Asp

<210> SEQ ID NO 189
<211> LENGTH: 10
<212> TYPE: PRT
<213> ORGANISM: Artificial Sequence
<220> FEATURE:
<223> OTHER INFORMATION: Humanized Anti-Human gpA33 Antibody ("gpA33 mAb
      1") Heavy Chain Variable Domain CDRH3

<400> SEQUENCE: 189

Ile Tyr Gly Asn Asn Val Tyr Phe Asp Val
1               5                   10

<210> SEQ ID NO 190
<211> LENGTH: 357
<212> TYPE: DNA
<213> ORGANISM: Artificial Sequence
<220> FEATURE:
<223> OTHER INFORMATION: Polynucelotide Encoding Humanized Anti-Human
      gpA33 Antibody ("gpA33 mAb 1") Heavy Chain Variable Domain

<400> SEQUENCE: 190
caggtccagc tggtccagag cggggccgaa gtcaaaaaac ccggagcaag cgtgaaggtc      60
tcctgcaaag catcaggcta catatttaca ggcagctgga tgaactgggt gaggcaggct     120
ccaggacagg gactggagtg gatcgggcgc atctaccctg gagacggcga aactaactat     180
aatggaaagt tcaaagaccg agtgaccatc acagccgata gtctactagt accgcctac      240 atggagctga gctccctgcg gtctgaagat accgccgtct actattgcgc tagaatttac     300
ggaaacaatg tctattttga cgtgtggggg cagggaacaa ctgtgactgt ctcctcc        357

<210> SEQ ID NO 191
<211> LENGTH: 109
<212> TYPE: PRT
<213> ORGANISM: Artificial Sequence
<220> FEATURE:
<223> OTHER INFORMATION: Humanized Anti-Human Her2 Antibody ("Her2 mAb
      1") Light Chain Variable Domain

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
                    20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Arg Thr
                100                 105
```

<210> SEQ ID NO 192
<211> LENGTH: 120
<212> TYPE: PRT
<213> ORGANISM: Artificial Sequence
<220> FEATURE:
<223> OTHER INFORMATION: Chimeric Anti-Human Her2 Antibody ("Her2 mAb
      1") Heavy Chain Variable Domain

<400> SEQUENCE: 192

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                    85                  90                  95

Ser Arg Trp Gly Gly Asp Gly Phe Tyr Ala Met Asp Tyr Trp Gly Gln
                100                 105                 110

Gly Ala Ser Val Thr Val Ser Ser
            115                 120
```

<210> SEQ ID NO 193
<211> LENGTH: 108
<212> TYPE: PRT
<213> ORGANISM: Artificial Sequence
<220> FEATURE:
<223> OTHER INFORMATION: Humanized Anti-Human Her2 Antibody
      (Trastuzumab) Light Chain Variable Domain

<400> SEQUENCE: 193

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                        85                  90                  95

Thr Phe Gly Gln Gly Thr Lys Val Glu Ile Lys Arg
                100                 105

<210> SEQ ID NO 194
<211> LENGTH: 120
<212> TYPE: PRT
<213> ORGANISM: Artificial Sequence
<220> FEATURE:
<223> OTHER INFORMATION: Humanized Anti-Human Her2 Antibody
      (Trastuzumab) Heavy Chain Variable Domain

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 195
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human B7-H3 Antibody ("B7-H3 mAb
      1") Light Chain Variable Domain

<400> SEQUENCE: 195

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105

<210> SEQ ID NO 196
<211> LENGTH: 122
<212> TYPE: PRT
<213> ORGANISM: Mus musculus
```

```
<220> FEATURE:
<221> NAME/KEY: MISC_FEATURE
<222> LOCATION: (1)..(122)
<223> OTHER INFORMATION: Murine Anti-Human B7-H3 Antibody ("B7-H3 mAb
      1") Heavy Chain Variable Domain

<400> SEQUENCE: 196

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

<210> SEQ ID NO 197
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human B7-H3 Antibody ("B7-H3 mAb
      2") Light Chain Variable Domain

<400> SEQUENCE: 197

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 198
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Murine Anti-Human B7-H3 Antibody ("B7-H3 mAb
      2") Heavy Chain Variable Domain

<400> SEQUENCE: 198
```

```
Gln Val Gln Leu Gln Gln Ser Gly Ala Glu Leu Ala Arg Pro Gly Ala
1               5                  10                 15

Ser Val Lys Leu Ser Cys Lys Ala Ser Gly Tyr Thr Phe Thr Ser Tyr
            20                 25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Arg Arg Gly Ile Pro Arg Leu Trp Tyr Phe Asp Val Trp Gly Ala
            100                 105                 110

Gly Thr Thr Val Thr Val Ser Ser
            115                 120
```

<210> SEQ ID NO 199
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Murine Anti-Human B7-H3 Antibody ("B7-H3 mAb
      3") Light Chain Variable Domain

<400> SEQUENCE: 199

```
Asp Ile Gln Met Thr Gln Ser Pro Ala Ser Leu Ser Val Ser Val Gly
1               5                  10                 15

Glu Thr Val Thr Ile Thr Cys Arg Ala Ser Glu Ser Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Arg Tyr Tyr Cys Gln His His Tyr Gly Thr Pro Pro
            85                  90                  95

Trp Thr Phe Gly Gly Gly Thr Asn Leu Glu Ile Lys
            100                 105
```

<210> SEQ ID NO 200
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: Murine Anti-Human B7-H3 Antibody ("B7-H3 mAb
      3") Heavy Chain Variable Domain

<400> SEQUENCE: 200

```
Glu Val Gln Gln Val Glu Ser Gly Gly Asp Leu Val Lys Pro Gly Gly
1               5                  10                 15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45
```

```
Ala Thr Ile Asn Ser Gly Gly Ser Asn Thr Tyr Tyr Pro Asp Ser Leu
            50                  55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
            115

<210> SEQ ID NO 201
<211> LENGTH: 108
<212> TYPE: PRT
<213> ORGANISM: Artificial Sequence
<220> FEATURE:
<223> OTHER INFORMATION: Chimeric Anti-Human EGFR Antibody (Cetuximab)
      Light Chain Variable Domain

<400> SEQUENCE: 201

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 202
<211> LENGTH: 119
<212> TYPE: PRT
<213> ORGANISM: Artificial Sequence
<220> FEATURE:
<223> OTHER INFORMATION: Chimeric Anti-Human EGFR Antibody (Cetuximab)
      Heavy Chain Variable Domain

<400> SEQUENCE: 202

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110
```

Thr Leu Val Thr Val Ser Ala
        115

<210> SEQ ID NO 203
<211> LENGTH: 108
<212> TYPE: PRT
<213> ORGANISM: Artificial Sequence
<220> FEATURE:
<223> OTHER INFORMATION: Humanized Anti-Human VEGF Antibody
      (Bevacizumab) Light Chain Variable Domain

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 204
<211> LENGTH: 123
<212> TYPE: PRT
<213> ORGANISM: Artificial Sequence
<220> FEATURE:
<223> OTHER INFORMATION: Humanized Anti-Human VEGF Antibody
      (Bevacizumab) Heavy Chain Variable Domain

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 205
<211> LENGTH: 108
<212> TYPE: PRT
<213> ORGANISM: Artificial Sequence
<220> FEATURE:
<223> OTHER INFORMATION: Humanized Anti-CD52 Antibody (Alemtuzumab)
      Light Chain Variable Domain

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg
            100                 105

<210> SEQ ID NO 206
<211> LENGTH: 121
<212> TYPE: PRT
<213> ORGANISM: Artificial Sequence
<220> FEATURE:
<223> OTHER INFORMATION: Humanized Anti-CD52 Antibody (Alemtuzumab)
      Heavy Chain Variable Domain

<400> SEQUENCE: 206

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
        115                 120

<210> SEQ ID NO 207
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 207

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val

<210> SEQ ID NO 208
<211> LENGTH: 98
<212> TYPE: PRT
<213> ORGANISM: Artificial Sequence
<220> FEATURE:
<223> OTHER INFORMATION: Variant Human IgG1 CH1 Domain

<400> SEQUENCE: 208

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val

<210> SEQ ID NO 209
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Human IgG1 Hinge Domain

<400> SEQUENCE: 209

Glu Pro Lys Ser Cys Asp Lys Thr His Thr Cys Pro Pro Cys Pro
1               5                   10                  15

<210> SEQ ID NO 210
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG1 CL Kappa Domain

<400> SEQUENCE: 210

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 211
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: human IgG2 CL Lambda2 Domain

<400> SEQUENCE: 211

```
Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                 20                  25                  30

Tyr Pro Gly Ala Val Thr Val Ala Trp Lys Ala Asp Ser Ser Pro Val
             35                  40                  45

Lys Ala Gly Val Glu Thr Thr Pro Ser Lys Gln Ser Asn Asn Lys Tyr
 50                  55                  60

Ala Ala Ser Ser Tyr Leu Ser Leu Thr Pro Glu Gln Trp Lys Ser His
 65                  70                  75                  80

Arg Ser Tyr Ser Cys Gln Val Thr His Glu Gly Ser Thr Val Glu Lys
                 85                  90                  95

Thr Val Ala Pro Thr Glu Cys Ser
            100
```

<210> SEQ ID NO 212
<211> LENGTH: 503
<212> TYPE: PRT
<213> ORGANISM: Artificial Sequence
<220> FEATURE:
<223> OTHER INFORMATION: First Polypeptide Chain of "gpA33 mAb 1 x CD3
      mAb 2 x DR5 mAb 1" Tri-Specific Binding Molecule

<400> SEQUENCE: 212

```
Asp Ile Gln Leu Thr Gln Ser Pro Ser Phe Leu Ser Ala Ser Val Gly
 1               5                  10                  15

Asp Arg Val Thr Ile Thr Cys Ser Ala Arg Ser Ser Ile Ser Phe Met
                 20                  25                  30

Tyr Trp Tyr Gln Gln Lys Pro Gly Lys Ala Pro Lys Leu Leu Ile Tyr
             35                  40                  45

Asp Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125
```

Gly Gly Ser Leu Arg Leu Ser Cys Ala Ala Ser Gly Phe Thr Phe Ser
            130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 213
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain of "gpA33 mAb 1 x CD3 mAb 2 x DR5 mAb 1" Tri-Specific Binding Molecule

<400> SEQUENCE: 213

```
gacattcagc tgactcagtc cccctctttt ctgtccgcat ccgtcggaga tcgagtgact    60
attacttgct ctgctaggtc ctcaatcagc ttcatgtact ggtatcagca gaagcccggc   120
aaagcaccta agctgctgat ctacgacaca agcaacctgg cctccggggt gccatctcgg   180
ttctctggca gtgggtcagg aactgagttt accctgacaa ttagctccct ggaggctgaa   240
gatgccgcta cctactattg ccagcagtgg agcagctatc ctctgacctt cggacagggg   300
actaaactgg aaatcaaggg tggaggatcc ggcggcggag gcgaggtgca gctggtggag   360
tctgggggag gcttggtcca gcctggaggg tccctgagac tctcctgtgc agcctctgga   420
ttcaccttca gcacatacgc tatgaattgg gtccgccagg ctccagggaa ggggctggag   480
tgggttggaa ggatcaggtc caagtacaac aattatgcaa cctactatgc cgactctgtg   540
aagggtagat tcaccatctc aagagatgat tcaaagaact cactgtatct gcaaatgaac   600
agcctgaaaa ccgaggacac ggccgtgtat tactgtgtga cacggtaa cttcggcaat   660
tcttacgtgt cttggtttgc ttattgggga caggggacac tggtgactgt gtcttccgga   720
ggatgtggcg gtggagaagt ggccgcactg gagaaagagg ttgctgcttt ggagaaggag   780
gtcgctgcac ttgaaaagga ggtcgcagcc ctggagaaag cggcggggga caaaactcac   840
acatgcccac cgtgcccagc acctgaagcc gcgggggac cgtcagtctt cctcttcccc   900
ccaaaaccca aggacaccct catgatctcc cggacccctg aggtcacatg cgtggtggtg   960
gacgtgagcc acgaagaccc tgaggtcaag ttcaactggt acgtggacgg cgtggaggtg  1020
cataatgcca agacaaagcc gcgggaggag cagtacaaca gcacgtaccg tgtggtcagc  1080
gtcctcaccg tcctgcacca ggactggctg aatggcaagg agtacaagtg caaggtctcc  1140
aacaaagccc tcccagcccc catcgagaaa accatctcca agccaaaagg cagccccga   1200
gaaccacagg tgtacaccct gcccccatcc cgggaggaga tgaccaagaa ccaggtcagc  1260
ctgtggtgcc tggtcaaagg cttctatccc agcgacatcg ccgtggagtg ggagagcaat  1320
gggcagccgg agaacaacta caagaccacg cctcccgtgc tggactccga cggctccttc  1380
ttcctctaca gcaagctcac cgtggacaag agcaggtggc agcagggaa cgtcttctca  1440
tgctccgtga tgcatgaggc tctgcacaac cactacacgc agaagagcct ctccctgtct  1500
ccgggtaaa                                                          1509
```

<210> SEQ ID NO 214
<211> LENGTH: 271
<212> TYPE: PRT
<213> ORGANISM: Artificial Sequence
<220> FEATURE:
<223> OTHER INFORMATION: Second Polypeptide Chain of "gpA33 mAb 1 x CD3 mAb 2 x DR5 mAb 1" Tri-Specific Binding Molecule

<400> SEQUENCE: 214

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

```
Ser Gly Ser Leu Leu Gly Gly Lys Ala Ala Leu Thr Ile Thr Gly Ala
 65                  70                  75                  80
Gln Ala Glu Asp Glu Ala Asp Tyr Tyr Cys Ala Leu Trp Tyr Ser Asn
                 85                  90                  95
Leu Trp Val Phe Gly Gly Gly Thr Lys Leu Thr Val Leu Gly Gly Gly
            100                 105                 110
Gly Ser Gly Gly Gly Gly Gln Val Gln Leu Val Gln Ser Gly Ala Glu
        115                 120                 125
Val Lys Lys Pro Gly Ala Ser Val Lys Val Ser Cys Lys Ala Ser Gly
    130                 135                 140
Tyr Thr Phe Thr Gly Ser Trp Met Asn Trp Val Arg Gln Ala Pro Gly
145                 150                 155                 160
Gln Gly Leu Glu Trp Ile Gly Arg Ile Tyr Pro Gly Asp Gly Glu Thr
                165                 170                 175
Asn Tyr Asn Gly Lys Phe Lys Asp Arg Val Thr Ile Thr Ala Asp Lys
            180                 185                 190
Ser Thr Ser Thr Ala Tyr Met Glu Leu Ser Ser Leu Arg Ser Glu Asp
        195                 200                 205
Thr Ala Val Tyr Tyr Cys Ala Arg Ile Tyr Gly Asn Asn Val Tyr Phe
    210                 215                 220
Asp Val Trp Gly Gln Gly Thr Thr Val Thr Val Ser Ser Gly Gly Cys
225                 230                 235                 240
Gly Gly Gly Lys Val Ala Ala Leu Lys Glu Lys Val Ala Ala Leu Lys
                245                 250                 255
Glu Lys Val Ala Ala Leu Lys Glu Lys Val Ala Ala Leu Lys Glu
                260                 265                 270

<210> SEQ ID NO 215
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of "gpA33 mAb 1 x CD3 mAb 2 x DR5 mAb 1" Tri-Specific
      Binding Molecule

<400> SEQUENCE: 215
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacaggtc      360
cagctggtcc agagcggggc cgaagtcaaa aacccggag caagcgtgaa ggtctcctgc     420
aaagcatcag gctatacatt tacaggcagc tggatgaact gggtgaggca ggctccagga     480
cagggactgg agtggatcgg gcgcatctac cctggagacg gcgaaactaa ctataatgga     540
aagttcaaag accgagtgac catcacagcc gataagtcta ctagtaccgc ctacatggag     600
ctgagctccc tgcggtctga agataccgcc gtctactatt gcgctagaat ttacggaaac     660
aatgtctatt ttgacgtgtg ggggcaggga acaactgtga ctgtctcctc cggaggatgt     720
ggcggtggaa aagtggccgc actgaaggag aaagttgctg ctttgaagga aaggtcgcc     780 gcacttaagg aaaaggtcgc agccctgaaa gag                                 813
```

<210> SEQ ID NO 216
<211> LENGTH: 451
<212> TYPE: PRT
<213> ORGANISM: Artificial Sequence
<220> FEATURE:
<223> OTHER INFORMATION: Third Polypeptide Chain of "gpA33 mAb 1 x CD3 mAb 2 x DR5 mAb 1" Tri-Specific Binding Molecule

<400> SEQUENCE: 216

```
Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Asn Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
```

```
                355                 360                 365
Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
        420                 425                 430

His Glu Ala Leu His Asn Arg Tyr Thr Gln Lys Ser Leu Ser Leu Ser
        435                 440                 445

Pro Gly Lys
    450

<210> SEQ ID NO 217
<211> LENGTH: 1353
<212> TYPE: DNA
<213> ORGANISM: Artificial Sequence
<220> FEATURE:
<223> OTHER INFORMATION: Polynucleotide Encoding Third Polypeptide Chain
      of "gpA33 mAb 1 x CD3 mAb 2 x DR5 mAb 1" Tri-Specific Binding
      Molecule

<400> SEQUENCE: 217
```

| | | | | | |
|---|---|---|---|---|---|
| gaggtgaagt | tctctcgagtc | tggaggtggc | ctggtgcagc | ctggaggatc | cctgaaactc | 60 |
| tcctgtgtag | cctcaggatt | cgattttagt | agatactgga | tgagttgggt | ccggcaggct | 120 |
| ccagggaaag | gctagaatg | gattggagaa | attaatccag | atagcaatac | gataaactat | 180 |
| acgccatctc | taaaggataa | attcatcatc | tccagagaca | acgccaaaaa | tacgctgtat | 240 |
| ctgcaaatga | ccaaagtgag | atctgaggac | acagcccttt | attattgtac | aagaagggcc | 300 |
| tactatggta | acccggcctg | gtttgcttac | tggggccaag | ggactctggt | cactgtctct | 360 |
| tccgcctcca | ccaagggccc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | gccgcgggg | 720 |
| ggaccgtcag | tcttcctctt | ccccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgagt | tgcgcagtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | gtcagcaagc | tcaccgtgga | caagagcagg | 1260 |
| tggcagcagg | ggaacgtctt | ctcatgctcc | gtgatgcatg | aggctctgca | caaccgctac | 1320 |
| acgcagaaga | gcctctccct | gtctccgggt | aaa | | | 1353 |

<210> SEQ ID NO 218
<211> LENGTH: 218
<212> TYPE: PRT
<213> ORGANISM: Artificial Sequence
<220> FEATURE:
<223> OTHER INFORMATION: Fourth Polypeptide Chain of "gpA33 mAb 1 x CD3 mAb 2 x DR5 mAb 1" Tri-Specific Binding Molecule

<400> SEQUENCE: 218

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 219
<211> LENGTH: 654
<212> TYPE: DNA
<213> ORGANISM: Artificial Sequence
<220> FEATURE:
<223> OTHER INFORMATION: Polynucleotide Encoding Fourth Polypeptide Chain of "gpA33 mAb 1 x CD3 mAb 2 x DR5 mAb 1" Tri-Specific Binding Molecule

<400> SEQUENCE: 219
gacattgtgc tgacacagtc tcctgcttcc ttagctgtat ctctcgggca gagggccacc      60
atctcatgca gggccagcaa aagtgtcagt tcctctggct atagttatat gcactggtac     120
caacagaaac caggacagcc acccaaagtc tcatctttc tttcatccaa cctagattct      180
ggggtccctg ccaggttcag tggcagtggg tctgggacag acttcaccct caacatccat     240
cctgtggagg atggggatgc tgcaacctat tactgtcagc acagtaggga tcttcctccg     300
acgttcggtg gaggcaccaa gctggaaatc aaacgtacgg tggctgcacc atcggtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480

```
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca caggggaga gtgt           654
```

<210> SEQ ID NO 220
<211> LENGTH: 503
<212> TYPE: PRT
<213> ORGANISM: Artificial Sequence
<220> FEATURE:
<223> OTHER INFORMATION: First Polypeptide Chain of "gpA33 mAb 1 x CD3
      mAb 2 x DR5 mAb 2" Tri-Specific Binding Molecule

<400> SEQUENCE: 220

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
```

```
                325                 330                 335
Gly Val Glu Val His Asn Ala Lys Thr Lys Pro Arg Glu Glu Gln Tyr
            340                 345                 350
Asn Ser Thr Tyr Arg Val Val Ser Val Leu Thr Val Leu His Gln Asp
                355                 360                 365
Trp Leu Asn Gly Lys Glu Tyr Lys Cys Lys Val Ser Asn Lys Ala Leu
            370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Trp Cys Leu Val Lys Gly Phe Tyr Pro Ser Asp
            420                 425                 430
Ile Ala Val Glu Trp Glu Ser Asn Gly Gln Pro Glu Asn Asn Tyr Lys
                435                 440                 445
Thr Thr Pro Pro Val Leu Asp Ser Asp Gly Ser Phe Phe Leu Tyr Ser
            450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly Lys
            500

<210> SEQ ID NO 221
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of "gpA33 mAb 1 x CD3 mAb 2 x DR5 mAb 2" Tri-Specific Binding
      Molecule

<400> SEQUENCE: 221
gacattcagc tgactcagtc cccctctttt ctgtccgcat ccgtcggaga tcgagtgact      60
attacttgct ctgctaggtc ctcaatcagc ttcatgtact ggtatcagca gaagcccggc     120
aaagcaccta agctgctgat ctacgacaca agcaacctgg cctccggggt gccatctcgg     180
ttctctggca gtgggtcagg aactgagttt accctgacaa ttagctccct ggaggctgaa     240
gatgccgcta cctactattg ccagcagtgg agcagctatc ctctgacctt cggacagggg     300
actaaactgg aaatcaaggg tggaggatcc ggcggcggag gcgaggtgca gctggtggag     360 tctggggag gcttggtcca gcctggaggg tccctgagac tctcctgtgc agcctctgga     420
ttcaccttca gcatatacgc tatgaattgg gtccgccagg ctccagggaa ggggctggag     480
tgggttggaa ggatcaggtc caagtacaac aattatgcaa cctactatgc cgactctgtg     540
aagggtagat tcaccatctc aagagatgat tcaaagaact cactgtatct gcaaatgaac     600
agcctgaaaa ccgaggacac ggccgtgtat tactgtgtga cacggtaa cttcggcaat     660 tcttacgtgt cttggttttgc ttattgggga caggggacac tggtgactgt gtcttccgga     720
ggatgtggcg gtgagaagt ggccgcactg gagaaagagg ttgctgcttt ggagaaggag     780
gtcgctgcac ttgaaaagga ggtcgcagcc ctggagaaag cggcggggga caaaactcac     840
acatgcccac cgtgcccagc acctgaagcc gcggggggac cgtcagtctt cctcttcccc     900
ccaaaaccca aggacaccct catgatctcc cggacccctg aggtcacatg cgtggtggtg     960
```

```
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa accatctcca aagccaaagg gcagccccga    1200
gaaccacagg tgtacaccct gcccccatcc cgggaggaga tgaccaagaa ccaggtcagc    1260
ctgtggtgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaa                                                             1509
```

<210> SEQ ID NO 222
<211> LENGTH: 271
<212> TYPE: PRT
<213> ORGANISM: Artificial Sequence
<220> FEATURE:
<223> OTHER INFORMATION: Second Polypeptide Chain of "gpA33 mAb 1 x CD3 mAb 2 x DR5 mAb 2" Tri-Specific Binding Molecule

<400> SEQUENCE: 222

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ile Tyr Gly Asn Asn Val Tyr Phe
    210                 215                 220

Asp Val Trp Gly Gln Gly Thr Thr Val Thr Val Ser Ser Gly Gly Cys
225                 230                 235                 240

Gly Gly Gly Lys Val Ala Ala Leu Lys Glu Lys Val Ala Ala Leu Lys
                245                 250                 255
```

Glu Lys Val Ala Ala Leu Lys Glu Lys Val Ala Ala Leu Lys Glu
            260                 265                 270

<210> SEQ ID NO 223
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of "gpA33 mAb 1 x CD3 mAb 2 x DR5 mAb 2" Tri-Specific
      Binding Molecule

<400> SEQUENCE: 223
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga gggggtggat ccggcggagg tggacaggtc     360
cagctggtcc agagcggggc cgaagtcaaa aacccggag caagcgtgaa ggtctcctgc     420
aaagcatcag gctatacatt tacaggcagc tggatgaact gggtgaggca ggctccagga     480
cagggactgg agtggatcgg cgcatctac cctggagacg gcgaaactaa ctataatgga     540
aagttcaaag accgagtgac catcacagcc gataagtcta ctagtaccgc ctacatggag     600
ctgagctccc tgcggtctga agataccgcc gtctactatt gcgctagaat ttacggaaac     660
aatgtctatt ttgacgtgtg ggggcaggga acaactgtga ctgtctcctc cggaggatgt     720
ggcggtggaa aagtggccgc actgaaggag aaagttgctg cttttgaaaga gaaggtcgcc     780 gcacttaagg aaaaggtcgc agccctgaaa gag                                  813

<210> SEQ ID NO 224
<211> LENGTH: 449
<212> TYPE: PRT
<213> ORGANISM: Artificial Sequence
<220> FEATURE:
<223> OTHER INFORMATION: Third Polypeptide Chain of "gpA33 mAb 1 x CD3
      mAb 2 x DR5 mAb 2" Tri-Specific Binding Molecule

<400> SEQUENCE: 224

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Glu Tyr
            20                  25                  30

Ile Leu His Trp Val Lys Gln Lys Ser Gly Gln Gly Leu Glu Trp Ile
        35                  40                  45

Gly Trp Phe Tyr Pro Gly Asn Asn Asn Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Gln Gly Pro Gly Tyr Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

| | | | |
|---|---|---|---|
| | 130 | 135 | 140 |

Gly Cys Leu Val Lys Asp Tyr Phe Pro Glu Pro Val Thr Val Ser Trp
145                      150                  155                  160

Asn Ser Gly Ala Leu Thr Ser Gly Val His Thr Phe Pro Ala Val Leu
                165                  170                  175

Gln Ser Ser Gly Leu Tyr Ser Leu Ser Ser Val Val Thr Val Pro Ser
                180                  185                  190

Ser Ser Leu Gly Thr Gln Thr Tyr Ile Cys Asn Val Asn His Lys Pro
                195                  200                  205

Ser Asn Thr Lys Val Asp Lys Arg Val Glu Pro Lys Ser Cys Asp Lys
210                      215                  220

Thr His Thr Cys Pro Pro Cys Pro Ala Pro Glu Ala Ala Gly Gly Pro
225                      230                  235                  240

Ser Val Phe Leu Phe Pro Pro Lys Pro Lys Asp Thr Leu Met Ile Ser
                245                  250                  255

Arg Thr Pro Glu Val Thr Cys Val Val Val Asp Val Ser His Glu Asp
                260                  265                  270

Pro Glu Val Lys Phe Asn Trp Tyr Val Asp Gly Val Glu Val His Asn
                275                  280                  285

Ala Lys Thr Lys Pro Arg Glu Glu Gln Tyr Asn Ser Thr Tyr Arg Val
290                      295                  300

Val Ser Val Leu Thr Val Leu His Gln Asp Trp Leu Asn Gly Lys Glu
305                      310                  315                  320

Tyr Lys Cys Lys Val Ser Asn Lys Ala Leu Pro Ala Pro Ile Glu Lys
                325                  330                  335

Thr Ile Ser Lys Ala Lys Gly Gln Pro Arg Glu Pro Gln Val Tyr Thr
                340                  345                  350

Leu Pro Pro Ser Arg Glu Glu Met Thr Lys Asn Gln Val Ser Leu Ser
                355                  360                  365

Cys Ala Val Lys Gly Phe Tyr Pro Ser Asp Ile Ala Val Glu Trp Glu
370                      375                  380

Ser Asn Gly Gln Pro Glu Asn Asn Tyr Lys Thr Thr Pro Pro Val Leu
385                      390                  395                  400

Asp Ser Asp Gly Ser Phe Phe Leu Val Ser Lys Leu Thr Val Asp Lys
                405                  410                  415

Ser Arg Trp Gln Gln Gly Asn Val Phe Ser Cys Ser Val Met His Glu
                420                  425                  430

Ala Leu His Asn Arg Tyr Thr Gln Lys Ser Leu Ser Leu Ser Pro Gly
                435                  440                  445

Lys

```
<210> SEQ ID NO 225
<211> LENGTH: 1347
<212> TYPE: DNA
<213> ORGANISM: Artificial Sequence
<220> FEATURE:
<223> OTHER INFORMATION: Polynucleotide Encoding Third Polypeptide Chain
      of "gpA33 mAb 1 x CD3 mAb 2 x DR5 mAb 2" Tri-Specific Binding
      Molecule

<400> SEQUENCE: 225
aaggtccagc tgcagcagtc tggagctgaa ctggtgaaac ccggggcatc agtgaagctg      60
tcctgcaagg cttctgggta caccttcact gagtatattt acactgggt aaagcagaag     120 tctggacagg gtcttgagtg gattgggtgg ttttatcctg gaaataataa tataaagtac     180
```

```
aatgagaaat tcaaggacaa ggccacactg actgcggaca atcctccag cacagtctat    240 atggaactta gtagattgac atctgaagac tctgcggtct atttctgtgc aagacacgaa    300
caaggaccag gttactttga ctactggggc caaggcacca ctctcacagt ctcctccgcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagccgc ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gagttgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtcagc aagctcaccg tggacaagag caggtggcag    1260
caggggaacg tcttctcatg ctccgtgatg catgaggctc tgcacaaccg ctacacgcag    1320
aagagcctct ccctgtctcc gggtaaa                                         1347
```

<210> SEQ ID NO 226
<211> LENGTH: 214
<212> TYPE: PRT
<213> ORGANISM: Artificial Sequence
<220> FEATURE:
<223> OTHER INFORMATION: Fourth Polypeptide Chain of "gpA33 mAb 1 x CD3 mAb 2 x DR5 mAb 2" Tri-Specific Binding Molecule

<400> SEQUENCE: 226

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 227
<211> LENGTH: 642
<212> TYPE: DNA
<213> ORGANISM: Artificial Sequence
<220> FEATURE:
<223> OTHER INFORMATION: Polynucleotide Encoding Fourth Polypeptide
      Chain of "gpA33 mAb 1 x CD3 mAb 2 x DR5 mAb 2" Tri-Specific
      Binding Molecule

<400> SEQUENCE: 227

```
gacattgtga tgacccagtc tcacaaattc atgtccactt cagtaggaga cagggtcagc      60
atcacctgca aggccagtca ggatgtgaat actgctgtag cctggtatca acaaaaacca     120
gggcaatctc ctaaactact gatttactgg gcatccaccc ggcacactgg agtccctgat     180
cgcttcacag gcagtggatc tgggacagat tatacactca ccatcaaaag tgtgcaggct     240
gaagacctga cactttatta ctgtcagcaa cactatatca ctccgtggac gttcggtgga     300
ggcaccaagc tggaaatcaa acgtacggtg gctgcaccat cggtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagctcgc ccgtcacaaa gagcttcaac aggggagagt gt                        642
```

<210> SEQ ID NO 228
<211> LENGTH: 503
<212> TYPE: PRT
<213> ORGANISM: Artificial Sequence
<220> FEATURE:
<223> OTHER INFORMATION: First Polypeptide Chain of "EphA2 mAb 1 x CD3
      mAb 2 x DR5 mAb 1" Tri-Specific Binding Molecule

<400> SEQUENCE: 228

```
Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
                85                  90                  95

Phe Gly Gly Gly Thr Lys Leu Glu Ile Lys Gly Gly Gly Ser Gly Gly
            100                 105                 110
```

```
Gly Gly Glu Val Gln Leu Val Glu Ser Gly Gly Leu Val Gln Pro
        115                 120                 125
Gly Gly Ser Leu Arg Leu Ser Cys Ala Ala Ser Gly Phe Thr Phe Ser
        130                 135                 140
Thr Tyr Ala Met Asn Trp Val Arg Gln Ala Pro Gly Lys Gly Leu Glu
145                 150                 155                 160
Trp Val Gly Arg Ile Arg Ser Lys Tyr Asn Asn Tyr Ala Thr Tyr Tyr
                165                 170                 175
Ala Asp Ser Val Lys Gly Arg Phe Thr Ile Ser Arg Asp Asp Ser Lys
                180                 185                 190
Asn Ser Leu Tyr Leu Gln Met Asn Ser Leu Lys Thr Glu Asp Thr Ala
            195                 200                 205
Val Tyr Tyr Cys Val Arg His Gly Asn Phe Gly Asn Ser Tyr Val Ser
        210                 215                 220
Trp Phe Ala Tyr Trp Gly Gln Gly Thr Leu Val Thr Val Ser Ser Gly
225                 230                 235                 240
Gly Cys Gly Gly Gly Glu Val Ala Ala Leu Glu Lys Glu Val Ala Ala
                245                 250                 255
Leu Glu Lys Glu Val Ala Ala Leu Glu Lys Glu Val Ala Ala Leu Glu
            260                 265                 270
Lys Gly Gly Gly Asp Lys Thr His Thr Cys Pro Pro Cys Pro Ala Pro
        275                 280                 285
Glu Ala Ala Gly Gly Pro Ser Val Phe Leu Phe Pro Pro Lys Pro Lys
        290                 295                 300
Asp Thr Leu Met Ile Ser Arg Thr Pro Glu Val Thr Cys Val Val Val
305                 310                 315                 320
Asp Val Ser His Glu Asp Pro Glu Val Lys Phe Asn Trp Tyr Val Asp
                325                 330                 335
Gly Val Glu Val His Asn Ala Lys Thr Lys Pro Arg Glu Glu Gln Tyr
                340                 345                 350
Asn Ser Thr Tyr Arg Val Val Ser Val Leu Thr Val Leu His Gln Asp
            355                 360                 365
Trp Leu Asn Gly Lys Glu Tyr Lys Cys Lys Val Ser Asn Lys Ala Leu
        370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Trp Cys Leu Val Lys Gly Phe Tyr Pro Ser Asp
                420                 425                 430
Ile Ala Val Glu Trp Glu Ser Asn Gly Gln Pro Glu Asn Asn Tyr Lys
            435                 440                 445
Thr Thr Pro Pro Val Leu Asp Ser Asp Gly Ser Phe Phe Leu Tyr Ser
        450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly Lys
            500

<210> SEQ ID NO 229
<211> LENGTH: 1508
```

<210> SEQ ID NO 229
<211> LENGTH: 1508
<212> TYPE: DNA
<213> ORGANISM: Artificial Sequence
<220> FEATURE:
<223> OTHER INFORMATION: Polynucleotide Encoding First Polypeptide Chain of "EphA2 mAb 1 x CD3 mAb 2 x DR5 mAb 1" Tri-Specific Binding Molecule

<400> SEQUENCE: 229

```
gatatccaga tgacacagac tacatcctcc ctgtctgcct ctctgggaga cagaatcacc      60
atcagttgca gggcaagtca ggacattagc aattatttaa actggtatca gcagaaacca     120
gatggaactg ttaaactcct gatctactac acatcaagat acactcagg  agtcccatca     180
aggttcagtg gcagtgggtc tggaacagat tattctctca ccattagcaa cctggagcaa     240
gaagatattg ccacttactt ttgccaacag ggttatacgc tgtacacgtt cggagggggg     300
accaagctgg aaataaaagg tggaggatcc ggcggcggag gcgaggtgca gctggtggag     360
tctgggggag gcttggtcca gcctggaggg tccctgagac tctcctgtgc agcctctgga     420
ttcaccttca gcacatacgc tatgaattgg gtccgccagg ctccagggaa ggggctggag     480
tgggttggaa ggatcaggtc caagtacaac aattatgcaa cctactatgc cgactctgtg     540
aagggtagat tcaccatctc aagagatgat tcaaagaact cactgtatct gcaaatgaac     600
agcctgaaaa ccgaggacac ggccgtgtat tactgtgtga cacggtaa cttcggcaat      660
tcttacgtgt cttggtttgc ttattgggga caggggacac tggtgactgt gtcttccgga     720
ggatgtggcg gtggagaagt ggccgcactg gagaaagagg ttgctgcttt ggagaaggag     780
gtcgctgcac ttgaaaagga ggtcgcagcc ctggagaaag cggcggggga caaaaactcac    840
acatgcccac cgtgcccagc acctgaagcc gcgggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa accatctcca aagccaaagg gcagccccga    1200
gaaccacagg tgtacaccct gcccccatcc cgggaggaga tgaccaagaa ccaggtcagc    1260
ctgtggtgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcagggaa  cgtcttctca    1440
tgctccgtga tgcatgaggc tctgcacaac cactacacgc agaagagcct ctccctgtct    1500
ccgggtaa                                                             1508
```

<210> SEQ ID NO 230
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 1 x CD3 mAb 2 x DR5 mAb 1" Tri-Specific Binding Molecule

<400> SEQUENCE: 230

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly

```
                35                  40                  45
Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Thr Lys Leu Thr Val Leu Gly Gly Gly
                100                 105                 110

Gly Ser Gly Gly Gly Gly Gln Val Gln Leu Lys Glu Ser Gly Pro Gly
                115                 120                 125

Leu Val Ala Pro Ser Gln Ser Leu Ser Ile Thr Cys Thr Val Ser Gly
                130                 135                 140

Phe Ser Leu Ser Arg Tyr Ser Val His Trp Val Arg Gln Pro Pro Gly
145                 150                 155                 160

Lys Gly Leu Glu Trp Leu Gly Met Ile Trp Gly Gly Ser Thr Asp
                165                 170                 175

Tyr Asn Ser Ala Leu Lys Ser Arg Leu Ser Ile Ser Lys Asp Asn Ser
                180                 185                 190

Lys Ser Gln Val Phe Leu Lys Met Asn Ser Leu Gln Thr Asp Asp Thr
                195                 200                 205

Ala Met Tyr Tyr Cys Ala Arg Lys His Gly Asn Tyr Tyr Thr Met Asp
210                 215                 220

Tyr Trp Gly Gln Gly Thr Ser Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
                260                 265                 270

<210> SEQ ID NO 231
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 1 x CD3 mAb 2 x DR5 mAb 1" Tri-Specific
      Binding Molecule

<400> SEQUENCE: 231
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacaggtg      360
cagctgaagg agtcaggacc tggcctggtg gcaccctcac agagcctgtc catcacatgc     420
actgtctctg ggttctcatt atccagatat agtgtacact gggttcgcca gcctccagga     480
aagggtctgg agtggctggg aatgatatgg ggtggtggaa gcacagacta taattcagct     540
ctcaaatcca gactgagtat cagcaaggac aactccaaga gccagttttt cttaaaaatg     600
aacagtctgc aaactgatga cacagccatg tactactgtg ccagaaaaca tggtaactac     660
tatactatgg actactgggg tcaaggaacc tcagtcaccg tctcctccgg aggatgtggc     720
```

```
ggtggaaaag tggccgcact gaaggagaaa gttgctgctt tgaaagagaa ggtcgccgca    780
cttaaggaaa aggtcgcagc cctgaaagag                                      810
```

<210> SEQ ID NO 232
<211> LENGTH: 451
<212> TYPE: PRT
<213> ORGANISM: Artificial Sequence
<220> FEATURE:
<223> OTHER INFORMATION: Third Polypeptide Chain of "EphA2 mAb 1 x CD3
      mAb 2 x DR5 mAb 1" Tri-Specific Binding Molecule

<400> SEQUENCE: 232

```
Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Asn Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Tyr Thr Gln Lys Ser Leu Ser Leu Ser
        435                 440                 445

Pro Gly Lys
    450
```

<210> SEQ ID NO 233
<211> LENGTH: 1353
<212> TYPE: DNA
<213> ORGANISM: Artificial Sequence
<220> FEATURE:
<223> OTHER INFORMATION: Polynucleotide Encoding Third Polypeptide Chain
      of "EphA2 mAb 1 x CD3 mAb 2 x DR5 mAb 1" Tri-Specific Binding
      Molecule

<400> SEQUENCE: 233

| | |
|---|---|
| gaggtgaagt tctcgagtc tggaggtggc ctggtgcagc ctggaggatc cctgaaactc | 60 |
| tcctgtgtag cctcaggatt cgatttagt agatactgga tgagttgggt ccggcaggct | 120 |
| ccagggaaag gctagaatg gattggagaa attaatccag atagcaatac gataaactat | 180 |
| acgccatctc taaaggataa attcatcatc tccagagaca cgccaaaaa tacgctgtat | 240 |
| ctgcaaatga ccaaagtgag atctgaggac acagcccttt attattgtac aagaagggcc | 300 |
| tactatggta acccggcctg gtttgcttac tggggccaag ggactctggt cactgtctct | 360 |
| tccgcctcca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga gccgcgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag ccccatcga gaaaaccatc | 1020 |
| tccaaagcca agggcagcc cgagaaacca caggtgtaca cctgccccc atcccgggag | 1080 |
| gagatgacca gaaccaggt cagcctgagt tgcgcagtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc gtcagcaagc tcaccgtgga caagagcagg | 1260 |
| tggcagcagg ggaacgtctt ctcatgctcc gtgatgcatg aggctctgca caaccgctac | 1320 | acgcagaaga gcctctccct gtctccgggt aaa                               1353

<210> SEQ ID NO 234
<211> LENGTH: 218
<212> TYPE: PRT
<213> ORGANISM: Artificial Sequence
<220> FEATURE:
<223> OTHER INFORMATION: Fourth Polypeptide Chain of "EphA2 mAb 1 x CD3
      mAb 2 x DR5 mAb 1" Tri-Specific Binding Molecule

<400> SEQUENCE: 234

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 235
<211> LENGTH: 654
<212> TYPE: DNA
<213> ORGANISM: Artificial Sequence
<220> FEATURE:
<223> OTHER INFORMATION: Polynucleotide Encoding Fourth Polypeptide
      Chain of "EphA2 mAb 1 x CD3 mAb 2 x DR5 mAb 1" Tri-Specific
      Binding Molecule

<400> SEQUENCE: 235
gacattgtgc tgacacagtc tcctgcttcc ttagctgtat ctctcgggca gagggccacc      60
atctcatgca gggccagcaa aagtgtcagt tcctctggct atagttatat gcactggtac     120
caacagaaac caggacagcc acccaaagtc ctcatctttc tttcatccaa cctagattct     180
ggggtccctg ccaggttcag tggcagtggg tctgggacag acttcaccct caacatccat     240
cctgtggagg atggggatgc tgcaacctat tactgtcagc acagtaggga tcttcctccg     300
acgttcggtg gaggcaccaa gctggaaatc aaacgtacgg tggctgcacc atcggtcttc     360

-continued

```
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt    654
```

```
<210> SEQ ID NO 236
<211> LENGTH: 508
<212> TYPE: PRT
<213> ORGANISM: Artificial Sequence
<220> FEATURE:
<223> OTHER INFORMATION: First Polypeptide Chain of "EphA2 mAb 2 x CD3
      mAb 2 x DR5 mAb 1" Tri-Specific Binding Molecule

<400> SEQUENCE: 236
```

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
225                 230                 235                 240

Thr Val Ser Ser Gly Gly Cys Gly Gly Gly Glu Val Ala Ala Leu Glu
                245                 250                 255

Lys Glu Val Ala Ala Leu Glu Lys Glu Val Ala Ala Leu Glu Lys Glu
            260                 265                 270

Val Ala Ala Leu Glu Lys Gly Gly Gly Asp Lys Thr His Thr Cys Pro
        275                 280                 285

Pro Cys Pro Ala Pro Glu Ala Ala Gly Gly Pro Ser Val Phe Leu Phe
    290                 295                 300
```

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Glu Glu Met Thr Lys Asn Gln Val Ser Leu Trp Cys Leu Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
            500                 505

<210> SEQ ID NO 237
<211> LENGTH: 1524
<212> TYPE: DNA
<213> ORGANISM: Artificial Sequence
<220> FEATURE:
<223> OTHER INFORMATION: Polynucleotide Encoding First Polypeptide Chain
      of "EphA2 mAb 2 x CD3 mAb 2 x DR5 mAb 1" Tri-Specific Binding
      Molecule

<400> SEQUENCE: 237
gatgttgtga tgacccaaac tccactctcc ctgcctgtca gtcttggaga tcaagcctcc      60
atctcttgca gatctagtca gagccttgta cacagtagtg aaacacccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccc    300
acgttcggct cggggacaaa gttggaaata aaaggtggag gatccggcgg cggaggcgag    360
gtgcagctgg tggagtctgg gggaggcttg gtccagcctg agggtccctg agactctcc    420 tgtgcagcct ctggattcac cttcagcaca tacgctatga attgggtccg ccaggctcca    480
gggaaggggc tggagtgggt tggaaggatc aggtccaagt acaacaatta tgcaacctac    540
tatgccgact ctgtgaaggg tagattcacc atctccaaga tgattcaaa gaactcactg    600 tatctgcaaa tgaacagcct gaaaaccgag gacacggccg tgtattactg tgtgagacac    660
ggtaacttcg gcaattctta cgtgtcttgg tttgcttatt ggggacaggg gacactggtg    720
actgtgtctt ccggaggatg tggcggtgga agtggccg cactgagaa agaggttgct    780 gctttggaga aggaggtcgc tgcacttgaa aaggaggtcg cagccctgga aaaggcggc    840

```
gggggacaaaa ctcacacatg cccaccgtgc ccagcacctg aagccgcggg gggaccgtca    900
gtcttcctct tccccccaaa acccaaggac accctcatga tctcccggac ccctgaggtc    960
acatgcgtgg tggtggacgt gagccacgaa gaccctgagg tcaagttcaa ctggtacgtg   1020
gacggcgtgg aggtgcataa tgccaagaca aagccgcggg aggagcagta caacagcacg   1080
taccgtgtgg tcagcgtcct caccgtcctg caccaggact ggctgaatgg caaggagtac   1140
aagtgcaagg tctccaacaa agccctccca gcccccatcg agaaaaccat ctccaaagcc   1200
aaagggcagc cccgagaacc acaggtgtac accctgcccc catcccggga ggagatgacc   1260
aagaaccagg tcagcctgtg tgtgcctggtc aaaggcttct atcccagcga catcgccgtg   1320
gagtgggaga gcaatgggca gccggagaac aactacaaga ccacgcctcc cgtgctggac   1380
tccgacggct ccttcttcct ctacagcaag ctcaccgtgg acaagagcag gtggcagcag   1440
gggaacgtct tctcatgctc cgtgatgcat gaggctctgc acaaccacta cacgcagaag   1500
agcctctccc tgtctccggg taaa                                          1524
```

<210> SEQ ID NO 238
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 2 x CD3
      mAb 2 x DR5 mAb 1" Tri-Specific Binding Molecule

<400> SEQUENCE: 238

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Ile Gln Leu Val Gln Ser Gly Pro Glu
        115                 120                 125

Leu Lys Lys Pro Gly Glu Thr Val Lys Ile Ser Cys Lys Ala Ser Gly
    130                 135                 140

Phe Thr Phe Thr Asn Tyr Gly Met Asn Trp Lys Gln Ala Pro Gly
145                 150                 155                 160

Lys Gly Leu Lys Trp Met Gly Trp Ile Asn Thr Tyr Ile Gly Glu Pro
                165                 170                 175

Thr Tyr Ala Asp Asp Phe Lys Gly Arg Phe Val Phe Ser Leu Glu Thr
            180                 185                 190

Ser Ala Ser Thr Ala Tyr Leu Gln Ile Asn Asn Leu Lys Asn Glu Asp
        195                 200                 205

Met Ala Thr Tyr Phe Cys Ala Arg Glu Leu Gly Pro Tyr Tyr Phe Asp
    210                 215                 220

Tyr Trp Gly Gln Gly Thr Thr Leu Thr Val Ser Ser Gly Gly Cys Gly
225                 230                 235                 240
```

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 239
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 2 x CD3 mAb 2 x DR5 mAb 1" Tri-Specific
      Binding Molecule

<400> SEQUENCE: 239
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacagatc      360
cagttggtgc agtctggacc tgagctgaag aagcctggag agacagtcaa gatctcctgc     420
aaggcttctg gtttaccctt cacaaactat ggaatgaact gggtgaagca ggctccagga     480
aagggtttaa agtggatggg ctggataaac acctatattg agagccgac atatgctgat      540 gacttcaagg gacggtttgt cttctctttg gaaacctctg ccagcactgc ctatttgcag     600
atcaacaacc tcaaaaatga ggacatggcc acatatttct gtgcaagaga actgggacca     660
tactactttg actactgggg ccaaggcacc actctcacag tctcctccgg aggatgtggc     720
ggtggaaaag tggccgcact gaaggagaaa gttgctgctt tgaaagagaa ggtcgccgca     780
cttaaggaaa aggtcgcagc cctgaaagag                                     810

<210> SEQ ID NO 240
<211> LENGTH: 451
<212> TYPE: PRT
<213> ORGANISM: Artificial Sequence
<220> FEATURE:
<223> OTHER INFORMATION: Third Polypeptide Chain of "EphA2 mAb 2 x CD3
      mAb 2 x DR5 mAb 1" Tri-Specific Binding Molecule

<400> SEQUENCE: 240

Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Asn Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

```
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Ser Cys Ala Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn Arg Tyr Thr Gln Lys Ser Leu Ser Leu Ser
        435                 440                 445
Pro Gly Lys
    450

<210> SEQ ID NO 241
<211> LENGTH: 1353
<212> TYPE: DNA
<213> ORGANISM: Artificial Sequence
<220> FEATURE:
<223> OTHER INFORMATION: Polynucleotide Encoding Third Polypeptide Chain
      of "EphA2 mAb 2 x CD3 mAb 2 x DR5 mAb 1" Tri-Specific Binding
      Molecule

<400> SEQUENCE: 241
gaggtgaagt tctcgagtc tggaggtggc ctggtgcagc ctggaggatc cctgaaactc    60
```

| | | | | |
|---|---|---|---|---|
| tcctgtgtag | cctcaggatt | cgattttagt | agatactgga | tgagttgggt ccggcaggct | 120 |
| ccagggaaag | ggctagaatg | gattggagaa | attaatccag | atagcaatac gataaactat | 180 |
| acgccatctc | taaaggataa | attcatcatc | tccagagaca | acgccaaaaa tacgctgtat | 240 |
| ctgcaaatga | ccaaagtgag | atctgaggac | acagcccttt | attattgtac aagaagggcc | 300 |
| tactatggta | acccggcctg | gtttgcttac | tggggccaag | ggactctggt cactgtctct | 360 |
| tccgcctcca | ccaagggccc | atcggtcttc | cccctggcac | cctcctccaa gagcacctct | 420 |
| ggggcacag | cggccctggg | ctgcctggtc | aaggactact | tccccgaacc ggtgacggtg | 480 |
| tcgtggaact | caggcgccct | gaccagcggc | gtgcacacct | tcccggctgt cctacagtcc | 540 |
| tcaggactct | actccctcag | cagcgtggtg | accgtgccct | ccagcagctt gggcacccag | 600 |
| acctacatct | gcaacgtgaa | tcacaagccc | agcaacacca | aggtggacaa gagagttgag | 660 |
| cccaaatctt | gtgacaaaac | tcacacatgc | ccaccgtgcc | cagcacctga gccgcgggg | 720 |
| ggaccgtcag | tcttcctctt | ccccccaaaa | cccaaggaca | ccctcatgat ctcccggacc | 780 |
| cctgaggtca | catgcgtggt | ggtggacgtg | agccacgaag | accctgaggt caagttcaac | 840 |
| tggtacgtgg | acggcgtgga | ggtgcataat | gccaagacaa | agccgcggga ggagcagtac | 900 |
| aacagcacgt | accgtgtggt | cagcgtcctc | accgtcctgc | accaggactg gctgaatggc | 960 |
| aaggagtaca | agtgcaaggt | ctccaacaaa | gccctcccag | cccccatcga gaaaaccatc | 1020 |
| tccaaagcca | aagggcagcc | ccgagaacca | caggtgtaca | ccctgccccc atcccgggag | 1080 |
| gagatgacca | agaaccaggt | cagcctgagt | tgcgcagtca | aaggcttcta tcccagcgac | 1140 |
| atcgccgtgg | agtgggagag | caatgggcag | ccggagaaca | actacaagac cacgcctccc | 1200 |
| gtgctggact | ccgacggctc | cttcttcctc | gtcagcaagc | tcaccgtgga caagagcagg | 1260 |
| tggcagcagg | ggaacgtctt | ctcatgctcc | gtgatgcatg | aggctctgca caaccgctac | 1320 |
| acgcagaaga | gcctctccct | gtctccgggt | aaa | | 1353 |

<210> SEQ ID NO 242
<211> LENGTH: 218
<212> TYPE: PRT
<213> ORGANISM: Artificial Sequence
<220> FEATURE:
<223> OTHER INFORMATION: Fourth Polypeptide Chain of "EphA2 mAb 2 x CD3
      mAb 2 x DR5 mAb 1" Tri-Specific Binding Molecule

<400> SEQUENCE: 242

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 243
<211> LENGTH: 654
<212> TYPE: DNA
<213> ORGANISM: Artificial Sequence
<220> FEATURE:
<223> OTHER INFORMATION: Polynucleotide Encoding Fourth Polypeptide
      Chain of "EphA2 mAb 2 x CD3 mAb 2 x DR5 mAb 1" Tri-Specific
      Binding Molecule

<400> SEQUENCE: 243

```
gacattgtgc tgacacagtc tcctgcttcc ttagctgtat ctctcgggca gagggccacc    60
atctcatgca gggccagcaa agtgtcagt tcctctggct atagttatat gcactggtac   120
caacagaaac caggacagcc acccaaagtc ctcatctttc tttcatccaa cctagattct   180
ggggtccctg ccaggttcag tggcagtggg tctgggacag acttcaccct caacatccat   240
cctgtggagg atgggggatgc tgcaacctat tactgtcagc acagtaggga tcttcctccg   300
acgttcggtg gaggcaccaa gctggaaatc aaacgtacgg tggctgcacc atcggtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600 acccatcagg gcctgagctc gcccgtcaca aagagcttca caggggaga gtgt         654
```

<210> SEQ ID NO 244
<211> LENGTH: 504
<212> TYPE: PRT
<213> ORGANISM: Artificial Sequence
<220> FEATURE:
<223> OTHER INFORMATION: First Polypeptide Chain of "EphA2 mAb 3 x CD3
      mAb 2 x DR5 mAb 1" Tri-Specific Binding Molecule

<400> SEQUENCE: 244

```
Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80
```

```
Gly Asp Leu Ala Leu Tyr Tyr Cys Gln Gln His Tyr Ser Thr Pro Tyr
                 85                  90                  95
Thr Phe Gly Gly Gly Thr Lys Leu Glu Ile Lys Gly Gly Gly Ser Gly
            100                 105                 110
Gly Gly Gly Glu Val Gln Leu Val Glu Ser Gly Gly Gly Leu Val Gln
        115                 120                 125
Pro Gly Gly Ser Leu Arg Leu Ser Cys Ala Ala Ser Gly Phe Thr Phe
    130                 135                 140
Ser Thr Tyr Ala Met Asn Trp Val Arg Gln Ala Pro Gly Lys Gly Leu
145                 150                 155                 160
Glu Trp Val Gly Arg Ile Arg Ser Lys Tyr Asn Asn Tyr Ala Thr Tyr
                165                 170                 175
Tyr Ala Asp Ser Val Lys Gly Arg Phe Thr Ile Ser Arg Asp Asp Ser
                180                 185                 190
Lys Asn Ser Leu Tyr Leu Gln Met Asn Ser Leu Lys Thr Glu Asp Thr
            195                 200                 205
Ala Val Tyr Tyr Cys Val Arg His Gly Asn Phe Gly Asn Ser Tyr Val
        210                 215                 220
Ser Trp Phe Ala Tyr Trp Gly Gln Gly Thr Leu Val Thr Val Ser Ser
225                 230                 235                 240
Gly Gly Cys Gly Gly Gly Glu Val Ala Ala Leu Glu Lys Glu Val Ala
                245                 250                 255
Ala Leu Glu Lys Glu Val Ala Ala Leu Glu Lys Glu Val Ala Ala Leu
                260                 265                 270
Glu Lys Gly Gly Gly Asp Lys Thr His Thr Cys Pro Pro Cys Pro Ala
            275                 280                 285
Pro Glu Ala Ala Gly Gly Pro Ser Val Phe Leu Phe Pro Pro Lys Pro
    290                 295                 300
Lys Asp Thr Leu Met Ile Ser Arg Thr Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
                340                 345                 350
Tyr Asn Ser Thr Tyr Arg Val Val Ser Val Leu Thr Val Leu His Gln
            355                 360                 365
Asp Trp Leu Asn Gly Lys Glu Tyr Lys Cys Lys Val Ser Asn Lys Ala
        370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Glu Glu Met Thr
                405                 410                 415
Lys Asn Gln Val Ser Leu Trp Cys Leu Val Lys Gly Phe Tyr Pro Ser
                420                 425                 430
Asp Ile Ala Val Glu Trp Glu Ser Asn Gly Gln Pro Glu Asn Asn Tyr
            435                 440                 445
Lys Thr Thr Pro Pro Val Leu Asp Ser Asp Gly Ser Phe Phe Leu Tyr
        450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys
```

<210> SEQ ID NO 245
<211> LENGTH: 1512
<212> TYPE: DNA
<213> ORGANISM: Artificial Sequence
<220> FEATURE:
<223> OTHER INFORMATION: Polynucleotide Encoding First Polypeptide Chain of "EphA2 mAb 3 x CD3 mAb 2 x DR5 mAb 1" Tri-Specific Binding Molecule

<400> SEQUENCE: 245

```
gacattgtgc tgacccagtc tcacagatcc atgtccacat cagtaggaga cagggtcaac      60
atcacctgca aggccagtca ggatgtgact actgctgtag cctggtatca acaaaaacca     120
gggcaatctc ctaaattact gattttctgg gcatccaccc ggcacgctgg agtccctgat     180
cgcttcacag gcagtggatc tgggacagat tttactctca ccatcagcag tgtgcaggct     240
ggagacctgg cactttatta ctgtcaacaa cattatagca ccgtacacat tcggaggg      300
gggaccaagc tggaaataaa aggtggagga tccggcggcg gaggcgaggt gcagctggtg     360
gagtctgggg gaggcttggt ccagcctgga gggtccctga ctctcctg tgcagcctct      420
ggattcacct tcagcacata cgctatgaat tgggtccgcc aggctccagg aaggggctg      480
gagtgggttg gaaggatcag gtccaagtac aacaattatg caacctacta tgccgactct     540
gtgaagggta gattcaccat ctcaagagat gattcaaaga actcactgta tctgcaaatg     600
aacagcctga aaccgagga cacggccgtg tattactgtg tgagacacgg taacttcgc     660
aattcttacg tgtcttggtt tgcttattgg ggacagggga cactggtgac tgtgtcttcc     720
ggaggatgtg gcggtggaga gtggccgca ctggagaaag aggttgctgc tttggagaag      780
gaggtcgctg cacttgaaaa ggaggtcgca gccctggaga aggcggcgg ggacaaaact      840
cacacatgcc caccgtgccc agcacctgaa ccgcgggg gaccgtcagt cttcctcttc       900
cccccaaaac ccaaggacac cctcatgatc tcccggaccc ctgaggtcac atgcgtggtg      960
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggagtacaa gtgcaaggtc    1140
tccaacaaag ccctcccagc ccccatcgag aaaaccatct ccaaagccaa agggcagccc    1200
cgagaaccac aggtgtacac cctgccccca tcccgggagg agatgaccaa gaaccaggtc    1260
agcctgtggt gcctggtcaa aggcttctat cccagcgaca tcgccgtgga gtgggagagc    1320
aatgggcagc cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggta aa                                                        1512
```

<210> SEQ ID NO 246
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 3 x CD3 mAb 2 x DR5 mAb 1" Tri-Specific Binding Molecule

<400> SEQUENCE: 246

Gln Ala Val Val Thr Gln Glu Pro Ser Leu Thr Val Ser Pro Gly Gly
1               5                   10                  15

```
Thr Val Thr Leu Thr Cys Arg Ser Ser Thr Gly Ala Val Thr Thr Ser
        20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
            115                 120                 125

Ser Val Lys Pro Gly Gly Ser Leu Lys Leu Ser Cys Ala Ala Ser Gly
130                 135                 140

Phe Thr Phe Thr Asp His Tyr Met Tyr Trp Val Arg Gln Thr Pro Glu
145                 150                 155                 160

Lys Arg Leu Glu Trp Val Ala Thr Ile Ser Asp Gly Gly Ser Phe Thr
                165                 170                 175

Ser Tyr Pro Asp Ser Val Lys Gly Arg Phe Thr Ile Ser Arg Asp Ile
            180                 185                 190

Ala Lys Asn Asn Leu Tyr Leu Gln Met Ser Ser Leu Lys Ser Glu Asp
            195                 200                 205

Thr Ala Met Tyr Tyr Cys Thr Arg Asp Glu Ser Asp Arg Pro Phe Pro
210                 215                 220

Tyr Trp Gly Gln Gly Thr Leu Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 247
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 3 x CD3 mAb 2 x DR5 mAb 1" Tri-Specific
      Binding Molecule

<400> SEQUENCE: 247
caggctgtgg tgactcagga gccttcactg accgtgtccc caggcggaac tgtgaccctg      60
acatgcagat ccagcacagg cgcagtgacc atatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300 ggggggtggca caaactgac tgtgctggga ggggtggat ccggcggagg tggagaagtg     360
cagctggtgg agtctggggg aggctcagtg aagcctggag ggtccctgaa actcctctgt     420
gcagcctctg gattcacttt cactgaccat tacatgtatt gggttcgcca gactccggaa     480
aagaggctgg agtgggtcgc aaccattagt gatggcggta gtttcacctc ctatccagac     540
```

```
agtgtgaagg ggcgattcac catctccaga gacattgcca agaacaacct gtacctccaa    600
atgagcagtc tgaagtctga ggacacagcc atgtattact gtacaagaga tgagagcgat    660
aggccgtttc cttactgggg ccaagggact ctggtcactg tctcctccgg aggatgtggc    720
ggtggaaaag tggccgcact gaaggagaaa gttgctgctt gaaagagaa ggtcgccgca     780 cttaaggaaa aggtcgcagc cctgaaagag                                     810
```

<210> SEQ ID NO 248
<211> LENGTH: 451
<212> TYPE: PRT
<213> ORGANISM: Artificial Sequence
<220> FEATURE:
<223> OTHER INFORMATION: Third Polypeptide Chain of "EphA2 mAb 3 x CD3
      mAb 2 x DR5 mAb 1" Tri-Specific Binding Molecule

<400> SEQUENCE: 248

```
Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Asn Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                305                 310                 315                 320

Lys Glu Tyr Lys Cys Lys Val Ser Asn Lys Ala Leu Pro Ala Pro Ile
                    325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn Arg Tyr Thr Gln Lys Ser Leu Ser Leu Ser
            435                 440                 445

Pro Gly Lys
    450

<210> SEQ ID NO 249
<211> LENGTH: 1353
<212> TYPE: DNA
<213> ORGANISM: Artificial Sequence
<220> FEATURE:
<223> OTHER INFORMATION: Polynucleotide Encoding Third Polypeptide Chain
      of "EphA2 mAb 3 x CD3 mAb 2 x DR5 mAb 1" Tri-Specific Binding
      Molecule

<400> SEQUENCE: 249
gaggtgaagt tctctcgagtc tggaggtggc ctggtgcagc ctggaggatc cctgaaactc       60
tcctgtgtag cctcaggatt cgatttagt agatactgga tgagttgggt ccggcaggct       120
ccagggaaag gctagaatg gattggagaa attaatccag atagcaatac gataaactat       180
acgccatctc taaaggataa attcatcatc tccagagaca acgccaaaaa tacgctgtat       240
ctgcaaatga ccaaagtgag atctgaggac acagcccttt attattgtac aagaagggcc       300
tactatggta acccggcctg gtttgcttac tggggccaag gactctggt cactgtctct       360 tccgcctcca ccaagggccc atcggtcttc cccctggcac cctcctccaa gagcacctct       420
gggggcacag cggccctggg ctgcctggtc aaggactact tccccgaacc ggtgacggtg       480
tcgtggaact caggcgccct gaccagcggc gtgcacacct tcccggctgt cctacagtcc       540
tcaggactct actccctcag cagcgtggtg accgtgccct ccagcagctt gggcacccag       600
acctacatct gcaacgtgaa tcacaagccc agcaacacca aggtggacaa gagagttgag       660
cccaaatctt gtgacaaaac tcacacatgc ccaccgtgcc cagcacctga gccgcgggg       720 ggaccgtcag tcttcctctt ccccccaaaa cccaaggaca ccctcatgat ctcccggacc       780
cctgaggtca catgcgtggt ggtggacgtg agccacgaag accctgaggt caagttcaac       840
tggtacgtgg acggcgtgga ggtgcataat gccaagacaa agccgcggga ggagcagtac       900
aacagcacgt accgtgtggt cagcgtcctc accgtcctgc accaggactg gctgaatggc       960
aaggagtaca agtgcaaggt ctccaacaaa gccctcccag cccccatcga gaaaaccatc      1020
tccaaagcca aagggcagcc ccgagaacca caggtgtaca ccctgccccc atcccgggag      1080
gagatgacca agaaccaggt cagcctgagt tgcgcagtca aaggcttcta tcccagcgac      1140
```

```
atcgccgtgg agtgggagag caatgggcag ccggagaaca actacaagac cacgcctccc    1200
gtgctggact ccgacggctc cttcttcctc gtcagcaagc tcaccgtgga caagagcagg    1260
tggcagcagg ggaacgtctt ctcatgctcc gtgatgcatg aggctctgca caaccgctac    1320
acgcagaaga gcctctccct gtctccgggt aaa                                 1353
```

<210> SEQ ID NO 250
<211> LENGTH: 218
<212> TYPE: PRT
<213> ORGANISM: Artificial Sequence
<220> FEATURE:
<223> OTHER INFORMATION: Fourth Polypeptide Chain of "EphA2 mAb 3 x CD3
      mAb 2 x DR5 mAb 1" Tri-Specific Binding Molecule

<400> SEQUENCE: 250

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 251
<211> LENGTH: 654
<212> TYPE: DNA
<213> ORGANISM: Artificial Sequence
<220> FEATURE:
<223> OTHER INFORMATION: Polynucleotide Encoding Fourth Polypeptide
      Chain of "EphA2 mAb 3 x CD3 mAb 2 x DR5 mAb 1" Tri-Specific
      Binding Molecule

<400> SEQUENCE: 251

```
gacattgtgc tgacacagtc tcctgcttcc ttagctgtat ctctcgggca gagggccacc    60
atctcatgca gggccagcaa aagtgtcagt tcctctggct atagttatat gcactggtac    120
caacagaaac caggacagcc acccaaagtc ctcatctttc tttcatccaa cctagattct    180
```

-continued

```
ggggtccctg ccaggttcag tggcagtggg tctgggacag acttcaccct caacatccat      240
cctgtggagg atggggatgc tgcaacctat tactgtcagc acagtaggga tcttcctccg      300
acgttcggtg gaggcaccaa gctggaaatc aaacgtacgg tggctgcacc atcggtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgt             654
```

```
<210> SEQ ID NO 252
<211> LENGTH: 503
<212> TYPE: PRT
<213> ORGANISM: Artificial Sequence
<220> FEATURE:
<223> OTHER INFORMATION: First Polypeptide Chain of "gpA33 mAb 1 x CD3
      mAb 2 x EphA2 mAb 1" Tri-Specific Binding Molecule

<400> SEQUENCE: 252
```

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro

```
            275                 280                 285
Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 253
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of "gpA33 mAb 1 x CD3 mAb 2 x EphA2 mAb 1" Tri-Specific Binding
      Molecule

<400> SEQUENCE: 253
gacattcagc tgactcagtc cccctctttt ctgtccgcat ccgtcggaga tcgagtgact     60
attacttgct ctgctaggtc tcaatcagct tcatgtact ggtatcagca gaagcccggc    120
aaagcaccta gctgctgat ctacgacaca gcaacctgg cctccggggt gccatctcgg     180
ttctctggca gtgggtcagg aactgagttt accctgacaa ttagctccct ggaggctgaa    240
gatgccgcta ctactattg ccagcagtgg agcagctatc ctctgacctt cggacagggg    300
actaaactgg aaatcaaggg tggaggatcc ggcggcggag cgaggtgca gctggtggag    360 tctgggggag gcttggtcca gcctggaggg tccctgagac tctcctgtgc agcctctgga    420
ttcaccttca gcacatacgc tatgaattgg gtccgccagg ctccaggaa ggggctggag    480 tgggttggaa ggatcaggtc caagtacaac aattatgcaa cctactatgc cgactctgtg    540
aagggtagat tcaccatctc aagagatgat tcaaagaact cactgtatct gcaaatgaac    600
agcctgaaaa ccgaggacac ggccgtgtat tactgtgtga cacggtaa cttcggcaat    660 tcttacgtgt cttggtttgc ttattgggga caggggacac tggtgactgt gtcttccgga    720
```

```
ggatgtggcg gtggagaagt ggccgcactg gagaaagagg ttgctgcttt ggagaaggag    780
gtcgctgcac ttgaaaagga ggtcgcagcc ctggagaaag gcggcgggga caaaactcac    840
acatgcccac cgtgcccagc acctgaagcc gcggggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca aagccaaagg gcagccccga   1200
gaaccacagg tgtacaccct gcccccatcc cgggaggaga tgaccaagaa ccaggtcagc   1260
ctgtggtgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtaaa                                                           1509
```

<210> SEQ ID NO 254
<211> LENGTH: 271
<212> TYPE: PRT
<213> ORGANISM: Artificial Sequence
<220> FEATURE:
<223> OTHER INFORMATION: Second Polypeptide Chain of "gpA33 mAb 1 x CD3
      mAb 2 x EphA2 mAb 1" Tri-Specific Binding Molecule

<400> SEQUENCE: 254

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205
```

Thr Ala Val Tyr Tyr Cys Ala Arg Ile Tyr Gly Asn Asn Val Tyr Phe
        210                 215                 220

Asp Val Trp Gly Gln Gly Thr Thr Val Thr Val Ser Ser Gly Gly Cys
225                 230                 235                 240

Gly Gly Gly Lys Val Ala Ala Leu Lys Glu Lys Val Ala Ala Leu Lys
            245                 250                 255

Glu Lys Val Ala Ala Leu Lys Glu Lys Val Ala Ala Leu Lys Glu
        260                 265                 270

<210> SEQ ID NO 255
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of "gpA33 mAb 1 x CD3 mAb 2 x EphA2 mAb 1" Tri-Specific
      Binding Molecule

<400> SEQUENCE: 255
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc ggggtacaa acaaaagggc tccctggacc    180
cctgcacggt tttctggaag tctgctgggc ggaaaggccg ctctgactat taccggggca   240
caggccgagg acgaagccga ttactattgt gctctgtggt atagcaatct gtgggtgttc   300
gggggtggca caaaactgac tgtgctggga ggggtggat ccggcggagg tggacaggtc    360
cagctggtcc agagcgggc cgaagtcaaa aacccggag caagcgtgaa ggtctcctgc     420
aaagcatcag gctatacatt tacaggcagc tggatgaact gggtgaggca ggctccagga   480
cagggactgg agtggatcgg cgcatctac cctggagacg gcgaaactaa ctataatgga    540
aagttcaaag accgagtgac catcacagcc gataagtcta ctagtaccgc tacatggag    600 ctgagctccc tgcggtctga agataccgcc gtctactatt gcgctagaat ttacggaaac   660
aatgtctatt ttgacgtgtg ggggcaggga acaactgtga ctgtctcctc cggaggatgt   720
ggcggtggaa agtggccgc actgaaggag aaagttgctg cttttgaaaga gaaggtcgcc   780 gcacttaagg aaaaggtcgc agccctgaaa gag                               813

<210> SEQ ID NO 256
<211> LENGTH: 448
<212> TYPE: PRT
<213> ORGANISM: Artificial Sequence
<220> FEATURE:
<223> OTHER INFORMATION: Third Polypeptide Chain of "gpA33 mAb 1 x CD3
      mAb 2 x EphA2 mAb 1" Tri-Specific Binding Molecule

<400> SEQUENCE: 256

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala 85                  90                  95
Arg Lys His Gly Asn Tyr Tyr Thr Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Ser Cys
    355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn Arg Tyr Thr Gln Lys Ser Leu Ser Leu Ser Pro Gly Lys
    435                 440                 445

<210> SEQ ID NO 257
<211> LENGTH: 1344
<212> TYPE: DNA
<213> ORGANISM: Artificial Sequence
<220> FEATURE:
<223> OTHER INFORMATION: Polynucleotide Encoding Third Polypeptide Chain
      of "gpA33 mAb 1 x CD3 mAb 2 x EphA2 mAb 1" Tri-Specific Binding
      Molecule

<400> SEQUENCE: 257

```
caggtgcagc tgaaggagtc aggacctggc ctggtggcac cctcacagag cctgtccatc    60
acatgcactg tctctgggtt ctcattatcc agatatagtg tacactgggt tcgccagcct   120
ccaggaaagg gtctggagtg gctgggaatg atatggggtg gtggaagcac agactataat   180
tcagctctca aatccagact gagtatcagc aaggacaact ccaagagcca agttttctta   240
aaaatgaaca gtctgcaaac tgatgacaca gccatgtact actgtgccag aaaacatggt   300
aactactata ctatggacta ctggggtcaa ggaacctcag tcaccgtctc ctccgcctcc   360
accaagggcc catcggtctt ccccctggca ccctcctcca agagcacctc tgggggcaca   420
gcggccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct tgggcaccca gacctacatc   600
tgcaacgtga atcacaagcc cagcaacacc aaggtggaca agagagttga gcccaaatct   660
tgtgacaaaa ctcacacatg cccaccgtgc ccagcacctg aagccgcggg gggaccgtca   720
gtcttcctct tccccccaaa acccaaggac accctcatga tctcccggac ccctgaggtc   780
acatgcgtgg tggtggacgt gagccacgaa gaccctgagg tcaagttcaa ctggtacgtg   840
gacggcgtgg aggtgcataa tgccaagaca aagccgcggg aggagcagta caacagcacg   900
taccgtgtgg tcagcgtcct caccgtcctg caccaggact ggctgaatgg caaggagtac   960
aagtgcaagg tctccaacaa agccctccca gcccccatcg agaaaaccat ctccaaagcc  1020
aaagggcagc cccgagaacc acaggtgtac accctgcccc catcccggga ggagatgacc  1080
aagaaccagg tcagcctgag ttgcgcagtc aaaggcttct atcccagcga catcgccgtg  1140
gagtgggaga gcaatgggca gccggagaac aactacaaga ccacgcctcc cgtgctggac  1200
tccgacggct ccttcttcct cgtcagcaag ctcaccgtgg acaagagcag gtggcagcag  1260
gggaacgtct tctcatgctc cgtgatgcat gaggctctgc acaaccgcta cacgcagaag  1320
agcctctccc tgtctccggg taaa                                         1344
```

<210> SEQ ID NO 258
<211> LENGTH: 213
<212> TYPE: PRT
<213> ORGANISM: Artificial Sequence
<220> FEATURE:
<223> OTHER INFORMATION: Fourth Polypeptide Chain of "gpA33 mAb 1 x CD3
      mAb 2 x EphA2 mAb 1" Tri-Specific Binding Molecule

<400> SEQUENCE: 258

Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 259
<211> LENGTH: 639
<212> TYPE: DNA
<213> ORGANISM: Artificial Sequence
<220> FEATURE:
<223> OTHER INFORMATION: Polynucleotide Encoding Fourth Polypeptide
      Chain of "gpA33 mAb 1 x CD3 mAb 2 x EphA2 mAb 1" Tri-Specific
      Binding Molecule

<400> SEQUENCE: 259
gatatccaga tgacacagac tacatcctcc ctgtctgcct ctctgggaga cagaatcacc     60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt tgccaacag ggttatacgc tgtacacgtt cggagggggg     300
accaagctgg aaataaaacg tacggtggct gcaccatcgg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639

<210> SEQ ID NO 260
<211> LENGTH: 503
<212> TYPE: PRT
<213> ORGANISM: Artificial Sequence
<220> FEATURE:
<223> OTHER INFORMATION: First Polypeptide Chain of "gpA33 mAb 1 x CD3
      mAb 2 x EphA2 mAb 2" Tri-Specific Binding Molecule

<400> SEQUENCE: 260

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu

```
                65                  70                  75                  80
Asp Ala Ala Thr Tyr Tyr Cys Gln Gln Trp Ser Ser Tyr Pro Leu Thr
                    85                  90                  95
Phe Gly Gln Gly Thr Lys Leu Glu Ile Lys Gly Gly Gly Ser Gly Gly
                100                 105                 110
Gly Gly Glu Val Gln Leu Val Glu Ser Gly Gly Gly Leu Val Gln Pro
                115                 120                 125
Gly Gly Ser Leu Arg Leu Ser Cys Ala Ala Ser Gly Phe Thr Phe Ser
            130                 135                 140
Thr Tyr Ala Met Asn Trp Val Arg Gln Ala Pro Gly Lys Gly Leu Glu
145                 150                 155                 160
Trp Val Gly Arg Ile Arg Ser Lys Tyr Asn Asn Tyr Ala Thr Tyr Tyr
                165                 170                 175
Ala Asp Ser Val Lys Gly Arg Phe Thr Ile Ser Arg Asp Asp Ser Lys
                180                 185                 190
Asn Ser Leu Tyr Leu Gln Met Asn Ser Leu Lys Thr Glu Asp Thr Ala
                195                 200                 205
Val Tyr Tyr Cys Val Arg His Gly Asn Phe Gly Asn Ser Tyr Val Ser
            210                 215                 220
Trp Phe Ala Tyr Trp Gly Gln Gly Thr Leu Val Thr Val Ser Ser Gly
225                 230                 235                 240
Gly Cys Gly Gly Gly Glu Val Ala Ala Leu Glu Lys Glu Val Ala Ala
                245                 250                 255
Leu Glu Lys Glu Val Ala Ala Leu Glu Lys Glu Val Ala Ala Leu Glu
                260                 265                 270
Lys Gly Gly Gly Asp Lys Thr His Thr Cys Pro Pro Cys Pro Ala Pro
            275                 280                 285
Glu Ala Ala Gly Gly Pro Ser Val Phe Leu Phe Pro Pro Lys Pro Lys
                290                 295                 300
Asp Thr Leu Met Ile Ser Arg Thr Pro Glu Val Thr Cys Val Val Val
305                 310                 315                 320
Asp Val Ser His Glu Asp Pro Glu Val Lys Phe Asn Trp Tyr Val Asp
                325                 330                 335
Gly Val Glu Val His Asn Ala Lys Thr Lys Pro Arg Glu Glu Gln Tyr
                340                 345                 350
Asn Ser Thr Tyr Arg Val Val Ser Val Leu Thr Val Leu His Gln Asp
            355                 360                 365
Trp Leu Asn Gly Lys Glu Tyr Lys Cys Lys Val Ser Asn Lys Ala Leu
            370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Trp Cys Leu Val Lys Gly Phe Tyr Pro Ser Asp
                420                 425                 430
Ile Ala Val Glu Trp Glu Ser Asn Gly Gln Pro Glu Asn Asn Tyr Lys
            435                 440                 445
Thr Thr Pro Pro Val Leu Asp Ser Asp Gly Ser Phe Phe Leu Tyr Ser
            450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
```

Leu Ser Leu Ser Pro Gly Lys
            500

<210> SEQ ID NO 261
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of "gpA33 mAb 1 x CD3 mAb 2 x EphA2 mAb 2" Tri-Specific Binding
      Molecule

<400> SEQUENCE: 261

```
gacattcagc tgactcagtc cccctctttt ctgtccgcat ccgtcggaga tcgagtgact      60
attacttgct ctgctaggtc ctcaatcagc ttcatgtact ggtatcagca gaagcccggc     120
aaagcaccta agctgctgat ctacgacaca agcaacctgg cctccggggt gccatctcgg     180
ttctctggca gtgggtcagg aactgagttt accctgacaa ttagctccct ggaggctgaa     240
gatgccgcta cctactattg ccagcagtgg agcagctatc tctgaccctt cggacagggg     300
actaaactgg aaatcaaggg tgaggatcc ggcggcggag cgaggtgca gctggtggag      360 tctggggag gcttggtcca gcctggaggg tccctgagac tctcctgtgc agcctctgga     420
ttcaccttca gcacatacgc tatgaattgg gtccgccagg ctccagggaa ggggctggag     480
tgggttggaa ggatcaggtc caagtacaac aattatgcaa cctactatgc cgactctgtg     540
aagggtagat tcaccatctc aagagatgat tcaaagaact cactgtatct gcaaatgaac     600
agcctgaaaa ccgaggacac ggccgtgtat tactgtgtga cacggtaa cttcggcaat      660 tcttacgtgt cttggtttgc ttattgggga caggggacac tggtgactgt gtcttccgga     720
ggatgtggcg gtgagaagt ggccgcactg agaaagagg ttgctgcttt ggagaaggag      780
gtcgctgcac ttgaaaagga ggtcgcagcc ctggagaaag cggcgggga caaaactcac     840 acatgcccac cgtgcccagc acctgaagcc gcgggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa accatctcca agccaaagg gcagccccga     1200 gaaccacagg tgtacaccct gcccccatcc cgggaggaga tgaccaagaa ccaggtcagc    1260
ctgtggtgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaa                                                            1509
```

<210> SEQ ID NO 262
<211> LENGTH: 271
<212> TYPE: PRT
<213> ORGANISM: Artificial Sequence
<220> FEATURE:
<223> OTHER INFORMATION: Second Polypeptide Chain of "gpA33 mAb 1 x CD3
      mAb 2 x EphA2 mAb 2" Tri-Specific Binding Molecule

<400> SEQUENCE: 262

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ile Tyr Gly Asn Asn Val Tyr Phe
    210                 215                 220

Asp Val Trp Gly Gln Gly Thr Thr Val Thr Val Ser Ser Gly Gly Cys
225                 230                 235                 240

Gly Gly Gly Lys Val Ala Ala Leu Lys Glu Lys Val Ala Ala Leu Lys
            245                 250                 255

Glu Lys Val Ala Ala Leu Lys Glu Lys Val Ala Ala Leu Lys Glu
            260                 265                 270
```

<210> SEQ ID NO 263
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of "gpA33 mAb 1 x CD3 mAb 2 x EphA2 mAb 2" Tri-Specific
      Binding Molecule

<400> SEQUENCE: 263

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300 ggggtggca caaaactgac tgtgctggga ggggtggat ccggcggagg tggacaggtc     360
cagctggtcc agagcggggc cgaagtcaaa aaacccggag caagcgtgaa ggtctcctgc     420
aaagcatcag gctatacatt tacaggcagc tggatgaact gggtgaggca ggctccagga     480
```

```
cagggactgg agtggatcgg gcgcatctac cctggagacg gcgaaactaa ctataatgga    540
aagttcaaag accgagtgac catcacagcc gataagtcta ctagtaccgc ctacatggag    600
ctgagctccc tgcggtctga agataccgcc gtctactatt gcgctagaat ttacggaaac    660
aatgtctatt ttgacgtgtg ggggcaggga acaactgtga ctgtctcctc cggaggatgt    720
ggcggtggaa aagtggccgc actgaaggag aaagttgctg ctttgaaaga aaggtcgcc    780 gcacttaagg aaaaggtcgc agccctgaaa gag                                813

<210> SEQ ID NO 264
<211> LENGTH: 448
<212> TYPE: PRT
<213> ORGANISM: Artificial Sequence
<220> FEATURE:
<223> OTHER INFORMATION: Third Polypeptide Chain of "gpA33 mAb 1 x CD3
      mAb 2 x EphA2 mAb 2" Tri-Specific Binding Molecule

<400> SEQUENCE: 264
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Ile Gly Glu Pro Thr Tyr Ala Asp Asp Phe
        50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Leu Gly Pro Tyr Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Arg Tyr Thr Gln Lys Ser Leu Ser Leu Ser Pro Gly Lys
            435                 440                 445
```

<210> SEQ ID NO 265
<211> LENGTH: 1344
<212> TYPE: DNA
<213> ORGANISM: Artificial Sequence
<220> FEATURE:
<223> OTHER INFORMATION: Polynucleotide Encoding Third Polypeptide Chain
      of "gpA33 mAb 1 x CD3 mAb 2 x EphA2 mAb 2" Tri-Specific Binding
      Molecule

<400> SEQUENCE: 265

```
cagatccagt tggtgcagtc tggacctgag ctgaagaagc tggagagaca agtcaagatc     60
tcctgcaagg cttctgggtt taccttcaca aactatggaa tgaactgggt gaagcaggct    120
ccaggaaagg gtttaaagtg gatgggctgg ataaacacct atattggaga gccgacatat    180
gctgatgact tcaagggacg gtttgtcttc tctttggaaa cctctgccag cactgcctat    240
ttgcagatca caaccctcaa aaatgaggac atggccacat atttctgtgc aagagaactg    300
ggaccatact actttgacta ctggggccaa ggcaccactc tcacagtctc ctccgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacccca gacctacatc    600
tgcaacgtga atcacaagcc cagcaacacc aaggtggaca gagagttga gcccaaatct    660 tgtgacaaaa ctcacacatg cccaccgtgc ccagcacctg aagccgcggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gccccatcg agaaaaccat ctccaaagcc   1020
aaagggcagc cccgagaacc acaggtgtac accctgcccc catcccggga ggagatgacc   1080
aagaaccagg tcagcctgag ttgcgcagtc aaaggcttct atcccagcga catcgccgtg   1140
gagtgggaga gcaatgggca gccggagaac aactacaaga ccacgcctcc cgtgctggac   1200
```
tccgacggct ccttcttcct cgtcagcaag ctcaccgtgg acaagagcag gtggcagcag  1260
gggaacgtct tctcatgctc cgtgatgcat gaggctctgc acaaccgcta cacgcagaag  1320
agcctctccc tgtctccggg taaa  1344

<210> SEQ ID NO 266
<211> LENGTH: 218
<212> TYPE: PRT
<213> ORGANISM: Artificial Sequence
<220> FEATURE:
<223> OTHER INFORMATION: Polynucleotide Encoding Fourth Polypeptide
      Chain of "gpA33 mAb 1 x CD3 mAb 2 x EphA2 mAb 2" Tri-Specific
      Binding Molecule

<400> SEQUENCE: 266

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 267
<211> LENGTH: 654
<212> TYPE: DNA
<213> ORGANISM: Artificial Sequence
<220> FEATURE:
<223> OTHER INFORMATION: Polynucleotide Encoding Fourth Polypeptide
      Chain of "gpA33 mAb 1 x CD3 mAb 2 x EphA2 mAb 2" Tri-Specific
      Binding Molecule

<400> SEQUENCE: 267
gatgttgtga tgacccaaac tccactctcc ctgcctgtca gtcttggaga tcaagcctcc  60
atctcttgca gatctagtca gagccttgta cacagtagtg aaacacccta tttacattgg  120
tacctgcaga agccaggcca gtctccaaag ctcctgatct acaaagtttc caaccgattt  180

-continued

```
tctggggtcc cagacaggtt cagtggcagt ggatcaggga cagatttcac actcaagatc        240
agcagagtgg aggctgagga tctgggagtt tatttctgct ctcaaagtac acatgttccc        300
acgttcggct cggggacaaa gttggaaata aaacgtacgg tggctgcacc atcggtcttc        360
atcttcccgc catctgatga gcagttgaaa tctggaactg cctctgttgt gtgcctgctg        420
aataacttct atcccagaga ggccaaagta cagtggaagg tggataacgc cctccaatcg        480
ggtaactccc aggagagtgt cacagagcag gacagcaagg acagcaccta cagcctcagc        540
agcaccctga cgctgagcaa agcagactac gagaacaca aagtctacgc ctgcgaagtc         600
acccatcagg gcctgagctc gcccgtcaca aagagcttca cagggggaga gtgt              654
```

<210> SEQ ID NO 268
<211> LENGTH: 503
<212> TYPE: PRT
<213> ORGANISM: Artificial Sequence
<220> FEATURE:
<223> OTHER INFORMATION: First Polypeptide Chain of "gpA33 mAb 1 x CD3
    mAb 2 x EphA2 mAb 3" Tri-Specific Binding Molecule

<400> SEQUENCE: 268

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
```

```
            275                 280                 285
Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 269
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of "gpA33 mAb 1 x CD3 mAb 2 x EphA2 mAb 3" Tri-Specific Binding
      Molecule

<400> SEQUENCE: 269
gacattcagc tgactcagtc cccctctttt ctgtccgcat ccgtcggaga tcgagtgact      60
attacttgct ctgctaggtc ctcaatcagc ttcatgtact ggtatcagca gaagcccggc     120
aaagcaccta gctgctgat ctacgacaca gcaacctgg cctccggggt gccatctcgg       180
ttctctggca gtgggtcagg aactgagttt accctgacaa ttagctccct ggaggctgaa     240
gatgccgcta cctactattg ccagcagtgg agcagctatc ctctgacctt cggacagggg     300
actaaactgg aaatcaaggg tggaggatcc ggcggcggag cgaggtgca gctggtggag      360 tctgggggag gcttggtcca gcctggaggg tccctgagac tctcctgtgc agcctctgga    420
ttcaccttca gcatacgc tatgaattgg gtccgccagg ctccaggaa ggggctggag       480 tgggttggaa ggatcaggtc caagtacaac aattatgcaa cctactatgc cgactctgtg    540
aagggtagat tcaccatctc aagagatgat tcaaagaact cactgtatct gcaaatgaac    600
agcctgaaaa ccgaggacac ggccgtgtat tactgtgtga cacggtaa cttcggcaat      660 tcttacgtgt cttggtttgc ttattgggga caggggacac tggtgactgt gtcttccgga    720
```

```
ggatgtggcg gtggagaagt ggccgcactg gagaaagagg ttgctgcttt ggagaaggag    780
gtcgctgcac ttgaaaagga ggtcgcagcc ctggagaaag gcggcgggga caaaactcac    840
acatgcccac cgtgcccagc acctgaagcc gcggggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca aagccaaagg cagccccga    1200 gaaccacagg tgtacaccct gcccccatcc cgggaggaga tgaccaagaa ccaggtcagc   1260
ctgtggtgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtaaa                                                          1509

<210> SEQ ID NO 270
<211> LENGTH: 271
<212> TYPE: PRT
<213> ORGANISM: Artificial Sequence
<220> FEATURE:
<223> OTHER INFORMATION: Second Polypeptide Chain of "gpA33 mAb 1 x CD3
      mAb 2 x EphA2 mAb 3" Tri-Specific Binding Molecule

<400> SEQUENCE: 270
```

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ile Tyr Gly Asn Asn Val Tyr Phe
    210                 215                 220

Asp Val Trp Gly Gln Gly Thr Thr Val Thr Val Ser Ser Gly Gly Cys
225                 230                 235                 240

Gly Gly Gly Lys Val Ala Ala Leu Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 271
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of "gpA33 mAb 1 x CD3 mAb 2 x EphA2 mAb 3" Tri-Specific
      Binding Molecule

<400> SEQUENCE: 271
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacaggtc     360
cagctggtcc agagcgggc cgaagtcaaa aacccggag caagcgtgaa ggtctcctgc     420
aaagcatcag gctatacatt tacaggcagc tggatgaact gggtgaggca ggctccagga     480
cagggactgg agtggatcgg cgcatctac cctggagacg gcgaaactaa ctataatgga     540
aagttcaaag accgagtgac catcacagcc gataagtcta ctagtaccgc tacatggag     600 ctgagctccc tgcggtctga agataccgcc gtcctactatt gcgctagaat ttacggaaac     660
aatgtctatt ttgacgtgtg ggggcaggga acaactgtga ctgtctcctc cggaggatgt     720
ggcggtggaa agtggccgc actgaaggag aaagttgctg ctttgaaaga gaaggtcgcc     780
gcacttaagg aaaaggtcgc agccctgaaa gag                                813

<210> SEQ ID NO 272
<211> LENGTH: 448
<212> TYPE: PRT
<213> ORGANISM: Artificial Sequence
<220> FEATURE:
<223> OTHER INFORMATION: Third Polypeptide Chain of "gpA33 mAb 1 x CD3
      mAb 2 x EphA2 mAb 3" Tri-Specific Binding Molecule

<400> SEQUENCE: 272

Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Thr Asp His
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Phe Thr Ser Tyr Pro Asp Ser Val
    50                  55                  60

Lys Gly Arg Phe Thr Ile Ser Arg Asp Ile Ala Lys Asn Asn Leu Tyr
65                  70                  75                  80

Leu Gln Met Ser Ser Leu Lys Ser Glu Asp Thr Ala Met Tyr Tyr Cys

```
                   85                  90                  95
Thr Arg Asp Glu Ser Asp Arg Pro Phe Pro Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445

<210> SEQ ID NO 273
<211> LENGTH: 1344
<212> TYPE: DNA
<213> ORGANISM: Artificial Sequence
<220> FEATURE:
<223> OTHER INFORMATION: Polynucleotide Encoding Third Polypeptide Chain
      of "gpA33 mAb 1 x CD3 mAb 2 x EphA2 mAb 3" Tri-Specific Binding
      Molecule

<400> SEQUENCE: 273
```

-continued

```
gaagtgcagc tggtggagtc tgggggaggc tcagtgaagc tggagggtc cctgaaactc        60 tcctgtgcag cctctggatt cactttcact gaccattaca tgtattgggt tcgccagact       120
ccggaaaaga ggctggagtg ggtcgcaacc attagtgatg gcggtagttt cacctcctat       180
ccagacagtg tgaaggggcg attcaccatc tccagagaca ttgccaagaa caacctgtac       240
ctccaaatga gcagtctgaa gtctgaggac acagccatgt attactgtac aagagatgag       300
agcgataggc cgtttcctta ctggggccaa gggactctgg tcactgtctc ctccgcctcc       360
accaagggcc catcggtctt ccccctggca ccctcctcca agagcacctc tgggggcaca       420
gcggccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcaccca gacctacatc        600 tgcaacgtga atcacaagcc cagcaacacc aaggtggaca gagagttga gcccaaatct       660 tgtgacaaaa ctcacacatg cccaccgtgc ccagcacctg aagccgcggg gggaccgtca       720
gtcttcctct tccccccaaa acccaaggac accctcatga tctcccggac ccctgaggtc       780
acatgcgtgg tggtggacgt gagccacgaa gaccctgagg tcaagttcaa ctggtacgtg       840
gacggcgtgg aggtgcataa tgccaagaca aagccgcggg aggagcagta caacagcacg       900
taccgtgtgg tcagcgtcct caccgtcctg caccaggact ggctgaatgg caaggagtac       960
aagtgcaagg tctccaacaa agccctccca gcccccatcg agaaaaccat ctccaaagcc     1020
aaagggcagc cccgagaacc acaggtgtac accctgcccc catcccggga ggagatgacc     1080
aagaaccagg tcagcctgag ttgcgcagtc aaaggcttct atcccagcga catcgccgtg     1140
gagtgggaga gcaatgggca gccggagaac aactacaaga ccacgcctcc cgtgctggac     1200
tccgacggct ccttcttcct cgtcagcaag ctcaccgtgg acaagagcag gtggcagcag     1260
gggaacgtct tctcatgctc cgtgatgcat gaggctctgc acaaccgcta cacgcagaag     1320
agcctctccc tgtctccggg taaa                                            1344
```

<210> SEQ ID NO 274
<211> LENGTH: 214
<212> TYPE: PRT
<213> ORGANISM: Artificial Sequence
<220> FEATURE:
<223> OTHER INFORMATION: Fourth Polypeptide Chain of "gpA33 mAb 1 x CD3
      mAb 2 x EphA2 mAb 3" Tri-Specific Binding Molecule

<400> SEQUENCE: 274

Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Gly Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 275
<211> LENGTH: 642
<212> TYPE: DNA
<213> ORGANISM: Artificial Sequence
<220> FEATURE:
<223> OTHER INFORMATION: Polynucleotide Encoding Fourth Polypeptide
      Chain of "gpA33 mAb 1 x CD3 mAb 2 x EphA2 mAb 3" Tri-Specific
      Binding Molecule

<400> SEQUENCE: 275

```
gacattgtgc tgacccagtc tcacagatcc atgtccacat cagtaggaga cagggtcaac   60
atcacctgca aggccagtca ggatgtgact actgctgtag cctggtatca acaaaaacca  120
gggcaatctc ctaaattact gattttctgg gcatccaccc ggcacgctgg agtccctgat  180
cgcttcacag gcagtggatc tgggacagat tttactctca ccatcagcag tgtgcaggct  240
ggagacctgg cactttatta ctgtcaacaa cattatagca caccgtacac attcggaggg  300
gggaccaagc tggaaataaa acgtacggtg gctgcaccat cggtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac agggagagt gt                      642
```

<210> SEQ ID NO 276
<211> LENGTH: 503
<212> TYPE: PRT
<213> ORGANISM: Artificial Sequence
<220> FEATURE:
<223> OTHER INFORMATION: First Polypeptide Chain of "EphA2 mAb 1 x CD3
      mAb 2 x gpA33 mAb 1" Tri-Specific Binding Molecule

<400> SEQUENCE: 276

```
Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
```

-continued

```
                65                  70                  75                  80
Glu Asp Ile Ala Thr Tyr Phe Cys Gln Gln Gly Tyr Thr Leu Tyr Thr
                    85                  90                  95

Phe Gly Gly Gly Thr Lys Leu Glu Ile Lys Gly Gly Ser Gly Gly
                100                 105                 110

Gly Gly Glu Val Gln Leu Val Glu Ser Gly Gly Gly Leu Val Gln Pro
                115                 120                 125

Gly Gly Ser Leu Arg Leu Ser Cys Ala Ala Ser Gly Phe Thr Phe Ser
                130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
                180                 185                 190

Asn Ser Leu Tyr Leu Gln Met Asn Ser Leu Lys Thr Glu Asp Thr Ala
                195                 200                 205

Val Tyr Tyr Cys Val Arg His Gly Asn Phe Gly Asn Ser Tyr Val Ser
                210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
                260                 265                 270

Lys Gly Gly Gly Asp Lys Thr His Thr Cys Pro Pro Cys Pro Ala Pro
                275                 280                 285

Glu Ala Ala Gly Gly Pro Ser Val Phe Leu Phe Pro Pro Lys Pro Lys
                290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
                355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
                420                 425                 430

Ile Ala Val Glu Trp Glu Ser Asn Gly Gln Pro Glu Asn Asn Tyr Lys
                435                 440                 445

Thr Thr Pro Pro Val Leu Asp Ser Asp Gly Ser Phe Phe Leu Tyr Ser
                450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495
```

Leu Ser Leu Ser Pro Gly Lys
            500

<210> SEQ ID NO 277
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of "EphA2 mAb 1 x CD3 mAb 2 x gpA33 mAb 1" Tri-Specific Binding
      Molecule

<400> SEQUENCE: 277

| | | | | | |
|---|---|---|---|---|---|
| gatatccaga | tgacacagac | tacatcctcc | ctgtctgcct | ctctgggaga | cagaatcacc | 60 |
| atcagttgca | ggcaagtca | ggacattagc | aattatttaa | actggtatca | gcagaaacca | 120 |
| gatggaactg | ttaaactcct | gatctactac | acatcaagat | tacactcagg | agtcccatca | 180 |
| aggttcagtg | gcagtgggtc | tggaacagat | tattctctca | ccattagcaa | cctggagcaa | 240 |
| gaagatattg | ccacttactt | ttgccaacag | ggttatacgc | tgtacacgtt | cggagggggg | 300 |
| accaagctgg | aaataaaagg | tggaggatcc | ggcggcggag | gcgaggtgca | gctggtggag | 360 |
| tctgggggag | gcttggtcca | gcctggaggg | tccctgagac | tctcctgtgc | agcctctgga | 420 |
| ttcaccttca | gcacatacgc | tatgaattgg | gtccgccagg | ctccagggaa | ggggctggag | 480 |
| tgggttggaa | ggatcaggtc | caagtacaac | aattatgcaa | cctactatgc | cgactctgtg | 540 |
| aagggtagat | tcaccatctc | aagagatgat | tcaaagaact | cactgtatct | gcaaatgaac | 600 |
| agcctgaaaa | ccgaggacac | ggccgtgtat | tactgtgtga | cacacggtaa | cttcggcaat | 660 |
| tcttacgtgt | cttggtttgc | ttattgggga | caggggacac | tggtgactgt | gtcttccgga | 720 |
| ggatgtggcg | gtgagaagt | ggccgcactg | gagaaagagg | ttgctgcttt | ggagaaggag | 780 |
| gtcgctgcac | ttgaaaagga | ggtcgcagcc | ctggagaaag | gcggcgggga | caaaactcac | 840 |
| acatgcccac | cgtgcccagc | acctgaagcc | gcgggggac | cgtcagtctt | cctcttcccc | 900 |
| ccaaaaccca | aggacaccct | catgatctcc | cggacccctg | aggtcacatg | cgtggtggtg | 960 |
| gacgtgagcc | acgaagaccc | tgaggtcaag | ttcaactggt | acgtggacgg | cgtggaggtg | 1020 |
| cataatgcca | agacaaagcc | gcgggaggag | cagtacaaca | gcacgtaccg | tgtggtcagc | 1080 |
| gtcctcaccg | tcctgcacca | ggactggctg | aatggcaagg | agtacaagtg | caaggtctcc | 1140 |
| aacaaagccc | tcccagcccc | catcgagaaa | accatctcca | aagccaaagg | gcagccccga | 1200 |
| gaaccacagg | tgtacaccct | gcccccatcc | cgggaggaga | tgaccaagaa | ccaggtcagc | 1260 |
| ctgtggtgcc | tggtcaaagg | cttctatccc | agcgacatcg | ccgtggagtg | ggagagcaat | 1320 |
| gggcagccgg | agaacaacta | caagaccacg | cctcccgtgc | tggactccga | cggctccttc | 1380 |
| ttcctctaca | gcaagctcac | cgtggacaag | agcaggtggc | agcaggggaa | cgtcttctca | 1440 |
| tgctccgtga | tgcatgaggc | tctgcacaac | cactacacgc | agaagagcct | ctccctgtct | 1500 |
| ccgggtaaa | | | | | | 1509 |

<210> SEQ ID NO 278
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 1 x CD3
      mAb 2 x gpA33 mAb 1" Tri-Specific Binding Molecule

<400> SEQUENCE: 278

```
Gln Ala Val Val Thr Gln Glu Pro Ser Leu Thr Val Ser Pro Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Gln Val Gln Leu Lys Glu Ser Gly Pro Gly
            115                 120                 125

Leu Val Ala Pro Ser Gln Ser Leu Ser Ile Thr Cys Thr Val Ser Gly
    130                 135                 140

Phe Ser Leu Ser Arg Tyr Ser Val His Trp Val Arg Gln Pro Pro Gly
145                 150                 155                 160

Lys Gly Leu Glu Trp Leu Gly Met Ile Trp Gly Gly Gly Ser Thr Asp
                165                 170                 175

Tyr Asn Ser Ala Leu Lys Ser Arg Leu Ser Ile Ser Lys Asp Asn Ser
                180                 185                 190

Lys Ser Gln Val Phe Leu Lys Met Asn Ser Leu Gln Thr Asp Asp Thr
                195                 200                 205

Ala Met Tyr Tyr Cys Ala Arg Lys His Gly Asn Tyr Tyr Thr Met Asp
    210                 215                 220

Tyr Trp Gly Gln Gly Thr Ser Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
                260                 265                 270

<210> SEQ ID NO 279
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 1 x CD3 mAb 2 x gpA33 mAb 1" Tri-Specific
      Binding Molecule

<400> SEQUENCE: 279
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggggtacaa acaaaagggc tccctggacc    180
cctgcacggt tttctggaag tctgctgggc ggaaaggccg ctctgactat taccggggca    240
caggccgagg acgaagccga ttactattgt gctctgtggt atagcaatct gtgggtgttc    300 ggggggtggca caaaactgac tgtgctggga ggggtggat ccggcggagg tggacaggtg    360
cagctgaagg agtcaggacc tggcctggtg gcaccctcac agagcctgtc catcacatgc    420
actgtctctg ggttctcatt atccagatat agtgtacact gggttcgcca gcctccagga    480
```

```
aagggtctgg agtggctggg aatgatatgg ggtggtggaa gcacagacta taattcagct    540
ctcaaatcca gactgagtat cagcaaggac aactccaaga gccaagtttt cttaaaaatg    600
aacagtctgc aaactgatga cacagccatg tactactgtg ccagaaaaca tggtaactac    660
tatactatgg actactgggg tcaaggaacc tcagtcaccg tctcctccgg aggatgtggc    720
ggtggaaaag tggccgcact gaaggagaaa gttgctgctt tgaaagagaa ggtcgccgca    780
cttaaggaaa aggtcgcagc cctgaaagag                                     810
```

<210> SEQ ID NO 280
<211> LENGTH: 449
<212> TYPE: PRT
<213> ORGANISM: Artificial Sequence
<220> FEATURE:
<223> OTHER INFORMATION: Third Polypeptide Chain of "EphA2 mAb 1 x CD3
      mAb 2 x gpA33 mAb 1" Tri-Specific Binding Molecule

<400> SEQUENCE: 280

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro Gly
        435                 440                 445

Lys

<210> SEQ ID NO 281
<211> LENGTH: 1347
<212> TYPE: DNA
<213> ORGANISM: Artificial Sequence
<220> FEATURE:
<223> OTHER INFORMATION: Polynucleotide Encoding Third Polypeptide Chain
      of "EphA2 mAb 1 x CD3 mAb 2 x gpA33 mAb 1" Tri-Specific Binding
      Molecule

<400> SEQUENCE: 281
caggtccagc tggtccagag cggggccgaa gtcaaaaaac ccggagcaag cgtgaaggtc     60
tcctgcaaag catcaggcta tacatttaca ggcagctgga tgaactgggt gaggcaggct    120
ccaggacagg gactggagtg gatcgggcgc atctaccctg agacggcga aactaactat     180 aatgaaaagt tcaaagaccg agtgaccatc acagccgata gtctactag taccgcctac    240 atggagctga gctccctgcg gtctgaagat accgccgtct actattgcgc tagaatttac    300
ggaaacaatg tctattttga cgtgtggggg cagggaacaa ctgtgactgt ctcctccgcc    360
tccaccaagg gcccatcggt cttccccctg gcaccctcct ccaagagcac ctctggggc    420 acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaagccgc ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gagttgcgca gtcaaaggct tctatccag cgacatcgcc   1140
```

```
gtggagtggg agagcaatgg gcagccggag aacaactaca agaccacgcc tcccgtgctg    1200
gactccgacg gctccttctt cctcgtcagc aagctcaccg tggacaagag caggtggcag    1260
caggggaacg tcttctcatg ctccgtgatg catgaggctc tgcacaaccg ctacacgcag    1320
aagagcctct ccctgtctcc gggtaaa                                        1347
```

<210> SEQ ID NO 282
<211> LENGTH: 213
<212> TYPE: PRT
<213> ORGANISM: Artificial Sequence
<220> FEATURE:
<223> OTHER INFORMATION: Fourth Polypeptide Chain of "EphA2 mAb 1 x CD3
      mAb 2 x gpA33 mAb 1" Tri-Specific Binding Molecule

<400> SEQUENCE: 282

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 283
<211> LENGTH: 639
<212> TYPE: DNA
<213> ORGANISM: Artificial Sequence
<220> FEATURE:
<223> OTHER INFORMATION: Polynucleotide Encoding Fourth Polypeptide
      Chain of "EphA2 mAb 1 x CD3 mAb 2 x gpA33 mAb 1" Tri-Specific
      Binding Molecule

<400> SEQUENCE: 283

```
gacattcagc tgactcagtc cccctctttt ctgtccgcat ccgtcggaga tcgagtgact    60
attacttgct ctgctaggtc ctcaatcagc ttcatgtact ggtatcagca gaagcccggc    120
aaagcaccta gctgctgat ctacgacaca agcaacctgg cctccggggt gccatctcgg    180
```

```
ttctctggca gtgggtcagg aactgagttt accctgacaa ttagctccct ggaggctgaa    240
gatgccgcta cctactattg ccagcagtgg agcagctatc ctctgacctt cggacagggg    300
actaaactgg aaatcaagcg tacggtggct gcaccatcgg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639
```

<210> SEQ ID NO 284
<211> LENGTH: 508
<212> TYPE: PRT
<213> ORGANISM: Artificial Sequence
<220> FEATURE:
<223> OTHER INFORMATION: First Polypeptide Chain of "EphA2 mAb 2 x CD3 mAb 2 x gpA33 mAb 1" Tri-Specific Binding Molecule

<400> SEQUENCE: 284

```
Asp Val Val Met Thr Gln Thr Pro Leu Ser Leu Pro Val Ser Leu Gly
1               5                  10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Ala Met Asn Trp Val Arg Gln Ala Pro
145                 150                 155                 160

Gly Lys Gly Leu Glu Trp Val Gly Arg Ile Arg Ser Lys Tyr Asn Asn
                165                 170                 175

Tyr Ala Thr Tyr Tyr Ala Asp Ser Val Lys Gly Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
225                 230                 235                 240

Thr Val Ser Ser Gly Gly Cys Gly Gly Gly Glu Val Ala Ala Leu Glu
                245                 250                 255

Lys Glu Val Ala Ala Leu Glu Lys Glu Val Ala Ala Leu Glu Lys Glu
            260                 265                 270
```

```
Val Ala Ala Leu Glu Lys Gly Gly Asp Lys Thr His Thr Cys Pro
                275                 280                 285

Pro Cys Pro Ala Pro Glu Ala Ala Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
                340                 345                 350

Arg Glu Glu Gln Tyr Asn Ser Thr Tyr Arg Val Val Ser Val Leu Thr
                355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Glu Glu Met Thr Lys Asn Gln Val Ser Leu Trp Cys Leu Val Lys Gly
                420                 425                 430

Phe Tyr Pro Ser Asp Ile Ala Val Glu Trp Glu Ser Asn Gly Gln Pro
    435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
                500                 505

<210> SEQ ID NO 285
<211> LENGTH: 1524
<212> TYPE: DNA
<213> ORGANISM: Artificial Sequence
<220> FEATURE:
<223> OTHER INFORMATION: Polynucleotide Encoding First Polypeptide Chain
      of "EphA2 mAb 2 x CD3 mAb 2 x gpA33 mAb 1" Tri-Specific Binding
      Molecule

<400> SEQUENCE: 285
gatgttgtga tgacccaaac tccactctcc ctgcctgtca gtcttggaga tcaagcctcc      60
atctcttgca gatctagtca gagccttgta cacagtagtg aaacaccta  tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccc    300
acgttcggct cggggacaaa gttggaaata aaaggtggag gatccggcgg cggaggcgag    360
gtgcagctgg tggagtctgg gggaggcttg gtccagcctg gagggtccct gagactctcc    420
tgtgcagcct ctggattcac cttcagcaca tacgctatga attgggtccg ccaggctcca    480
gggaaggggc tggagtgggt tggaaggatc aggtccaagt acaacaatta tgcaacctac    540
tatgccgact ctgtgaaggg tagattcacc atctcaagag atgattcaaa gaactcactg    600
tatctgcaaa tgaacagcct gaaaaccgag gacacggccg tgtattactg tgtgagacac    660
```

```
ggtaacttcg gcaattctta cgtgtcttgg tttgcttatt ggggacaggg gacactggtg    720
actgtgtctt ccggaggatg tggcggtgga gaagtggccg cactggagaa agaggttgct    780
gctttggaga aggaggtcgc tgcacttgaa aaggaggtcg cagccctgga gaaaggcggc    840
ggggacaaaa ctcacacatg cccaccgtgc ccagcacctg aagccgcggg gggaccgtca    900
gtcttcctct tccccccaaa acccaaggac accctcatga tctcccggac ccctgaggtc    960
acatgcgtgg tggtggacgt gagccacgaa gaccctgagg tcaagttcaa ctggtacgtg   1020
gacggcgtgg aggtgcataa tgccaagaca aagccgcggg aggagcagta caacagcacg   1080
taccgtgtgg tcagcgtcct caccgtcctg caccaggact ggctgaatgg caaggagtac   1140
aagtgcaagg tctccaacaa agccctccca gcccccatcg agaaaaccat ctccaaagcc   1200
aaagggcagc cccgagaacc acaggtgtac accctgcccc catcccggga ggagatgacc   1260
aagaaccagg tcagcctgtg cgtgcctggtc aaaggcttct atcccagcga catcgccgtg   1320
gagtgggaga gcaatgggca gccggagaac aactacaaga ccacgcctcc cgtgctggac   1380
tccgacggct ccttcttcct ctacagcaag ctcaccgtgg acaagagcag gtggcagcag   1440
gggaacgtct tctcatgctc cgtgatgcat gaggctctgc acaaccacta cacgcagaag   1500
agcctctccc tgtctccggg taaa                                          1524
```

<210> SEQ ID NO 286
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 2 x CD3
      mAb 2 x gpA33 mAb 1" Tri-Specific Binding Molecule

<400> SEQUENCE: 286

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Ile Gln Leu Val Gln Ser Gly Pro Glu
        115                 120                 125

Leu Lys Lys Pro Gly Glu Thr Val Lys Ile Ser Cys Lys Ala Ser Gly
130                 135                 140

Phe Thr Phe Thr Asn Tyr Gly Met Asn Trp Val Lys Gln Ala Pro Gly
145                 150                 155                 160

Lys Gly Leu Lys Trp Met Gly Trp Ile Asn Thr Tyr Ile Gly Glu Pro
                165                 170                 175

Thr Tyr Ala Asp Asp Phe Lys Gly Arg Phe Val Phe Ser Leu Glu Thr
            180                 185                 190

Ser Ala Ser Thr Ala Tyr Leu Gln Ile Asn Asn Leu Lys Asn Glu Asp
        195                 200                 205

Met Ala Thr Tyr Phe Cys Ala Arg Glu Leu Gly Pro Tyr Tyr Phe Asp
            210                 215                 220

Tyr Trp Gly Gln Gly Thr Thr Leu Thr Val Ser Ser Gly Gly Cys Gly
225                 230                 235                 240

Gly Gly Lys Val Ala Ala Leu Lys Glu Lys Val Ala Ala Leu Lys Glu
            245                 250                 255

Lys Val Ala Ala Leu Lys Glu Lys Val Ala Ala Leu Lys Glu
            260                 265                 270

<210> SEQ ID NO 287
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 2 x CD3 mAb 2 x gpA33 mAb 1" Tri-Specific
      Binding Molecule

<400> SEQUENCE: 287
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc gggggtacaa acaaaagggc tccctggacc   180
cctgcacggt tttctggaag tctgctgggc ggaaaggccg ctctgactat taccggggca   240
caggccgagg acgaagccga ttactattgt gctctgtggt atagcaatct gtgggtgttc   300 ggggtggca caaaactgac tgtgctggga ggggtggat ccggcggagg tggacagatc   360
cagttggtgc agtctggacc tgagctgaag aagcctggag agacagtcaa gatctcctgc   420
aaggcttctg gtttaccttt cacaaactat ggaatgaact gggtgaagca ggctccagga   480
aagggtttaa agtggatggg ctggataaac acctatattg agagccgac atatgctgat   540 gacttcaagg gacggtttgt cttctctttg gaaacctctg ccagcactgc ctatttgcag   600
atcaacaacc tcaaaaatga ggacatggcc acatatttct gtgcaagaga actgggacca   660
tactactttg actactgggg ccaaggcacc actctcacag tctcctccgg aggatgtggc   720
ggtggaaaag tggccgcact gaaggagaaa gttgctgctt tgaaagagaa ggtcgccgca   780
cttaaggaaa aggtcgcagc cctgaaagag                                    810

<210> SEQ ID NO 288
<211> LENGTH: 449
<212> TYPE: PRT
<213> ORGANISM: Artificial Sequence
<220> FEATURE:
<223> OTHER INFORMATION: Third Polypeptide Chain of "EphA2 mAb 2 x CD3
      mAb 2 x gpA33 mAb 1" Tri-Specific Binding Molecule

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Ser
                355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn Arg Tyr Thr Gln Lys Ser Leu Ser Leu Ser Pro Gly
                435                 440                 445

Lys

<210> SEQ ID NO 289
<211> LENGTH: 1347
<212> TYPE: DNA
<213> ORGANISM: Artificial Sequence
<220> FEATURE:
<223> OTHER INFORMATION: Polynucleotide Encoding Third Polypeptide Chain
      of "EphA2 mAb 2 x CD3 mAb 2 x gpA33 mAb 1" Tri-Specific Binding
```

Molecule

<400> SEQUENCE: 289

```
caggtccagc tggtccagag cggggccgaa gtcaaaaaac ccggagcaag cgtgaaggtc      60
tcctgcaaag catcaggcta tacatttaca ggcagctgga tgaactgggt gaggcaggct     120
ccaggacagg gactggagtg gatcgggcgc atctaccctg agacggcga aactaactat      180
aatgaaagt tcaaagaccg agtgaccatc agccgata agtctactag taccgcctac        240
atggagctga gctccctgcg gtctgaagat accgccgtct actattgcgc tagaatttac     300
ggaaacaatg tctattttga cgtgtggggg cagggaacaa ctgtgactgt ctcctccgcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagccgc ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc cccatcccg ggaggagatg     1080
accaagaacc aggtcagcct gagttgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtcagc aagctcaccg tggacaagag caggtggcag    1260
caggggaacg tcttctcatg ctccgtgatg catgaggctc tgcacaaccg ctacacgcag    1320
aagagcctct ccctgtctcc gggtaaa                                        1347
```

<210> SEQ ID NO 290
<211> LENGTH: 213
<212> TYPE: PRT
<213> ORGANISM: Artificial Sequence
<220> FEATURE:
<223> OTHER INFORMATION: Fourth Polypeptide Chain of "EphA2 mAb 2 x CD3 mAb 2 x gpA33 mAb 1" Tri-Specific Binding Molecule

<400> SEQUENCE: 290

```
Asp Ile Gln Leu Thr Gln Ser Pro Ser Phe Leu Ser Ala Ser Val Gly
 1               5                  10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95
```

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 291
<211> LENGTH: 639
<212> TYPE: DNA
<213> ORGANISM: Artificial Sequence
<220> FEATURE:
<223> OTHER INFORMATION: Polynucleotide Encoding Fourth Polypeptide
      Chain of "EphA2 mAb 2 x CD3 mAb 2 x gpA33 mAb 1" Tri-Specific
      Binding Molecule

<400> SEQUENCE: 291
gacattcagc tgactcagtc cccctctttt ctgtccgcat ccgtcggaga tcgagtgact      60
attacttgct ctgctaggtc ctcaatcagc ttcatgtact ggtatcagca gaagcccggc     120
aaagcaccta agctgctgat ctacgacaca agcaacctgg cctccggggt gccatctcgg     180
ttctctggca gtgggtcagg aactgagttt accctgacaa ttagctccct ggaggctgaa     240
gatgccgcta cctactattg ccagcagtgg agcagctatc ctctgacctt cggacagggg     300
actaaactgg aaatcaagcg tacggtggct gcaccatcgg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639

<210> SEQ ID NO 292
<211> LENGTH: 504
<212> TYPE: PRT
<213> ORGANISM: Artificial Sequence
<220> FEATURE:
<223> OTHER INFORMATION: First Polypeptide Chain of "EphA2 mAb 3 x CD3
      mAb 2 x gpA33 mAb 1" Tri-Specific Binding Molecule

<400> SEQUENCE: 292

Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly

```
            50                  55                  60
Ser Gly Ser Gly Thr Asp Phe Thr Leu Thr Ile Ser Ser Val Gln Ala
 65                  70                  75                  80

Gly Asp Leu Ala Leu Tyr Tyr Cys Gln Gln His Tyr Ser Thr Pro Tyr
                     85                  90                  95

Thr Phe Gly Gly Gly Thr Lys Leu Glu Ile Lys Gly Gly Gly Ser Gly
                    100                 105                 110

Gly Gly Gly Glu Val Gln Leu Val Glu Ser Gly Gly Gly Leu Val Gln
                115                 120                 125

Pro Gly Gly Ser Leu Arg Leu Ser Cys Ala Ala Ser Gly Phe Thr Phe
                130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                    165                 170                 175

Tyr Ala Asp Ser Val Lys Gly Arg Phe Thr Ile Ser Arg Asp Asp Ser
                180                 185                 190

Lys Asn Ser Leu Tyr Leu Gln Met Asn Ser Leu Lys Thr Glu Asp Thr
                195                 200                 205

Ala Val Tyr Tyr Cys Val Arg His Gly Asn Phe Gly Asn Ser Tyr Val
210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                    245                 250                 255

Ala Leu Glu Lys Glu Val Ala Ala Leu Glu Lys Glu Val Ala Ala Leu
                260                 265                 270

Glu Lys Gly Gly Gly Asp Lys Thr His Thr Cys Pro Pro Cys Pro Ala
                275                 280                 285

Pro Glu Ala Ala Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
                355                 360                 365

Asp Trp Leu Asn Gly Lys Glu Tyr Lys Cys Lys Val Ser Asn Lys Ala
                370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                    405                 410                 415

Lys Asn Gln Val Ser Leu Trp Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
                450                 455                 460

Ser Lys Leu Thr Val Asp Lys Ser Arg Trp Gln Gln Gly Asn Val Phe
465                 470                 475                 480
```

Ser Cys Ser Val Met His Glu Ala Leu His Asn His Tyr Thr Gln Lys
            485                 490                 495

Ser Leu Ser Leu Ser Pro Gly Lys
            500

<210> SEQ ID NO 293
<211> LENGTH: 1512
<212> TYPE: DNA
<213> ORGANISM: Artificial Sequence
<220> FEATURE:
<223> OTHER INFORMATION: Polynucleotide Encoding First Polypeptide Chain
      of "EphA2 mAb 3 x CD3 mAb 2 x gpA33 mAb 1" Tri-Specific Binding
      Molecule

<400> SEQUENCE: 293

| | | | | | |
|---|---|---|---|---|---|
| gacattgtgc | tgacccagtc | tcacagatcc | atgtccacat | cagtaggaga | cagggtcaac | 60 |
| atcacctgca | aggccagtca | ggatgtgact | actgctgtag | cctggtatca | acaaaaacca | 120 |
| gggcaatctc | ctaaattact | gattttctgg | catccaccc | gcacgctgg | agtccctgat | 180 |
| cgcttcacag | gcagtggatc | tgggacagat | tttactctca | ccatcagcag | tgtgcaggct | 240 |
| ggagacctgg | cactttatta | ctgtcaacaa | cattatagca | caccgtacac | attcggaggg | 300 |
| gggaccaagc | tggaaataaa | aggtggagga | tccggcggcg | gaggcgaggt | gcagctggtg | 360 |
| gagtctgggg | gaggcttggt | ccagcctgga | gggtccctga | dactctcctg | tgcagcctct | 420 |
| ggattcaccct | tcagcacata | cgctatgaat | tgggtccgcc | aggctccagg | gaaggggctg | 480 |
| gagtgggttg | gaaggatcag | gtccaagtac | aacaattatg | caacctacta | tgccgactct | 540 |
| gtgaaggga | gattcaccat | ctcaagagat | gattcaaaga | actcactgta | tctgcaaatg | 600 |
| aacagcctga | aaccgagga | cacggccgtg | tattactgtg | tgagacacgg | taacttcggc | 660 |
| aattcttacg | tgtcttggtt | tgcttattgg | ggacagggga | cactggtgac | tgtgtcttcc | 720 |
| ggaggatgtg | gcgtggaga | agtggccgca | ctggagaaag | aggttgctgc | tttggagaag | 780 |
| gaggtcgctg | cacttgaaaa | ggaggtcgca | gccctggaga | aggcggcgg | ggacaaaact | 840 |
| cacacatgcc | caccgtgccc | agcacctgaa | gccgcggggg | gaccgtcagt | cttcctcttc | 900 |
| cccccaaaac | ccaaggacac | cctcatgatc | tcccggaccc | ctgaggtcac | atgcgtggtg | 960 |
| gtggacgtga | gccacgaaga | ccctgaggtc | aagttcaact | ggtacgtgga | cggcgtggag | 1020 |
| gtgcataatg | ccaagacaaa | gccgcgggag | gagcagtaca | acagcacgta | ccgtgtggtc | 1080 |
| agcgtcctca | ccgtcctgca | ccaggactgg | ctgaatggca | aggagtacaa | gtgcaaggtc | 1140 |
| tccaacaaag | ccctcccagc | ccccatcgag | aaaaccatct | ccaaagccaa | agggcagccc | 1200 |
| cgagaaccac | aggtgtacac | cctgcccca | tcccgggagg | agatgaccaa | gaaccaggtc | 1260 |
| agcctgtggt | gcctggtcaa | aggcttctat | cccagcgaca | tcgccgtgga | gtgggagagc | 1320 |
| aatgggcagc | cggagaacaa | ctacaagacc | acgcctcccg | tgctggactc | cgacggctcc | 1380 |
| ttcttcctct | acagcaagct | caccgtggac | aagagcaggt | ggcagcaggg | gaacgtcttc | 1440 |
| tcatgctccg | tgatgcatga | ggctctgcac | aaccactaca | cgcagaagag | cctctccctg | 1500 |
| tctccgggta | aa | | | | | 1512 |

<210> SEQ ID NO 294
<211> LENGTH: 270
<212> TYPE: PRT
<213> ORGANISM: Artificial Sequence
<220> FEATURE:
<223> OTHER INFORMATION: Second Polypeptide Chain of "EphA2 mAb 3 x CD3
      mAb 2 x gpA33 mAb 1" Tri-Specific Binding Molecule

<400> SEQUENCE: 294

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Ser Val Lys Pro Gly Gly Ser Leu Lys Leu Ser Cys Ala Ala Ser Gly
130                 135                 140

Phe Thr Phe Thr Asp His Tyr Met Tyr Trp Val Arg Gln Thr Pro Glu
145                 150                 155                 160

Lys Arg Leu Glu Trp Val Ala Thr Ile Ser Asp Gly Gly Ser Phe Thr
                165                 170                 175

Ser Tyr Pro Asp Ser Val Lys Gly Arg Phe Thr Ile Ser Arg Asp Ile
            180                 185                 190

Ala Lys Asn Asn Leu Tyr Leu Gln Met Ser Ser Leu Lys Ser Glu Asp
        195                 200                 205

Thr Ala Met Tyr Tyr Cys Thr Arg Asp Glu Ser Asp Arg Pro Phe Pro
    210                 215                 220

Tyr Trp Gly Gln Gly Thr Leu Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 295
<211> LENGTH: 810
<212> TYPE: DNA
<213> ORGANISM: Artificial Sequence
<220> FEATURE:
<223> OTHER INFORMATION: Polynucleotide Encoding Second Polypeptide
      Chain of "EphA2 mAb 3 x CD3 mAb 2 x gpA33 mAb 1" Tri-Specific
      Binding Molecule

<400> SEQUENCE: 295
caggctgtgg tgactcagga gccttcactg accgtgtccc caggcggaac tgtgaccctg      60
acatgcagat ccagcacagg cgcagtgacc atctctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaactgac tgtgctggga ggggtggat ccggcggagg tggagaagtg      360
cagctggtgg agtctggggg aggctcagtg aagcctggag ggtccctgaa actctcctgt     420

```
gcagcctctg gattcacttt cactgaccat tacatgtatt gggttcgcca gactccggaa    480
aagaggctgg agtgggtcgc aaccattagt gatggcggta gtttcacctc ctatccagac    540
agtgtgaagg gccgattcac catctccaga gacattgcca agaacaacct gtacctccaa    600
atgagcagtc tgaagtctga ggacacagcc atgtattact gtacaagaga tgagagcgat    660
aggccgtttc cttactgggg ccaagggact ctggtcactg tctcctccgg aggatgtggc    720
ggtggaaaag tggccgcact gaaggagaaa gttgctgctt tgaaagagaa ggtcgccgca    780
cttaaggaaa aggtcgcagc cctgaaagag                                     810
```

<210> SEQ ID NO 296
<211> LENGTH: 449
<212> TYPE: PRT
<213> ORGANISM: Artificial Sequence
<220> FEATURE:
<223> OTHER INFORMATION: Third Polypeptide Chain of "EphA2 mAb 3 x CD3
      mAb 2 x gpA33 mAb 1" Tri-Specific Binding Molecule

<400> SEQUENCE: 296

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Ser
        355                 360                 365
Cys Ala Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn Arg Tyr Thr Gln Lys Ser Leu Ser Leu Ser Pro Gly
        435                 440                 445
Lys
```

<210> SEQ ID NO 297
<211> LENGTH: 1347
<212> TYPE: DNA
<213> ORGANISM: Artificial Sequence
<220> FEATURE:
<223> OTHER INFORMATION: Polynucleotide Encoding Third Polypeptide Chain
  of "EphA2 mAb 3 x CD3 mAb 2 x gpA33 mAb 1" Tri-Specific Binding
  Molecule

<400> SEQUENCE: 297

```
caggtccagc tggtccagag cggggccgaa gtcaaaaaac ccggagcaag cgtgaaggtc      60
tcctgcaaag catcaggcta tacatttaca ggcagctgga tgaactgggt gaggcaggct     120
ccaggacagg gactggagtg gatcgggcgc atctaccctg agacggcga aactaactat      180
aatggaaagt tcaaagaccg agtgaccatc acagccgata agtctactag taccgcctac     240
atggagctga gctccctgcg gtctgaagat accgccgtct actattgcgc tagaatttac     300
ggaaacaatg tctattttga cgtgtggggg cagggaacaa ctgtgactgt ctcctccgcc     360
tccaccaagg gcccatcggt cttccccctg caccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaagccgc ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
```

```
gccaaagggc agccccgaga accacaggtg tacaccctgc ccccatcccg ggaggagatg    1080
accaagaacc aggtcagcct gagttgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtcagc aagctcaccg tggacaagag caggtggcag    1260
caggggaacg tcttctcatg ctccgtgatg catgaggctc tgcacaaccg ctacacgcag    1320
aagagcctct ccctgtctcc gggtaaa                                        1347
```

<210> SEQ ID NO 298
<211> LENGTH: 213
<212> TYPE: PRT
<213> ORGANISM: Artificial Sequence
<220> FEATURE:
<223> OTHER INFORMATION: Fourth Polypeptide Chain of "EphA2 mAb 3 x CD3 mAb 2 x gpA33 mAb 1" Tri-Specific Binding Molecule

<400> SEQUENCE: 298

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 299
<211> LENGTH: 639
<212> TYPE: DNA
<213> ORGANISM: Artificial Sequence
<220> FEATURE:
<223> OTHER INFORMATION: Polynucleotide Encoding Fourth Polypeptide Chain of "EphA2 mAb 3 x CD3 mAb 2 x gpA33 mAb 1" Tri-Specific Binding Molecule

<400> SEQUENCE: 299

```
gacattcagc tgactcagtc cccctctttt ctgtccgcat ccgtcggaga tcgagtgact    60
```

```
attacttgct ctgctaggtc ctcaatcagc ttcatgtact ggtatcagca gaagcccggc    120
aaagcaccta agctgctgat ctacgacaca agcaacctgg cctccggggt gccatctcgg    180
ttctctggca gtgggtcagg aactgagttt accctgacaa ttagctccct ggaggctgaa    240
gatgccgcta cctactattg ccagcagtgg agcagctatc ctctgacctt cggacagggg    300
actaaactgg aaatcaagcg tacggtggct gcaccatcgg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639
```

<210> SEQ ID NO 300
<211> LENGTH: 279
<212> TYPE: PRT
<213> ORGANISM: Artificial Sequence
<220> FEATURE:
<223> OTHER INFORMATION: First Polypeptide Chain of "4-4-20 x CD3 mAb 2"
      Diabody

<400> SEQUENCE: 300

```
Asp Val Val Met Thr Gln Thr Pro Phe Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Asn Thr Tyr Ala Met Asn Trp Val Arg Gln Ala
145                 150                 155                 160

Pro Gly Lys Gly Leu Glu Trp Val Ala Arg Ile Arg Ser Lys Tyr Asn
                165                 170                 175

Asn Tyr Ala Thr Tyr Tyr Ala Asp Ser Val Lys Asp Arg Phe Thr Ile
            180                 185                 190

Ser Arg Asp Asp Ser Lys Asn Ser Leu Tyr Leu Gln Met Asn Ser Leu
        195                 200                 205

Lys Thr Glu Asp Thr Ala Val Tyr Tyr Cys Val Arg His Gly Asn Phe
    210                 215                 220

Gly Asn Ser Tyr Val Ser Trp Phe Ala Tyr Trp Gly Gln Gly Thr Leu
225                 230                 235                 240

Val Thr Val Ser Ser Gly Gly Cys Gly Gly Glu Val Ala Ala Leu
                245                 250                 255
```

Glu Lys Glu Val Ala Ala Leu Glu Lys Val Ala Ala Leu Lys
            260                 265                 270

Glu Val Ala Ala Leu Glu Lys
        275

<210> SEQ ID NO 301
<211> LENGTH: 270
<212> TYPE: PRT
<213> ORGANISM: Artificial Sequence
<220> FEATURE:
<223> OTHER INFORMATION: Second Polypeptide Chain of "4-4-20 x CD3 mAb
      2" Diabody

<400> SEQUENCE: 301

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 302
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Murine Anti-Human CD317 Antibody ("HM1.24 mAb
      1") Light Chain Variable Domain

```
<400> SEQUENCE: 302

Asp Ile Val Met Thr Gln Ser His Lys Phe Met Ser Thr Ser Val Gly
1               5                   10                  15

Asp Arg Val Ser Ile Thr Cys Lys Lys Ala Ser Gln Asp Val Asn Thr
            20                  25                  30

Ala Val Ala Trp Tyr Gln Lys Pro Gly Gln Ser Pro Lys Leu Leu
        35                  40                  45

Ile Tyr Ser Ala Ser Asn Arg Tyr Thr Gly Val Pro Asp Arg Ile Thr
    50                  55                  60

Gly Ser Gly Ser Gly Thr Asp Phe Thr Phe Thr Ile Ser Ser Val Gln
65                  70                  75                  80

Ala Glu Asp Leu Ala Leu Thr Thr Cys Gln Gln His Tyr Ser Thr Pro
                85                  90                  95

Phe Thr Phe Gly Ser Gly Thr Lys Leu Glu Ile Lys
            100                 105

<210> SEQ ID NO 303
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Murine Anti-Human CD317 Antibody ("HM1.24 mAb
      1") Heavy Chain Variable Domain

<400> SEQUENCE: 303

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly Ser Ile Phe Pro Gly Asp Gly Asp Thr Arg Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ile Leu Ala Phe Glu Asp Ser Ala Val Tyr Tyr Cys
                85                  90                  95

Ala Arg Gly Leu Arg Arg Gly Gly Tyr Tyr Phe Asp Tyr Trp Gly Gln
            100                 105                 110

Gly Thr Thr Leu Thr Val Ser Ser
        115                 120

<210> SEQ ID NO 304
<211> LENGTH: 107
<212> TYPE: PRT
<213> ORGANISM: Artificial Sequence
<220> FEATURE:
<223> OTHER INFORMATION: Murine Anti-Human CEACAM5 / CEACAM6 Antibody
      (16C3; EP 2585476) Light Chain Variable Domain

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45
```

```
Trp Gly Ala Ser Asn Leu Ala Asp Gly Met Pro Ser Arg Phe Ser Gly
             50                  55                  60

Ser Gly Ser Gly Arg Gln Tyr Thr Leu Thr Ile Ser Ser Leu Gln Pro
 65                  70                  75                  80

Glu Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
            100                 105

<210> SEQ ID NO 305
<211> LENGTH: 121
<212> TYPE: PRT
<213> ORGANISM: Artificial Sequence
<220> FEATURE:
<223> OTHER INFORMATION: Humanized Anti-Human CEACAM5 / CEACAM6 Antibody
      (16C3; EP 2585476) Heavy Chain Variable Domain

<400> SEQUENCE: 305

Gln Val Gln Leu Gln Gln Ser Gly Pro Glu Val Val Arg Pro Gly Val
 1               5                  10                  15

Ser Val Lys Ile Ser Cys Lys Gly Ser Gly Tyr Thr Phe Thr Asp Tyr
             20                  25                  30

Ala Met His Trp Val Lys Gln Ser His Ala Lys Ser Leu Glu Trp Ile
         35                  40                  45

Gly Leu Ile Ser Thr Tyr Ser Gly Asp Thr Lys Tyr Asn Gln Asn Phe
     50                  55                  60

Lys Gly Lys Ala Thr Met Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 306
<211> LENGTH: 107
<212> TYPE: PRT
<213> ORGANISM: Artificial Sequence
<220> FEATURE:
<223> OTHER INFORMATION: Humanized Anti-Human CEACAM5 / CEACAM6 Antibody
      (hMN15; WO 2011/034660) Light Chain Variable Domain

<400> SEQUENCE: 306

Asp Ile Gln Leu Thr Gln Ser Pro Ser Ser Leu Ser Ala Ser Val Gly
 1               5                  10                  15

Asp Arg Val Thr Met Thr Cys Ser Ala Ser Ser Arg Val Ser Tyr Ile
             20                  25                  30

His Trp Tyr Gln Gln Lys Pro Gly Lys Ala Pro Lys Arg Trp Ile Tyr
         35                  40                  45

Gly Thr Ser Thr Leu Ala Ser Gly Val Pro Ala Arg Phe Ser Gly Ser
     50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Tyr Asn Pro Pro Thr
                 85                  90                  95

Phe Gly Gln Gly Thr Lys Val Glu Ile Lys Arg
            100                 105
```

<210> SEQ ID NO 307
<211> LENGTH: 121
<212> TYPE: PRT
<213> ORGANISM: Artificial Sequence
<220> FEATURE:
<223> OTHER INFORMATION: Humanized Anti-Human CEACAM5 / CEACAM6 Antibody
      (hMN15; WO 2011/034660) Heavy Chain Variable Domain

<400> SEQUENCE: 307

Gln Val Gln Leu Val Glu Ser Gly Gly Gly Val Val Gln Pro Gly Arg
1               5                   10                  15

Ser Leu Arg Leu Ser Cys Ser Ser Gly Phe Ala Leu Thr Asp Tyr
            20                  25                  30

Tyr Met Ser Trp Val Arg Gln Ala Pro Gly Lys Gly Leu Glu Trp Leu
        35                  40                  45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
                85                  90                  95

Phe Cys Ala Arg Asp Met Gly Ile Arg Trp Asn Phe Asp Val Trp Gly
            100                 105                 110

Gln Gly Thr Pro Val Thr Val Ser Ser
        115                 120

<210> SEQ ID NO 308
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-Human 5T4 Antibody ("5T4 mAb 1")
      Light Chain Variable Domain

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys
            100                 105

<210> SEQ ID NO 309
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Murine Anti-Human 5T4 Antibody ("5T4 mAb 1")

-continued

Heavy Chain Variable Domain

<400> SEQUENCE: 309

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
    50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser
        115

<210> SEQ ID NO 310
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Murine Anti-Human 5T4 Antibody ("5T4 mAb 2")
      Light Chain Variable Domain

<400> SEQUENCE: 310

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 311
<211> LENGTH: 127
<212> TYPE: PRT
<213> ORGANISM: Mus musculus
<220> FEATURE:
<221> NAME/KEY: MISC_FEATURE
<222> LOCATION: (1)..(127)
<223> OTHER INFORMATION: Murine Anti-Human 5T4 Antibody ("5T4 mAb 2")
      Heavy Chain Variable Domain

<400> SEQUENCE: 311

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr

```
                    20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Arg Ala Asn Tyr Asn Glu Lys Phe
        50                  55                  60

Lys Ser Lys Ala Thr Leu Thr Val Asp Thr Ser Ser Ser Thr Ala Tyr
 65                 70                  75                  80

Met Gln Leu Ser Ser Leu Thr Ser Glu Asp Ser Ala Val Tyr Asn Cys
                85                  90                  95

Ala Arg Tyr Gly Pro Leu Phe Thr Thr Val Val Asp Pro Asn Ser Tyr
            100                 105                 110

Ala Met Asp Tyr Trp Gly Gln Gly Thr Ser Val Thr Val Ser Ser
        115                 120                 125

<210> SEQ ID NO 312
<211> LENGTH: 108
<212> TYPE: PRT
<213> ORGANISM: Artificial Sequence
<220> FEATURE:
<223> OTHER INFORMATION: Humanized Anti-Human ITGB6 Antibody (Derived
      from Antibody 3G9, PCT Publication No. WO 2007/008712) Light Chain
      Variable Domain

<400> SEQUENCE: 312

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Gly Phe Thr Leu Thr Ile Ser Ser Leu Glu
 65                 70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105

<210> SEQ ID NO 313
<211> LENGTH: 120
<212> TYPE: PRT
<213> ORGANISM: Artificial Sequence
<220> FEATURE:
<223> OTHER INFORMATION: Humanized Anti-Human ITGB6 Antibody (Derived
      from Antibody 3G9, PCT Publication No. WO 2007/008712) Heavy Chain
      Variable Domain

<400> SEQUENCE: 313

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Phe Thr Val Lys
    50                  55                  60

Gly Arg Phe Thr Ile Ser Arg Asp Asn Ala Lys Asn Ser Leu Tyr Leu
 65                 70                  75                  80
```

Gln Met Asn Ser Leu Arg Ala Glu Asp Thr Ala Val Tyr Tyr Cys Ala
                85                  90                  95

Arg Gly Ser Ile Tyr Asp Gly Tyr Tyr Val Phe Pro Tyr Trp Gly Gln
            100                 105                 110

Gly Thr Leu Val Thr Val Ser Ser
        115                 120

<210> SEQ ID NO 314
<211> LENGTH: 111
<212> TYPE: PRT
<213> ORGANISM: Artificial Sequence
<220> FEATURE:
<223> OTHER INFORMATION: Humanized Anti-Human ITGB6 Antibody (Derived
      from Antibody 8G6; PCT Publication No. WO 2007/008712) Light Chain
      Variable Domain

<400> SEQUENCE: 314

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Leu Leu Ile Tyr Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95

Glu Ile Pro Phe Thr Phe Gly Gly Gly Thr Lys Val Glu Ile Lys
            100                 105                 110

<210> SEQ ID NO 315
<211> LENGTH: 126
<212> TYPE: PRT
<213> ORGANISM: Artificial Sequence
<220> FEATURE:
<223> OTHER INFORMATION: Humanized Anti-Human ITGB6 Antibody (Derived
      from Antibody 8G6; PCT Publication No. WO 2007/008712) Heavy Chain
      Variable Domain

<400> SEQUENCE: 315

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Val Ile Ser Thr Tyr Tyr Gly Asn Thr Asn Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Leu Arg Arg Gly Asp Arg Pro Ser Leu Gln Tyr Ala
            100                 105                 110

Met Asp Tyr Trp Gly Gln Gly Thr Leu Val Thr Val Ser Ser
        115                 120                 125

<210> SEQ ID NO 316
<211> LENGTH: 272
<212> TYPE: PRT
<213> ORGANISM: Artificial Sequence
<220> FEATURE:
<223> OTHER INFORMATION: First Polypeptide Chain of "gpA33 x CD3 mAb 2"
      Diabody

<400> SEQUENCE: 316

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
210                 215                 220

Trp Phe Ala Tyr Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

<210> SEQ ID NO 317
<211> LENGTH: 270
<212> TYPE: PRT
<213> ORGANISM: Artificial Sequence
<220> FEATURE:
<223> OTHER INFORMATION: Second Polypeptide Chain of "gpA33 x CD3 mAb 2"
      Diabody

<400> SEQUENCE: 317

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Gln Val Gln Leu Val Gln Ser Gly Ala Glu
                115                 120                 125

Val Lys Lys Pro Gly Ala Ser Val Lys Val Ser Cys Lys Ala Ser Gly
130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
                180                 185                 190

Ser Thr Ser Thr Ala Tyr Met Glu Leu Ser Ser Leu Arg Ser Glu Asp
                195                 200                 205

Thr Ala Val Tyr Tyr Cys Ala Arg Ile Tyr Gly Asn Asn Val Tyr Phe
210                 215                 220

Asp Val Trp Gly Gln Gly Thr Thr Val Thr Val Ser Ser Ala Ser Thr
225                 230                 235                 240

Lys Gly Lys Val Ala Ala Cys Lys Glu Lys Val Ala Ala Leu Lys Glu
                245                 250                 255

Lys Val Ala Ala Leu Lys Glu Lys Val Ala Ala Leu Lys Glu
                260                 265                 270

<210> SEQ ID NO 318
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide encoding Murine Anti-Human EphA2
      Antibody ("EphA2 mAb 2") Light Chain Variable Domain (SEQ ID
      NO:163)

<400> SEQUENCE: 318
gatgttgtga tgacccaaac tccactctcc ctgcctgtca gtcttggaga tcaagcctcc        60
atctcttgca gatctagtca gagccttgta cacagtagtg aaacacccta tttacattgg      120
tacctgcaga agccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tatttctgct ctcaaagtac acatgttccc      300
acgttcggct cggggacaaa gttggaaata aaa                                    333

<210> SEQ ID NO 319
<211> LENGTH: 354
<212> TYPE: DNA
<213> ORGANISM: Mus musculus
<220> FEATURE:
<221> NAME/KEY: misc_feature
<222> LOCATION: (1)..(354)

<223> OTHER INFORMATION: Polynucelotide Encoding Murine Anti-Human EphA2
Antibody ("EphA2 mAb 3") Heavy Chain Variable Domain (SEQ ID
NO:177)

<400> SEQUENCE: 319

```
gaagtgcagc tggtggagtc tgggggaggc tcagtgaagc tggagggtc cctgaaactc      60 tcctgtgcag cctctggatt cactttcact gaccattaca tgtattgggt tcgccagact     120
ccggaaaaga ggctggagtg ggtcgcaacc attagtgatg gcggtagttt cacctcctat    180
ccagacagtg tgaaggggcg attcaccatc tccagagaca ttgccaagaa caacctgtac    240
ctccaaatga gcagtctgaa gtctgaggac acagccatgt attactgtac aagagatgag    300
agcgataggc cgtttcctta ctggggccaa gggactctgg tcactgtctc ctcc          354
```

<210> SEQ ID NO 320
<211> LENGTH: 11
<212> TYPE: PRT
<213> ORGANISM: Artificial Sequence
<220> FEATURE:
<223> OTHER INFORMATION: humanized Anti-Human DR5 Antibody ("DR5 mAb 2")
Light Chain Variable Domain CDRL1

<400> SEQUENCE: 320

```
Arg Ala Ser Gln Asp Val Asn Thr Ala Val Ala
1               5                   10
```

<210> SEQ ID NO 321
<211> LENGTH: 107
<212> TYPE: PRT
<213> ORGANISM: Artificial Sequence
<220> FEATURE:
<223> OTHER INFORMATION: humanized anti-IL13RA2 Antibody ("HU08") Light
Chain Variable

<400> SEQUENCE: 321

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Ser Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105
```

<210> SEQ ID NO 322
<211> LENGTH: 122
<212> TYPE: PRT
<213> ORGANISM: Artificial Sequence
<220> FEATURE:
<223> OTHER INFORMATION: humanized anti-IL13RA2 Antibody ("HU08") Heavy
Chain Variable

<400> SEQUENCE: 322

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
```

-continued

```
                    20                  25                  30
Gly Met Ser Trp Val Arg Gln Ala Pro Gly Lys Gly Leu Glu Trp Val
            35                  40                  45

Ala Thr Val Ser Ser Gly Gly Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
            115                 120
```

TRI-SPECIFIC BINDING MOLECULES THAT SPECIFICALLY BIND TO MULTIPLE CANCER ANTIGENS

CROSS-REFERENCE TO RELATED APPLICATIONS

This patent application is a divisional application of U.S. application Ser. No. 15/313,765, filed Nov. 23, 2016, entitled MULTI-CHAIN POLYPEPTIDE-CONTAINING TRI-SPECIFIC BINDING MOLECULES THAT SPECIFICALLY BIND TO MULTIPLE CANCER ANTIGENS, naming Ezio BONVINI et al. as inventors, which is a 35 U.S.C. 371 national phase patent application of International Application No. PCT/US2015/033081, filed on May 29, 2015, entitled TRI-SPECIFIC BINDING MOLECULES THAT SPECIFICALLY BIND TO MULTIPLE CANCER ANTIGENS AND METHODS OF USE THEREOF, naming Ezio BONVINI et al. as inventors, which claims priority to U.S. Patent Applications No. 62/107,824 (filed Jan. 26, 2015), 62/008,229 (filed Jun. 5, 2014), and 62/004,571 (filed May 29, 2014), each of which applications is herein incorporated by reference in its entirety.

REFERENCE TO SEQUENCE LISTING

The instant application contains a Sequence Listings which has been submitted electronically in ASCII format and is hereby incorporated by reference in its entirety. The ASCII copy, created on Feb. 4, 2019, is named MAC-0060-US_SubSL_2019-02-05.txt, and is 417,468 bytes in size.

BACKGROUND OF THE INVENTION

Field of the Invention

The present invention relates to Tri-Specific Binding Molecules, which are multi-chain polypeptide molecules that possess three Binding Domains and are thus capable of mediating coordinated binding to three epitopes. The Tri-Specific Binding Molecule is preferably characterized in possessing binding domains that permit it to immunospecifically bind to: (1) an epitope of a first Cancer Antigen, (2) an epitope of a second Cancer Antigen, and (3) an epitope of a molecule that is expressed on the surface of an immune system effector cell, and are thus capable of localizing an immune system effector cell to a cell that expresses a Cancer Antigen, so as to thereby facilitate the killing of such cancer cell.

Description of Related Art

I. The Mammalian Immune System

The mammalian immune system serves as a defense against a variety of conditions, including, e.g., injury, infection and neoplasia. The efficiency with which humans and other mammals develop an immunological response to pathogens, foreign substances and cancer antigens rests on two characteristics: the exquisite specificity of the immune response for antigen recognition, and the immunological memory that allows for faster and more vigorous responses upon re-activation with the same antigen (Portolés, P. et al. (2009) "*The TCR/CD3 Complex: Opening the Gate to Successful Vaccination*," Current Pharmaceutical Design 15:3290-3300; Guy, C. S. et al. (2009) "*Organization of Proximal Signal Initiation at the TCR:CD3 Complex*," Immunol Rev. 232(1):7-21).

The mammalian immune system is mediated by two separate but interrelated systems: the cellular and humoral immune systems. Generally speaking, the humoral system is mediated by soluble products (antibodies or immunoglobulins) that have the ability to combine with and neutralize products recognized by the system as being foreign to the body. In contrast, the cellular immune system involves the mobilization of certain cells, termed "T cells," that serve a variety of therapeutic roles. T cells are lymphocytes that are derived from the thymus and circulate between the tissues, lymphatic system and the circulatory system. In response to the presence and recognition of foreign structures (antigens), T cells become "activated" to initiate an immune response. In many instances these foreign antigens are expressed on host cells as a result of neoplasia or infection. Although T cells do not themselves secrete antibodies, they are usually required for antibody secretion by the second class of lymphocytes, B cells (which derive from bone marrow). Critically, T cells exhibit extraordinary immunological specificity so as to be capable of discerning one antigen from another). Two types of T cells, "T helper cells" and "cytotoxic T cells," are of particular relevance.

T helper cells are characterized by their expression of the glycoprotein, CD4 (i.e., they are "CD4$^+$"). CD4$^+$ T cells are the essential organizers of most mammalian immune and autoimmune responses (Dong, C. et al. (2003) "*Immune Regulation by Novel Costimulatory Molecules*," Immunolog. Res. 28(1):39-48). The activation of CD4$^+$ T cells has been found to be mediated through co-stimulatory interactions between an antigen:major histocompability class II (MHC II) molecule complex that is arrayed on the surface of an Antigen Presenting Cell (such as a B cell, a macrophage or a dendritic cell) and a complex of two molecules, the T Cell Receptor ("TCR") and a CD3 cell surface receptor ligand, that are arrayed on surface of a naive CD4$^+$ T cell. Activated T helper cells are capable of proliferating into Th1 cells that are capable of mediating an inflammatory response to the target cell.

Cytotoxic T cells are characterized by their expression of CD8 (i.e., they are "CD8+" as well as CD3$^+$). The activation of CD8$^+$ T cells has been found to be mediated through co-stimulatory interactions between an antigen:major histocompability class I (MHC I) molecule complex that is arrayed on the surface of a target cell and a complex of CD8 and the T Cell Receptor, that are arrayed on surface of the CD8$^+$ T cell. Unlike MHC II molecules, which are expressed by only certain immune system cells, MHC I molecules are very widely expressed. Thus, cytotoxic T cells are capable of binding to a wide variety of cell types. Activated cytotoxic T cells mediate cell killing through their release of the cytotoxins perforin, granzymes, and granulysin. Through the action of perforin, granzymes enter the cytoplasm of the target cell and their serine protease function triggers the caspase cascade, which is a series of cysteine proteases that eventually lead to apoptosis (programmed cell death) of targeted cells.

The T cell receptor ("TCR") is a covalently linked heterodimer of α and β chains ("TCRαβ"). These chains are class I membrane polypeptides of 259 (α) and 296 (β) amino acids in length. The CD3 molecule is a T cell co-receptor composed of five distinct polypeptide chains (a CD3 γ chain, a CD3 δ chain, two CD3 ε chains and two zeta chains). The individual polypeptide chains associate to form a complex of three dimers (εγ, εδ, ζζ) (Wucherpfennig, K. W. et al. (2010) "*Structural Biology Of The T Cell Receptor: Insights into Receptor Assembly, Ligand Recognition, And Initiation of Signaling*," Cold Spring Harb. Perspect. Biol. 2(4):a005140;

pages 1-14; Chetty, R. et al. (1994) "*CD3: Structure, Function And The Role Of Immunostaining In Clinical Practice*," J. Pathol. 173:303-307; Guy, C. S. et al. (2009) "*Organization of Proximal Signal Initiation at the TCR:CD3 Complex*," Immunol Rev. 232(1):7-21; Call, M. E. et al. (2007) "*Common Themes In The Assembly And Architecture Of Activating Immune Receptors*," Nat. Rev. Immunol. 7:841-850; Weiss, A. (1993) "*T Cell Antigen Receptor Signal Transduction: A Tale Of Tails And Cytoplasmic Protein-Tyrosine Kinases*," Cell 73:209-212). The CD3 complex associates with TCR in order to generate an activation signal in T lymphocytes. In the absence of CD3, TCRs do not assemble properly and are degraded (Thomas, S. et al. (2010) "*Molecular Immunology Lessons From Therapeutic T Cell Receptor Gene Transfer*," Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2):133-139).

The TCR and CD3 complex, along with the CD3 ζ chain zeta chain (also known as T cell receptor T3 zeta chain or CD247) comprise the TCR complex (van der Merwe, P. A. etc. (epub Dec. 3, 2010) "*Mechanisms For T Cell Receptor Triggering*," Nat. Rev. Immunol. 11:47-55; Wucherpfennig, K. W. et al. (2010) "*Structural Biology of the T cell Receptor: Insights into Receptor Assembly, Ligand Recognition, and Initiation of Signaling*," Cold Spring Harb. Perspect. Biol. 2:a005140). The complex is particularly significant since it contains a large number (ten) of immunoreceptor tyrosine-based activation motifs (ITAMs).

Two interactions are required for T cell activation (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). In the first interaction, a Cell must display the relevant target antigen bound to the cell's major histocompatibility complex so that it can bind to the T cell Receptor ("TCR") of a naive T lymphocyte. In the second interaction, a ligand of the Cell must bind to a co-receptor of the T lymphocyte (Dong, C. et al. (2003) "*Immune Regulation by Novel Costimulatory Molecules*," Immunolog. Res. 28(1): 39-48; Lindley, P. S. et al. (2009) "*The Clinical Utility Of Inhibiting CD28-Mediated Costimulation*," Immunol. Rev. 229:307-321). T cells experiencing both stimulatory signals are then capable of responding to cytokines (such as Interleukin-2 and Interleukin-12). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors*," Exper. Pharmacol. 181:291-328). In pathologic states, T cells are the key players of various organ-specific autoimmune diseases, such as type I diabetes, rheumatoid arthritis, and multiple sclerosis (Dong, C. et al. (2003) "*Immune Regulation by Novel Costimulatory Molecules*," Immunolog. Res. 28(1):39-48).

The need for two signals to activate T cells such that they achieve an adaptive immune response is believed to provide a mechanism for avoiding responses to self-antigens that may be present on an Antigen Presenting Cell at locations in the system where it can be recognized by a T cell. Where contact of a T cell with a Cell results in the generation of only one of two required signals, the T cell does not become activated and an adaptive immune response does not occur.

II. Antibodies and Other Epitope-Binding Molecules

A. Antibodies

"Antibodies" are immunoglobulin molecules capable of specific binding to a target, such as a carbohydrate, polynucleotide, lipid, polypeptide, etc., through at least one antigen recognition site, located in the Variable Domain of the immunoglobulin molecule. As used herein, the term encompasses not only intact polyclonal or monoclonal antibodies, camelized antibodies, single-chain antibodies, and anti-idiotypic (anti-Id) antibodies (including, e.g., anti-Id and anti-anti-Id antibodies to antibodies of the invention), but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242. As used herein, an "antigen-binding fragment of an antibody" is a portion of an antibody that possesses an at least one antigen recognition site. As used herein, the term encompasses fragments (e.g., Fab, Fab', F(ab')2 Fv), disulfide-linked bispecific Fvs (sdFv), intrabodies, and single-chain molecules (e.g., scFv). In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Natural antibodies (such as IgG antibodies) are composed of two Light Chains complexed with two Heavy Chains. Each Light Chain contains a Variable Domain (VL) and a Constant Domain (CL). Each heavy chain contains a Variable Domain (VH), three Constant Domains (CH1, CH2 and CH3), and a Hinge Domain located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N") portion of each chain includes a variable region of about 100 to 110 or more amino acids primarily responsible for antigen recognition. The carboxy-terminal ("C") portion of each chain defines a constant region, with light chains having a single Constant Domain and heavy chains usually having three Constant Domains and a hinge region. Thus, the structure of the light chains of an IgG molecule is n-VL-CL-c and the structure of the IgG heavy chains is n-VH-CH1-H-CH2-CH3-c (where H is the hinge region, and n and c represent, respectively, the N-terminus and the C-terminus of the polypeptide).

The ability of an intact, unmodified antibody (e.g., an IgG antibody) to bind an epitope of an antigen depends upon the presence of Variable Domains on the immunoglobulin light and heavy chains (i.e., the VL Domain and VH Domain, respectively). Interaction of an antibody Light Chain and an antibody heavy chain and, in particular, interaction of its VL and VH Domains forms one of the epitope-binding sites of the antibody. The variable regions of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to an specific epitope regardless of whether such protein is an antibody having light and heavy chains or a diabody or a single-chain binding molecule (e.g., an scFv, a BiTe, etc.), or is another type of protein. In contrast to such antibodies, the scFv construct comprises a VL and VH Domain of an antibody contained in a single polypeptide chain wherein the Domains are separated by a flexible linker of sufficient length to allow self-assembly of the two Domains into a functional epitope-binding site. Where self-assembly of the VL and VH Domains is rendered impossible due to a linker of insufficient length (less than about 12 amino acid residues), two of the scFv constructs may interact with one another other to form a bivalent molecule in which the VL of one chain associates with the VH of the other (reviewed in Marvin et al. (2005) "*Recombinant Approaches To IgG-Like Bispecific Antibodies*," Acta Pharmacol. Sin. 26:649-658).

In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Nearly 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', $F(ab')_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125).

In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate a chimeric antibody, a humanized antibody, or a caninized antibody, or to improve the affinity, or other characteristics of the antibody. The term "humanized" antibody refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

The epitope-binding domain of such antibodies may comprise either complete Variable Domains fused onto Constant Domains or only the complementarity determining regions (CDRs) grafted onto appropriate framework regions in the Variable Domains. Antigen-binding sites may be wild-type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains (see, for example, Winter et al. (1991) "*Man-made Antibodies*," Nature 349: 293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody constant domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

B. Bi-Specific Antibodies, Multi-Specific Diabodies and DART™ Diabodies

Natural antibodies are capable of binding to only one epitope species (i.e., they are "mono-specific"), although they may be able to bind multiple copies of that species (i.e., they may exhibit bi-valency or multi-valency). A wide variety of recombinant bi-specific antibody formats have been developed (see, e.g., PCT Publication Nos. WO 2008/003116, WO 2009/132876, WO 2008/003103, WO 2007/146968, WO 2007/146968, WO 2009/018386, WO 2012/009544, WO 2013/070565), most of which use linker peptides either to fuse the antibody core (IgA, IgD, IgE, IgG or IgM) to a further binding protein (e.g., scFv, VL VH, etc.) to, or within, the antibody core, or to fuse multiple antibody portions or to fuse (e.g. two Fab fragments or scFv) to a Heterodimerization-Promoting Domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a tri-specific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Domains have been replaced with additional VL and VH Domains, so as to form tri-valent binding molecules. PCT Publications Nos. WO 2003/025018 and WO2003012069 disclose recombinant diabodies whose individual chains contain scFv domains. PCT Publications No. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2007/075270, WO 1998/002463, WO 1992/022583 and WO 1991/003493 disclose adding additional Binding Domains or functional groups to an antibody or an antibody portion (e.g., adding a diabody to the antibody's Light Chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "'Diabodies': Small Bivalent And Bispecific Antibody Fragments," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672; WO 02/02781 (Mertens et al.); Olafsen, T. et al. (2004) "Covalent Disulfide-Linked Anti-CEA Diabody Allows Site-Specific Conjugation And Radiolabeling For Tumor Targeting Applications," Protein Eng Des Sel. 17(1):21-27; Wu, A. et al. (2001) "Multimerization Of A Chimeric Anti-CD20 Singlechain Fv-Fv Fusion Protein Is Mediated Through Variable Domain Exchange," Protein Engineering 14(2): 1025-1033; Asano et al. (2004) "A Diabody For Cancer Immunotherapy And Its Functional Enhancement By Fusion Of Human Fc Domain," Abstract 3P-683, J. Biochem. 76(8):992; Takemura, S. et al. (2000) "Construction Of A Diabody (Small Recombinant Bispecific Antibody) Using A Refolding System," Protein Eng. 13(8):583-588; Baeuerle, P. A. et al. (2009) "Bispecific T-Cell Engaging Antibodies For Cancer Therapy," Cancer Res. 69(12):4941-4944).

The design of a diabody is based on the structure of single-chain Variable Domain fragments (scFv). Such molecules are made by linking light and/or Heavy Chain Variable Domains to one another via a short linking peptide. Bird et al. (1988) ("Single-Chain Antigen-Binding Proteins," Science 242:423-426) describes an example of linking peptides which bridge approximately 3.5 nm between the carboxy terminus of one Variable Domain and the amino terminus of the other Variable Domain. Linkers of other sequences have been designed and used (Bird et al. (1988) "Single-Chain Antigen-Binding Proteins," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

U.S. Pat. No. 7,585,952 and United States Patent Publication No. 2010-0173978 concern scFv molecules that are immunospecific for ErbB2. Bi-specific T cell engagers ("BiTEs"), a type of scFv molecule has been described (WO 05/061547; Baeuerle, P et al. (2008) "BiTE: A New Class Of Antibodies That Recruit T Cells," Drugs of the Future 33: 137-147; Bargou, et al. 2008) "Tumor Regression in Cancer Patients by Very Low Doses of a T Cell-Engaging Antibody," Science 321: 974-977). Such molecules are composed of a single polypeptide chain molecule having two Antigen-Binding Domains, one of which immunospecifically binds to a CD3 epitope and the second of which immunospecifically binds to an antigen present on the surface of a target cell.

The provision of non-mono-specific diabodies provides a significant advantage: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "Improved Tumour Targeting By Disulphide Stabilized Diabodies Expressed In Pichia pastoris," Protein Eng. 10:1221). Of particular importance is the co-ligating of differing cells, for example, the cross-linking of cytotoxic T cells to tumor cells (Staerz et al. (1985) "Hybrid Antibodies Can Target Sites For Attack By T Cells," Nature 314:628-631, and Holliger et al. (1996) "Specific Killing Of Lymphoma Cells By Cytotoxic T-Cells Mediated By A Bispecific Diabody," Protein Eng. 9:299-305).

Diabody epitope-binding domains may be directed to a surface determinant of any immune effector cell such as CD3, CD16, CD32, CD64, etc., which are expressed on T lymphocytes, Natural Killer (NK) cells or other mononuclear cells. In many studies, diabody binding to effector cell determinants, e.g., Fcγ receptors (FcγR), was also found to activate the effector cell (Holliger et al. (1996) "Specific Killing Of Lymphoma Cells By Cytotoxic T-Cells Mediated By A Bispecific Diabody," Protein Eng. 9:299-305; Holliger et al. (1999) "Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "Bispecific Antibody Conjugates In Therapeutics," Adv. Drug. Deliv. Rev. 55:171-197).

For example, U.S. Pat. No. 6,171,586, concerns the production of bi-specific antibodies by proteolytically cleaving two antibodies to obtain their F(ab')2 fragments, reducing such fragments under conditions for preventing intermolecular disulfide bond formation, and then mixing the fragments to generate the bi-specific antibody). U.S. Pat. Nos. 6,551,592; 6,994,853 and 8,277,806 and PCT Publications Nos. WO 2012/156430, WO 2002/020039, WO 2000/018806 and WO 1998/003670 concern the production of tri-specific antibodies capable of simultaneously binding to T cells and other antigens on a tumor cell, and, via the Fc portion of the bi-specific antibody, to the Fc receptor of cells possessing such a receptor. PCT Publications Nos. WO 2000/018806, WO 1998/003670 and WO 2006/072152 concern the production of tri-specific antibodies capable of simultaneously binding to T cells and other antigens. United States Patent Publication No. 2008-0057054 discloses bi-specific conjugates specific for a binding element against amyloid beta oligomers and a binding element against transmembrane protein telencephalin. United States Patent Publication No. 2010-0291112 concerns bi-specific and tri-specific single-chain Fv molecules that specifically bind to a one (or two) tumor antigen(s) and an effector cell antigen (such as CD3, CD16 CD32, CD64, etc.).

PCT Publication Nos. WO 1999/042597 and WO 1998/006749 disclose antibody derivatives that comprise human Major Histocompatibility Complex binding domains, with or without bound MHC binding peptides. PCT Publication No. WO 02/072141 concerns multi-specific binding molecules whose on-rates (rates at which they bind to target molecules) and off-rates (rates at which they release target molecules) differ so as to preferentially bind to one target compared to their binding to the other such target molecule. Tri-specific molecules, for example molecules having a monovalent first portion which is an Anti-CD3 or anti-CD28 antibody, and a second portion comprising a divalent immune function exerting moiety which immunospecifically binds to one or more target ligands on a target diseased cell or immune cell.

U.S. Pat. No. 7,695,936 and Patent Publication 2007/0196363 concern bi-specific antibodies that are formed from the heavy chains of two antibodies, one of which possess a protuberance engineered into its heavy chain and the second of which possess a complementary cavity engineered into its heavy chain. The presence of such complementary "knobs" and "holes" is taught to preferentially form bi-specific hetero-antibodies (having one heavy chain of each such antibody) relative to mono-specific homo-antibodies that contain two heavy chains of the same antibody. Various bi-specific hetero-antibodies are proposed, including those that are immunospecific for CD3 and a tumor cell antigen. Various tri-specific hetero-antibodies are also proposed, including some that are immunospecific for CD3, CD8 and CD37 (a transmembrane protein expressed predominantly on B cells that is involved the regulation of T cell proliferation (Robak, T. et al. (2014) "*Anti-CD37 Antibodies For Chronic Lymphocytic Leukemia*," Expert Opin. Biol. Ther. 14(5):651-661), however, no mechanism for their production and no disclosure of their structure is provided.

PCT Publication WO2012-162561 concerns bi-specific, tetravalent binding molecules that comprise two polypeptides, each of which comprises two diabody structures, separated by an intervening CH2-CH3 Domain. The document also concerns tetravalent binding molecules composed of four polypeptide chains in which two of the polypeptide chains contain variable light and variable heavy Domains for two antigens, and in which the other two polypeptide chains contain the complementary variable heavy and variable light Domains for the antigens and a terminal CH2-CH3 Domain. The bi-specific, tetravalent binding molecules form through the association of their respective CH2-CH3 Domains. In the four polypeptide chain construct, the "light" chains are not covalently bound to the heavy chains, thus leading to instability (see, Lu, D. et al. (2005) "*A Fully Human Recombinant IgG-like Bispecific Antibody To Both The Epidermal Growth Factor Receptor And The Insulin-Like Growth Factor Receptor For Enhanced Antitumor Activity*," J. Biol. Chem. 280(20):19665-19672). The document discloses a third construct in which the chains are altered to provide such covalent bonding, but at the cost of eliminating their bi-specificity (i.e., the molecules are mono-specific). Molecules having specificity for CD2, CD3, CD4, CD8, CD161, a chemokine receptor, CD95, CCR5, etc. are disclosed. A bi-specific molecule capable of binding to both CD3 and CD8 is not disclosed.

However, the above advantages come at salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i. e., two polypeptide species) must be provided in order to form a non-mono-specific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (Takemura, S. et al. (2000) "*Construction Of A Diabody (Small Recombinant Bispecific Antibody) Using A Refolding System*," Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bi-specific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-mono-specific diabodies, termed DARTs™ (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010)

"Therapeutic Control Of B Cell Activation Via Recruitment Of Fcgamma Receptor IIb (CD32B) Inhibitory Function With A Novel Bispecific Antibody Scaffold," Arthritis Rheum. 62(7):1933-1943; Johnson, S. et al. (2010) "Effector Cell Recruitment With Novel Fv-Based Dual Affinity Re-Targeting Protein Leads To Potent Tumor Cytolysis And in vivo B-Cell Depletion," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond two polypeptide chains. For example, the addition of a cysteine residue to the C-terminus of such constructs has been shown to allow disulfide bonding between the polypeptide chains, stabilizing the resulting heterodimer without interfering with the binding characteristics of the bivalent molecule.

There are many DART™ embodiments. Each of the two polypeptides of the simplest DART™ embodiment comprises three Domains (FIG. 1). The first polypeptide comprises: (i) a first domain that comprises a binding region of a Light Chain Variable Domain of the a first immunoglobulin (VL1), (ii) a second domain that comprises a binding region of a Heavy Chain Variable Domain of a second immunoglobulin (VH2), and (iii) a third domain that contains a cysteine residue (or a Cysteine-Containing Domain) and a Heterodimerization-Promoting Domain that serves to promote heterodimerization with the second polypeptide chain. The cysteine residue (or a Cysteine-Containing Domain) of the third domain serves to promote the covalent bonding of the first polypeptide chain to the second polypeptide chain of the diabody. The second polypeptide contains: (i) a complementary first domain (a VL2-containing Domain), (ii) a complementary second domain (a VH1-containing Domain) and (iii) a third domain that contains a cysteine residue (or a Cysteine-Containing Domain) and, optionally, a complementary Heterodimerization-Promoting Domain that complexes with the Heterodimerization-Promoting Domain of the first polypeptide chain in order to promote heterodimerization with the first polypeptide chain. The cysteine residue (or a Cysteine-Containing Domain) of the third domain of the second polypeptide chain serves to promote the covalent bonding of the second polypeptide chain to the first polypeptide chain of the diabody. Such molecules are stable, potent and have the ability to simultaneously bind two or more antigens. They are able to promote re-directed T cell mediated killing of cells expressing target antigens.

In one embodiment, the third domains of the first and second polypeptides each contain a cysteine residue, which serves to bind the polypeptides together via a disulfide bond. The third domain of one or both of the polypeptides may additionally possesses the sequence of a CH2-CH3 Domain, such that complexing of the diabody polypeptides forms an Fc Domain that is capable of binding to the Fc receptor of cells (such as B lymphocytes, dendritic cells, Natural Killer cells, macrophages, neutrophils, eosinophils, basophils and mast cells) (FIGS. 2A-2B).

Many variations of such molecules have been described (see, e.g., United States Patent Publications No. 2013-0295121; 2010-0174053 and 2009-0060910; European Patent Publication No. EP 2714079; EP 2601216; EP 2376109; EP 2158221 and PCT Publications Nos. WO 2012/162068; WO 2012/018687; WO 2010/080538). These Fc-bearing DARTs may comprise three polypeptide chains (e.g., FIG. 2B). The first polypeptide chain of such a diabody contains three domains: (i) a VL1-containing Domain, (ii) a VH2-containing Domain and (iii) a domain containing a cysteine residue (or a Cysteine-Containing Domain) and a Heterodimerization-Promoting Domain, and (iv) a cysteine residue (or a Cysteine-Containing Domain and a CH2-CH3 Domain. The second polypeptide chain of such DART™ contains: (i) a VL2-containing Domain, (ii) a VH1-containing Domain and (iii) a Domain that contains a cysteine residue (or a Cysteine-Containing Domain) and a Heterodimerization-Promoting Domain that promotes heterodimerization with the first polypeptide chain. The cysteine residue (or a Cysteine-Containing Domain) of the third domain of the second polypeptide chain serves to promote the covalent bonding of the second polypeptide chain to the first polypeptide chain of the diabody. The third polypeptide of such DART™ comprises a cysteine residue (or a Cysteine-Containing Domain) and a CH2-CH3 Domain. Thus, the first and second polypeptide chains of such DART™ associate together to form a VL1/VH1 binding site that is capable of binding to the epitope, as well as a VL2/VH2 binding site that is capable of binding to the second epitope. The first and second polypeptides are bonded to one another through a disulfide bond involving cysteine residues in their respective third domains. Notably, the first and third polypeptide chains complex with one another to form an Fc Domain that is stabilized via a disulfide bond. Such diabodies have enhanced potency. Such Fc-bearing DARTs™ may have either of two orientations (Table 1):

TABLE 1

| First Orientation | 3rd Chain | NH$_2$—CH2—CH3—COOH |
|---|---|---|
| | 1st Chain | NH$_2$-VL1-VH2-Cys-Heterodimer-Promoting Domain-CH2—CH3—COOH |
| | 2nd Chain | NH$_2$-VL2-VH1-Cys-Heterodimer-Promoting Domain-COOH |
| Second Orientation | 3rd Chain | NH$_2$—CH2—CH3—COOH |
| | 1st Chain | NH$_2$—CH2—CH3-VL1-VH2-Cys-Heterodimer-Promoting Domain-COOH |
| | 2nd Chain | NH$_2$-VL2-VH1-Cys-Heterodimer-Promoting Domain-COOH |

Even more complex DART™ diabodies, termed Ig-DART™ (FIGS. 3A-3B) and Fc-DART™ diabodies (FIG. 3C) have been described (WO 2012/018687). Fc-DARTs™ have four polypeptide chains. The first and third polypeptide chains of such a diabody contain three Domains: (i) a VL1-containing Domain, (ii) a VH2-containing Domain and (iii) a Domain containing a CH2-CH3 sequence. The second and fourth polypeptide of the Fc-DART™ contain: (i) a VL2-containing Domain, (ii) a VH1-containing Domain and (iii) a Domain that promotes heterodimerization and covalent bonding with the Fc-DART's™ first polypeptide chain. The third and fourth, and the first and second polypeptide chains may be the same or different so as to permit tetravalent binding that is either mono-specific, bi-specific or tetra-specific. Such more complex DART™ molecules also possess Cysteine-Containing Domains which function to form a covalently bonded complex. Fc-DART™ diabodies contain CH1 and CL Domains.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700)

which are formed by the homo-dimerization of two identical chains each possessing a VH1, VL2, VH2, and VL2 Domain.

However, despite all prior advances, a need remains for compositions that could provide improved therapeutic value to patients suffering from cancer or other diseases and conditions. The present invention is directed to this and other goals.

SUMMARY OF THE INVENTION

The present invention relates to Tri-Specific Binding Molecules, which are multi-chain polypeptide molecules that possess three Binding Domains and are thus capable of mediating coordinated binding to three epitopes. The Tri-Specific Binding Molecule is preferably characterized in possessing binding domains that permit it to immunospecifically bind to: (1) an epitope of a first Cancer Antigen, (2) an epitope of a second Cancer Antigen, and (3) an epitope of a molecule that is expressed on the surface of an immune system effector cell, and are thus capable of localizing an immune system effector cell to a cell that expresses a Cancer Antigen, so as to thereby facilitate the killing of such cancer cell.

In detail, the invention provides a Tri-Specific Binding Molecule capable of immunospecifically binding to three different epitopes, said Epitopes being Epitope I, Epitope II, and Epitope III, wherein two of three epitopes are epitopes of Cancer Antigen(s), and the third of said epitopes is an epitope of an Effector Cell Antigen.

The invention particularly concerns the embodiment of such Tri-Specific Binding Molecule wherein the molecule comprises four different polypeptide chains covalently complexed together and comprises:

(I) an Antigen-Binding Domain I that is capable of immunospecifically binding to an Epitope I present on a first antigen, and an Antigen-Binding Domain II that is capable of immunospecifically binding to an Epitope II present on a second antigen, wherein the Antigen-Binding Domain I and the Antigen-Binding Domain II are both Diabody-Type Binding Domains;

(II) an Antigen-Binding Domain III that is capable of immunospecifically binding to an Epitope III present on a third antigen; and (III) an Fc Domain that is formed by the complexing of two CH2-CH3 Domains to one another;

wherein one of Epitope I, Epitope II or Epitope III is an epitope of an Effector Cell Antigen, a second of Epitope I, Epitope II or Epitope III is an epitope of a first Cancer Antigen, and the third of Epitope I, Epitope II or Epitope III is an epitope of a second Cancer Antigen, and wherein the Antigen-Binding Domains I, II and III of the Binding Molecules mediate coordinated binding of an immune system effector cell expressing the Effector Cell Antigen and a cancer cell expressing the first and second Cancer Antigens.

The invention particularly concerns the embodiment of such Tri-Specific Binding Molecules wherein the Fc Domain is capable of binding to an Fc Receptor arrayed on the surface of a cell.

The invention additionally concerns the embodiment of such Tri-Specific Binding Molecules wherein the Effector Cell Antigen is arrayed on the surface of an effector cell and wherein the Cancer Antigens are arrayed on the surface of a cancer cell, and wherein the immunospecific binding is sufficient to co-localize the Effector Cell Antigen, and the Cancer Antigens, thereby facilitating the activation of the effector cell against the cancer cell.

The invention additionally concerns the embodiment of such Tri-Specific Binding Molecules wherein the Effector Cell Antigen is selected from the group consisting of: CD2, CD3, CD16, CD19, CD20, CD22, CD32B, CD64, the B cell Receptor (BCR), the T cell Receptor (TCR), and the NKG2D Receptor.

The invention additionally concerns the embodiment of such Tri-Specific Binding Molecules wherein the first and second Cancer Antigens are independently selected from the group consisting of: colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7-H3; beta-catenin; blood group $ALe^b/Le^y$; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-1A; CO-43 (blood group $Le^b$); CO-514 (blood group $Le^a$); CTA-1; CTLA4; Cytokeratin 8; antigen D1.1; antigen $D_1$56-22; DR5; $E_1$ series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; $G_{D2}$; $G_{D3}$; GICA 19-9; $G_{M2}$; gp100; human leukemia T cell antigen Gp37; melanoma antigen gp75; gpA33; HER2 antigen ($p185^{HER2}$); human milk fat globule antigen (HMFG); human papillomavirus-E6/human papillomavirus-E7; high molecular weight melanoma antigen (HMW-MAA); I antigen (differentiation antigen) I(Ma); Integrin Alpha-V-Beta-6 Integrinβ6 (ITGB6); Interleukin-13; Receptor α2 (IL13Rα2); JAM-3; KID3; KID31; KS 1/4 pan-carcinoma antigen; human lung carcinoma antigens L6 and L20; LEA; LUCA-2; M1:22:25:8; M18; M39; MAGE-1; MAGE-3; MART; MUC-1; MUM-1; Myl; N-acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R24; ROR1; sphingolipids; SSEA-1; SSEA-3; SSEA-4; sTn; T cell receptor derived peptide; $T_5A_7$; TAG-72; TL5 (blood group A); TNF-α receptor; TNF-β receptor; TNF-γ receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, $Le^y$.

The invention additionally concerns the embodiment of such Tri-Specific Binding Molecules wherein the first and second Cancer Antigens are selected from the group consisting of: CD2, CD317, CEACAM5, CEACAM6, DR5, EphA2, gpA33, Her2, B7-H3; EGF, EGFR, VEGF and VEGFR.

The invention additionally concerns the embodiment of such Tri-Specific Binding Molecules wherein the Non-Diabody-Type Binding Domain III comprises the Fab-Type Binding Domain ($VL_{III}/VH_{III}$) that is capable of immunospecifically binding to an Epitope III, wherein the molecule comprises:

(A) a first polypeptide chain that comprises in the N-terminus to C-terminus direction:
  (1) a light chain variable Domain of an immunoglobulin capable of binding to a first of the three epitopes ($VL_I$);

(2) a heavy chain variable Domain of an immunoglobulin capable of binding to a second of the three epitopes ($VH_{II}$);
(3) a Heterodimer-Promoting Domain; and
(4) CH2 and CH3 Domains of an IgG;
(B) a second polypeptide chain that comprises, in the N-terminus to C-terminus direction:
(1) a light chain variable Domain of an immunoglobulin capable of binding to the second of the three epitopes ($VL_{II}$);
(2) a heavy chain variable Domain of an immunoglobulin capable of binding to the first of the three epitopes ($VH_I$); and
(3) a complementary Heterodimer-Promoting Domain;
(C) a third polypeptide chain that comprises, in the N-terminus to C-terminus direction:
(1) a heavy chain variable Domain of an immunoglobulin capable of binding to a third of the three epitopes ($VH_{III}$); and
(2) a CH1 Domain, a Hinge Domain, and a CH2-CH3 Domain of an IgG; and
(D) a fourth polypeptide chain that comprises, in the N-terminus to C-terminus direction:
(1) a light chain variable Domain of an immunoglobulin capable of binding to the third of the three epitopes ($VL_{III}$); and
(2) a light chain constant Domain (CL);
wherein:
(i) the $VL_I$ and $VH_I$ Domains associate to form a Domain capable of binding the first epitope;
(ii) the $VL_{II}$ and $VH_{II}$ Domains associate to form a Domain capable of binding the second epitope;
(iii) the $VL_{III}$ and $VH_{III}$ Domains associate to form a Domain capable of binding the third epitope;
(iv) the CH2-CH3 Domain of the first polypeptide chain and the CH2-CH3 Domain of the third polypeptide chain associate to form an Fc Domain;
(v) the first and second polypeptide chains are covalently bonded to one another;
(vi) the first and third polypeptide chains are covalently bonded to one another; and
(vii) the third and fourth polypeptide chains are covalently bonded to one another.

The invention additionally concerns the embodiment of such Tri-Specific Binding Molecules wherein:
(A) the Heterodimer-Promoting Domain is an E-coil and the complementary Heterodimer-Promoting Domain is a K-coil; or
(B) the Heterodimer-Promoting Domain is a K-coil and the complementary Heterodimer-Promoting Domain is an E-coil.

The invention additionally concerns the embodiment of such Tri-Specific Binding Molecules wherein:
(A) the CH2-CH3 Domains of the first and third polypeptide chains each have the sequence of SEQ ID NO:1, such that the Fc Domain formed from their association exhibits normal FcγR-mediated effector function; or
(B) the CH2-CH3 Domain of the first and third polypeptide chains comprise at least one amino acid substitution, relative to the sequence of SEQ ID NO:1, such that the Fc Domain formed from their association exhibits altered FcγR-mediated effector function.

The invention additionally concerns the embodiment of such Tri-Specific Binding Molecules wherein the at least one amino acid substitution comprises at least one amino acid substitution selected from the group consisting of: L235V, F243L, R292P, Y300L, V305I, and P396L, wherein the numbering is that of the EU index as in Kabat.

The invention additionally concerns the embodiment of such Tri-Specific Binding Molecules wherein the at least one amino acid substitution comprises:
(A) at least one substitution selected from the group consisting of F243L, R292P, Y300L, V305I, and P396L;
(B) at least two substitutions selected from the group consisting of:
(1) F243L and P396L;
(2) F243L and R292P; and
(3) R292P and V305I;
(C) at least three substitutions selected from the group consisting of:
(1) F243L, R292P and Y300L;
(2) F243L, R292P and V305I;
(3) F243L, R292P and P396L; and
(4) R292P, V305I and P396L;
(D) at least four substitutions selected from the group consisting of:
(1) F243L, R292P, Y300L and P396L; and
(2) F243L, R292P, V305I and P396L;
or
(E) at least the five substitutions selected from the group consisting of:
(1) F243L, R292P, Y300L, V305I and P396L; and
(2) L235V, F243L, R292P, Y300L and P396L.

The invention additionally concerns the embodiment of such Tri-Specific Binding Molecules wherein the CH2-CH3 Domain of the first and third polypeptide chains differ from one another and have an amino acid sequence selected from the group consisting of SEQ ID NO:52 and SEQ ID NO:53.

The invention additionally concerns the embodiment of such Tri-Specific Binding Molecules wherein:
(A) the Epitope I, Epitope II and Epitope III are, respectively, an epitope of the first Cancer Antigen, an epitope of the second Cancer Antigen and an epitope of the Effector Cell Antigen;
(B) the Epitope I, Epitope II and Epitope III are, respectively, an epitope of the first Cancer Antigen, an epitope of the Effector Cell Antigen and an epitope of the second Cancer Antigen;
(C) the Epitope I, Epitope II and Epitope III are, respectively, an epitope of second Cancer Antigen, an epitope of the first Cancer Antigen, and an epitope of the Effector Cell Antigen;
(D) the Epitope I, Epitope II and Epitope III are, respectively, an epitope of the second Cancer Antigen, an epitope of the Effector Cell Antigen and an epitope of the first Cancer Antigen;
(E) the Epitope I, Epitope II and Epitope III are, respectively, an epitope of the Effector Cell Antigen, an epitope of the first Cancer Antigen, and an epitope of the second Cancer Antigen;
and
(F) the Epitope I, Epitope II and Epitope III are, respectively, an epitope of the Effector Cell Antigen, an epitope of second Cancer Antigen, and an epitope of the first Cancer Antigen.

The invention additionally concerns the embodiment of such Tri-Specific Binding Molecules wherein:
(A) the epitope of an Effector Cell Antigen is a CD2 epitope recognized by antibody Lo-CD2a;
(B) the epitope of an Effector Cell Antigen is a CD3 epitope recognized by antibody OKT3, M291, YTH12.5, Anti-CD3 mAb 1 or Anti-CD3 mAb 2;

(C) the epitope of an Effector Cell Antigen is a CD16 epitope recognized by antibody 3G8 or A9;
(D) the epitope of an Effector Cell Antigen is a CD19 epitope recognized by antibody MD1342, MEDI-551, blinatumomab or HD37;
(E) the epitope of an Effector Cell Antigen is a CD20 epitope recognized by antibody rituximab, ibritumomab, ofatumumab, and tositumomab;
(F) the epitope of an Effector Cell Antigen is a CD22 epitope recognized by antibody epratuzumab;
(G) the epitope of an Effector Cell Antigen is a CD32B epitope recognized by antibody CD32B mAb 1;
(H) the epitope of an Effector Cell Antigen is a CD64 epitope recognized by antibody CD64 mAb 1;
(I) the epitope of an Effector Cell Antigen is a BCR/CD79 epitope recognized by antibody CD79 mAb 1;
(J) the epitope of an Effector Cell Antigen is a TCR epitope recognized by antibody BMA 031;
or
(K) the epitope of an Effector Cell Antigen is a NKG2D Receptor epitope recognized by antibody KYK-2.0.

The invention additionally concerns a pharmaceutical composition that comprises any of the above-described Tri-Specific Binding Molecules, and a pharmaceutically acceptable carrier, excipient or diluent.

The invention additionally concerns the embodiment of such pharmaceutical composition or of any such Tri-Specific Binding Molecules wherein the Tri-Specific Binding Molecule is used in the treatment of cancer.

The invention additionally concerns the embodiment of such pharmaceutical compositions or such Tri-Specific Binding Molecules wherein the cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention additionally concerns the embodiment of such pharmaceutical compositions or such Tri-Specific Binding Molecules wherein the cancer is acolorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer or a rectal cancer.

The invention additionally concerns the embodiment of such pharmaceutical compositions or such Tri-Specific Binding Molecules the cancer is acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

BRIEF DESCRIPTION OF THE DRAWINGS

FIG. 1A shows a diagrammatic representation of the Domains of a basic DART™ diabody. FIG. 1B provides a schematic of a covalently bonded diabody composed of two polypeptide chains, each having a Heterodimer-Promoting Domain VL and VH domains that recognize the same epitope are shown using the same shading.

FIG. 3A shows an Ig diabody. FIG. 3B shows an Ig diabody, which contains E-coil and K-coil heterodimer-promoting domains. FIG. 3C, shows an Fc-DART™ diabody that contains antibody CH1 and CL domains. The notation "VL1" and "VH1" denote respectively, the Variable Light Chain Domain and Variable Heavy Chain Domain that bind the "first" epitope. Similarly, the notation "VL2" and "VH2" denote respectively, the Variable Light Chain Domain and Variable Heavy Chain Domain that bind the "second" epitope.

FIGS. 4A, 4B and 4G illustrate embodiments in which the Tri-Specific Binding Molecule is composed of four polypeptide chains. FIGS. 4C, 4D, 4E and 4F illustrate embodiments in which the binding molecule is composed of three polypeptide chains. The molecule may possess Hinge and/or CL domains (FIGS. 4A, 4B, 4C, 4E) or may contain an alternative linker peptide (FIG. 4D, 4F, 4G).

FIGS. 5A and 5B illustrate embodiments in which the Tri-Specific Binding Molecule is composed of four polypeptide chains. FIG. 5C and FIG. 5E illustrate an embodiment in which the binding molecule is composed of three polypeptide chains. FIG. 5D illustrates an embodiment in which the binding molecule is composed of five polypeptide chains. The molecule may possess Hinge and/or CL domains or may contain alternative linker peptides.

FIG. 9A shows the binding obtained when trispecific molecules: EphA2 mAb 1×CD3 mAb 2×DR5 mAb 1; EphA2 mAb 1×CD3 mAb 2×gpA33 mAb 1; and gpA33 mAb 1×CD3 mAb 2×DR5 mAb 1 are incubated in the presence of EphA2-expressing CHO cells. FIG. 9B shows the binding obtained when such trispecific molecules are incubated in the presence of DR5-expressing CHO cells. FIG. 9C shows the binding obtained when such trispecific molecules are incubated in the presence of DU145 human prostate cells that express EphA2 and DR5, but not gpA33.

FIG. 10A shows the percent cytotoxicity obtained by incubating trispecific molecules: EphA2 mAb 1×CD3 mAb 2×DR5 mAb 1; EphA2 mAb 1×CD3 mAb 2×gpA33 mAb 1; and gpA33 mAb 1×CD3 mAb 2×DR5 mAb 1 are incubated in the presence of EphA2-expressing CHO cells and cytotoxic lymphocytes. FIG. 10B shows the percent cytotoxicity obtained when such trispecific molecules are incubated in the presence of DR5-expressing CHO cells and cytotoxic lymphocytes. FIG. 10C shows the cytotoxicity obtained when such trispecific molecules are incubated in the presence of DU145 human prostate cells and cytotoxic lymphocytes. DU145 cells express EphA2 and DR5, but not gpA33. Cytotoxicity was measured by the increase in luminescence caused by the release of luciferase upon cell lysis.

DETAILED DESCRIPTION OF THE INVENTION

Figure 1A:
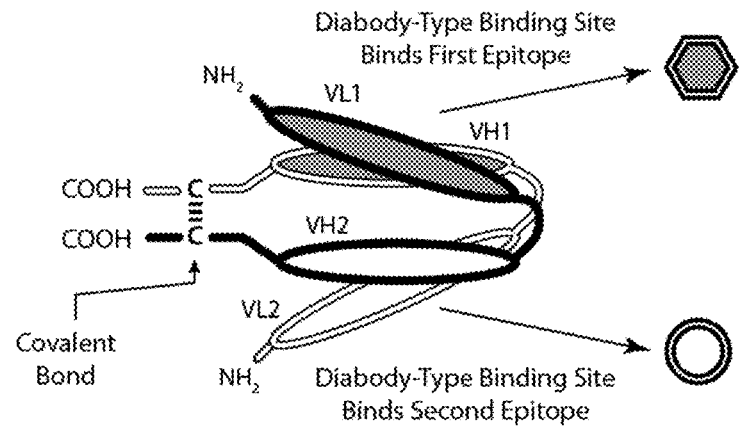
FIGS. 1A-1B show diagrammatic representation of the Domains of DART™ diabodies.
Figure 1B:
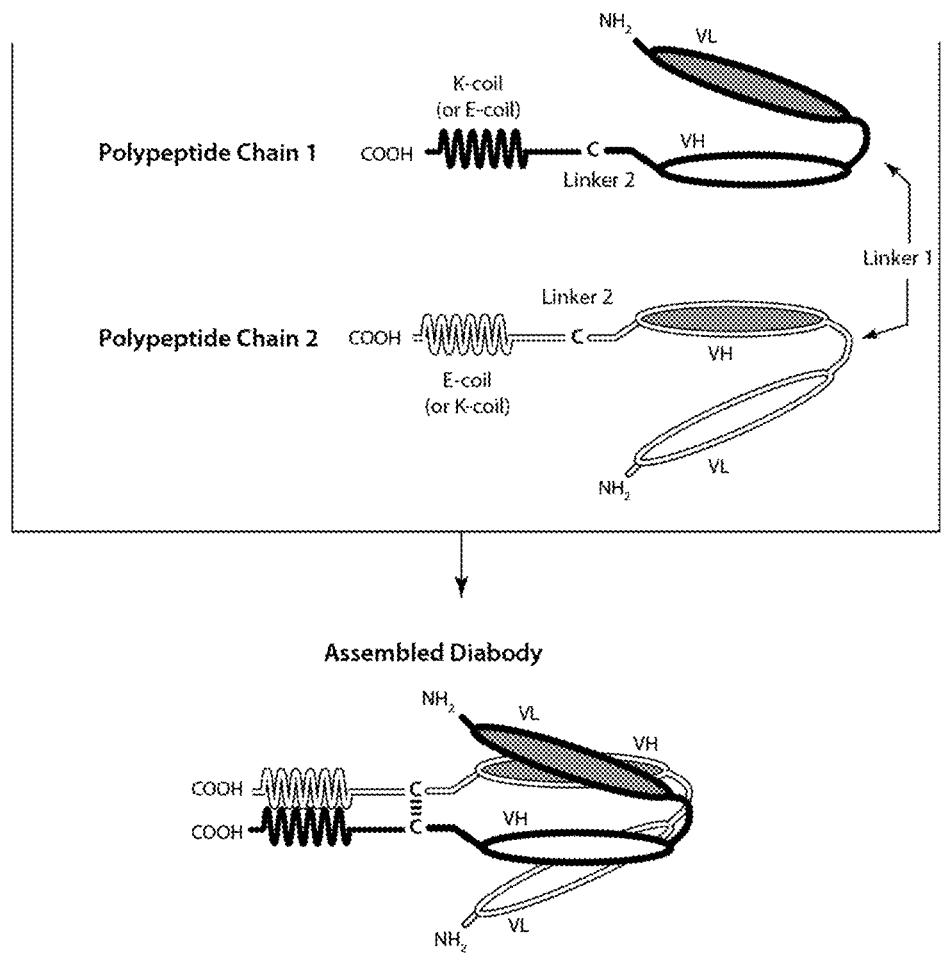
Figure 2A:
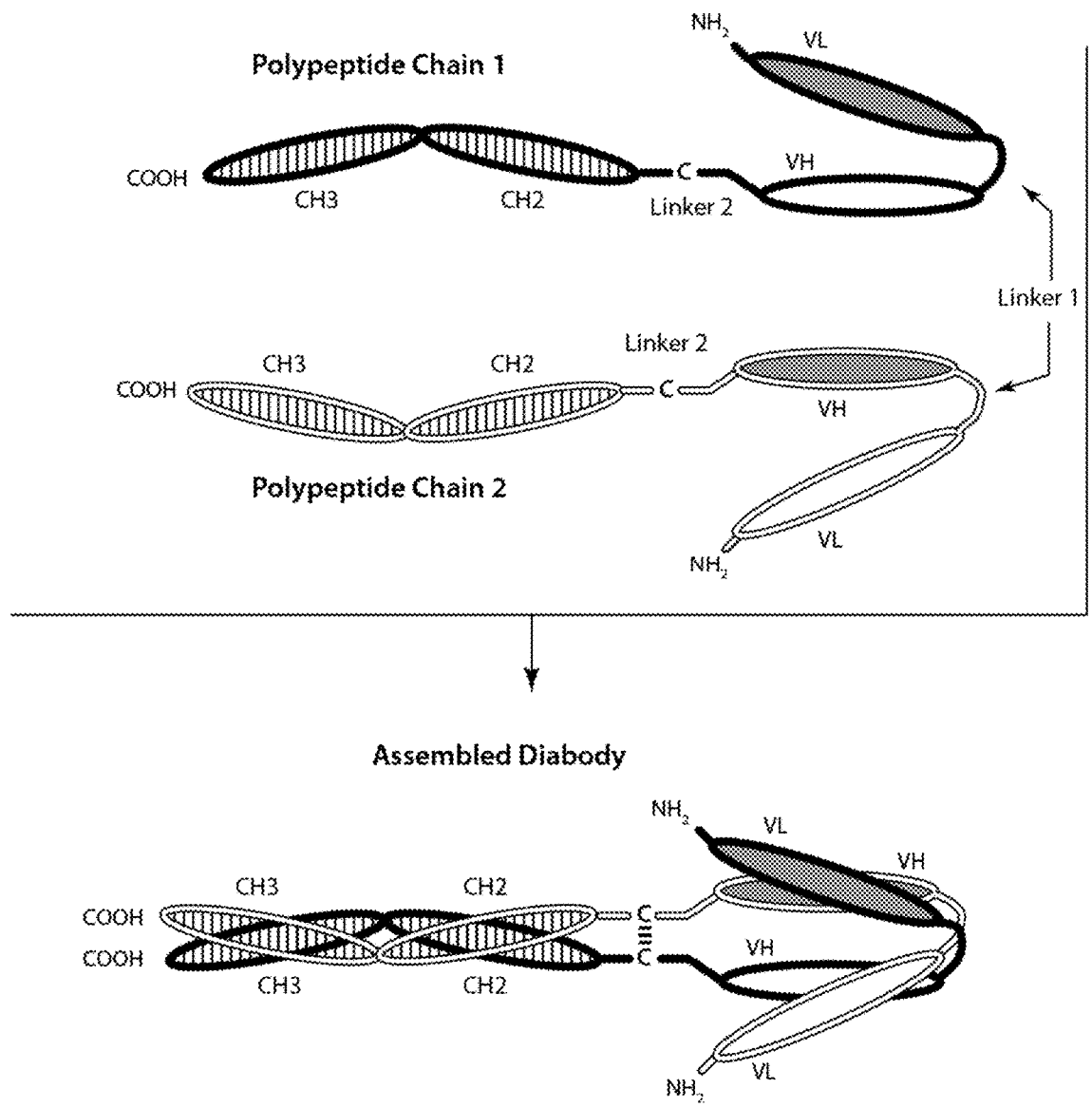
FIGS. 2A-2B provide a schematic of covalently bonded diabodies composed of two polypeptide chains, each having a CH2 and CH3 Domain (FIG. 2A) or in which only one has a CH2 and CH3 Domain (FIG. 2B), such that the associated chains form an Fc Domain that comprises all or part of a naturally occurring Fc Domain. VL and VH domains that recognize the same epitope are shown using the same shading.
Figure 2B:
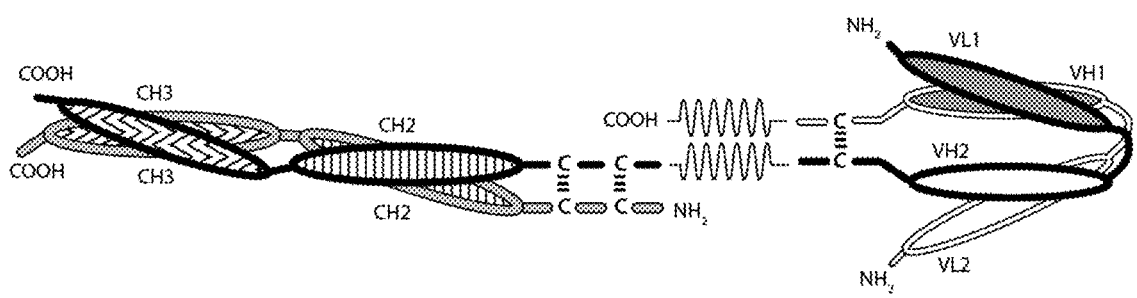
Figure 3A:
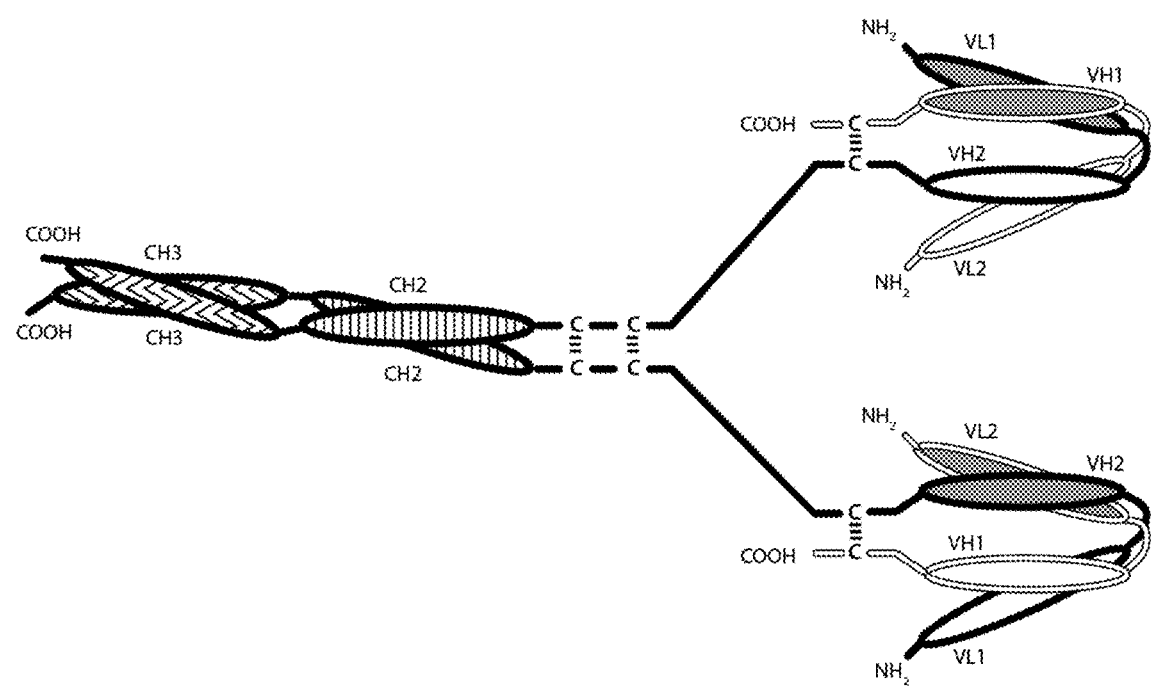
FIGS. 3A-3C provide schematics showing tetravalent diabodies composed of two pairs of polypeptide chains. The pairs are different, thus resulting in a bi-specific molecule that is bivalent with respect to each of two epitopes, in which one is an epitope of DR5 and the other is an epitope of a molecule present on the surface of an effector cell. One polypeptide of each pair possesses a CH2 and CH3 Domain, such that the associated chains form an Fc Domain that comprises all or part of a naturally occurring Fc Domain. VL and VH domains that recognize the same epitope are shown using the same shading. Only one pair of epitopes (shown with the same shading) is capable of binding to DR5.
Figure 3B:
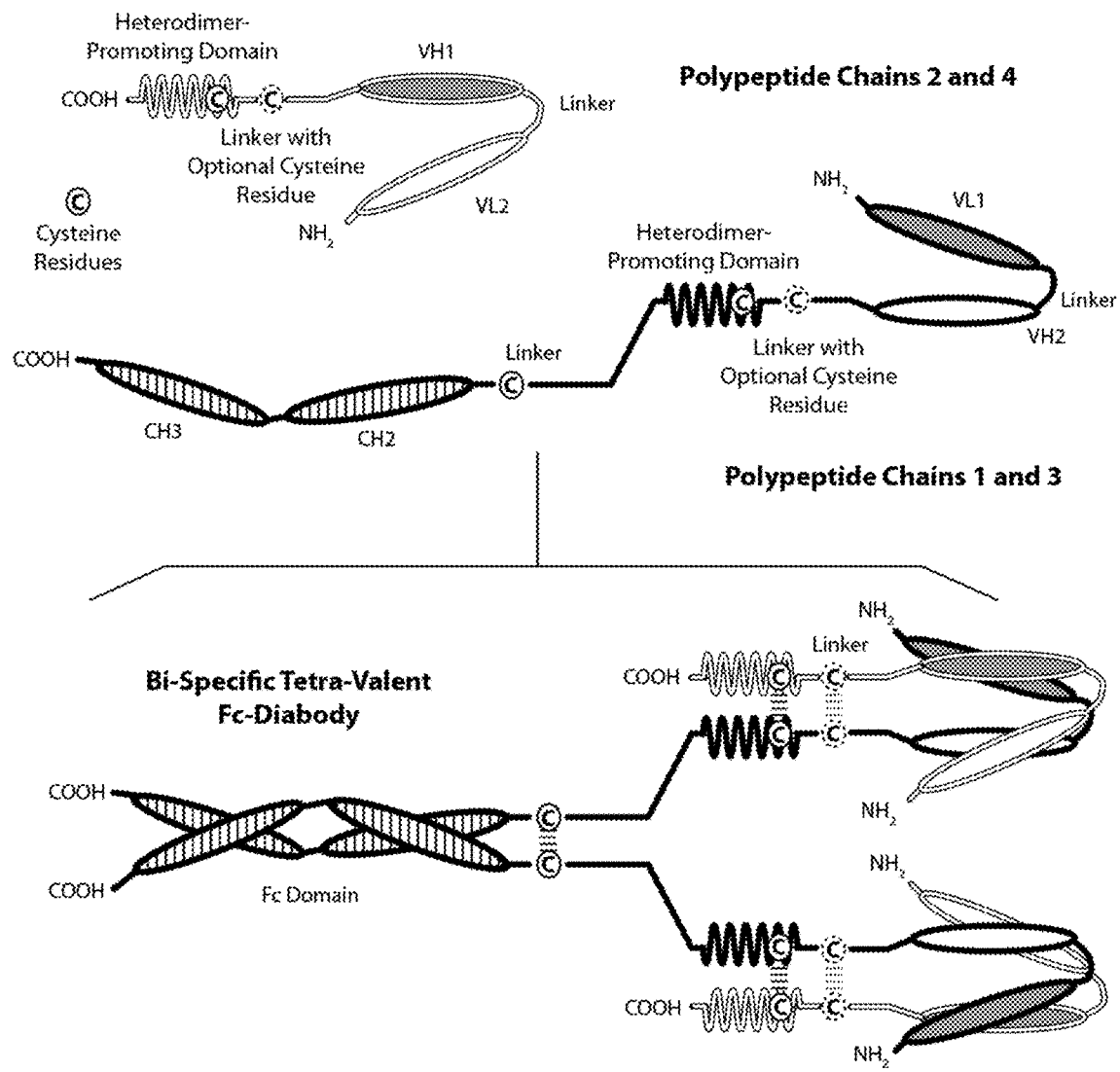
Figure 3C:
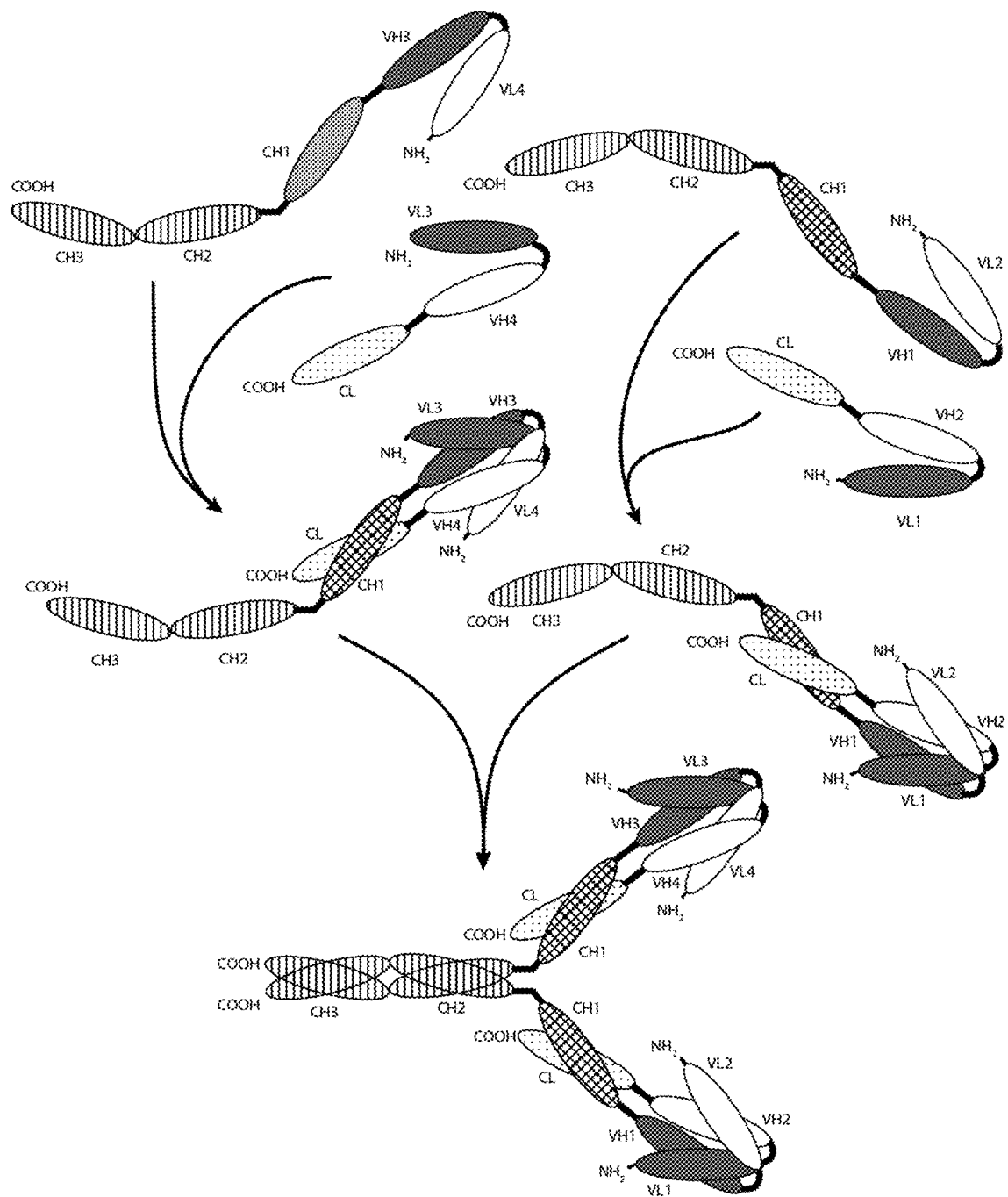
Figure 4A:
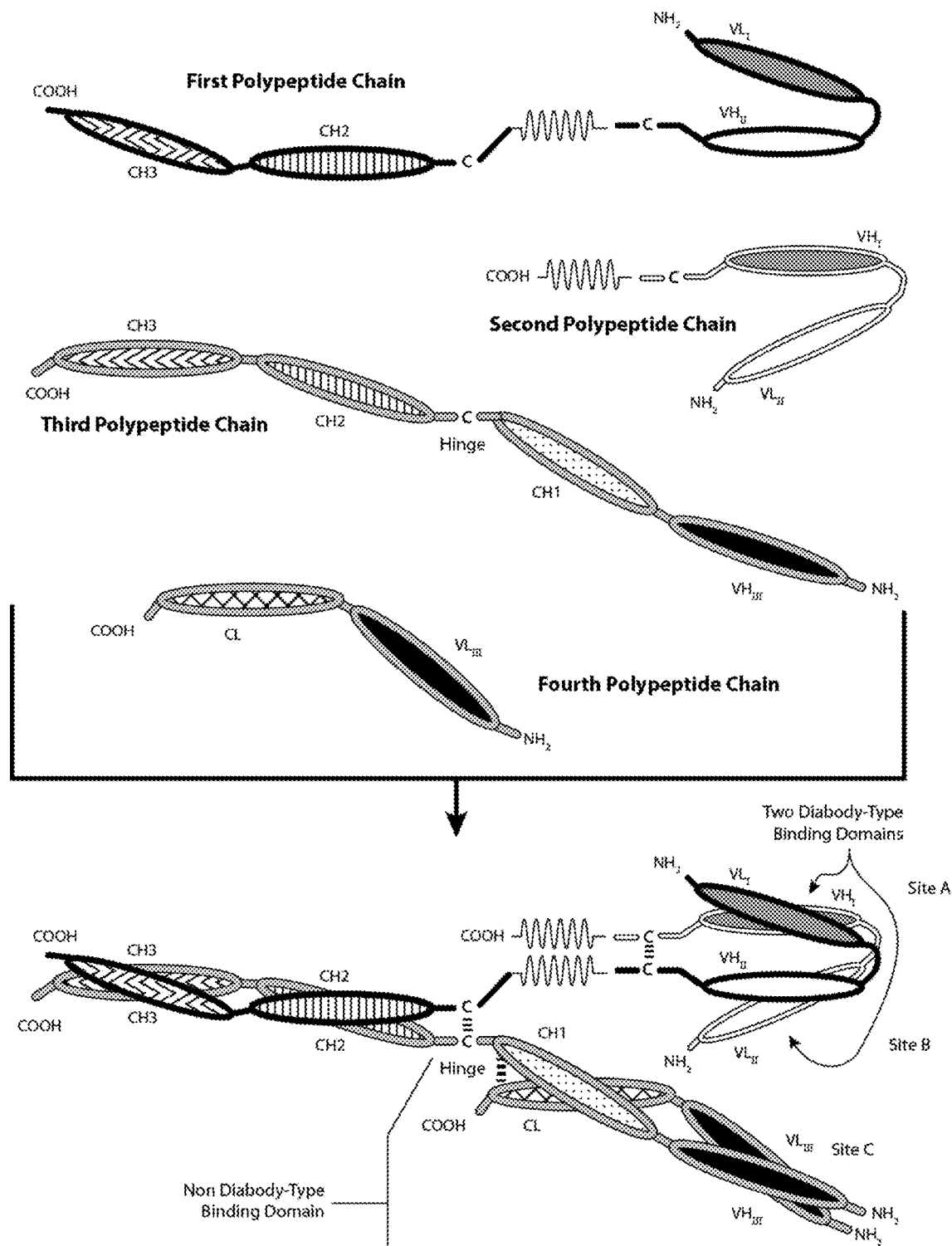
FIGS. 4A-4G provide a diagrammatic representation of the Domains of preferred Tri-Specific Binding Molecules of the present invention. The Figures illustrate schematically the order and orientation of the Domains of embodiments of the preferred Tri-Specific Binding Molecules of the present invention.
Figure 4B:
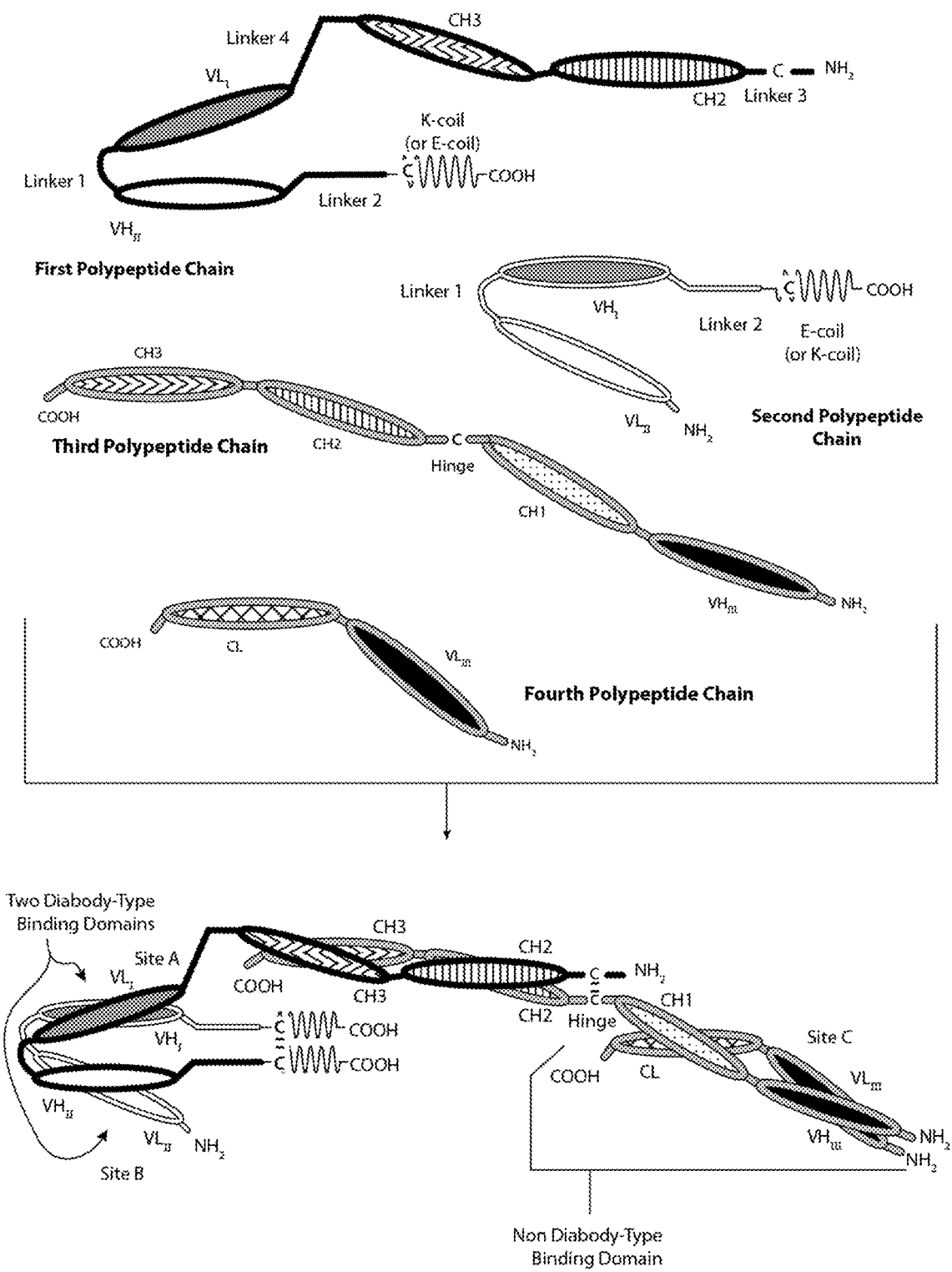
Figure 4C:
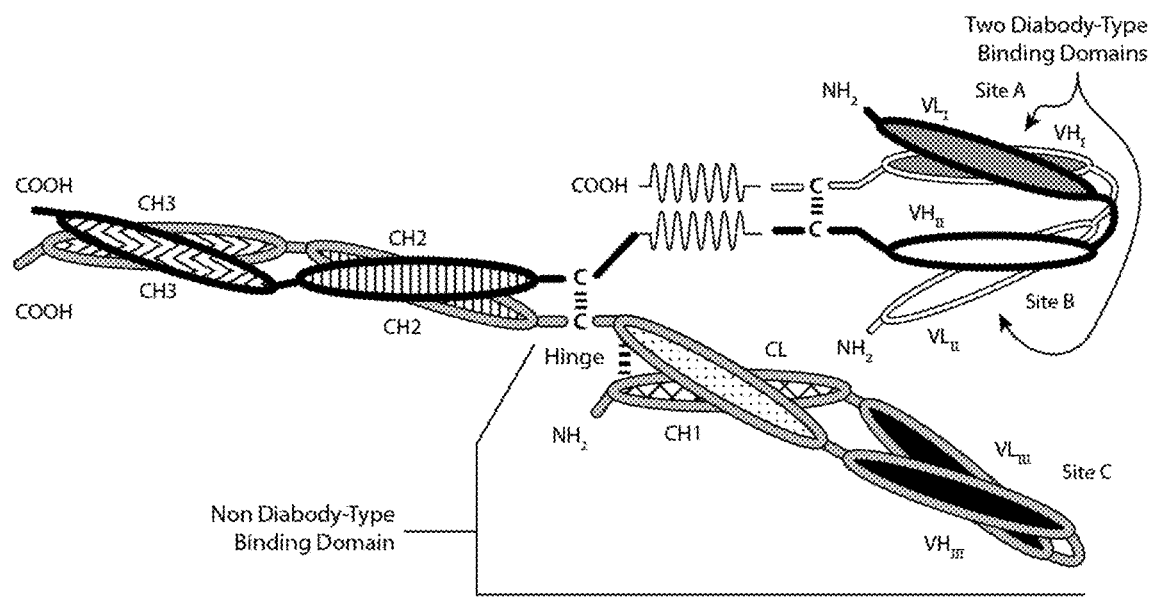
Figure 4D:
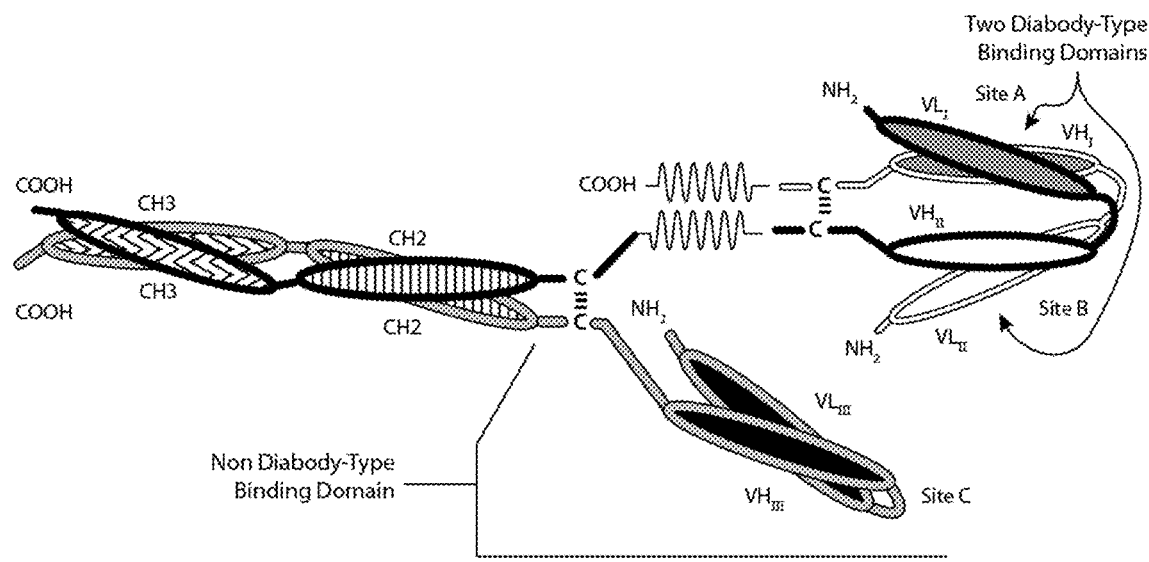
Figure 4E:
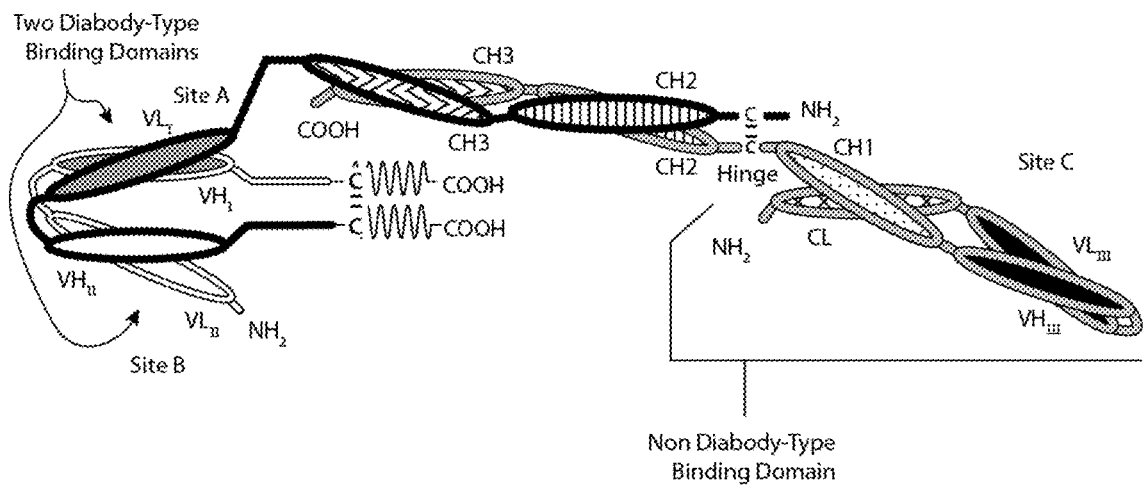
Figure 4F:
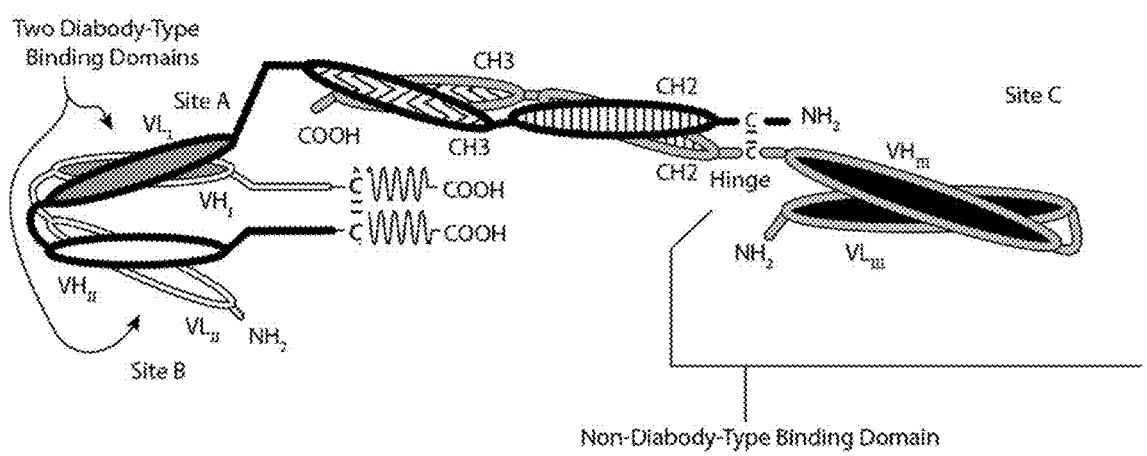
Figure 4G:
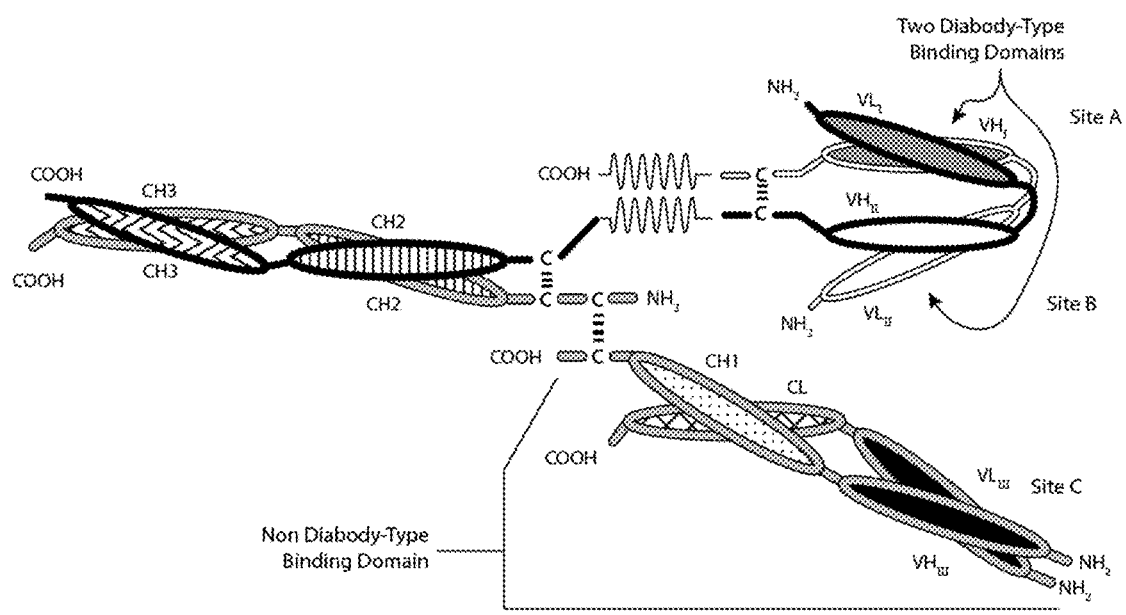
Figure 5A:
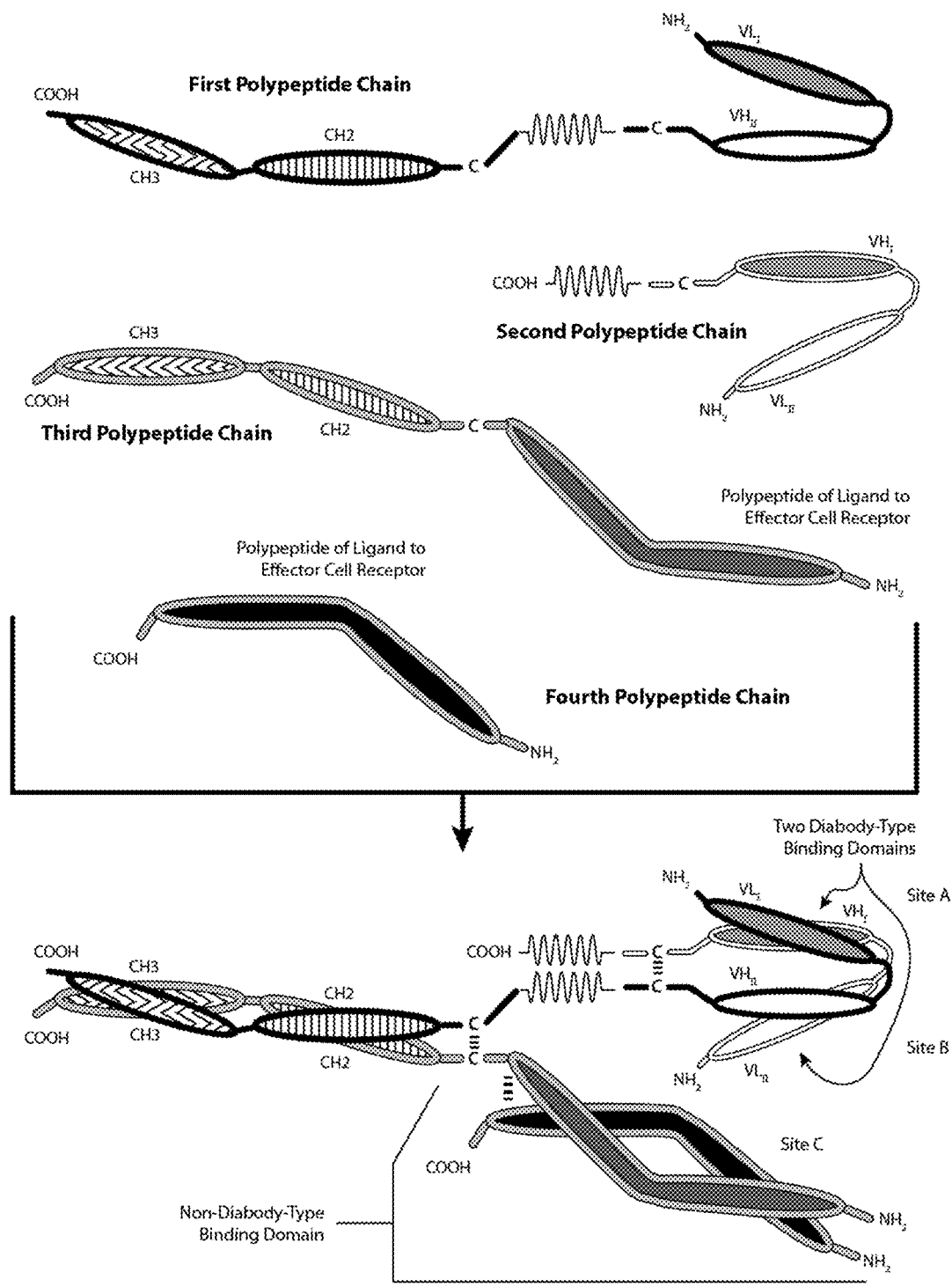
FIGS. 5A-5E provide a diagrammatic representation of the Domains of an alternative embodiment of the Tri- Specific Binding Molecules of the present invention, in which the Effector Cell-Binding Domain is composed of an Effector Cell Receptor-Type Binding Domai rather than a Diabody-Type Binding Domain or a Fab-Type Binding Domain.
Figure 5B:
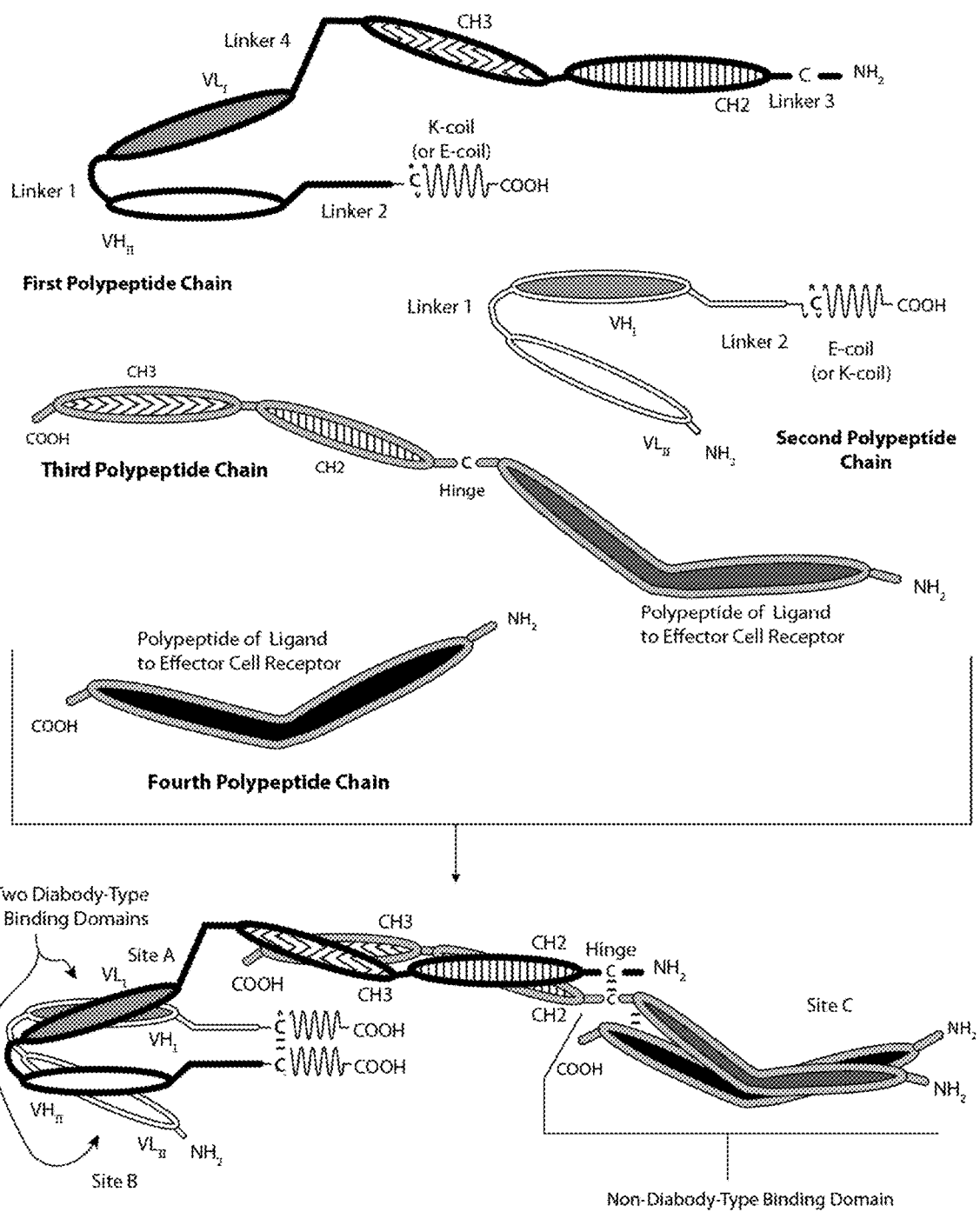
Figure 5C:
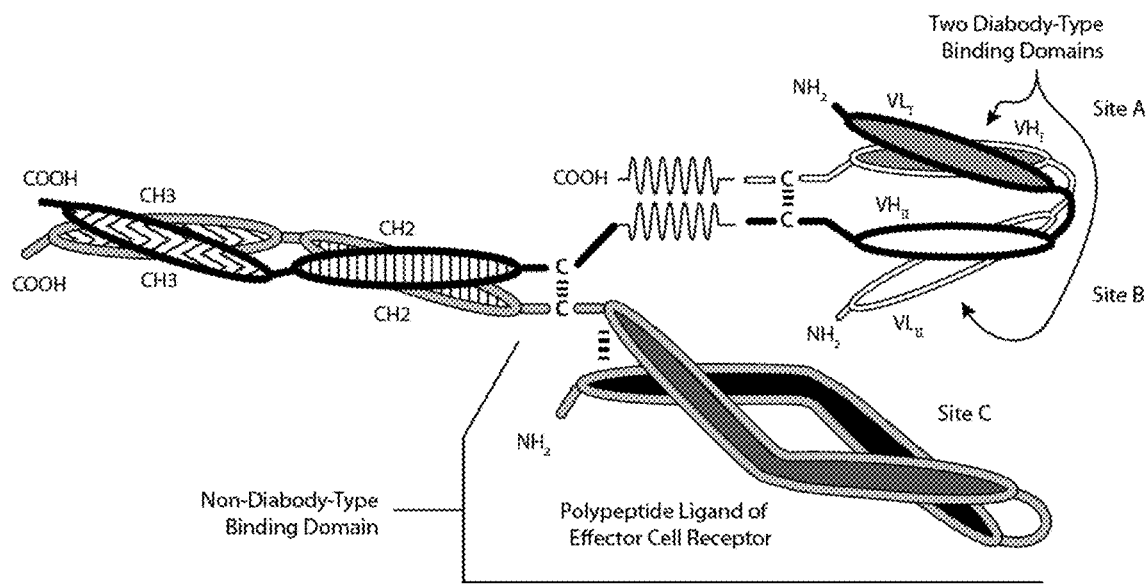
Figure 5D:
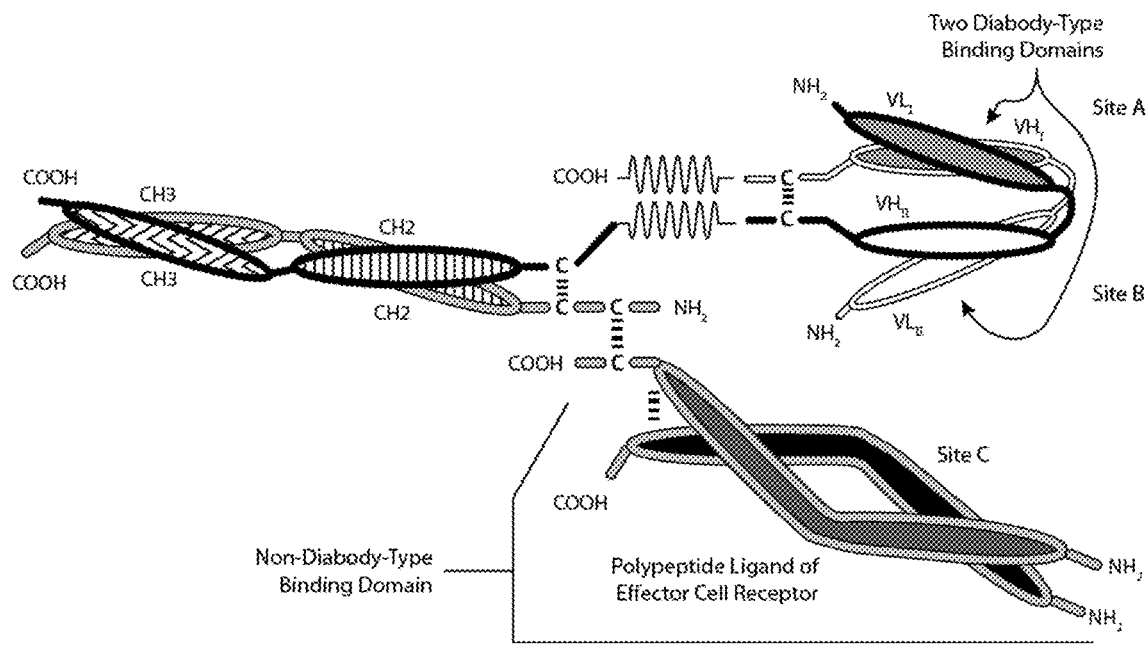
Figure 5E:
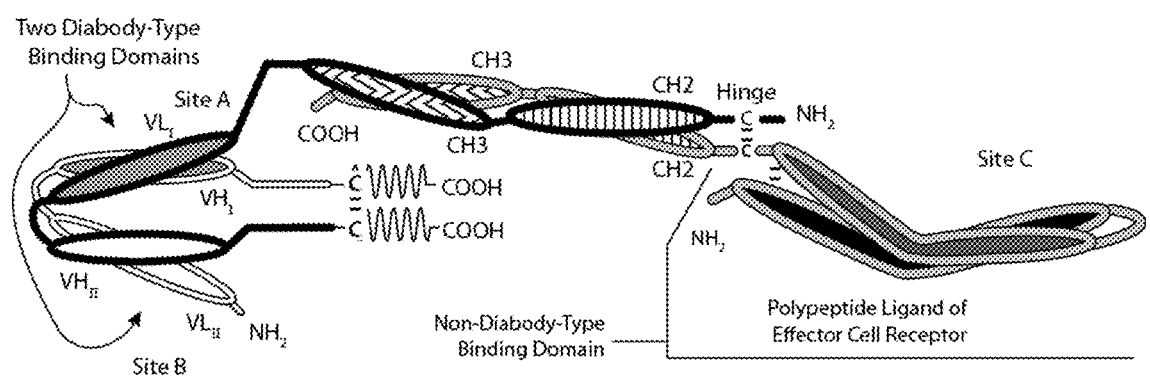

The present invention relates to Tri-Specific Binding Molecules, which are multi-chain polypeptide molecules that possess three Binding Domains and are thus capable of mediating coordinated binding to three epitopes. The Tri-Specific Binding Molecule is preferably characterized in possessing binding domains that permit it to immunospecifically bind to: (1) an epitope of a first Cancer Antigen, (2) an epitope of a second Cancer Antigen, and (3) an epitope of a molecule that is expressed on the surface of an immune system effector cell, and are thus capable of localizing an immune system effector cell to a cell that expresses a Cancer Antigen, so as to thereby facilitate the killing of such cancer cell.

The Tri-Specific Binding Molecules of the present invention may include Epitope-Binding Domains of humanized, chimeric or caninized derivatives of the above-discussed antibodies, for example, DR5 mAb 1 or DR5 mAb 2.

I. General Techniques and General Definitions

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhauser, Boston Mass.; CURRENT PROTOCOLS IN IMMUNOLOGY (Coligan, J. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

II. Preferred Tri-Specific Binding Molecules of the Present Invention

A. Binding Capabilities

The preferred Tri-Specific Binding Molecules of the present invention are able to coordinately and simultaneously bind to three different epitopes. The preferred Tri-Specific Binding Molecules of the present invention comprise:

(I) a "Binding Domain I" that is capable of immunospecifically binding to an "Epitope I" present on a first antigen, and a "Binding Domain II" that is capable of immunospecifically binding to an "Epitope II" present on a second antigen, wherein said Binding Domain I and said Binding Domain II are both "Diabody-Type Binding Domains;"

(II) a "Binding Domain III" that is capable of immunospecifically binding to an "Epitope III" present on a third antigen; and (III) an Fc Domain that is formed by the complexing of two CH2-CH3 Domains to one another;

wherein:

(A) one of Epitope I, Epitope II or Epitope III is an epitope of a first "Cancer Antigen" Cancer Antigen;

(B) a second of Epitope I, Epitope II or Epitope III is an epitope of a second Cancer Antigen; and (C) the third of Epitope I, Epitope II or Epitope III is an epitope of a molecule expressed on the surface of an immune system effector cell ("Effector Cell Antigen");

and wherein the Binding Domains I, II and III of the binding molecules mediate coordinated binding of the immune system effector cell and a cell expressing both the first and second Cancer Antigens to thereby co-localize such cells.

Diabody Epitope-Binding Domains may also be directed to a surface determinant of a B cell, such as CD19, CD20, CD22, CD30, CD37, CD40, and CD74 (Moore, P. A. et al. (2011) "*Application Of Dual Affinity Retargeting Molecules To Achieve Optimal Redirected T-Cell Killing Of B-Cell Lymphoma*," Blood 117(17):4542-4551; Cheson, B. D. et al. (2008) "*Monoclonal Antibody Therapy For B-Cell Non Hodgkin's Lymphoma*," N. Engl. J. Med. 359(6):613-626; Castillo, J. et al. (2008) "Newer monoclonal antibodies for hematological malignancies," Exp. Hematol. 36(7):755-768. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bi-specific Diabody*," Protein Eng. 9:299-305; Holliger et al. (1999) "*Carcinoembryonic Antigen (CEA)-Specific T-Cell Activation In Colon Carcinoma Induced By Anti-CD3×Anti-CEA Bi-specific Diabodies And B7×Anti-CEA Bi-specific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bi-specific Antibody Conjugates In Therapeutics*," Adv. Drug. Deliv. Rev. 55:171-197).

Although such Tri-Specific Binding Molecules are particularly preferred, the invention additionally specifically contemplates Tri-Specific Binding Molecules that comprise any combination of Binding Domains sufficient to produce a molecule having three binding specificities, of which two are binding specificities directed against Cancer Antigens, and one is a binding specificity directed against an Effector Cell Antigen. Thus, for example, the invention contemplates: a Tri-Specific Binding Molecule that comprises three Fab-Type Binding Domains, a Tri-Specific Binding Molecule that comprises one bivalent, bi-specific antibody domain (formed for example, by complexing two different light chains and two different heavy chains) and one Fab-Type Binding Domain, a Tri-Specific Binding Molecule that comprises two bivalent, bi-specific antibody domains (formed for example, by complexing four different light chains and two different heavy chains), but in which one of antibody domains has been rendered inactive, etc.

The terms "polypeptide," "polypeptide chain," and "peptide" are used interchangeably herein to refer to polymers of amino acids of any length, but especially lengths greater than 3, 5, 10, 15, 20 or 25 amino acid residues, in which two, and more preferably all, amino acid residues are joined via an amide (peptide) bond (—NH—C(O)—). The polymer may however be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The polypeptides of this invention can occur as single-chains or as complexed chains.

A "Diabody-Type Binding Domain" is the Epitope-Binding Domain of a diabody, and especially, a DART® diabody. The terms "diabody" and "DART® diabody" has been discussed above, and refers to a molecule that comprises at least two polypeptide chains that preferably complex with one another through a covalent interaction to form at least two epitope binding sites, which may recognize the same or different epitopes. Two of the polypeptide chains of a diabody or DART® diabody each comprise immunoglobulin Light Chain Variable Region and an immunoglobulin Heavy Chain Variable Region, but these regions do not interact to form an epitope binding site (i.e., they are not mutually "complementary"). Rather, the immunoglobulin Heavy Chain Variable Region of one (e.g., the first) of the diabody, or DART® diabody, chains interacts with the immunoglobulin Light Chain Variable Region of a different (e.g., the second) diabody or, DART® diabody, polypeptide chain to form an epitope binding site. Similarly, the immunoglobulin Light Chain Variable Region of one (e.g., the first) of the diabody, or DART® diabody, polypeptide chains interacts with the immunoglobulin Heavy Chain Variable Region of a different (e.g., the second) diabody, or DART® diabody, polypeptide chain to form an epitope binding site. DART® diabody molecules are disclosed in United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; WO 2006/113665, WO 2008/157379 and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bi-specific Antibody Scaffold*," Arthritis Rheum. 62(7):1933-1943; and Johnson, S. et al. (2010) "*Effector Cell Recruitment With Novel Fv-Based Dual Affinity Re-Targeting Protein Leads To Potent Tumor Cytolysis And in vivo B-Cell Depletion*," J. Mol. Biol. 399(3):436-449.

Binding Domain III is preferably a "Non-Diabody-Type" Binding Domain, which is intended to denote that Binding Domain III does not have the structure of a Diabody-Type Binding Domain. Preferably, Binding Domain III is a Non-Diabody-Type Binding Domain that is a Fab-Type Binding Domain or an Effector Cell Receptor-Type Binding Domain. Thus, in one embodiment, exemplified in FIGS. 4A-4G, the Binding Domain III is a Fab-Type Binding Domain. FIGS. 5A-5E exemplify the embodiment in which Binding Domain III is an Effector Cell Receptor-Type Binding Domain. As used herein, the term an "Fab-Type Binding Domain" refers to an epitope Binding Domain that is formed by the interaction of the VL Domain of an immunoglobulin light chain and a complementing VH Domain of an immunoglobulin heavy chain. Fab-Type Binding Domains differ from Diabody-Type Binding Domain in that the two polypeptide chains that form a Fab-Type Binding Domain comprise only a single epitope Binding Domain, whereas the two polypeptide chains that form a Diabody-Type Binding Domain comprise at least two epitope Binding Domains. Thus, as used herein Fab-Type Binding Domains are distinct from Diabody-Type Binding Domain. When a binding domain is a Fab-Type Binding Domain or a Diabody-Type Binding Domain, it will be composed of a VL Domain and a VH Domain, which may be located on the same or on different polypetide chains. The selection of such VL and VH domains is coordinated, such that the domains form an epitope binding domain. As used herein, the term "Effector Cell Receptor-Type Binding Domain" refers to an epitope binding domain that is formed by the interaction of a variable domain of a T Cell Receptor alpha chain and a variable domain of a T Cell Receptor beta chain. Such receptors recognize peptides displayed in the context of MHC and are thus capable of recognizing intracellular epitopes.

The Tri-Specific Binding Molecules of the present invention are thus distinguished from tetravalent binding molecules, such as those produced from the dimerization of a bivalent antibody, and preferably possess three and not four Binding Domains. As discussed below, the trispecific molecules of the present invention may possess additional binding domains (such as an Albumin-Binding Domain, an FcγR-Binding Domain, etc.). Such additional Binding Domains are not intended to be considered or counted as being one of the three Binding Domains of the Tri-Specific Binding Molecules of the present invention.

As used herein, the terms "association" or "associating," with regard to polypeptides (e.g., one diabody polypeptide to another, an immunoglobulin light chain to an immunoglobulin heavy chain, one CH2-CH3 Domain to another CH2-CH3 Domain, etc.) is intended to denote a non-covalent combining of the polypeptides. The terms "complexes" or "complexing" are intended to denote a covalent combining of the polypeptides.

As used herein, Binding Domains of a Binding Molecule of the invention is said to mediate "coordinated binding" if at least two of its Binding Domains and preferably all of its Binding Domains, are capable of concurrently being bound to their respective recognized epitopes or binding ligand. Such binding may be simultaneous. However, one aspect of the present invention relates to modifying the "on" and/or "off" rates with which such Binding Domains bind to their recognized epitopes. As used here, the "on rate" of binding is a measure of the affinity with which such Binding Domains recognize and initiate binding to their recognized epitopes. In contrast, the "off rate" of binding is a measure of the degree of stability of the Binding Domain:epitope complex. The "on" and/or "off" rates of binding can be modified by altering the amino acid sequence of the CDRs of a Binding Domain. As discussed below, independent of any CDR modifications, the extent of coordinated binding of the molecules of the present invention may be modulated by changing the configuration of the their Binding Domains so that a particular Binding Domain (i.e., a VLx/VHx Domain) is present as Binding Domain III or as an internal or external Diabody-Type Binding Domain relative to Binding Domain III (discussed in detail below).

The on- and off-rates of the Binding Domains of the Binding Molecules of the present invention can be readily measured by methods well-known in the art, for example by BIACORE® analysis (Jason-Moller, L. et al. (2006) "*Overview Of Biacore Systems And Their Applications,*" Curr. Protoc. Protein Sci. Chapter 19:Unit 19.13; Swanson, S. J. (2005) "*Characterization Of An Immune Response,*" Dev. Biol. (Basel). 122:95-101; Buijs, J. et al. (2005) "*SPR-MS In Functional Proteomics,*" Brief Funct. Genomic Proteomic. 4(1):39-47; Karlsson, R. et al. (2004) "*SPR For Molecular Interaction Analysis: A Review Of Emerging Application Areas,*" J. Mol. Recognit. 17(3):151-161; Van Regenmortel, M. H. (2003) "*Improving The Quality Of BIACORE-Based Affinity Measurements,*" Dev. Biol. (Basel) 112:141-151; Malmqvist, M. (1999) "*BIACORE: An Affinity Biosensor System For Characterization Of Biomolecular Interactions,*" Biochem. Soc. Trans. 27(2):335-340; Malmqvist, M. et al. (1997) "*Biomolecular Interaction Analysis: Affinity Biosensor Technologies For Functional Analysis Of Proteins,*" Curr. Opin. Chem. Biol. 1(3):378-383; Fivash, M. et al. (1998) "*Biacore For Macromolecular Interaction,*" Curr. Opin. Biotechnol. 9(1):97-101; Malmborg, A. C. et al. (1995) "*Biacore As A Tool In Antibody Engineering,*" J. Immunol. Methods. 183(1):7-13). The on- and off-rates of the Binding Domains of the Binding Molecules of the present invention can be readily altered by random or directed mutagenesis of nucleic acid molecules that encode such Binding Domains, followed by the routine screening of recovered nucleic acid molecules for their ability to encode mutated proteins that exhibit such altered binding kinetics.

The Binding Domains of the Tri-Specific Binding Molecules of the present invention bind to epitopes in an "immunospecific" manner. As used herein, an antibody, diabody or other epitope binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "specific binding" does not necessarily require (although it can include) exclusive binding. Generally, but not necessarily, reference to binding means "specific" binding. Two molecules are said to be capable of binding to one another in a "physiospecific" manner, if such binding exhibits the specificity with which receptors bind to their respective ligands.

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

Thus, in their simplest embodiment, the preferred binding molecules of the present invention are at least trispecific. Significantly, such molecules have at least three Sites that are capable of binding antigen: an "external" Diabody-Type Binding Domain that is located furthest from Binding Domain III, an "internal" Diabody-Type Binding Domain that is located nearest to Binding Domain III, and Binding Domain III itself. The positions of such Domains are respectively designated as "Site A," Site B" and "Site C" (FIGS. 4A-4G; FIGS. 5A-5E).

The Tri-Specific Binding Molecules of the present invention are able to coordinately bind to three different epitopes by comprising three binding domains. Two of the binding domains of such molecules are capable of binding to epitopes of "Cancer Antigens," such that the molecule is capable of binding to two different Cancer Antigens. The third binding domain of such molecules is capable of binding to an epitope of a molecule expressed on the surface of an immune system effector cell (i.e., an "Effector Cell Antigen"). Thus, the Tri-Specific Binding Molecules of the present invention are able to mediate coordinated and simultaneous binding to a cancer cell expressing two Cancer Antigens and to an immune system effector cell expressing the Effector Cell Antigen. The epitopes recognized by the Tri-Specific Binding Molecules of the present invention may be continuous or discontinuous (e.g., conformational).

The first and second Cancer Antigens that are bound by the Cancer Antigen-Binding Domains of the trispecific binding molecules of the present invention may be selected from any molecule that is characteristically present on the surface of a cancer cell. One aspect of the present invention relates to the ability to target "Low Expression Cancer Antigens" (i.e., a Cancer Antigen that may be expressed on a cancer cell at a level too low to permit a monospecific binding molecule to provide an effective cancer therapy). In contrast to such monospecific binding molecules, the Tri-Specific Binding Molecules of the present invention, by targeting two Cancer Antigens instead of one, exhibit synergistic and cooperative enhanced binding avidity that may compensate for low affinity of binding and thus may be advantageously used to target cancers characterized even by a Low Expression Cancer Antigen. A second aspect of the present invention relates to the ability to target "Low Specificity Cancer Antigens" (i.e., a Cancer Antigen that may be expressed on a normal cell in addition to being expressed on a cancer cell). The Tri-Specific Binding Molecules of the present invention, by providing synergistic and cooperative enhanced binding avidity to two Cancer Antigens, exhibits higher avidity of binding even for Low Specificity Cancer Antigens and thus provides a means for treating cancers that are characterized by such Cancer Antigens. Thus, the Tri-Specific Binding Molecules of the present invention may be used to impart an anti-cancer therapy even in circumstances where one or both of the target Cancer Antigens is ineffective on its own to provide such therapy.

For example, CD32B (the FcγRIIB receptor) is widely expressed on hematopoietic cells, including monocytes, macrophages, B cells, NK cells, neutrophils, mast cells, and platelets. Upon binding to IgG Fc Domain, CD32B inhibits the host immune system to thereby depress an ongoing immune response. Although such inhibition is desirable in helping the host recover from inflammatory reactions, it serves to exacerbate the immune deficiencies of subjects suffering from cancer or infectious disease. Antibodies that bind to CD32B, so as to block the binding of IgG Fc molecules, serve to prevent such inhibition and thus have utility as adjunct molecules in the treatment of cancer and infectious disease (Veri, M. C. et al. (2007) "*Monoclonal Antibodies Capable Of Discriminating The Human Inhibitory Fcgamma-Receptor IIB (CD32B) From The Activating Fcgamma-Receptor IIA (CD32A): Biochemical, Biological And Functional Characterization*," Immunology 121 (3): 392-404). Unfortunately, CD32B is also expressed on liver sinusoidal endothelial cells ("LSE cells") (Shahani, T. et al. (2014) "*Human Liver Sinusoidal Endothelial Cells But Not Hepatocytes Contain Factor VIII*," J. Thromb. Haemost. 12(1):36-42; Géraud, C. et al. (2013) "*Endothelial Transdifferentiation In Hepatocellular Carcinoma: Loss Of Stabilin-2 Expression In Peri-Tumourous Liver Correlates With Increased Survival*," Liver Int. 33(9):1428-1440; Takabe, Y. et al. (2012) "*Immunomagnetic Exclusion Of E-Cadherin-Positive Hepatoblasts In Fetal Mouse Liver Cell Cultures Impairs Morphogenesis And Gene Expression Of Sinusoidal Endothelial Cells*," J. Anat. 221(3):229-239). Thus, antibodies that bind CD32B attack LSE cells. However, by forming a Tri-Specific Binding Molecule of the present invention that binds to CD32B and to antigens (i.e., the first and second Cancer Antigens) that are not expressed on LSE cells, or are expressed at low levels by such cells (i.e., Low Expression Cancer Antigen(s)), or are expressed with low specificity on cancer cells and such LSE cells (i.e., Low Specificity Cancer Antigen(s)), the present invention provides compositions and methods that would be used to depress CD32B-mediated immune system inhibition.

B. Exemplary Cancer Antigen-Binding Domains

Examples of suitable Cancer Antigens include: 19.9 as found in colon cancer, gastric cancer mucins; 4.2; A33 (a colorectal carcinoma antigen; Almqvist, Y. 2006, *Nucl Med Biol*. November; 33(8):991-998); ADAM-9 (United States Patent Publication No. 2006/0172350; PCT Publication No. WO 06/084075); AH6 as found in gastric cancer; ALCAM (PCT Publication No. WO 03/093443); APO-1 (malignant human lymphocyte antigen) (Trauth et al. (1989) "*Monoclonal Antibody-Mediated Tumor Regression By Induction Of Apoptosis*," Science 245:301-304); B1 (Egloff, A. M. et al. 2006, Cancer Res. 66(1):6-9); BAGE (Bodey, B. 2002 *Expert Opin Biol Ther*. 2(6):577-84); B7-H3; beta-catenin (Prange W. et al. 2003 *J Pathol*. 201(2):250-9); blood group ALe$^b$/Le$^y$ as found in colonic adenocarcinoma; Burkitt's lymphoma antigen-38.13, C14 as found in colonic adenocarcinoma; CA125 (ovarian carcinoma antigen) (Bast, R. C. Jr. et al. 2005 *Int J Gynecol Cancer* 15 Suppl 3:274-81; Yu et al. (1991) "*Coexpression Of Different Antigenic Markers On Moieties That Bear CA 125 Determinants*," Cancer Res. 51(2):468-475); Carboxypeptidase M (United States Patent Publication No. 2006/0166291); CD5 (Calin, G. A. et al. 2006 *Semin Oncol*. 33(2):167-73; CD19 (Ghetie et al. (1994) "*Anti-CD19 Inhibits The Growth Of Human B-Cell Tumor Lines In Vitro And Of Daudi Cells In SCID Mice By Inducing Cell Cycle Arrest*," Blood 83:1329-1336; Troussard, X. et al. 1998 *Hematol Cell Ther*. 40(4):139-48); CD20 (Thomas, D. A. et al. 2006 Hematol Oncol Clin North Am. 20(5):1125-36); CD22 (Kreitman, R. J. 2006 AAPS J. 18; 8(3):E532-51); CD23 (Rosati, S. et al. 2005 *Curr Top Microbiol Immunol*. 5; 294:91-107); CD25 (Troussard, X. et al. 1998 *Hematol Cell Ther*. 40(4):139-48); CD27 (Bataille, R. 2006 *Haematologica* 91(9):1234-40); CD28 (Bataille, R. 2006 *Haematologica* 91(9):1234-40); CD33 (Sgouros et al. (1993) "*Modeling And Dosimetry Of Monoclonal Antibody M195 (Anti-CD33) In Acute Myelogenous Leukemia*," J.

Nucl. Med. 34:422-430); CD36 (Ge, Y. 2005 *Lab Hematol.* 11(1):31-7); CD40/CD154 (Messmer, D. et al. 2005 *Ann N Y Acad Sci.* 1062:51-60); CD45 (Jurcic, J. G. 2005 *Curr Oncol Rep.* 7(5):339-46); CD56 (Bataille, R. 2006 *Haematologica* 91(9):1234-40); CD46 (U.S. Pat. No. 7,148,038; PCT Publication No. WO 03/032814); CD79a/CD79b (Troussard, X. et al. 1998 *Hematol Cell Ther.* 40(4):139-48; Chu, P. G. et al. 2001 Appl Immunohistochem Mol Morphol. 9(2):97-106); CD103 (Troussard, X. et al. 1998 *Hematol Cell Ther.* 40(4):139-48); CDK4 (Lee, Y. M. et al. 2006 *Cell Cycle* 5(18):2110-4); CEA (carcinoembryonic antigen) (Foon et al. (1995) *"Immune Response To The Carcinoembryonic Antigen In Patients Treated With An Anti-Idiotype Antibody Vaccine,"* J. Clin. Invest. 96(1):334-42); CEA (carcinoembryonic antigen; Mathelin, C. 2006 *Gynecol Obstet Fertil.* 34(7-8):638-46; Tellez-Avila, F. I. et al. 2005 *Rev Invest Clin.* 57(6):814-9); CO17-1A (Ragnhammar et al. (1993) *"Effect Of Monoclonal Antibody 17-1A And GM-CSF In Patients With Advanced Colorectal Carcinoma—Long-Lasting, Complete Remissions Can Be Induced"* Int. J. Cancer 53:751-758); CO-43 (blood group Le$^b$); CO-514 (blood group Le$^a$) as found in adenocarcinoma; CTA-1; CTLA4 (Peggs, K. S. et al. 2006 *Curr Opin Immunol.* 18(2):206-13); Cytokeratin 8 (PCT Publication No. WO 03/024191); D1.1; D$_1$56-22; DR5 (Abdulghani, J. et al. (2010) *"TRAIL Receptor Signaling And Therapeutics,"* Expert Opin. Ther. Targets 14(10):1091-1108; Andera, L. (2009) *"Signaling Activated By The Death Receptors Of The TNFR Family,"* Biomed. Pap. Med. Fac. Univ. Palacky Olomouc Czech. Repub. 153(3):173-180; Carlo-Stella, C. et al. (2007) *"Targeting TRAIL Agonistic Receptors for Cancer Therapy,"* Clin, Cancer 13(8):2313-2317; Chaudhari, B. R. et al. (2006) *"Following the TRAIL to Apoptosis,"* Immunologic Res. 35(3):249-262); E$_1$ series (blood group B) as found in pancreatic cancer; EGFR (Epidermal Growth Factor Receptor) (Adenis, A. et al. 2003 Bull Cancer. 90 Spec No: S228-32); Ephrin receptors (and in particular EphA2 (U.S. Pat. No. 7,569,672; PCT Publication No. WO 06/084226); Erb (ErbB1; ErbB3; ErbB4; Zhou, H. et al. 2002 *Oncogene* 21(57):8732-8740; Rimon, E. et al. 2004 Int J Oncol. 24(5):1325-1338); GAGE (GAGE-1; GAGE-2; Akcakanat, A. et al. 2006 *Int J Cancer.* 118(1):123-128); GD2/GD3/GM2 (Livingston, P. O. et al. 2005 Cancer Immunol Immunother. 54(10):1018-1025); F3 as found in lung adenocarcinoma; FC10.2 as found in embryonal carcinoma cells and gastric adenocarcinoma; G49, ganglioside GD2 (Saleh et al. (1993) *"Generation Of A Human Anti-Idiotypic Antibody That Mimics The GD2 Antigen,"* J. Immunol., 151, 3390-3398); ganglioside GD3 (Shitara et al. (1993) *"A Mouse/Human Chimeric Anti-(Ganglioside GD3) Antibody With Enhanced Antitumor Activities,"* Cancer Immunol. Immunother. 36:373-380); ganglioside GM2 (Livingston et al. (1994) *"Improved Survival In Stage III Melanoma Patients With GM2 Antibodies: A Randomized Trial Of Adjuvant Vaccination With GM2 Ganglioside,"* J. Clin. Oncol. 12:1036-1044); ganglioside GM3 (Hoon et al. (1993) *"Molecular Cloning Of A Human Monoclonal Antibody Reactive To Ganglioside GM3 Antigen On Human Cancers,"* Cancer Res. 53:5244-5250); G$_{D2}$; G$_{D3}$; GICA 19-9 (Herlyn et al. (1982) *"Monoclonal Antibody Detection Of A Circulating Tumor Associated Antigen. I. Presence Of Antigen In Sera Of Patients With Colorectal, Gastric, And Pancreatic Carcinoma,"* J. Clin. Immunol. 2:135-140); G$_{M2}$; gp100 (Lotem, M. et al. 2006 *J Immunother.* 29(6):616-27); Gp37 (human leukemia T cell antigen) (Bhattacharya-Chatterjee et al. (1988) *"Idiotype Vaccines Against Human T Cell Leukemia. II. Generation And Characterization Of A Monoclonal Idiotype Cascade (Ab1, Ab2, and Ab3),"* J. Immunol. 141:1398-1403); gp75 (melanoma antigen) (Vijayasardahl et al. (1990) *"The Melanoma Antigen Gp75 Is The Human Homologue Of The Mouse B (Brown) Locus Gene Product,"* J. Exp. Med. 171 (4): 1375-1380); gpA33; HER2 antigen (p185$^{HER2}$) (Kumar, Pal S et al. 2006 Semin Oncol. 33(4): 386-91); human B-lymphoma antigen-CD20 (Reff et al. (1994) *"Depletion Of B Cells In Vivo By A Chimeric Mouse Human Monoclonal Antibody To CD20,"* Blood 83:435-445); human milk fat globule antigen; human papillomavirus-E6/human papillomavirus-E7 (DiMaio, D. et al. 2006 *Adv Virus Res.* 66:125-59; HMW-MAA (high molecular weight melanoma antigen) (Natali et al. (1987) *"Immunohistochemical Detection Of Antigen In Human Primary And Metastatic Melanomas By The Monoclonal Antibody 140.240 And Its Possible Prognostic Significance,"* Cancer 59:55-63; Mittelman et al. (1990) *"Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies,"* J. Clin. Invest. 86:2136-2144); I antigen (differentiation antigen) (Feizi (1985) *"Demonstration By Monoclonal Antibodies That Carbohydrate Structures Of Glycoproteins And Glycolipids Are Onco-Developmental Antigens,"* Nature 314:53-57) such as I(Ma) as found in gastric adenocarcinomas; Integrin Alpha-V-Beta-6 (PCT Publication No. WO 03/087340); JAM-3 (PCT Publication No. WO 06/084078); KID3 (PCT Publication No. WO 05/028498); KID31 (PCT Publication No. WO 06/076584); KS 1/4 pan-carcinoma antigen (Perez et al. (1989) *"Isolation And Characterization Of A cDNA Encoding The Ks1/4 Epithelial Carcinoma Marker,"* J. Immunol. 142:3662-3667; Möller et al. (1991) *"Bi-specific-Monoclonal-Antibody-Directed Lysis Of Ovarian Carcinoma Cells By Activated Human T Lymphocytes,"* Cancer Immunol. Immunother. 33(4):210-216; Ragupathi, G. 2005 *Cancer Treat Res.* 123:157-80); L6 and L20 (human lung carcinoma antigens) (Hellström et al. (1986) *"Monoclonal Mouse Antibodies Raised Against Human Lung Carcinoma,"* Cancer Res. 46:3917-3923); LEA; LUCA-2 (United States Patent Publication No. 2006/0172349; PCT Publication No. WO 06/083852); M1:22:25:8; M18; M39; MAGE (MAGE-1; MAGE-3; (Bodey, B. 2002 *Expert Opin Biol Ther.* 2(6):577-84); MART (Kounalakis, N. et al. 2005 *Curr Oncol Rep.* 7(5):377-82; MUC-1 (Mathelin, C. 2006 *Gynecol Obstet Fertil.* 34(7-8):638-46); MUM-1 (Castelli, C. et al. 2000 *J Cell Physiol.* 182(3): 323-31); Myl; N-acetylglucosaminyltransferase (Dennis, J. W. 1999 *Biochim Biophys Acta.* 6; 1473(1):21-34); neoglycoprotein; NS-10 as found in adenocarcinomas; OFA-1; OFA-2; Oncostatin M (Oncostatin Receptor Beta) (U.S. Pat. No. 7,572,896; PCT Publication No. WO 06/084092); p15 (Gil, J. et al. 2006 *Nat Rev Mol Cell Biol.* 7(9):667-77); p97 (melanoma-associated antigen) (Estin et al. (1989) *"Transfected Mouse Melanoma Lines That Express Various Levels Of Human Melanoma Associated Antigen p97,"* J. Natl. Cancer Instit. 81(6):445-454); PEM (polymorphic epithelial mucin) (Hilkens et al. (1992) *"Cell Membrane-Associated Mucins And Their Adhesion Modulating Property,"* Trends in Biochem. Sci. 17:359-363); PEMA (polymorphic epithelial mucin antigen); PIPA (U.S. Pat. No. 7,405,061; PCT Publication No. WO 04/043239); PSA (prostate-specific antigen) (Henttu et al. (1989) *"cDNA Coding For The Entire Human Prostate Specific Antigen Shows High Homologies To The Human Tissue Kallikrein Genes,"* Biochem. Biophys. Res. Comm. 10(2):903-910; Israeli et al. (1993) *"Molecular Cloning Of A Complementary DNA Encoding A Prostate-Specific Mem-* brane Antigen," Cancer Res. 53:227-230; Cracco, C. M. et al. 2005 *Minerva Urol Nefrol.* 57(4):301-11); PSMA (prostate-specific membrane antigen) (Ragupathi, G. 2005 *Cancer Treat Res.* 123:157-180); prostatic acid phosphate (Tailor et al. (1990) "*Nucleotide Sequence Of Human Prostatic Acid Phosphatase Determined From A Full-Length cDNA Clone,*" Nucl. Acids Res. 18(16):4928); $R_{24}$ as found in melanoma; ROR1 (U.S. Pat. No. 5,843,749); sphingolipids; SSEA-1; SSEA-3; SSEA-4; sTn (Holmberg, L. A. 2001 *Expert Opin Biol Ther.* 1(5):881-91); T cell receptor derived peptide from a cutaneous T cell lymphoma (see Edelson (1998) "*Cutaneous T-Cell Lymphoma: A Model For Selective Immunotherapy,*" Cancer J Sci Am. 4:62-71); $T_5A_7$ found in myeloid cells; TAG-72 (Yokota et al. (1992) "*Rapid Tumor Penetration Of A Single-Chain Fv And Comparison With Other Immunoglobulin Forms,*" Cancer Res. 52:3402-3408); TL5 (blood group A); TNF-receptor (TNF-α receptor, TNF-β receptor; TNF-γ receptor (van Horssen, R. et al. 2006 Oncologist. 11(4):397-408; Gardnerova, M. et al. 2000 *Curr Drug Targets.* 1(4):327-64); TRA-1-85 (blood group H); Transferrin Receptor (U.S. Pat. No. 7,572,895; PCT Publication No. WO 05/121179); TSTA (tumor-specific transplantation antigen) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al. (1985) "*Monoclonal Antibodies To Cell Surface Antigens Shared By Chemically Induced Mouse Bladder Carcinomas,*" Cancer. Res. 45:2210-2188); VEGF receptor (O'Dwyer. P. J. 2006 Oncologist. 11(9):992-998); VEP8; VEP9; VIM-D5; and Y hapten, Le as found in embryonal carcinoma cells.

1. Campath-1 (CD52) Binding Domain (Alemtuzumab)

The amino acid sequence of the VL Domain of the humanized anti-CD52 antibody "Alemtuzumab" (SEQ ID NO:205) is shown below (CDR residues are shown underlined):

```
DIQMTQSPSS LSASVGDRVT ITCKASQNID KYLNWYQQKP

GKAPKLLIYN TNNLQTGVPS RFSGSGSGTD FTFTISSLQP

EDIATYYCLQ HISRPRTFGQ GTKVEIKR
```

The amino acid sequence of the VH Domain of the humanized anti-CD52 antibody "Alemtuzumab" (SEQ ID NO:206) is shown below (CDR residues are shown underlined):

```
QVQLQESGPG LVRPSQTLSL TCTVSGFTFT DFYMNWVRQP

PGRGLEWIGF IRDKAKGYTT EYNPSVKGRV TMLVDTSKNQ

FSLRLSSVTA ADTAVYYCAR EGHTAAPFDY WGQGSLVTVS

S
```

2. CD317 (BMST2)-Binding Domains

CD317 (also known as Bone Marrow Stromal Cell Antigen 2; BMST) is overexpressed on various cancer cells isolated from breast, lung, kidney, endometrium, and skin (Kawai, S. et al. (2008) "Interferon-α enhances CD317 expression and the antitumor activity of anti-CD317 monoclonal antibody in renal cell carcinoma xenograft models," Cancer Science 99(12):2461-2466; Cai, D. et al. (2009) "*Up-Regulation Of Bone Marrow Stromal Protein 2 (BST2) In Breast Cancer With Bone Metastasis,*" BMC Cancer 9:102, pp. 1-10; Wang, W. et al. (2009) *HM1.24 (CD317) Is A Novel Target Against Lung Cancer For Immunotherapy Using Anti-HM1.24 Antibody,*" Cancer Immunology, Immunotherapy 58(6):967-976; Wang, W. et al. (2009) "*Chimeric And Humanized Anti-HM1.24 Antibodies Mediate Antibody-Dependent Cellular Cytotoxicity Against Lung Cancer Cells. Lung Cancer,*" 63(1):23-31; Sayeed, A. et al. (2013) "*Aberrant Regulation Of The BST2 (Tetherin) Promoter Enhances Cell Proliferation And Apoptosis Evasion In High Grade Breast Cancer Cells,*" PLoS ONE 8(6)e67191, pp. 1-10; Yi, E. H. et al. (2013) "*BST-2 Is A Potential Activator Of Invasion And Migration In Tamoxifen-Resistant Breast Cancer Cells,*" Biochem. Biophys. Res. Commun. 435(4): 685-690; Staudinger, M. (2014) "*The Novel Immunotoxin HM1.24-ETA' Induces Apoptosis In Multiple Myeloma Cells,*" Blood Cancer J. 13; 4:e219, pp. 1-11). Antibodies that immunospecifically bind to CD317 are commercially available (Novus Biologicals LLC; BioLegend, Inc.; see also U.S. Pat. No. 8,834,876, which references the deposit of the heavy and light chains of antibody HM1.24 as FERM BP-5644 and FERM BP-5646; see also U.S. Pat. No. 8,394,374). The amino acid sequence of the VL Domain of the anti-CD317 antibody "HM1.24" (SEQ ID NO:302) is shown below (CDR residues are shown underlined):

```
DIVMTQSHKF MSTSVGDRVS ITCKKASQDV NTAVAWYQQK

PGQSPKLLIY SASNRYTGVP DRITGSGSGT DFTFTISSVQ

AEDLALTTCQ QHYSTPFTFG SGTKLEIK
```

The amino acid sequence of the VH Domain of the anti-CD317 antibody "HM1.24" (SEQ ID NO:303) is shown below (CDR residues are shown underlined):

```
QVQLQQSGAE LARPGASVKL SCKASGYTFT PYWMQWVKQR

PGQGLEWIGS IFPGDGDTRY SQKFKGKATL TADKSSSTAY

MQLSILAFED SAVYYCARGL RRGGYYFDYW GQGTTLTVSS
```

3. CEACAM5- and CEACAM6-Binding Domains

Carcinoembryonic Antigen-Related Cell Adhesion Molecules 5 (CEACAM5) and 6 (CEACAM6) have been found to be associated with various types of cancers including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Pubmication No. WO 2011/034660), and particularly colorectal, gastrointestinal, pancreatic, non-small cell lung cancer (NSCL), breast, thyroid, stomach, ovarian and uterine carcinomas (Zheng, C. et al. (2011) "*A Novel Anti-CEACAM5 Monoclonal Antibody, CC4, Suppresses Colorectal Tumor Growth and Enhances NK Cells Mediated Tumor Immunity,*" PLoS One 6(6):e21146, pp. 1-11).

CEACAM5 has been found to be overexpressed in 90% of gastrointestinal, colorectal and pancreatic cancers, 70% of non-small cell lung cancer cells and 50% of breast cancers (Thompson, J. A. et al. (1991) "*Carcinoembryonic Antigen Gene Family: Molecular Biology And Clinical Perspectives,*" J. Clin. Lab. Anal. 5:344-366).

Overexpressed carcinoembryonic antigen-related cellular adhesion molecule 6 (CEACAM6) plays important roles in the invasion and metastasis of a variety of human cancers, including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Pubmication No. WO 2011/034660; Deng, X. et al. (2014) "*Expression Profiling Of CEACAM6 Associated With The Tumorigenesis And Progression In Gastric Adenocarcinoma,*" Genet. Mol. Res. 13(3):7686-7697; Cameron, S. et al. (2012) "*Focal Overexpression Of CEACAM6 Contributes To Enhanced Tumourigenesis In Head And Neck Cancer Via Suppression Of Apoptosis,*" Mol. Cancer 11:74, pp. 1-11; Chapin, C. et al. (2012) "*Distribution And Surfactant Association Of Carcinoembryonic Cell Adhesion Molecule 6 In Human Lung,*" Amer. J. Physiol. Lung Cell. Mol. Physiol. 302(2):L216-L25; Riley, C. J. et al. (2009) "*Design And Activity Of A Murine And Humanized Anti-CEACAM6 Single-Chain Variable Fragment In The Treatment Of Pancreatic Cancer,*" Cancer Res. 69(5):1933-1940; Lewis-Wambi, J. S. et al. (2008) "*Overexpression Of CEACAM6 Promotes Migration And Invasion Of Oestrogen-Deprived Breast Cancer Cells,*" Eur. J. Cancer 44(12):1770-1779; Blumenthal, R. D. et al. (2007) "*Expression Patterns Of CEACAM5 And CEACAM6 In Primary And Metastatic Cancers,*" BMC Cancer. 7:2, pp. 1-15). Antibodies that immunospecifically bind to CEACAM5 and CEACAM6 are commercially available (Santa Cruz Biotechnology, Inc., Novus Biologicals LLC; Abnova Corporation). The amino acid sequence of the VL Domain of the humanized anti-CEACAM5/ANTI-CEACAM6 antibody 16C3 (EP 2585476) (SEQ ID NO:304) is shown below (CDR residues are shown underlined):

```
DIQMTQSPSS LSASVGDRVT ITCGASENIY GALNWYQRKP

GKSPKLLIWG ASNLADGMPS RFSGSGSGRQ YTLTISSLQP

EDVATYYCQN VLSSPYTFGG GTKLEIK
```

The amino acid sequence of the VH Domain of the humanized anti-CEACAM5/ANTI-CEACAM6 antibody 16C3 (EP 2585476) (SEQ ID NO:305) is shown below (CDR residues are shown underlined):

```
QVQLQQSGPE VVRPGVSVKI SCKGSGYTFT DYAMHWVKQS

HAKSLEWIGL ISTYSGDTKY NQNFKGKATM TVDKSASTAY

MELSSLRSED TAVYYCARGD YSGSRYWFAY WGQGTLVTVS

S
```

The amino acid sequence of the VL Domain of the humanized anti-CEACAM5/CEACAM6 antibody hMN15 (WO 2011/034660) (SEQ ID NO:306) is shown below (CDR residues are shown underlined):

```
DIQLTQSPSS LSASVGDRVT MTCSASSRVS YIHWYQQKPG

KAPKRWIYGT STLASGVPAR FSGSGSGTDF TFTISSLQPE

DIATYYCQQW SYNPPTFGQG TKVEIKR
```

The amino acid sequence of the VH Domain of the humanized anti-CEACAM5/CEACAM6 antibody hMN15 (WO 2011/034660) (SEQ ID NO:307) is shown below (CDR residues are shown underlined):

```
QVQLVESGGG VVQPGRSLRL SCSSSGFALT DYYMSWVRQA

PGKGLEWLGF IANKANGHTT DYSPSVKGRF TISRDNSKNT

LFLQMDSLRP EDTGVYFCAR DMGIRWNFDV WGQGTPVTVS

S
```

4. DR5-Binding Domains

DR5 is a preferred Cancer Antigen of the present invention. The preferred anti-human DR5-binding molecules of the present invention possess the VL and/or VH Domains of murine anti-human DR5 monoclonal antibodies "DR5 mAb 1" and/or "DR5 mAb 2," and more preferably possess 1, 2 or all 3 of the CDRs of the VL Domain and/or 1, 2 or all 3 of the CDRs of the VH Domain of such anti-human DR5 monoclonal antibodies. Alternatively, any anti-human DR5 monoclonal antibody may be employed, particularly: drozitumab (designated herein as "DR5 mAb 3"), conatumumab (designated herein as "DR5 mAb 4"), tigatuzumab (designated herein as "DR5 mAb 5"), LBY135-1 (designated herein as "DR5 mAb 6"), LBY135-2 (designated herein as "DR5 mAb 7") and KMTR2 (designated herein as "DR5 mAb 8").

a. The Anti-Human DR5 Antibody DR5 mAb 1

DR5 has potential utility in the treatment of a wide range of cancers (e.g., colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer. The amino acid sequence of human DR5 precursor (NCBI Sequence NP_003833.4) (SEQ ID NO:2) is:

```
MEQRGQNAPA ASGARKRHGP GPREARGARP GLRVPKTLVL

VVAAVLLLVS AESALITQQD LAPQQRVAPQ QKRSSPSEGL

CPPGHHISED GRDCISCKYG QDYSTHWNDL LFCLRCTRCD

SGEVELSPCT TTRNTVCQCE EGTFREEDSP EMCRKCRTGC

PRGMVKVGDC TPWSDIECVH KESGTKHSGE APAVEETVTS

SPGTPASPCS LSGIIIGVTV AAVVLIVAVF VCKSLLWKKV

LPYLKGICSG GGGDPERVDR SSQRPGAEDN VLNEIVSILQ

PTQVPEQEME VQEPAEPTGV NMLSPGESEH LLEPAEAERS

QRRRLLVPAN EGDPTETLRQ CFDDFADLVP FDSWEPLMRK

LGLMDNEIKV AKAEAAGHRD TLYTMLIKWV NKTGRDASVH

TLLDALETLG ERLAKQKIED HLLSSGKFMY LEGNADSAMS
```

The amino acid sequence of the VL Domain of DR5 mAb 1 (SEQ ID NO:3) is shown below (CDR residues are shown underlined):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI K
```

CDR$_L$1 of DR5 mAb 1 (SEQ ID NO: 4):
RASKSVSSSGYSYMH

CDR$_L$2 of DR5 mAb 1 (SEQ ID NO: 5):
LSSNLDS

-continued

CDR_L3 of DR5 mAb 1 (SEQ ID NO: 6):
QHSRDLPPT

The VL Domain of DR5 mAb 1 is preferably encoded by a polynucleotide (SEQ ID NO:7) having the sequence shown below (polynucleotides encoding the CDRs are shown in underline):

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaa
```

The amino acid sequence of the VH Domain of DR5 mAb 1 (SEQ ID NO:8) is shown below (CDR residues are shown underlined). The C-terminal amino acid may be substituted with alanine to facilitate subcloning of this VH Domain.

```
EVKFLESGGG LVQPGGSLKL SCVASGFDFS RYWMSWVRQA

PGKGLEWIGE INPDSNTINY TPSLKDKFII SRDNAKNTLY

LQMTKVRSED TALYYCTRRA YYGNPAWFAY WGQGTLVTVSS
```

CDR_H1 of DR5 mAb 1 (SEQ ID NO: 9):
GFDFSRYWMS

CDR_H2 of DR5 mAb 1 (SEQ ID NO: 10):
EINPDSNTINYTPSLKD

CDR_H3 of DR5 mAb 1 (SEQ ID NO: 11):
RAYYGNPAWFAY

The VH Domain of DR5 mAb 1 is preferably encoded by a polynucleotide (SEQ ID NO:12) having the sequence shown below (polynucleotides encoding the CDRs are shown in underline):

```
gaggtgaagt tctcgagtc tggaggtggc ctggtgcagc ctggaggatc cctgaaactc tcctgtgtag cctcaggatt cgatttagt agatactgga tgagttgggt ccggcaggct ccagggaaag ggctagaatg gattggagaa attaatccag atagcaatac gataaactat acgccatctc taaaggataa attcatcatc tccagagaca cgccaaaaa tacgctgtat ctgcaaatga ccaaagtgag atctgaggac acagccttt attattgtac aagaagggcc tactatggta acccggcctg gtttgcttac tggggccaag ggactctggt cactgtctct tcc
``` b. The Anti-Human DR5 Antibody DR5 mAb 2
(1) Murine Anti-Human Antibody DR5 mAb 2
The amino acid sequence of the VL Domain of DR5 mAb 2 (SEQ ID NO:13) is shown below (CDR residues are shown underlined):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIK
```

CDRL1 of DR5 mAb 2 (SEQ ID NO: 14):
KASQDVNTAVA

CDRL2 of DR5 mAb 2 (SEQ ID NO: 15):
WASTRHT

CDRL3 of DR5 mAb 2 (SEQ ID NO: 16):
QQHYITPWT

The VL Domain of DR5 mAb 2 is preferably encoded by a polynucleotide (SEQ ID NO:17) having the sequence shown below (polynucleotides encoding the CDRs are shown in underline):

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaaa
```

The amino acid sequence of the VH Domain of DR5 mAb 2 (SEQ ID NO:18) is shown below (CDR residues are shown underlined):

```
KVQLQQSGAE LVKPGASVKL SCKASGYTFT EYILHWVKQK

SGQGLEWIGW FYPGNNNIKY NEKFKDKATL TADKSSSTVY

MELSRLTSED SAVYFCARHE QGPGYFDYWG QGTTLTVSS
```

CDRH1 of DR5 mAb 2 (SEQ ID NO: 19):
GYTFTEYILH

CDRH2 of DR5 mAb 2 (SEQ ID NO: 20):
WFYPGNNNIKYNEKFKD

CDRH3 of DR5 mAb 2 (SEQ ID NO: 21):
HEQGPGYFDY

The VH Domain of DR5 mAb 2 is preferably encoded by a polynucleotide (SEQ ID NO:22) having the sequence shown below (polynucleotides encoding the CDRs are shown in underline):

```
aaggtccagc tgcagcagtc tggagctgaa ctggtgaaac ccggggcatc agtgaagctg tcctgcaagg cttctgggta caccttcact gagtatattt tacactgggt aaagcagaag tctggacagg gtcttgagtg gattgggtgg ttttatcctg gaaataataa tataaagtac aatgagaaat tcaaggacaa
```

```
ggccacactg actgcggaca aatcctccag cacagtctat atggaactta gtagattgac atctgaagac tctgcggtct atttctgtgc aagacacgaa caaggaccag gttactttga ctactggggc caaggcacca ctctcacagt ctcctcc
```

(2) Humanized DR5 mAb 2 ("hDR5 mAb 2")

The above-described murine anti-human DR5 antibody DR5 mAb 2 was humanized in order to demonstrate the capability of humanizing an anti-human DR5 antibody so as to decrease its antigenicity upon administration to a human recipient. The humanization yielded four humanized VL Domains designated herein as "hDR5 mAb 2 VL-2," "hDR5 mAb 2 VL-3," "hDR5 mAb 2 VL-4," and "hDR5 mAb 2 VL-5," and one humanized VH Domain, designated herein as "hDR5 mAb 2 VH-2." Any of the humanized VL Domains may be paired with the humanized VH Domain. Accordingly, any antibody comprising one of the humanized VL Domains paired with the humanized VH Domain is referred to generically as "hDR5 mAb 2," and particular combinations of humanized VL/VH Domains are referred to by reference to the VL domain.

The amino acid sequence of the VL Domain of hDR5 mAb 2 VL-2 (SEQ ID NO:23) is shown below (CDR residues are shown underlined):

```
DIQMTQSPSF LSASVGDRVT ITCKASQDVN TAVAWYQQKP

GKAPKLLIYW ASTRHTGVPS RFSGSGSGTD FTLTISSLQP

EDVATYYCQQ HYITPWTFGG GTKLEIK
``` hDR5 mAb 2 VL-2 is preferably encoded by a polynucleotide (SEQ ID NO:24) having the sequence shown below:

```
gatattcaga tgacccagag tccctcattt ctgtccgcct ccgtcggtga ccgcgtgact attacttgta aagcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa a
```

The amino acid sequence of the VL Domain of hDR5 mAb 2 VL-3 (SEQ ID NO:25) is shown below (CDR residues are shown underlined):

```
DIQMTQSPSF LSASVGDRVT ITCRASQDVN TAVAWYQQKP

GKAPKLLIYW ASTRHTGVPD RFSGSGSGTD FTLTISSLQP

EDVATYYCQQ HYITPWTFGG GTKLEIK
``` hDR5 mAb 2 VL-3 is preferably encoded by a polynucleotide (SEQ ID NO:26) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa a
```

The amino acid sequence of the VL Domain of hDR5 mAb 2 VL-4 (SEQ ID NO:27) is shown below (CDR residues are shown underlined):

```
DIQMTQSPSF LSASVGDRVT ITCRASQDVN TAVAWYQQKP

GKAPKLLIYW ASTRHTGVPS RFSGSGSGTD FTLTISSLQP

EDIATYYCQQ HYITPWTFGG GTKLEIK
``` hDR5 mAb 2 VL-4 is preferably encoded by a polynucleotide (SEQ ID NO:28) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagcca gaggatatcg ctacatacta ttgtcagcag cactacatca ctccttggac cttcggcggg ggcacaaaac tggaaatcaa a
```

The amino acid sequence of the VL Domain of hDR5 mAb 2 VL-5 (SEQ ID NO:29) is shown below (CDR residues are shown underlined):

```
DIQMTQSPSF LSASVGDRVT ITCRASQDVN TAVAWYQQKP

GKAPKLLIYW ASTRHTGVPD RFSGSGSGTD FTLTISSLQP

EDIATYYCQQ HYITPWTFGG GTKLEIK
``` hDR5 mAb 2 VL-5 is preferably encoded by a polynucleotide (SEQ ID NO:30) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagcc
```

-continued
```
gaggatatcg ctacttacta ttgtcagcag cactacatca ctccttggac cttcgcggg ggcacaaaac tggaaatcaa a
```

The amino acid sequence of the VH Domain of hDR5 mAb 2 VH-2 (SEQ ID NO:31) is shown below (CDR residues are shown underlined):

```
QVQLVQSGAE VKKPGASVKV SCKASGYTFT EYILHWVRQA

PGQGLEWMGW FYPGNNNIKY NEKFKDRVTI TADKSTSTVY

MELSSLRSED TAVYYCARHE QGPGYFDYWG QGTLVTVSS
``` hDR5 mAb 2 VH-2 is preferably encoded by a polynucleotide (SEQ ID NO:32) having the sequence shown below:

```
caggtccagc tggtgcagag tggggcagag gtgaaaaagc cagggcatc agtgaaagtg tcttgtaaag catcaggtta tacatttact gagtacatcc tgcactgggt gcgacaggca ccaggacagg gactggaatg gatggggtgg ttctaccctg gcaacaacaa cattaagtac aacgagaagt ttaaagaccg ggtgaccatc acagcggata gtctaccag tacagtctat atggagctga gctccctgag aagcgaagac accgccgtct actattgcgc tcgccacgaa cagggtccag gttactttga ttattggggg cagggaactc tggtcacagt cagctcc
```

The CDR1 of the VL Domain of hDR5 mAb 2 VL-3, hDR5 mAb 2 VL-4 and hDR5 mAb VL-5 has the amino acid sequence: RASQDVNTAVA (SEQ ID NO:320).

c. Drozitumab ("DR5 mAb 3")

The amino acid sequence of the VL Domain of drozitumab ("DR5 mAb 3") (SEQ ID NO:54) is shown below (CDR residues are shown underlined):

```
SELTQDPAVS VALGQTVRIT CSGDSLRSYY ASWYQQKPG

QAPVLVIYGA NNRPSGIPDR FSGSSSGNTA SLTITGAQAE

DEADYYCNSA DSSGNHVVFG GGTKLTVLG
```

CDRL1 of DR5 mAb 3 (SEQ ID NO: 55):
SGDSLRSYYAS

CDRL2 of DR5 mAb 3 (SEQ ID NO: 56):
GANNRPS

CDRL3 of DR5 mAb 3 (SEQ ID NO: 57):
NSADSSGNHVV

The amino acid sequence of the VH Domain of drozitumab ("DR5 mAb 3") (SEQ ID NO:58) is shown below (CDR residues are shown underlined):

```
EVQLVQSGGG VERPGGSLRL SCAASGFTFD DYAMSWVRQA

PGKGLEWVSG INWQGGSTGY ADSVKGRVTI SRDNAKNSLY

LQMNSLRAED TAVYYCAKIL GAGRGWYFDY WGKGTTVTVS

S
```

CDR$_H$1 of DR5 mAb 3 (SEQ ID NO: 59):
GFTFDDYAMS

CDR$_H$2 of DR5 mAb 3 (SEQ ID NO: 60):
INWQGGSTGYADSVKG

CDR$_H$3 of DR5 mAb 3 (SEQ ID NO: 61):
ILGAGRGWYFDY d. Conatumumab ("DR5 mAb 4")

The amino acid sequence of the VL Domain of conatumumab ("DR5 mAb 4") (SEQ ID NO:62) is shown below (CDR residues are shown underlined):

```
EIVLTQSPGT LSLSPGERAT LSCRASQGIS RSYLAWYQQK

PGQAPSLLIY GASSRATGIP DRFSGSGSGT DFTLTISRLE

PEDFAVYYCQ QFGSSPWTFG QGTKVEIK
```

CDR$_L$1 of DR5 mAb 4 (SEQ ID NO: 63):
RASQGISRSYLA

CDR$_L$2 of DR5 mAb 4 (SEQ ID NO: 64):
GASSRAT

CDR$_L$3 of DR5 mAb 4 (SEQ ID NO: 65):
QQFGSSPWT

The amino acid sequence of the VH Domain of conatumumab ("DR5 mAb 4") (SEQ ID NO:66) is shown below (CDR residues are shown underlined):

```
QVQLQESGPG LVKPSQTLSL TCTVSGGSIS SGDYFWSWIR

QLPGKGLEWI GHIHNSGTTY YNPSLKSRVT ISVDTSKKQF

SLRLSSVTAA DTAVYYCARD RGGDYYYGMD VWGQGTTVTV

SS
```

CDR$_H$1 of DR5 mAb 4 (SEQ ID NO: 67):
GGSISSGDYFWS

CDR$_H$2 of DR5 mAb 4 (SEQ ID NO: 68):
HIHNSGTTYYNPSLKS

CDR$_H$3 of DR5 mAb 4 (SEQ ID NO: 69):
DRGGDYYYGMDV e. Tigatumumab ("DR5 mAb 5")

The amino acid sequence of the VL Domain of tigatumumab ("DR5 mAb 5") (SEQ ID NO:70) is shown below (CDR residues are shown underlined):

```
DIQMTQSPSS LSASVGDRVT ITCKASQDVG TAVAWYQQKP

GKAPKLLIYW ASTRHTGVPS RFSGSGSGTD FTLTISSLQP

EDFATYYCQQ YSSYRTFGQG TKVEIK
```

CDR$_L$1 of DR5 mAb 5 (SEQ ID NO: 71):
KASQDVGTAVA

CDR$_L$2 of DR5 mAb 5 (SEQ ID NO: 72):
WASTRHT

CDR$_L$3 of DR5 mAb 5 (SEQ ID NO: 73):
QQYSSYRT

The amino acid sequence of the VH Domain of tigatumumab ("DR5 mAbS") (SEQ ID NO:74) is shown below (CDR residues are shown underlined):

```
EVQLVESGGG LVQPGGSLRL SCAASGFTFS SYVMSWVRQA

PGKGLEWVAT ISSGGSYTYY PDSVKGRFTI SRDNAKNTLY

LQMNSLRAED TAVYYCARRG DSMITTDYWG QGTLVTVSS

CDR_H1 of DR5 mAb 5 (SEQ ID NO: 75):
GFTFSSYVMS

CDR_H2 of DR5 mAb 5 (SEQ ID NO: 76):
TISSGGSYTYYPDSVKG

CDR_H3 of DR5 mAb 5 (SEQ ID NO: 77):
RGDSMITTDY
``` f. LBY135-1 ("DR5 mAb 6")

The amino acid sequence of the VL Domain of LBY135-1 ("DR5 mAb 6") (SEQ ID NO:78) is shown below (CDR residues are shown underlined):

```
DIAMTQSHKF MSTLVGDRVS ITCKASQDVN TAIAWYQQKP

GQSPKLLIYW ASTRHTGVPD RFYGSGSGTD YTLTISSMEA

EDAATYYCQQ WSSNPLTFGA GTKLELKRA

CDR_L1 of DR5 mAb 6 (SEQ ID NO: 79):
QDVNTAIA

CDR_L2 of DR5 mAb 6 (SEQ ID NO: 80):
WASTRHT

CDR_L3 of DR5 mAb 6 (SEQ ID NO: 81):
QQWSSNPLT
```

The amino acid sequence of the VH Domain of LBY135-1 ("DR5 mAb 6") (SEQ ID NO:82) is shown below (CDR residues are shown underlined):

```
KVQLQQSGAE LVKPGASVKL SCKASGYTFT DYTIHWVKQR

SGQGLEWIGW FYPGGGYIKY NEKFKDRATL TADKSSNTVY

MELSRLTSEG SAVYFCARHE EGIYFDYWGQ GTTLVTVSS

CDR_H1 of DR5 mAb 6 (SEQ ID NO: 83):
GYTFTDYTIH

CDR_H2 of DR5 mAb 6 (SEQ ID NO: 84):
WFYPGGGYIKYNEKFKD

CDR_H3 of DR5 mAb 6 (SEQ ID NO: 85):
HEEGIYFDY
``` g. LBY135-2 ("DR5 mAb 7")

The amino acid sequence of the VL Domain of LBY135-2 ("DR5 mAb 7") (SEQ ID NO:86) is shown below (CDR residues are shown underlined):

```
DIVMTQSHKF MSTSVGDRVS ITCKASQDVN TAIAWYQQKP

GQSPKLLIYW ASTRHTGVPD RFTGSGSGTD YTLTISSVQA

EDLALYYCQQ HYTTPFTFGS GTKL

CDR_L1 of DR5 mAb 7 (SEQ ID NO: 87):
KASQDVNTAIA

CDR_L2 of DR5 mAb 7 (SEQ ID NO: 88):
WASTRHT

CDR_L3 of DR5 mAb 7 (SEQ ID NO: 89):
QQHYTTPFT
```

The amino acid sequence of the VH Domain of LBY135-2 ("DR5 mAb 7") (SEQ ID NO:90) is shown below (CDR residues are shown underlined):

```
KVQLQQSGAE LVKPGASVKL SCKASGYTFT DYTIHWVKQR

SGQGLEWIGW FYPGGGYIKY NEKFKDRATL TADKSSNTVY

MELSRLTSED SAVYFCARHE EGIYFDYWGQ GTTLTVSS

CDR_H1 of DR5 mAb 7 (SEQ ID NO: 91):
GYTFTDYTIH

CDR_H2 of DR5 mAb 7 (SEQ ID NO: 92):
WFYPGGGYIKYNEKFKD

CDR_H3 of DR5 mAb 7 (SEQ ID NO: 93):
HEEGIYFDY
``` h. KMTR2 ("DR5 mAb 8")

The amino acid sequence of the VL Domain of KMTR2 ("DR5 mAb 8") (SEQ ID NO:94) is shown below (CDR residues are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RSNWPLTFGG GTKVEIKR

CDR_L1 of DR5 mAb 8 (SEQ ID NO: 95):
RASQSVSSYLA

CDR_L2 of DR5 mAb 8 (SEQ ID NO: 96):
DASNRAT

CDR_L3 of DR5 mAb 8 (SEQ ID NO: 97):
QQRSNWPLT
```

The amino acid sequence of the VH Domain of KMTR2 ("DR5 mAb 8") (SEQ ID NO:98) is shown below (CDR residues are shown underlined):

```
QVQLVQSGAE MKKPGASVKV SCKTSGYTFT NYKINWVRQA

PGQGLEWMGW MNPDTDSTGY PQKFQGRVTM TRNTSISTAY

MELSSLRSED TAVYYCARSY GSGSYYRDYY YGMDVWGQGT

TVTVSS

CDR_H1 of DR5 mAb 8 (SEQ ID NO: 99):
GYTFTNYKIN

CDR_H2 of DR5 mAb 8 (SEQ ID NO: 100):
WMNPDTDSTGYPQKFQG

CDR_H3 of DR5 mAb 8 (SEQ ID NO: 101):
SYGSGSYYRDYYYGMDV
```

5. EphA2-Binding Domains

The receptor tyrosine kinase, ephrin type-A receptor 2 (EphA2) is a preferred cancer antigen of the present invention. EphA2 is normally expressed at sites of cell-to-cell contact in adult epithelial tissues, however, recent studies have shown that it is also overexpressed in various types of epithelial carcinomas, with the greatest level of EphA2 expression observed in metastatic lesions. High expression levels of EphA2 have been found in a wide range of cancers and in numerous tumor cell lines, including prostate cancer, breast cancer, non-small cell lung cancer and melanoma (Xu, J. et al. (2014) "*High Epha2 Protein Expression In Renal Cell Carcinoma Is Associated With A Poor Disease Outcome,*" Oncol. Lett. August 2014; 8(2): 687-692; Miao, B. et al. (2014) "*EphA2 is a Mediator of Vemurafenib Resistance and a Novel Therapeutic Target in Melanoma*," Cancer Discov. pii: CD-14-0295. EphA2 does not appear to be merely a marker for cancer, but rather appears to be persistently overexpressed and functionally changed in numerous human cancers (Chen, P. et al. (2014) "*Epha2 Enhances The Proliferation And Invasion Ability Of Lncap Prostate Cancer Cells*," Oncol. Lett. 8(1):41-46).

The invention particularly contemplates the selection of EphA2 as a Cancer Antigen, and the use of anti-EphA2 antibodies to provide the Cancer Antigen-Binding Domain of the Tri-Specific Binding Molecules of the present invention. Exemplary anti-EphA2 antibodies include "EphA2 mAb 1," "EphA2 mAb 2" and "EphA2 mAb 3".

a. EphA2 mAb 1

The amino acid sequence of the VL Domain of a preferred anti-human EphA2 antibody ("EphA2 mAb 1") (SEQ ID NO:153) is shown below (CDR residues are shown underlined):

```
DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIK

CDR_L1 of EphA2 mAb 1 (SEQ ID NO: 154):
RASQDISNYLN

CDR_L2 of EphA2 mAb 1 (SEQ ID NO: 155):
YTSRLHS

CDR_L3 of EphA2 mAb 1 (SEQ ID NO: 156):
QQGYTLYT
```

The VL Domain of EphA2 mAb 1 is preferably encoded by a polynucleotide (SEQ ID NO:157) having the sequence shown below (polynucleotides encoding the CDRs are shown in underline):

```
gatatccaga tgacacagac tacatcctcc ctgtctgcct ctctgggaga cagaatcacc atcagttgca gggcaagtca ggacattagc aattatttaa actggtatca gcagaaacca gatggaactg ttaaactcct gatctactac acatcaagat tacactcagg agtcccatca aggttcagtg gcagtgggtc tggaacagat tattctctca ccattagcaa cctggagcaa gaagatattg ccacttactt ttgccaacag ggttatacgc tgtacacgtt cggaggggggg accaagctgg aaataaaa
```

The amino acid sequence of the VH Domain of EphA2 mAb 1 (SEQ ID NO:158) is shown below (CDR residues are shown underlined):

```
QVQLKESGPG LVAPSQSLSI TCTVSGFSLS RYSVHWVRQP

PGKGLEWLGM IWGGGSTDYN SALKSRLSIS KDNSKSQVFL

KMNSLQTDDT AMYYCARKHG NYYTMDYWGQ GTSVTVSS

CDR_H1 of EphA2 mAb 1 (SEQ ID NO: 159):
GFSLSRYSVH

CDR_H2 of EphA2 mAb 1 (SEQ ID NO: 160):
MIWGGGSTDYNSALKS

CDR_H3 of EphA2 mAb 1 (SEQ ID NO: 161):
KHGNYYTMDY
```

The VH Domain of EphA2 mAb 1 is preferably encoded by a polynucleotide (SEQ ID NO:162) having the sequence shown below (polynucleotides encoding the CDRs are shown in underline):

```
caggtgcagc tgaaggagtc aggacctggc ctggtggcac cctcacagag cctgtccatc acatgcactg tctctgggtt ctcattatcc agatatagtg tacactgggt tcgccagcct ccaggaaagg gtctggagtg gctgggaatg atatggggtg gtggaagcac agactataat tcagctctca aatccagact gagtatcagc aaggacaact ccaagagcca agttttctta aaaatgaaca gtctgcaaac tgatgacaca gccatgtact actgtgccag aaaacatggt aactactata ctatggacta ctggggtcaa ggaacctcag tcaccgtctc ctcc
``` b. EphA2 mAb 2

The amino acid sequence of the VL Domain of a second preferred anti-human EphA2 antibody ("EphA2 mAb 2") (SEQ ID NO:163) is shown below (CDR residues are shown underlined):

DVVMTQTPLS LPVSLGDQAS ISC<u>RSSQSLV HSSGNTYLH</u>W

YLQKPGQSPK LLIY<u>KVSNRF S</u>GVPDRFSGS GSGTDFTLKI

SRVEAEDLGV YFC<u>SQSTHVP T</u>FGSGTKLEI K

CDR<sub>L</sub>1 of EphA2 mAb 2 (SEQ ID NO: 164):
RSSQSLVHSSGNTYLH

CDR<sub>L</sub>2 of EphA2 mAb 2 (SEQ ID NO: 165):
KVSNRFS

CDR<sub>L</sub>3 of EphA2 mAb 2 (SEQ ID NO: 166):
SQSTHVPT

The VL Domain of EphA2 mAb 2 is preferably encoded by a polynucleotide (SEQ ID NO:318) having the sequence shown below (polynucleotides encoding the CDRs are shown in underline):

gatgttgtga tgacccaaac tccactctcc ctgcctgtca gtcttggaga tcaagcctcc atctcttgc<u>a gatctagtca gagccttgta cacagtagtg gaaacaccta tttacat</u>tgg tacctgcaga agccaggcca gtctccaaag ctcctgatct ac<u>aaagtttc caaccgattt tct</u>ggggtcc cagacaggtt cagtggcagt ggatcaggga cagatttcac actcaagatc agcagagtgg aggctgagga tctgggagtt tatttctgc<u>t ctcaaagtac acatgttccc acg</u>ttcggct cggggacaaa gttggaaata aaa The amino acid sequence of the VH Domain of EphA2 mAb 2 (SEQ ID NO:167) is shown below (CDR residues are shown underlined):

QIQLVQSGPE LKKPGETVKI SCKAS<u>GFTFT NYGMN</u>WVKQA

PGKGLKWMG<u>W INTYIGEPTY ADDFKG</u>RFVF SLETSASTAY

LQINNLKNED MATYFCAR<u>EL GPYYFDY</u>WGQ GTTLTVSS

CDR<sub>H</sub>1 of EphA2 mAb 2 (SEQ ID NO: 168):
GFTFTNYGMN

CDR<sub>H</sub>2 of EphA2 mAb 2 (SEQ ID NO: 169):
WINTYIGEPTYADDFKG

CDR<sub>H</sub>3 of EphA2 mAb 2 (SEQ ID NO: 170):
ELGPYYFDY

The VH Domain of EphA2 mAb 2 is preferably encoded by a polynucleotide (SEQ ID NO:171) having the sequence shown below (polynucleotides encoding the CDRs are shown in underline):

cagatccagt tggtgcagtc tggacctgag ctgaagaagc ctggagagac agtcaagatc tcctgcaagg cttct<u>ggtt taccttcaca aactatggaa tgaac</u>tgggt gaagcaggct ccaggaaagg gtttaaagtg gatgggc<u>tgg ataaacacct atattggaga gccgacatat gctgatgact tcaaggga</u>cg gtttgtcttc tctttggaaa cctctgccag cactgcctat ttgcagatca acaacctcaa aaatgaggac atggccacat atttctgtgc aaga<u>gaactg ggaccatact actttgacta c</u>tggggccaa ggcaccactc tcacagtctc ctcc c. EphA2 mAb 3

The amino acid sequence of the VL Domain of a further preferred anti-human EphA2 antibody ("EphA2 mAb 3") (SEQ ID NO:172) is shown below (CDR residues are shown underlined):

DIVLTQSHRS MSTSVGDRVN ITC<u>KASQDVT TAVA</u>WYQQKP

GQSPKLLIF<u>W ASTRHA</u>GVPD RFTGSGSGTD FTLTISSVQA

GDLALYYC<u>QQ HYSTPYT</u>FGG GTKLEIK

CDR<sub>L</sub>1 of EphA2 mAb 3 (SEQ ID NO: 173):
KASQDVTTAVA

CDR<sub>L</sub>2 of EphA2 mAb 3 (SEQ ID NO: 174):
WASTRHA

CDR<sub>L</sub>3 of EphA2 mAb 3 (SEQ ID NO: 175):
QQHYSTPYT

The VL Domain of EphA2 mAb 3 is preferably encoded by a polynucleotide (SEQ ID NO:176) having the sequence shown below (polynucleotides encoding the CDRs are shown in underline):

gacattgtgc tgacccagtc tcacagatcc atgtccacat cagtaggaga cagggtcaac atcacctgc<u>a aggccagtca ggatgtgact actgctgtag cc</u>tggtatca acaaaaacca gggcaatctc ctaaattact gatttt<u>ctgg gcatccaccc ggcacgct</u>gg agtccctgat cgcttcacag gcagtggatc tgggacagat tttactctca ccatcagcag tgtgcaggct ggagacctgg cactttatta ctgt<u>caacaa cattatagca caccgtacac a</u>ttcggaggg gggaccaagc tggaaataaa a The amino acid sequence of the VH Domain of EphA2 mAb 3 (SEQ ID NO:177) is shown below (CDR residues are shown underlined):

EVQLVESGGG SVKPGGSLKL SCAAS<u>GFTFT DHYMY</u>WVRQT

PEKRLEWVA<u>T ISDGGSFTSY PDSVKG</u>RFTI SRDIAKNNLY

LQMSSLKSED TAMYYCTR<u>DE SDRPFPY</u>WGQ GTLVTVSS

CDR<sub>H</sub>1 of EphA2 mAb 3 (SEQ ID NO: 178):
GFTFTDHYMY

CDR<sub>H</sub>2 of EphA2 mAb 3 (SEQ ID NO: 179):
TISDGGSFTSYPDSVKG

CDR$_H$3 of EphA2 mAb 3 (SEQ ID NO: 180):
DESDRPFPY

The VH Domain of EphA2 mAb 3 is preferably encoded by a polynucleotide (SEQ ID NO:319) having the sequence shown below (polynucleotides encoding the CDRs are shown in underline):

```
gaagtgcagc tggtggagtc tgggggaggc tcagtgaagc ctggagggtc cctgaaactc tcctgtgcag cctctggatt cactttcact gaccattaca tgtattgggt tcgccagact ccggaaaaga ggctggagtg ggtcgcaacc attagtgatg gcggtagttt cacctcctat ccagacagtg tgaaggggcg attcaccatc tccagagaca ttgccaagaa caacctgtac ctccaaatga gcagtctgaa gtctgaggac acagccatgt attactgtac aagagatgag agcgataggc cgtttccta ctggggccaa gggactctgg tcactgtctc ctcc
```

6. gpA33-Binding Domains gpA33 is also a preferred cancer antigen of the present invention. Colorectal cancer is among the most common malignancies of the Western world and is a leading cause of cancer deaths (Silverberg, E. et al. (1989) "*Cancer Statistics, 1989,*" CA Cancer J Clin. 39(1):3-20). One potentially useful target for colon cancer is the 43 kD transmembrane glycoprotein A33 (gpA33), which is expressed in >95% of all colorectal carcinomas (Heath, J. K. et al. (1997) "*The Human A33 Antigen Is A Transmembrane Glycoprotein And A Novel Member Of The Immunoglobulin Superfamily,*" Proc. Natl. Acad. Sci. (U.S.A.) 94(2):469-474; Ritter, G. et al. (1997) "*Characterization Of Posttranslational Modifications Of Human A33Antigen, A Novel Palmitoylated Surface Glycoprotein Of Human Gastrointestinal* Epithelium," Biochem. Biophys. Res. Commun. 236(3):682-686; Wong, N. A. et al. (2006) "*EpCAM and gpA33 Are Markers Of Barrett's Metaplasia,*" J. Clin. Pathol. 59(3):260-263). gpA33 was first discovered through raising monoclonal murine antibodies against the human pancreatic carcinoma derived cell line ASPC1.

The invention particularly contemplates the selection of gpA33 as a Cancer Antigen, and the use of anti-gpA33 antibodies to provide the Cancer Antigen-Binding Domain of the Tri-Specific Binding Molecules of the present invention. An exemplary anti-gpA33 antibody is "gpA33 mAb 1."

The amino acid sequence of the VL Domain of a preferred anti-human gpA33 antibody ("gpA33 mAb 1") (SEQ ID NO:181) is shown below (CDR residues are shown underlined):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIK
```

CDR$_L$1 of gpA33 mAb 1 (SEQ ID NO: 182):
SARSSISFMY

CDR$_L$2 of gpA33 mAb 1 (SEQ ID NO: 183):
DTSNLAS

CDR$_L$3 of gpA33 mAb 1 (SEQ ID NO: 184):
QQWSSYPLT

The VL Domain of gpA33 mAb 1 is preferably encoded by a polynucleotide (SEQ ID NO:185) having the sequence shown below (polynucleotides encoding the CDRs are shown in underline):

```
gacattcagc tgactcagtc cccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca agcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacagggg actaaactgg aaatcaag
```

The amino acid sequence of the VH Domain of gpA33 mAb 1 (SEQ ID NO:186) is shown below (CDR residues are shown underlined):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSS
```

CDR$_H$1 of gpA33 mAb 1 (SEQ ID NO: 187):
GYTFTGSWMN

CDR$_H$2 of gpA33 mAb 1 (SEQ ID NO: 188):
RIYPGDGETNYNGKFKD

CDR$_H$3 of gpA33 mAb 1 (SEQ ID NO: 189):
IYGNNVYFDV

The VH Domain of gpA33 mAb 1 is preferably encoded by a polynucleotide (SEQ ID NO:190) having the sequence shown below (polynucleotides encoding the CDRs are shown in underline):

```
caggtccagc tggtccagag cggggccgaa gtcaaaaaac ccggagcaag cgtgaaggtc tcctgcaaag catcaggcta tacatttaca ggcagctgga tgaactgggt gaggcaggct ccaggacagg gactggagtg gatcgggcgc atctaccctg gagacggcga aactaactat aatggaaagt tcaaagaccg agtgaccatc acagccgata gtctactag taccgcctac atggagctga gctccctgcg gtctgaagat accgccgtct actattgcgc tagaatttac ggaaacaatg tctattttga cgtgtggggg cagggaacaa ctgtgactgt ctcctcc
```

7. Her2-Binding Domains

The invention also particularly contemplates the selection of Her2 as a Cancer Antigen, and the use of anti-Her2 antibodies to provide the Cancer Antigen-Binding Domain of the Tri-Specific Binding Molecules of the present invention. Exemplary anti-Her2 antibodies include "Her2 mAb 1" and Trastuzumab.

a. Her2 mAb 1

The amino acid sequence of the VL Domain of anti-Her2 antibody "Her2 mAb 1" (SEQ ID NO:191) is shown below (CDR residues are shown underlined):

DIQMTQSPSS LSASVGDRVT ITCRASQDVN TAVAWYQQKP
GKAPKLLIYS ASFLESGVPS RFSGSRSGTD FTLTISSLQP
EDFATYYCQQ HYTTPPTFGQ GTKVEIKRT

The amino acid sequence of the VH Domain of anti-Her2 antibody "Her2 mAb 1" (SEQ ID NO:192) is shown below (CDR residues are shown underlined):

QVQLQQSGPE LVKPGASLKL SCTASGFNIK DTYIHWVKQR
PEQGLEWIGR IYPTNGYTRY DPKFQDKATI TADTSSNTAY
LQVSRLTSED TAVYYCSRWG GDGFYAMDYW GQGASVTVSS b. Trastusumab

The amino acid sequence of the VL Domain of the humanized anti-Her2 antibody "Trastuzumab" (SEQ ID NO:193) is shown below (CDR residues are shown underlined):

DIQMTQSPSS LSASVGDRVT ITCRASQDVN TAVAWYQQKP
GKAPKLLIYS ASFLYSGVPS RFSGSRSGTD FTLTISSLQP
EDFATYYCQQ HYTTPPTFGQ GTKVEIKR

The amino acid sequence of the VH Domain of the humanized anti-Her2 antibody "Trastuzumab" (SEQ ID NO:194) is shown below (CDR residues are shown underlined):

EVQLVESGGG LVQPGGSLRL SCAASGFNIK DTYIHWVRQA
PGKGLEWVAR IYPTNGYTRY ADSVKGRFTI SADTSKNTAY
LQMNSLRAED TAVYYCSRWG GDGFYAMDYW GQGTLVTVSS

8. B7-H3-Binding Domains

In addition to its expression on neuroblastoma cells, human B7-H3 is also known to be expressed on a variety of other cancer cells (e.g., gastric, ovarian and non-small cell lung cancers). B7-H3 protein expression has been immunohistologically detected in tumor cell lines (Chapoval, A. et al. (2001) "*B7-H3: A Costimulatory Molecule For T Cell Activation and IFN-γ Production*," Nature Immunol. 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645; Sun, M. et al. (2002) "*Characterization of Mouse and Human B7-H3 Genes*," J. Immunol. 168:6294-6297). mRNA expression has been found in heart, kidney, testes, lung, liver, pancreas, prostate, colon, and osteoblast cells (Collins, M. et al. (2005) "*The B7 Family Of Immune-Regulatory Ligands*," Genome Biol. 6:223.1-223.7). At the protein level, B7-H3 is found in human liver, lung, bladder, testis, prostate, breast, placenta, and lymphoid organs (Hofmeyer, K. et al. (2008) "*The Contrasting Role Of B7-H3*," Proc. Natl. Acad. Sci. (U.S.A.) 105(30):10277-10278).

The invention also particularly contemplates the selection of B7-H3 as a Cancer Antigen, and the use of anti-B7-H3 antibodies to provide the Cancer Antigen-Binding Domain of the Tri-Specific Binding Molecules of the present invention. Exemplary anti-B7-H3 antibodies include "B7-H3 mAb 1," "B7-H3 mAb 2," and "B7-H3 mAb 3."

a. B7-H3 mAb 1

The amino acid sequence of the VL Domain of anti-B7-H3 antibody "B7-H3 mAb 1" (SEQ ID NO:195) is shown below (CDR residues are shown underlined):

DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIK

The amino acid sequence of the VH Domain of anti-B7-H3 antibody "B7-H3 mAb 1" (SEQ ID NO:196) is shown below (CDR residues are shown underlined):

DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SS b. B7-H3 mAb 2

The amino acid sequence of the VL Domain of anti-B7-H3 antibody "B7-H3 mAb 2" (SEQ ID NO:197) is shown below (CDR residues are shown underlined):

DIQMTQTTSS LSASLGDRVT ISCRASQDIS NYLNWYQQKP
DGTVKLLIYY TSRLHSGVPS RFSGSGSGTD YSLTIDNLEQ
EDIATYFCQQ GNTLPPTFGG GTKLEIK

The amino acid sequence of the VH Domain of anti-B7-H3 antibody "B7-H3 mAb 2" (SEQ ID NO:198) is shown below (CDR residues are shown underlined):

QVQLQQSGAE LARPGASVKL SCKASGYTFT SYWMQWVKQR
PGQGLEWIGT IYPGDGDTRY TQKFKGKATL TADKSSSTAY
MQLSSLASED SAVYYCARRG IPRLWYFDVW GAGTTVTVSS c. B7-H3 mAb 3

The amino acid sequence of the VL Domain of anti-B7-H3 antibody "B7-H3 mAb 3" (SEQ ID NO:199) is shown below (CDR residues are shown underlined):

DIQMTQSPAS LSVSVGETVT ITCRASESIY SYLAWYQQKQ
GKSPQLLVYN TKTLPEGVPS RFSGSGSGTQ FSLKINSLQP
EDFGRYYCQH HYGTPPWTFG GGTNLEIK

The amino acid sequence of the VH Domain of anti-B7-H3 antibody "B7-H3 mAb 3" (SEQ ID NO:200) is shown below (CDR residues are shown underlined):

EVQQVESGGD LVKPGGSLKL SCAASGFTFS SYGMSWVRQT
PDKRLEWVAT INSGGSNTYY PDSLKGRFTI SRDNAKNTLY
LQMRSLKSED TAMYYCARHD GGAMDYWGQG TSVTVSS

9. EGF Receptor-Binding Domains (Cetuximab)

The amino acid sequence of the VL Domain of the chimeric anti-EGFR antibody "Cetuximab" (SEQ ID NO:201) is shown below (CDR residues are shown underlined):

```
DILLTQSPVI LSVSPGERVS FSCRASQSIG TNIHWYQQRT
NGSPRLLIKY ASESISGIRS RFSGSGSGTD FTLSINSVES
EDIADYYCQQ NNNWPTTFGA GTKLELKR
```

The amino acid sequence of the VH Domain of the chimeric anti-EGFR antibody "Cetuximab" (SEQ ID NO:202) is shown below (CDR residues are shown underlined):

```
QVQLKQSGPG LVQPSQSLSI TCTVSGFSLT NYGVHWVRQS
PGKGLEWLGV IWSGGNTDYN TPFTSRLSIN KDNSKSQVFF
KMNSLQSNDT AIYYCARALT YYDYEFAYWG QGTLVTVSA
```

Panitumumab (e.g., VECTIBIX®, Amgen) is an alternative EGF receptor-binding antibody that may be used in accordance with the present invention.

10. VEGF-Binding Domains (Bevacizumab)

The amino acid sequence of the VL Domain of the humanized anti-VEGF antibody "Bevacizumab" (SEQ ID NO:203) is shown below (CDR residues are shown underlined):

```
DIQMTQSPSS LSASVGDRVT ITCSASQDIS NYLNWYQQKP
GKAPKVLIYF TSSLHSGVPS RFSGSGSGTD FTLTISSLQP
EDFATYYCQQ YSTVPWTFGQ GTKVEIKR
```

The amino acid sequence of the VH Domain of the humanized anti-VEGF antibody "Bevacizumab" (SEQ ID NO:204) is shown below (CDR residues are shown underlined):

```
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
```

11. 5T4-Binding Domains

The oncofetal protein, 5T4, is a tumor-associated protein displayed on the cell membrane of many carcinomas, including kidney, colon, prostate, lung, carcinoma and in acute lymphoblastic leukemia (see, Boghaert, E. R. et al. (2008) "*The Oncofetal Protein, 5T4, Is A Suitable Target For Antibody-Guided Anti-Cancer Chemotherapy With Calicheamicin,*" Int. J. Oncol. 32(1):221-234; Eisen, T. et al. (2014) "*Naptumomab Estafenatox: Targeted Immunotherapy with a Novel Immunotoxin,*" Curr. Oncol. Rep. 16:370, pp. 1-6). The amino acid sequence of the Light Chain Variable Domain of an exemplary anti-5T4 antibody ("5T4 mAb 1") is shown below (CDR residues are shown underlined): (SEQ ID NO:308):

```
DIQMTQSPSS LSASVGDRVT ITCRASQGIS NYLAWFQQKP
GKAPKSLIYR ANRLQSGVPS RFSGSGSGTD FTLTISSLQP
EDVATYYCLQ YDDFPWTFGQ GTKLEIK
```

The amino acid sequence of the Heavy Chain Variable Domain of such exemplary anti-5T4 antibody is shown below (CDR residues are shown underlined): (SEQ ID NO:309):

```
QVQLVQSGAE VKKPGASVKV SCKASGYTFT SFWMHWVRQA
PGQGLEWMGR IDPNRGGTEY NEKAKSRVTM TADKSTSTAY
MELSSLRSED TAVYYCAGGN PYYPMDYWGQ GTTVTVSS
```

The amino acid sequence of the Light Chain Variable Domain of a second exemplary anti-5T4 antibody ("5T4 mAb 2") is shown below (CDR residues are shown underlined): (SEQ ID NO:310):

```
DVLMTQTPLS LPVSLGDQAS ISCRSSQSIV YSNGNTYLEW
YLQKPGQSPK LLIYKVSNRF SGVPDRFSGS GSGTDFTLKI
SRVEAEDLGV YYCFQGSHVP FTFGSGTKLE IK
```

The amino acid sequence of the Heavy Chain Variable Domain of such second exemplary anti-5T4 antibody is shown below (CDR residues are shown underlined) (SEQ ID NO:311):

```
QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN SYAMDYWGQG

TSVTVSS
```

12. IL13Rα2-Binding Domains

Interleukin-13 Receptor α2 (IL13Rα2) is overexpressed in a variety of cancers, including glioblastoma, colorectal cancer, cervical cancer, pancreatic cancer, multiple melanoma, osteosarcoma, leukemia, lymphoma, prostate cancer and lung cancer (PCT Pubmication No. WO 2008/146911; Brown, C. E. et al. (2013) "Glioma IL13Rα2 Is Associated With Mesenchymal Signature Gene Expression And Poor Patient Prognosis," PLoS One. 18; 8(10):e77769; Barderas, R. et al. (2012) "High Expression Of IL-13 Receptor A2 In Colorectal Cancer Is Associated With Invasion, Liver Metastasis, And Poor Prognosis," Cancer Res. 72(11):2780-2790; Kasaian, M. T. et al. (2011) "IL-13 Antibodies Influence IL-13 Clearance In Humans By Modulating Scavenger Activity Of IL-13Rα2," J. Immunol. 187(1):561-569; Bozinov, O. et al. (2010) "Decreasing Expression Of The Interleukin-13 Receptor IL-13Ralpha2 In Treated Recurrent Malignant Gliomas," Neurol. Med. Chir. (Tokyo) 50(8):617-621; Fujisawa, T. et al. (2009) "A novel role of interleukin-13 receptor alpha2 in pancreatic cancer invasion and metastasis," Cancer Res. 69(22):8678-8685). Antibodies that immunospecifically bind to IL13Rα2 are commercially available (Abnova Corporation, Biorbyt, LifeSpan BioSciences, United States Biologicals; see also PCT Publication No. WO 2008/146911). The amino acid sequence of the Light Chain Variable Domain of an exemplary anti-IL13Rα2 antibody ("hu08," PCT Publication No. WO 2014/072888) is shown below (CDR residues are shown underlined): (SEQ ID NO:321):

```
DIQMTQSPSS LSASVGDRVT ITCKASQDVG TAVAWYQQKP

GKAPKLLIYS ASYRSTGVPS RFSGSGSGTD FTLTISSLQP

EDFATYYCQH HYSAPWTFGG GTKVEIK
```

The amino acid sequence of the Heavy Chain Variable Domain of such exemplary anti-IL13Rα2 antibody ("hu08," PCT Publication No. WO 2014/072888) is shown below (CDR residues are shown underlined): (SEQ ID NO:322):

```
EVQLVESGGG LVQPGGSLRL SCAASGFTFS RNGMSWVRQA

PGKGLEWVAT VSSGGSYIYY ADSVKGRFTI SRDNAKNSLY
```

```
LQMNSLRAED TAVYYCARQG TTALATRFFD VWGQGTLVTV

SS
```

13. Integrin Beta6-Binding Domains

Integrinβ6 (ITGB6) is a subtype of integrin that is expressed exclusively on the surfaces of epithelial cells and is a receptor for extracellular matrix (ECM) proteins. ITGB6 expression is specifically expressed in tumor tissues (such as those of colon, prostate, kidney cancer), but is generally undetectable in healthy epithelial tissue (Liang, B. et al. (2014) "*Integrinβ6-targeted Immunoliposomes Mediate Tumor Specific Drug Delivery and Enhance Therapeutic Efficacy in Colon Carcinoma,*" Clin. Cancer Res. December 30. pii: clincanres.1194.2014). Monoclonal antibodies that immunospecifically bind to ITGB6 are available commercially (e.g., MAB2075Z clone R6G9,EMD Millipore; see also, Weinacker, A. et al. (1994) "*Role Of The Integrin Alpha V Beta 6 In Cell Attachment To Fibronectin. Heterologous Expression Of Intact And Secreted Forms Of The Receptor,*" J. Biol. Chem. 269:6940-6948). Anti-ITGB6 monoclonal antibodies 3G9 and 8G6, and variants thereof are disclosed in PCT Publication Nos. WO 03/100033 and WO 2007/008712.

The amino acid sequence of the Light Chain Variable Domain of an exemplary humanized anti-ITGB6 antibody (derived from antibody 3G9, PCT Publication No. WO 2007/008712) is shown below (CDR residues are shown underlined): (SEQ ID NO:312):

```
EIVLTQSPAT LSLSPGERAT LSCSASSSVS SSYLYWYQQK

PGQAPRLLIY STSNLASGIP ARFSGSGSGT GFTLTISSLE

PEDFAVYYCH QWSTYPPTFG GGTKVEIK
```

The amino acid sequence of the Heavy Chain Variable Domain of such exemplary humanized anti-ITGB6 antibody (derived from antibody 3G9, PCT Publication No. WO 2007/008712) is shown below (CDR residues are shown underlined): (SEQ ID NO:313):

```
EVQLVESGGG LVQPGGSLRL SCAASGFTFS RYWMSWVRQA

PGKGLEWVAS ISSGGRMYYP FTVKGRFTIS RDNAKNSLYL

QMNSLRAEDT AVYYCARGSI YDGYYVFPYW GQGTLVTVSS
```

The amino acid sequence of the Light Chain Variable Domain of an exemplary anti-ITGB6 antibody (derived from antibody 8G6, PCT Publication No. WO 2007/008712) is shown below (CDR residues are shown underlined): (SEQ ID NO:314):

```
EIVLTQSPAT LSLSPGERAT LSCRASQSVS TSSYSYMYWY

QQKPGQAPRL LIYYASNLES GIPARFSGSG SGTDFTLTIS

SLEPEDFAVY YCQHNWEIPF TFGGGTKVEI K
```

The amino acid sequence of the Heavy Chain Variable Domain of such exemplary anti-ITGB6 antibody (derived from antibody 8G6, PCT Publication No. WO 2007/008712) is shown below (CDR residues are shown underlined): (SEQ ID NO:315):

```
QVQLVQSGAEVKKPGASVKVSCKASGYTFTDYAMHWVRQAPGQGLEWMGV

ISTYYGNTNYNQKFKGRVTMTRDTSISTAYMELSRLRSDDTAVYYCARGG

LRRGDRPSLQYAMDYWGQGTLVTVSS
```

14. Additional Anti-Cancer Antigen-Binding Domains

Additional anti-cancer antigen antibodies that may be used in accordance with the present invention include the following commercially available antibodies: Brentuximab (e.g., ADCETRIS®), which binds to CD30; Gemtuzumab (e.g., MYLOTARG®, Wyeth), which binds to CD33; and Ipilimumab (e.g., YERVOY®), which binds to CTLA-4.

C. Exemplary Effector Cell-Binding Domains

Antibodies that are capable of binding to immune system effector cells may be used to provide the Effector Cell-Binding Domains of the Tri-Specific Binding Molecules of the present invention. Particularly suitable are antibodies that bind to CD2, CD3, CD16, CD19, CD20, CD22, CD32B, CD64, the B cell Receptor (BCR), the T cell Receptor (TCR), and the NKG2D Receptor.

1. CD2-Binding Domains

CD2 is a cell adhesion molecule found on the surface of T cells and natural killer (NK) cells. CD2 enhances NK cell cytotoxicity, possibly as a promoter of NK cell nanotube formation (Mace, E. M. et al. (2014) "*Cell Biological Steps And Checkpoints In Accessing NK Cell Cytotoxicity,*" Immunol. Cell. Biol. 92(3):245-255; Comerci, C. J. et al. (2012) "*CD2 Promotes Human Natural Killer Cell Membrane Nanotube Formation,*" PLoS One 7(10):e47664:1-12). The amino acid sequence of the VL Domain of anti-CD2 antibody (Lo-CD2a; ATCC Accession No: 11423) is (SEQ ID NO:102) (CDR residues are shown underlined):

```
DVVLTQTPPT LLATIGQSVS ISCRSSQSLL HSSGNTYLNW

LLQRTGQSPQ PLIYLVSKLE SGVPNRFSGS GSGTDFTLKI

SGVEAEDLGV YYCMQFTHYP YTFGAGTKLE LK
```

The amino acid sequence of the VH Domain of anti-CD2 antibody (Lo-CD2a; ATCC Accession No: 11423) is (SEQ ID NO:103) (CDR residues are shown underlined):

```
EVQLQQSGPE LQRPGASVKL SCKASGYIFT EYYMYWVKQR

PKQGLELVGR IDPEDGSIDY VEKFKKKATL TADTSSNTAY

MQLSSLTSED TATYFCARGK FNYRFAYWGQ GTLVTVSS
```

2. CD3-Binding Domains

In a preferred embodiment, the second epitope that is bound by the Tri-Specific Binding Molecules of the present invention will be an epitope of CD3. CD3 is a T cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling,*" Cold Spring Harb. Perspect. Biol. 2(4):a005140; pages 1-14). In mammals, the complex contains a CD3γ chain, a CD3δ chain, and two CD3ε chains. These chains associate with a molecule known as the T cell receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer,*" Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2): 133-139).

As discussed below, in order to illustrate the present invention, bi-specific anti-human CD3×anti-human DR5-binding molecules were produced. An anti-human CD3 antibody used for such constructs is designated herein as "CD3 mAb 2." The amino acid sequence of the VL Domain of CD3 mAb 2 (SEQ ID NO:104) is shown below (CDR residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG

CDR_L1 of CD3 mAb 2 (SEQ ID NO: 105):
RSSTGAVTTSNYAN

CDR_L2 of CD3 mAb 2 (SEQ ID NO: 106):
GTNKRAP

CDR_L3 of CD3 mAb 2 (SEQ ID NO: 107):
ALWYSNLWV
```

The amino acid sequence of the VH Domain of CD3 mAb 2 (SEQ ID NO:108) is shown below (CDR residues are shown underlined):

```
EVQLVESGGG LVQPGGSLRL SCAASGFTFS TYAMNWVRQA

PGKGLEWVGR IRSKYNNYAT YYADSVKDRF TISRDDSKNS

LYLQMNSLKT EDTAVYYCVR HGNFGNSYVS WFAYWGQGTL

VTVSS

CDR_H1 of CD3 mAb 2 (SEQ ID NO: 109):
TYAMN

CDR_H2 of CD3 mAb 2 (SEQ ID NO: 110):
RIRSKYNNYATYYADSVKD

CDR_H3 of CD3 mAb 2 (SEQ ID NO: 111):
HGNFGNSYVSWFAY
```

In some of the CD3 constructs, a variant VH Domain was employed for CD3 mAb 2. The variant VH domain possesses a D65G substitution, thus having the amino acid sequence shown below (SEQ ID NO:112) (CDR residues are shown underlined):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSS
```

The substitution causes the CDR_H2 to have the amino acid sequence (SEQ ID NO:113) RIRSKYNNYATYYADSVKG. The substituted position (D65G) is shown in double underline.

A second anti-CD3 antibody used herein is antibody Muromonab-CD3 "OKT3" (Xu et al. (2000) "*In Vitro Characterization Of Five Humanized OKT3 Effector Function Variant Antibodies*," Cell. Immunol. 200:16-26); Norman, D. J. (1995) "*Mechanisms Of Action And Overview Of OKT3*," Ther. Drug Monit. 17(6):615-620; Canafax, D. M. et al. (1987) "*Monoclonal Antilymphocyte Antibody (OKT3) Treatment Of Acute Renal Allograft Rejection*," Pharmacotherapy 7(4):121-124; Swinnen, L. J. et al. (1993) "*OKT3 Monoclonal Antibodies Induce Interleukin-6 And Interleukin-10: A Possible Cause Of Lymphoproliferative Disorders Associated With Transplantation*," Curr. Opin. Nephrol. Hypertens. 2(4):670-678). The amino acid sequence of the VL Domain of OKT3 (SEQ ID NO:114) is shown below (CDR residues are shown underlined):

```
QIVLTQSPAI MSASPGEKVT MTCSASSSVS YMNWYQQKSG

TSPKRWIYDT SKLASGVPAH FRGSGSGTSY SLTISGMEAE

DAATYYCQQW SSNPFTFGSG TKLEINR
```

The amino acid sequence of the VH Domain of OKT3 (SEQ ID NO:115) is shown below (CDR residues are shown underlined):

```
QVQLQQSGAE LARPGASVKM SCKASGYTFT RYTMHWVKQR

PGQGLEWIGY INPSRGYTNY NQKFKDKATL TTDKSSSTAY

MQLSSLTSED SAVYYCARYY DDHYCLDYWG QGTTLTVSS
```

3. CD16-Binding Domains

CD16 is the FcγRIIIA receptor. CD16 is expressed by neutrophils, eosinophils, natural killer (NK) cells, and tissue macrophages that bind aggregated but not monomeric human IgG (Peltz, G. A. et al. (1989) "*Human Fc Gamma RIII: Cloning, Expression, And Identification Of The Chromosomal Locus Of Two Fc Receptors For IgG*," Proc. Natl. Acad. Sci. (U.S.A.) 86(3):1013-1017; Bachanova, V. et al. (2014) "*NK Cells In Therapy Of Cancer*," Crit. Rev. Oncog. 19(1-2):133-141; Miller, J. S. (2013) "*Therapeutic Applications: Natural Killer Cells In The Clinic*," Hematology Am. Soc. Hematol. Educ. Program. 2013:247-253; Youinou, P. et al. (2002) "*Pathogenic Effects Of Anti-Fc Gamma Receptor IIIB (CD16) On Polymorphonuclear Neutrophils In Non-Organ-Specific Autoimmune Diseases*," Autoimmun Rev. 1(1-2):13-19; Peipp, M. et al. (2002) "*Bi-specific Antibodies Targeting Cancer Cells*," Biochem. Soc. Trans. 30(4):507-511).

The amino acid sequence of a Variable Light Chain Domain of anti-CD16 antibody 3G8 is (SEQ ID NO:116) (CDR residues are shown underlined):

```
DTVLTQSPAS LAVSLGQRAT ISCKASQSVD FDGDSFMNWY

QQKPGQPPKL LIYTTSNLES GIPARFSASG SGTDFTLNIH

PVEEEDTATY YCQQSNEDPY TFGGGTKLEI K
```

The amino acid sequence of the Variable Heavy Chain Domain of anti-CD16 antibody 3G8 is (SEQ ID NO:117) (CDR residues are shown underlined):

QVTLKESGPG ILQPSQTLSL TCSFSGFSLR TSGMGVGWIR

QPSGKGLEWL AHIWWDDDKR YNPALKSRLT ISKDTSSNQV

FLKIASVDTA DTATYYCAQI NPAWFAYWGQ GTLVTVSA

The amino acid sequence of a Variable Light Chain Domain of anti-CD16 antibody A9 is (SEQ ID NO:118) (CDR residues are shown underlined):

DIQAVVTQES ALTTSPGETV TLTCRSNTGT VTTSNYANWV

QEKPDHLFTG LIGHTNNRAP GVPARFSGSL IGDKAALTIT

GAQTEDEAIY FCALWYNNHW VFGGGTKLTVL

The amino acid sequence of the Variable Heavy Chain Domain of anti-CD16 antibody A9 is (SEQ ID NO:119) (CDR residues are shown underlined):

QVQLQQSGAE LVRPGTSVKI SCKASGYTFT NYWLGWVKQR

PGHGLEWIGD IYPGGGYTNY NEKFKGKATV TADTSSRTAY

VQVRSLTSED SAVYFCARSA SWYFDVWGAR TTVTVSS

4. CD19-Binding Domains

CD19 antigen is a type I transmembrane glycoprotein belonging to the immunoglobulin Ig superfamily. CD19 is expressed on follicular dendritic cells and B cells. It is considered a pan B cell marker expressed throughout B cell development but with threefold higher expression in mature cells as compared to immature B cells (Raufi A. et al. (2013) "*Targeting CD19 In B-Cell Lymphoma: Emerging Role Of SAR3419*," Cancer Manag. Res. 5:225-233). Many CD19 antibodies have been described (e.g., MD1342, MEDI-551, etc.) (Mei, H. E. et al. (2012) "*Rationale Of Anti-CD19 Immunotherapy: An Option To Target Autoreactive Plasma Cells In Autoimmunity*," Arthritis Res. Ther. 14(Suppl 5):S1: 1-16). The anti-CD19 binding molecule "blinatumomab" is disclosed in EP 2186527.

The amino acid sequence of the VL Domain of a preferred anti-CD19 antibody (HD37) is (SEQ ID NO:120) (CDR residues are shown underlined):

DILITQSPKS MSMSVGERVT LTCKASENVV TYVSWYQQKP

EQSPKLLIYG ASNRYTGVPD RFTGSGSATD FTLTISSVQA

EDLADYHCGQ GYSYPYTFGG GTKLEIKR

The amino acid sequence of the VH Domain of anti-CD19 antibody HD37 is (SEQ ID NO:121) (CDR residues are shown underlined):

QVQLQQSGAE LVRPGSSVKI SCKASGYAFS SYWMNWVKQR

PGQGLEWIGQ IWPGDGDTNY NGKFKGKATL TADESSSTAY

MQLSSLASED SAVYFCARRE TTTVGRYYA MDYWGQGTSV

TVSS

5. CD20-Binding Domains

CD20 is a B cell-specific differentiation antigen that is expressed on mature B cells and in most B cell non-Hodgkin's lymphomas but not on early B cell progenitors or later mature plasma cells (Maloney, D. G. (2012) "*Anti-CD20 Antibody Therapy for B-Cell Lymphomas*," N. Engl. J. Med. 366:2008-2016). Rituximab is an illustrative anti-human CD20 antibody. The amino acid sequence of the VL Domain of a chimeric anti-CD20 antibody (rituximab) is (SEQ ID NO:122) (CDR residues are shown underlined):

QIVLSQSPAI LSASPGEKVT MTCRASSSVS YIHWFQQKPG

SSPKPWIYAT SNLASGVPVR FSGSGSGTSY SLTISRVEAE

DAATYYCQQW TSNPPTFGGG TKLEIKR

The amino acid sequence of the VH Domain of anti-CD20 antibody (rituximab) is (SEQ ID NO:123) (CDR residues are shown underlined):

QVQLQQPGAE LVKPGASVKM SCKASGYTFT SYNMHWVKQT

PGRGLEWIGA IYPGNGDTSY NQKFKGKATL TADKSSSTAY

MQLSSLTSED SAVYYCARST YYGGDWYFNV WGAGTTVTVS

A

Alternative anti-CD20 antibodies that may be used in accordance with the present invention include the following commercially available antibodies: Ibritumomab (e.g., ZEVALIN®, Spectrum Pharmaceuticals, Inc.), Ofatumumab (e.g., ARZERRA®, SmithKlineGlaxo) and Tositumomab (e.g., BEXXAR®,GlaxoSmithKline).

6. CD22-Binding Domains

CD22 is a sugar binding transmembrane protein found on the surface of mature B cells and to a lesser extent on some immature B cells (WO 2011/032633; Poe, J. C. et al. (2012) "*CD22 And Siglec-G In B Cell Function And Tolerance*," Trends Immunol. 33(8):413-420; Chen, W. C. et al. (2012) "*Targeting B Lymphoma With Nanoparticles Bearing Glycan Ligands Of CD22*," Leuk. Lymphoma 53(2):208-210; Walker, J. A. (2008) "*CD22: An Inhibitory Enigma*," Immunology 123(3):314-325; Coleman, M. et al. (2003) "*Epratuzumab: Targeting B-Cell Malignancies Through CD22*," Clin. Cancer Res. 9(10 Pt 2):39915-39945).

The amino acid sequence of the VL Domain of anti-CD22 antibody (epratuzumab) is (SEQ ID NO:124) (CDR residues are shown underlined):

DIQLTQSPSS LSASVGDRVT MSCKSSQSVL YSANHKNYLA

WYQQKPGKAP KLLIYWASTR ESGVPSRFSG SGSGTDFTFT

ISSLQPEDIA TYYCHQYLSS WTFGGGTKVQ IKR

The amino acid sequence of the VH Domain of anti-CD22 antibody (epratuzumab) is (SEQ ID NO:125) (CDR residues are shown underlined):

QVQLVQSGAE VKKPGSSVKV SCKASGYTFT SYWLHWVRQA

PGQGLEWIGY INPRNDYTEY NQNFKDKATI TADESTNTAY

MELSSLRSED TAFYFCARRD ITTFYWGQGT TVTVSS

7. CD32B-Binding Domains

A preferred sequence for the VL domain of an antibody that binds to human CD32B is CD32B mAb 1 (SEQ ID NO:126) (CDR residues are shown underlined):

DIQMTQSPSS LLAALGERVS LTCRASQEIS GYLSWLQQKP

DGTIKRLIYA ASTLDSGVPK RFSGSESGSD YSLTISSLES

EDFADYYCLQ YFSYPLTFGA GTKLELK

A preferred sequence for the VH domain of the CD32B mAb 1 antibody that binds to human CD32B is (SEQ ID NO:127) (CDR residues are shown underlined):

EVKLEESGGG LVQPGGSMKL SCEASGFTFS DAWMDWVRQS

PEKGLEWVAE IRNKAKNHAT YYAESVIGRF TISRDDSKSS

VYLQMNSLRA EDTGIYYCGA LGLDYWGQGT TLTVSS

8. CD64-Binding Domains

CD64 is the FcγRI receptor and is expressed on monocytes/macrophages, dendritic cells, and activated granulocytes. The expression can be upregulated by IFN-γ stimulation. CD64 binds IgG immune complex. CD64 plays a role in antigen capture, phagocytosis of IgG/antigen complexes, and antibody-dependent cellular cytotoxicity (WO 2006/002438).

A preferred sequence for the VL domain of an antibody that binds to human CD64 is CD64 mAb 1 (SEQ ID NO:128) (CDR residues are shown underlined):

EIVLTQSPAT LSLSPGERAT LSCRASQSVS SYLAWYQQKP

GQAPRLLIYD ASSRATGIPA RFGGSGSGGT DFTLTISSLE

PEDFAVYYCQ LRSNWPPYTF GQGTKLEIK

A preferred sequence for the VH domain of an antibody that binds to human CD64 is (SEQ ID NO:129) (CDR residues are shown underlined):

QVQLVESGGG VVQPGRSLRL SCAASGFIFS GYGMHWVRQA

PGKGLEWVTV IWYDGSNKYY ADSVKGRFTI SRDNSKNTLY

LQMNSLRAED TAVYYCARDT GDRFFDYWGQ GTLVTVSS

9. BCR/CD79-Binding Domains

The BCR is composed of a membrane immunoglobulin which, together with non-covalently associated α and β subunits of CD79 ("CD79a" and "CD79b," respectively), forms the BCR complex. CD79a and CD79b are signal transducing subunits that contain a conserved immunoreceptor tyrosine-based activation motif ("ITAM") required for signal transduction (Dylke, J. et al. (2007) "*Role Of The Extracellular And Transmembrane Domain Of Ig-Alpha/Beta In Assembly Of The B Cell Antigen Receptor (BCR),*" Immunol. Lett. 112(1):47-57; Cambier, J. C. (1995) "*New Nomenclature For The Reth Motif (or ARH1/TAM/ARAM/YXXL),*" Immunol. Today 16:110). Aggregation of the BCR complex by multivalent antigen initiates transphosphorylation of the CD79a and CD79b ITAMs and activation of receptor-associated kinases (DeFranco, A. L. (1997) "*The Complexity Of Signaling Pathways Activated By The BCR,*" Curr. Opin. Immunol. 9:296-308; Kurosaki, T. (1997) "*Molecular Mechanisms In B Cell Antigen Receptor Signaling,*" Curr. Opin. Immunol. 9:309-318; Kim, K. M. et al. (1993) "*Signalling Function Of The B-Cell Antigen Receptors,*" Immun. Rev. 132:125-146). Phosphorylated ITAMs recruit additional effectors such as PI$_3$K, PLC-γ and members of the Ras/MAPK pathway. These signaling events are responsible for both the B cell proliferation and increased expression of activation markers (such as MHCII and CD86) that are required to prime B cells for their subsequent interactions with T helper ("T$_h$") cells.

A preferred sequence for the VL domain of an antibody that binds to the human B Cell Receptor (CD79) is CD79 mAb 1 (SEQ ID NO:130) (CDR residues are shown underlined):

DVVMTQTPLT LSVNIGQPAS ISCKSSQSLL DTDGKTYLNW

LLQRPQGSPN RLIYLVSKLD SGVPDRFTGS GSGTDFTLKI

SRVEAEDLGI YYCWQGTHFP LTFGAGTKLE LK

A preferred sequence for the VH domain of the CD79 mAb 1 antibody that binds to the human B Cell Receptor (CD79) is (SEQ ID NO:131) (CDR residues are shown underlined):

QVQLQQPGAE LVRPGASVKL SCKASGYTFT SYWMNWVKQR

PGQGLEWIGM VDPSDSETHY NQMFKDKATL TVDKSSSTAY

MQLSSLTSED SAVYYCARAM GYWGQGTSVT VSS

10. T Cell Receptor-Binding Domains

In an alternate embodiment, the second epitope that is bound by the Tri-Specific Binding Molecules of the present invention will be an epitope of the T cell Receptor (TCR). The T cell Receptor is natively expressed by CD4+ or CD8+ T cells, and permits such cells to recognize antigenic peptides that are bound and presented by class I or class II MHC proteins of antigen presenting cells. Recognition of a pMHC (peptide-MHC) complex by a TCR initiates the propagation of a cellular immune response that leads to the production of cytokines and the lysis of the antigen presenting cell (see, e.g., Armstrong, K. M. et al. (2008) "*Conformational Changes And Flexibility In T-Cell Receptor Recognition Of Peptide-MHC Complexes,*" Biochem. J. 415(Pt 2):183-196; Willemsen, R. (2008) "*Selection Of Human Antibody Fragments Directed Against Tumor T-Cell Epitopes For Adoptive T-Cell Therapy,*" Cytometry A. 73(11):1093-1099; Beier, K. C. et al. (2007) "*Master Switches Of T-Cell Activation And Differentiation,*" Eur. Respir. J. 29:804-812; Mallone, R. et al. (2005) "*Targeting T Lymphocytes For Immune Monitoring And Intervention In Autoimmune Diabetes,*" Am. J. Ther. 12(6):534-550). CD3 is the receptor that binds to the TCR (Thomas, S. et al. (2010) "*Molecular Immunology Lessons From Therapeutic T-Cell Receptor Gene Transfer,*" Immunology 129(2):170-177; Guy, C. S. et al. (2009) "*Organization Of Proximal Signal Initiation At The TCR:CD3 Complex,*" Immunol. Rev. 232(1):7-21; St. Clair, E. W. (Epub 2009 Oct. 12) "*Novel Targeted Therapies For Autoimmunity,*" Curr. Opin. Immunol. 21(6):648-657; Baeuerle, P. A. et al. (Epub 2009 Jun. 9) "*Bi-specific T-Cell Engaging Antibodies For Cancer Therapy,*" Cancer Res. 69(12):4941-4944; Smith-Garvin, J. E. et al. (2009) "*T Cell Activation,*" Annu. Rev. Immunol. 27:591-619; Renders, L. et al. (2003) "*Engineered CD3 Antibodies For Immunosuppression,*" Clin. Exp. Immunol. 133(3):307-309).

Antibodies that specifically bind to the T cell Receptor include the anti-TCR antibody BMA 031 (EP 0403156; Kurrle, R. et al. (1989) "*BMA 031—A TCR-Specific Monoclonal Antibody For Clinical Application,*" Transplant Proc. 21(1 Pt 1):1017-1019; Nashan, B. et al. (1987) "Fine Specificity Of A Panel Of Antibodies Against The TCR/CD3

Complex," Transplant Proc. 19(5):4270-4272; Shearman, C. W. et al. (1991) "Construction, Expression, And Biologic Activity Of Murine/Human Chimeric Antibodies With Specificity For The Human α/β T Cell," J. Immunol. 146(3):928-935; Shearman, C. W. et al. (1991) "Construction, Expression And Characterization of Humanized Antibodies Directed Against The Human α/β T Cell Receptor," J. Immunol. 147(12):4366-4373).

The amino acid sequence of the VL Domain of anti-TCR antibody BMA 031 is (SEQ ID NO:132) (CDR residues are shown underlined):

```
EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIK
```

The amino acid sequence of a VH Domain of anti-TCR antibody BMA 031 is (SEQ ID NO:133) (CDR residues are shown underlined):

```
QVQLVQSGAE VKKPGASVKV SCKASGYKFT SYVMHWVRQA

PGQGLEWIGY INPYNDVTKY NEKFKGRVTI TADKSTSTAY

LQMNSLRSED TAVHYCARGS YYDYDGFVYW GQGTLVTVSS
```

11. NKG2D Receptor-Binding Domains

In an alternate embodiment, the second epitope that is bound by the Tri-Specific Binding Molecules of the present invention will be an epitope of the NKG2D receptor. The NKG2D receptor is expressed on all human (and other mammalian) Natural Killer cells (Bauer, S. et al. (1999) "Activation Of NK Cells And T Cells By NKG2D, A Receptor For Stress-Inducible MICA," Science 285(5428):727-729; Jamieson, A. M. et al. (2002) "The Role Of The NKG2D Immunoreceptor In Immune Cell Activation And Natural Killing," Immunity 17(1):19-29) as well as on all CD8+ T cells (Groh, V. et al. (2001) "Costimulation Of CD8αβ T Cells By NKG2D Via Engagement By MIC Induced On Virus-Infected Cells," Nat. Immunol. 2(3):255-260; Jamieson, A. M. et al. (2002) "The Role Of The NKG2D Immunoreceptor In Immune Cell Activation And Natural Killing," Immunity 17(1):19-29). Such binding ligands, and particularly those which are not expressed on normal cells, include the histocompatibility 60 (H60) molecule, the product of the retinoic acid early inducible gene-1 (RAE-1), and the murine UL16-binding protein like transcript 1 (MULTI) (Raulet D. H. (2003) "Roles Of The NKG2D Immunoreceptor And Its Ligands," Nature Rev. Immunol. 3:781-790; Coudert, J. D. et al. (2005) "Altered NKG2D Function In NK Cells Induced By Chronic Exposure To Altered NKG2D Ligand-Expressing Tumor Cells," Blood 106:1711-1717). Antibodies that specifically bind to the NKG2D Receptor include KYK-2.0 (Kwong, K Y et al. (2008) "Generation, Affinity Maturation, And Characterization Of A Human Anti Human NKG2D Monoclonal Antibody With Dual Antagonistic And Agonistic Activity," J. Mol. Biol. 384:1143-1156; and PCT/US09/54911).

The amino acid sequence of the VL Domain of anti-NKG2D antibody KYK-1.0 is (SEQ ID NO:134) (CDR residues are shown underlined):

```
QPVLTQPSSV SVAPGETARI PCGGDDIETK SVHWYQQKPG

QAPVLVIYDD DDRPSGIPER FFGSNSGNTA TLSISRVEAG

DEADYYCQVW DDNNDEWVFG GGTQLTVL
```

The amino acid sequence of the VH Domain of anti-NKG2D antibody KYK-1.0 is (SEQ ID NO:135) (CDR residues are shown underlined):

```
EVQLVESGGG VVQPGGSLRL SCAASGFTFS SYGMHWVRQA

PGKGLEWVAF IRYDGSNKYY ADSVKGRFTI SRDNSKNTKY

LQMNSLRAED TAVYYCAKDR FGYYLDYWGQ GTLVTVSS
```

The amino acid sequence of a VL Domain of anti-NKG2D antibody KYK-2.0 is (SEQ ID NO:136) (CDR residues are shown underlined):

```
QSALTQPASV SGSPGQSITI SCSGSSSNIG NNAVNWYQQL

PGKAPKLLIY YDDLLPSGVS DRFSGSKSGT SAFLAISGLQ

SEDEADYYCA AWDDSLNGPV FGGGTKLTVL
```

The amino acid sequence of a VH Domain of anti-NKG2D antibody KYK-2.0 is (SEQ ID NO:137) (CDR residues are shown underlined):

```
QVQLVESGGG LVKPGGSLRL SCAASGFTFS SYGMHWVRQA

PGKGLEWVAF IRYDGSNKYY ADSVKGRFTI SRDNSKNTLY

LQMNSLRAED TAVYYCAKDR GLGDGTYFDY WGQGTTVTVS

S
```

D. Preferred Trispecific Binding Molecules of the Present Invention

1. Preferred Fc Domains

The CH2 and CH3 Domains of the two heavy chains interact to form the Fc Domain, which is a domain that is recognized by cellular Fc Receptors (FcγRs). As used herein, the term "Fc Domain" is used to define a C-terminal region of an IgG heavy chain. The amino acid sequence of the CH2-CH3 domain of an exemplary human IgG1 is (SEQ ID NO:1):

```
|CH2→
APELLGGPS  VFLFPPKPKD  TLMISRTPEV  TCVVVDVSHE  DPEVKFNWYV  DGVEVHNAKT
231        240         250         260         270         280

→CH2 | CH3→
KPREEQYNST YRVVSVLTVL  HQDWLNGKEY  KCKVSNKALP  APIEKTISKA  K GQPREPQVY
290        300         310         320         330         340

TLPPSREEMT KNQVSLTCLV  KGFYPSDIAV  EWESNGQPEN  NYKTTPPVLD  SDGSFFLYSK
350        360         370         380         390         400
```

```
                          ←CH3|
LTVDKSRWQQ GNVFSCSVMH EALHNHYTQK SLSLSPGK
410        420        430        440
```

Throughout the present specification, the numbering of the residues in an IgG heavy chain is that of the EU index as in Kabat et al., *Sequences of Proteins of Immunological Interest,* 5th Ed. Public Health Service, NH1, MD (1991), expressly incorporated herein by references. The "EU index as in Kabat" refers to the numbering of the human IgG1 EU antibody. Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Although boundaries may vary slightly, the CH2 domain of a human IgG Fc Domain usually extends from amino acids 231 to amino acid 341 of a human IgG according to the numbering system of Kabat. The CH3 domain of a human IgG usually extends from amino acids 342 to 447 according to the numbering system of Kabat. The "hinge region" or "hinge domain" is generally defined as stretching from Glu216 to Pro230 of human IgG1.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211). It is specifically contemplated that the antibodies of the present invention may be incorporate any allotype, isoallotype, or haplotype of any immunoglobulin gene, and are not limited to the allotype, isoallotype or haplotype of the sequences provided herein.

Activating and inhibitory signals are transduced through the Fc Receptors (FcγRs) following their ligation to an Fc Domain. These diametrically opposing functions result from structural differences among the different receptor isoforms. Two distinct domains within the cytoplasmic signaling domains of the receptor called immunoreceptor tyrosine-based activation motifs (ITAMs) or immunoreceptor tyrosine-based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB. Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI$_3$K). Cellular activation leads to release of proinflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular Ca$^{++}$. Thus cross-linking of FcγRIIB dampens the activating response to FcγR ligation and inhibits cellular responsiveness. B cell activation, B cell proliferation and antibody secretion is thus aborted.

The Fc Domain of the binding molecules of the present invention may be either a complete Fc Domain (e.g., a complete IgG Fc Domain) or only a fragment of a complete Fc Domain. Although the Fc Domain of the bi-specific monovalent Fc diabodies of the present invention may possess the ability to bind to one or more Fc receptors (e.g., FcγR(s)), more preferably such Fc Domain will cause altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Domain) or will substantially eliminate the ability of such Fc Domain to bind to inhibitory receptor(s). Thus, the Fc Domain of the Fc Domain-containing diabodies of the present invention may include some or all of the CH2 Domain and/or some or all of the CH3 Domain of a complete Fc Domain, or may comprise a variant CH2 and/or a variant CH3 sequence (that may include, for example, one or more insertions and/or one or more deletions with respect to the CH2 or CH3 domains of a complete Fc Domain). Such Fc Domains may comprise non-Fc polypeptide portions, or may comprise portions of non-naturally complete Fc Domains, or may comprise non-naturally occurring orientations of CH2 and/or CH3 domains (such as, for example, two CH2 domains or two CH3 Domains, or in the N-terminal to C-terminal direction, a CH3 Domain linked to a CH2 Domain, etc.).

Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low Affinity Activating Fcgamma Receptors,*" Cancer Res. 57(18):8882-8890).

In particular, it is preferred for the CH2-CH3 domains of the polypeptide chains of the Fc Domain-containing diabodies of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Domain (SEQ ID NO:1). Fc variants and mutant forms capable of mediating such altered binding are described above. In a preferred embodiment the CH2-CH3 Domain of the first and/or third polypeptide chains of such diabodies include any 1, 2, 3, 4, 5, 6, or 7 of the substitutions: L234A, L235A, F243L, R292P, Y300L, V305I and P396L. Exemplary variants of human IgG1 Fc Domains with reduced binding to CD32B and/or increased binding to CD16A contain F243L, R292P, Y300L, V305I or P296L substitutions. These amino acid substitutions may be present in a human IgG1 Fc Domain in any combination. In one embodiment, the human IgG1 Fc Domain variant contains a F243L, R292P and Y300L substitution. In another embodiment, the human IgG1 Fc Domain variant contains a F243L, R292P, Y300L, V305I and P296L substitution. In one embodiment the CH2-CH3 Domain of the first and/or third polypeptide chains of such diabodies include any 1, 2, or 3, of the substitutions: L234A, L235A, N297G, N297Q. In another embodiment, the human IgG1 Fc Domain variant contains an N297Q substitution, L234A and L235A substitutions or a D265A substitution, as these mutations abolish FcR binding. Alternatively, a CH2-CH3 domain which inherently exhibits decreased (or substantially no) binding to FcγRIIIA (CD16a) and/or reduced effector function (relative to the binding exhibited by the wild-type IgG1 Fc Domain (SEQ ID NO:1)) is utilized. In a specific embodiment, the Fc Domain-containing diabodies of the present invention comprise an IgG2 Fc Domain or an IgG4 Fc Domain. Where an IgG4 Fc Domain in utilized the instant invention also encompasses the introduction of a stabilizing mutation such as S228P, as numbered by the EU index as set forth in Kabat (Lu et al., (2008) "*The Effect Of A Point Mutation On The Stability Of Igg4 As Monitored By Analytical Ultracentrifugation*," J Pharmaceutical Sciences 97:960-969) to reduce the incidence of strand exchange. Other stabilizing mutations known in the art may be introduced into an IgG4 Fc Domain (Peters, P et al., (2012) "*Engineering an Improved IgG4 Molecule with Reduced Disulfide Bond Heterogeneity and Increased Fab Domain Thermal Stability*," J. Biol. Chem., 287:24525-24533; PCT Patent Publication No: WO 2008/145142). Since the N297A, L234A, L235A and D265A substitutions abolish effector function, in circumstances in which effector function is desired, these substitutions would preferably not be employed.

The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any two of the polypeptides of the Tri-Specific Binding Molecule. Methods of protein engineering to favor heterodimerization over homodimerization are well-known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bi-specific Antibody: Highly Efficient Heterodimerization, Expression And Tumor Cell Lysis*," J. Immunol. Methods 296:95-101; each of which is hereby incorporated herein by reference in its entirety). Preferably the "knob" is engineered into the CH2-CH3 Domains of the first polypeptide chain and the "hole" is engineered into the CH2-CH3 Domains of the other CH2-CH3-containing polypeptide chain. Thus, the "knob" will help in preventing the first polypeptide chain from homodimerizing via its CH2 and/or CH3 Domains. The CH2-CH3 "hole-bearing" polypeptide chain will heterodimerize with the CH2-CH3 "knob-bearing" polypeptide chain, and will also homodimerize with itself. A preferred knob is created by modifying a native IgG Fc Domain to contain the modification T366W. A preferred hole is created by modifying a native IgG Fc Domain to contain the modification T366S, L368A and Y407V. To aid in purifying the "hole-bearing" polypeptide chain homodimer from the final Tri-Specific Binding Molecule, the protein A binding site of the CH2 and CH3 Domains of the "hole-bearing" Fc Domain is preferably mutated by amino acid substitution at position 435 (H435R). Thus, the "hole-bearing" Fc Domain homodimer will not bind to protein A, whereas the desired Tri-Specific Binding Molecule will retain its ability to bind protein A via the protein A binding site on the first polypeptide chain.

A preferred sequence for the CH2 and CH3 Domains of the first polypeptide chain of an Fc Domain-containing diabody of the present invention will have the "knob-bearing" sequence (SEQ ID NO:52):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

A preferred sequence for the CH2 and CH3 Domains of the second polypeptide chain of an Fc Domain-containing diabody of the present invention having two polypeptide chains (or the third polypeptide chain of an Fc Domain-containing diabody having three polypeptide chains) will have the "hole-bearing" sequence (SEQ ID NO:53):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

As will be noted, the CH2-CH3 Domains of SEQ ID NO:52 and SEQ ID NO:53 include a substitution at position 234 with alanine and 235 with alanine, and thus form an Fc Domain exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Domain (SEQ ID NO:1).

It is preferred that the first polypeptide chain will have a "knob-bearing" CH2-CH3 sequence, such as that of SEQ ID NO:52. However, as will be recognized, a "hole-bearing" CH2-CH3 Domain (e.g., SEQ ID NO:53) could be employed in the first polypeptide chain, in which case, a "knob-bearing" CH2-CH3 Domain (e.g., SEQ ID NO:52) would be employed in the second polypeptide chain of an Fc Domain-containing diabody of the present invention having two polypeptide chains (or the third polypeptide chain of an Fc Domain-containing diabody having three polypeptide chains).

2. Preferred First Polypeptide Chain

A first polypeptide chain of a preferred binding molecule of the present invention will comprise a Variable Light Chain Domain capable of binding to Epitope I ($VL_I$), a Variable Heavy Chain Domain capable of binding to Epitope II ($VH_{II}$), a Heterodimer-Promoting Domain and a CH2-CH3 Domain.

Since the Variable Light Chain and Variable Heavy Chain Domains of the first polypeptide are directed toward different epitopes, they cannot associate together to form a Binding Domain that is able to bind either Epitope I or Epitope II. The Variable Light Chain and Variable Heavy Chain Domains of the first polypeptide are spaced apart from one another by an intervening linker peptide that is sufficiently short as to substantially prevent the association of these Domains. An exemplary linker, termed "Linker 1," has the sequence (SEQ ID NO:33): GGGSGGGG.

The Variable Heavy Chain Domain of the first polypeptide and the Heterodimer-Promoting Domain of that polypeptide are preferably spaced apart from one another by an intervening linker peptide that contains 1, 2, 3 or more cysteine residues. A preferred cysteine-containing spacer peptide ("Linker 2") has the sequence is SEQ ID NO:34: GGCGGG.

Linkers that may be employed to link a CH2-CH3 Domain to a polypeptide chain of the molecules of the present invention include: ASTKG (SEQ ID NO:47), DKTHTCPPCP (SEQ ID NO:48), LEPKSS (SEQ ID NO:49), and APSSSPME (SEQ ID NO:50), APSSS (SEQ ID NO:152) and GGG or GCG. SEQ ID NO:49 may be used in lieu of GGG or GCG for ease of cloning. Additionally, SEQ ID NO:49 may be immediately followed by SEQ ID NO:47 to form an alternate linker (LEPKSSDKTHTCPPCP; SEQ ID NO:51).

The Heterodimer-Promoting Domain of the first polypeptide and the Heterodimer-Promoting Domain of the second polypeptide are coordinately selected. The Domains differ from one another and are designed to associate with one another so as to promote the association of the first and second polypeptide chains. For example, one of the Heterodimer-Promoting Domains will be engineered to have a negative charge at pH 7, while the other of the two polypeptide chains will be engineered to have a positive charge at pH 7. The presence of such charged Domains promotes association between the first and second polypeptides, and thus fosters heterodimerization. It is immaterial which Heterodimer-Promoting Domains is provided to which chain, as long as the Domains employed on the first and second polypeptide chains differ so as to foster heterodimerization between such chains.

The Heterodimer-Promoting Domains may be the IgG CL and CH1 domains or may be a peptide having the amino acid sequence GVEPKSC (SEQ ID NO:35) or VEPKSC (SEQ ID NO:36), derived from the hinge domain of a human IgG, and in lieu of the CL domain, one may employ the C-terminal 6 amino acids of the human kappa light chain, GFNRGEC (SEQ ID NO:37) or FNRGEC (SEQ ID NO:38).

More preferably, however, the Heterodimer-Promoting Domains of such diabodies are formed from one, two, three or four tandemly repeated coil domains of opposing charge that comprise a sequence of at least six, at least seven or at least eight charged amino acid residues (Apostolovic, B. et al. (2008) "*pH-Sensitivity of the E3/K3 Heterodimeric Coiled Coil*," Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228; Arndt, K. M. et al. (2002) "*Comparison of In Vivo Selection and Rational Design of Heterodimeric Coiled Coils*," Structure 10:1235-1248; Boucher, C. et al. (2010) "*Protein Detection By Western Blot Via Coiled-Coil Interactions*," Analytical Biochemistry 399:138-140; Cachia, P. J. et al. (2004) "*Synthetic Peptide Vaccine Development: Measurement Of Polyclonal Antibody Affinity And Cross Reactivity Using A New Peptide Capture And Release System For Surface Plasmon Resonance Spectroscopy*," J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763; Fernandez-Rodriquez, J. et al. (2012) "*Induced Heterodimerization And Purification Of Two Target Proteins By A Synthetic Coiled-Coil Tag*," Protein Science 21:511-519; Ghosh, T. S. et al. (2009) "*End-To-End And End-To-Middle Interhelical Interactions: New Classes Of Interacting Helix Pairs In Protein Structures*," Acta Crystallographica D65:1032-1041; Grigoryan, G. et al. (2008) "*Structural Specificity In Coiled-Coil Interactions*," Curr. Opin. Struc. Biol. 18:477-483; Litowski, J. R. et al. (2002) "*Designing Heterodimeric Two-Stranded α-Helical Coiled-Coils: The Effects Of Hydrophobicity And α-Helical Propensity On Protein Folding, Stability, And Specificity*," J. Biol. Chem. 277:37272-37279; Steinkruger, J. D. et al. (2012) "*The d'-d-d' Vertical Triad is Less Discriminating Than the a'-a-a' Vertical Triad in the Antiparallel Coiled-coil Dimer Motif*" J. Amer. Chem. Soc. 134(5):2626-2633; Straussman, R. et al. (2007) "*Kinking the Coiled Coil Negatively Charged Residues at the Coiled-coil Interface*," J. Molec. Biol. 366:1232-1242; Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; Woolfson, D. N. (2005) "*The Design Of Coiled-Coil Structures And Assemblies*," Adv. Prot. Chem. 70:79-112; Zeng, Y. et al. (2008) "*A Ligand-Pseudoreceptor System Based On de novo Designed Peptides For The Generation Of Adenoviral Vectors With Altered Tropism*," J. Gene Med. 10:355-367).

Such repeated coil domains may be exact repeats or may have substitutions. For example, the Heterodimer-Promoting Domain of the first polypeptide chain may comprise a sequence of eight negatively charged amino acid residues and the Heterodimer-Promoting Domain of the second polypeptide chain may comprise a sequence of eight negatively charged amino acid residues. It is immaterial which coil is provided to the first or second polypeptide chains, provided that a coil of opposite charge is used for the other polypeptide chain. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid. It is possible for only a single Heterodimer-Promoting Domain to be employed (since such domain will inhibit homodimerization and thereby promote heterodimerization), however, it is preferred for both the first and second polypeptide chains of the diabodies of the present invention to contain Heterodimer-Promoting Domains.

In a preferred embodiment, one of the Heterodimer-Promoting Domains will comprise four tandem "E-coil" helical domains (SEQ ID NO:39: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:40: KVAALKE-KVAALKE-KVAALKE-KVAALKE), whose lysine residues will form a positive charge at pH 7. The presence of such charged domains promotes association between the first and second polypeptides, and thus fosters heterodimerization. Especially preferred is a Heterodimer-Promoting Domain in which one of the four tandem "E-coil" helical domains of SEQ ID NO:39 has been modified to contain a cysteine residue: EVAACEK-EVAALEK-EVAALEK-EVAALEK (SEQ ID NO:41). Likewise, especially preferred is a Heterodimer-Promoting Domain in which one of the four tandem "K-coil" helical domains of SEQ ID NO:40 has been modified to contain a cysteine residue: KVAACKE-KVAALKE-KVAALKE-KVAALKE (SEQ ID NO:42).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules,*" J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:43): LAEAKVLANR ELDKYGVSDY YKNLID-NAKS AEGVKALIDE ILAALP.

As disclosed in WO 2012/162068 (herein incorporated by reference), "deimmunized" variants of SEQ ID NO:43 have the ability to attenuate or eliminate MHC class II binding. Based on combinational mutation results, the following combinations of substitutions are considered to be preferred substitutions for forming such a deimmunized albumin-binding domain: 66S/70S+71A; 66S/70S+79A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

(SEQ ID NO: 44)
LAEAKVLANR ELDKYGVSDY YKNA$_{64}$A$_{65}$NNAKT VEGVKALIA$_{79}$E ILAALP, or the amino acid sequence:

(SEQ ID NO: 45)
LAEAKVLANR ELDKYGVSDY YKNLIS$_{66}$NAKS$_{70}$ VEGVKALIA$_{79}$E ILAALP, are particularly preferred as such deimmunized Albumin-Binding Domains exhibit substantially wild-type binding while providing attenuated MHC class II binding. Thus, the first polypeptide chain of such a diabody having an Albumin-Binding Domain contains a third linker (Linker 3) preferably positioned C-terminally to the E-coil (or K-coil) Domain of such polypeptide chain so as to intervene between the E-coil (or K-coil) Domain and the Albumin-Binding Domain (which is preferably a deimmunized Albumin-Binding Domain). A preferred sequence for such Linker 3 is SEQ ID NO:46: GGGS.

Thus, in sum, a preferred first polypeptide chain of a preferred Tri-Specific Binding Molecule of the present invention will comprise the Domains and linkers: (VL$_I$ Domain)-(Linker 1)-(VH$_{II}$ Domain)-(Linker 2)-(E-coil Heterodimer-Promoting Domain)-(Linker 3)-(Knob-Bearing CH2-CH3 Domain).

3. Alternative First Polypeptide Chain

In one embodiment, the orientations of the above-described Domains will be in the N-terminal to C-terminal direction. The present invention, however, also contemplates a variation thereof, wherein the orientations of the Domains of the first polypeptide chain are: NH$_2$-(Knob-Bearing CH3-CH2 Domain)-(VL$_I$ Domain)-(Linker 1)-(VH$_{II}$ Domain)-(Linker 2)-(E-coil Heterodimer-Promoting Domain). Preferably, a cysteine-containing peptide is present, N-terminal to such CH2-CH3 Domain. The sequence of an exemplary peptide is sequence (SEQ ID NO:48): DKTHTCPPCP. Preferably in this embodiment, the CH3 Domain is spaced apart from the VL$_I$ Domain by an intervening peptide linker (Linker 4), such as one having the amino acid sequence of (SEQ ID NO:152): APSSS, and more preferably, the amino acid sequence (SEQ ID NO:50): APSSSPME.

4. Preferred Second Polypeptide Chain

A second polypeptide chain of such preferred Tri-Specific Binding Molecules will comprise, in the N-terminal to C-terminal direction, a Variable Light Chain Domain capable of binding to Epitope II (VL$_{II}$), a Variable Heavy Chain Domain capable of binding to Epitope I (VH$_I$), and a Heterodimer-Promoting Domain.

Since the Variable Light Chain and Variable Heavy Chain Domains of the second polypeptide are directed toward different epitopes, they cannot associate together to form a Binding Domain that is able to bind either Epitope I or Epitope II. The Variable Light Chain and Variable Heavy Chain Domains of the second polypeptide are spaced apart from one another by an intervening linker peptide that is sufficiently short as to substantially prevent the association of these Domains. "Linker 1," having the sequence (SEQ ID NO:33): GGGSGGGG is an exemplary linker for this purpose.

As in the case of the first polypeptide chain, the Variable Heavy Chain Domain of the second polypeptide and the Heterodimer-Promoting Domain of that polypeptide are preferably spaced apart from one another by an intervening linker peptide that contains 1, 2, 3 or more cysteine residues. "Linker 2," having the sequence (SEQ ID NO:34) GGCGGG is an exemplary linker for this purpose. Such cysteine residues can form disulfide bonds with cysteine residues in the cysteine-containing spacer peptide that separates the Variable Heavy Chain Domain of the first polypeptide and the Heterodimer-Promoting Domain of that polypeptide. Thus, the first and second polypeptides of the Binding Molecules of the present invention are covalently bonded to one another.

As discussed above, the Heterodimer-Promoting Domain of the second polypeptide chain is selected so as coordinate with the Heterodimer-Promoting Domain of the first polypeptide chain. Thus, in a preferred embodiment, the Heterodimer-Promoting Domain of the first polypeptide chain is either a "K-coil" Domain (SEQ ID NO:40) or an "E-coil" Domain (SEQ ID NO:39). If the cysteine-containing E-coil (SEQ ID NO:41) is employed in the first polypeptide chain, then the cysteine-containing K-coil (SEQ ID NO:42) is preferably employed in the second polypeptide chain. Conversely, if the cysteine-containing K-coil (SEQ ID NO:42) is employed in the first polypeptide chain, then the cysteine-containing E-coil (SEQ ID NO:41) is preferably employed in the second polypeptide chain. Since the first polypeptide chain will preferably possess an "E-coil" Domain, the second polypeptide chain will preferably contain a "K-coil" Domain.

As the first and second polypeptide chains are polypeptide chains of a diabody, they are able to associate together to form a Domain I Binding Domain ($VL_A$/$VH_A$) that recognizes and immunospecifically binds to Epitope I, and a Domain II Binding Domain ($VL_B$/$VH_B$) that recognizes and immunospecifically binds to Epitope II.

Thus, in sum, a preferred second polypeptide chain of a preferred Binding Molecule of the present invention will comprise the Domains and linkers: ($VL_{II}$ Domain)-(Linker Domain)-(Linker 2)-(K-coil Heterodimer-Promoting Domain).

5. Preferred Third Polypeptide Chain

A third polypeptide chain of a preferred Binding Molecule of the present invention is a polypeptide that comprises, in the N-terminal to C-terminal direction, a Binding Domain, an optional CH1-Hinge Domain, and a CH2-CH3 Domain. The Binding Domain of the third polypeptide chain of a preferred Binding Molecule of the present invention may be a Variable Heavy Chain Domain capable of binding to Epitope III ($VH_{III}$), in which case, the fourth polypeptide chain of the preferred Binding Molecules of the present invention (discussed below) is a polypeptide that comprises a Variable Light Chain Domain capable of binding to Epitope III ($VL_{III}$), such that the Binding Domain is capable of immunospecific binding to an antigen possessing Epitope III. Alternatively, the Binding Domain of the third polypeptide chain of the preferred Binding Molecules of the present invention may comprise an Effector Cell Receptor-Type Binding Domain, in which case, the fourth polypeptide chain of the preferred Binding Molecules of the present invention (discussed below) is a polypeptide that comprises a complementary Effector Cell Receptor-Type Binding Domain, such that the interaction of two polypeptide chains forms a Binding Domain that is capable of physiospecific binding to molecule present on the surface of the effector cell. The third polypeptide chain may be isolated from naturally occurring antibodies. Alternatively, it may be constructed recombinantly. An exemplary CH1 Domain is a human IgG1 CH1 Domain having the amino acid sequence (SEQ ID NO:207):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKV
```

A variant of the human IgG1 CH1 Domain of SEQ ID NO:207 is (SEQ ID NO:208):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

An exemplary Hinge Domain is a human IgG1 Hinge Domain having the amino acid sequence (SEQ ID NO:209): EPKSCDKTHTCPPCP. As will be recognized, the exemplary Hinge Domain comprises multiple cysteine residues (Elkabetz et al. (2005) "*Cysteines In CH1 Underlie Retention Of Unassembled Ig Heavy Chains*," J. Biol. Chem. 280:14402-14412) that may participate in interchain covalent bonding.

Although a wild-type CH2-CH3 Domain may be employed, it is preferred, as described above, to employ a modified CH2-CH3 Domain that promotes heterodimerization with the CH2-CH3 Domain of the first polypeptide chain.

Preferably, therefore the CH2-CH3 Domain of the third polypeptide chain will be a "hole-bearing" CH2-CH3 Domain whose amino acid sequence is complementary to the "knob-bearing" CH2-CH3 Domain (SEQ ID NO:52) employed in the first polypeptide. As discussed above, the "hole-bearing" CH2-CH3 domain preferably should comprise a substitution at position 435 (H435R) to remove the Protein A binding site. An exemplary "hole-bearing" CH2-CH3 Domain with the H435R substitution for the third polypeptide is SEQ ID NO:53.

As will be recognized, a "knob-bearing" CH2-CH3 Domain (e.g., SEQ ID NO:52) could be employed in the third polypeptide chain, in which case, a "hole-bearing" CH2-CH3 Domain (e.g., SEQ ID NO:53) would be employed in the first polypeptide chain.

In the embodiment in which the third (and fourth) polypeptide chains of the preferred Tri-Specific Binding Molecules of the present invention each comprise a polypeptide chain of an Effector Cell Receptor-Type Binding Domain, methods for producing such Effector Cell Receptor-Type Binding Domains are well-known (e.g., US2012/0294874A1).

Thus, in sum, a third polypeptide chain of the preferred Binding Molecules of the present invention will comprise the Domains and linkers: ($VH_{III}$ Domain)-(Optional CH1 Domain)-(Optional Hinge Domain)-("Hole-Bearing" CH2-CH3 Domain), or (T Cell Receptor-Type Binding Domain; first or second polypeptide thereof)-(Optional CH1 Domain)-(Optional Hinge Domain)-("Hole-Bearing" CH2-CH3 Domain).

6. Preferred Fourth Polypeptide Chain

A fourth polypeptide chain of the preferred Tri-Specific Binding Molecules of the present invention is either a polypeptide of an Effector Cell Receptor-Type Binding Domain (wherein the third and fourth polypeptides form a ligand for a receptor found on the surface of an effector cell, or more preferably, a light chain of the above-indicated antibody that immunospecifically binds to Epitope III or which are complementary to the binding domain of the third polypeptide chain.

Thus, wherein the third and fourth polypeptides form a Fab-Type Binding Domain such fourth polypeptide chain comprises, in the N-terminal to C-terminal direction, a Variable Light Chain Domain capable of binding to Epitope III (VL$_{III}$), and a Domain for promoting covalent bonding to the third polypeptide chain or a Binding Domain and such Domain for promoting covalent bonding to the third polypeptide chain. Such Domain may be a CL Domain, or a cysteine-containing portion thereof, such as (SEQ ID NO:38) FNRGEC or a linker such as Linker 2 (having the sequence (SEQ ID NO:34) GGCGGG. An exemplary a cysteine-containing peptide that forms disulfide bonds with such Linker 2 comprises the amino acid sequence VEPKSC (SEQ ID NO:36) or a Hinge Domain.

The fourth polypeptide chain may be isolated from naturally occurring antibodies. Alternatively, it may be constructed recombinantly. A preferred CL Domain is a human IgG1 CL Kappa Domain having the amino acid sequence (SEQ ID NO:210):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG1 CL Lambda2 Domain having the amino acid sequence (SEQ ID NO:211):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

As will be noticed, the CL Domain, or other Cysteine-Containing Domain, of the fourth polypeptide chain comprises cysteine residues. Such cysteine residues are able to covalently bond to cysteine residues of the CH1 Domain of the third polypeptide chain to thereby covalently complex the third and fourth polypeptide chains of the binding molecules of the present invention to one another. Thus the third and fourth polypeptide chains are covalently bonded to one another.

Additionally, cysteine residues of the CH2-CH3 Domain of the first polypeptide chain can form disulfide bonds with cysteine residues of the CH2-CH3 Domain of the third polypeptide chain. Thus the first and third polypeptide chains are covalently bonded to one another.

E. Variant Fc Domains

In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc Domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. The amino acid sequence of an exemplary IgG1 Fc Domain (SEQ ID NO:1) is presented above.

Modification of the Fc Domain normally leads to an altered phenotype, for example altered serum half-life, altered stability, altered susceptibility to cellular enzymes or altered effector function. It may be desirable to modify the antibody of the invention with respect to effector function, so as to enhance the effectiveness of the antibody in treating cancer, for example. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkins lymphoma, CLL, and Burkitt's lymphoma). In said embodiments, molecules of the invention with conferred or altered effector function activity are useful for the treatment and/or prevention of a disease, disorder or infection where an enhanced efficacy of effector function activity is desired.

In certain embodiments, the Tri-Specific Binding Molecules of the present invention comprise an Fc Domain that possesses one or more modifications (e.g., substitutions, deletions, or insertions) to the sequence of amino acids of a wild-type Fc Domain (SEQ ID NO:1), which reduce the affinity and avidity of the Fc Domain and, thus, the molecule of the invention, for one or more FcγR receptors. In other embodiments, the molecules of the invention comprise an Fc Domain that possesses one or more modifications to the amino acids of the wild-type Fc Domain, which increase the affinity and avidity of the Fc Domain and, thus, the molecule of the invention, for one or more FcγR receptors. In other embodiments, the molecules comprise a variant Fc Domain wherein said variant confers or mediates increased ADCC activity and/or an increased binding to FcγRIIA, relative to a molecule comprising no Fc Domain or comprising a wild-type Fc Domain. In alternate embodiments, the molecules comprise a variant Fc Domain wherein said variant confers or mediates decreased ADCC activity (or other effector function) and/or an increased binding to FcγRIIB, relative to a molecule comprising no Fc Domain or comprising a wild-type Fc Domain. In some embodiments, the invention encompasses Tri-Specific Binding Molecules comprising a variant Fc Domain, which variant Fc Domain does not show a detectable binding to any FcγR, relative to a comparable molecule comprising the wild-type Fc Domain. In other embodiments, the invention encompasses Tri-Specific Binding Molecules comprising a variant Fc Domain, which variant Fc Domain only binds a single FcγR, preferably one of FcγRIIA, FcγRIIB, or FcγRIIIA. Any such increased affinity and/or avidity is preferably assessed by measuring in vitro the extent of detectable binding to the FcγR or FcγR-related activity in cells that express low levels of the FcγR when binding activity of the parent molecule (without the modified Fc Domain) cannot be detected in the cells, or in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

The Tri-Specific Binding Molecules of the present invention may comprise altered affinities for an activating and/or inhibitory Fcγ receptor. In one embodiment, the Tri-Specific Binding Molecule comprises a variant Fc Domain that has increased affinity for FcγRIIB and decreased affinity for FcγRIIIA and/or FcγRIIA, relative to a comparable molecule with a wild-type Fc Domain. In another embodiment, the Tri-Specific Binding Molecule of the present invention comprise a variant Fc Domain, which has decreased affinity for FcγRIIB and increased affinity for FcγRIIIA and/or FcγRIIA, relative to a comparable molecule with a wild-type Fc Domain. In yet another embodiment, the Tri-Specific Binding Molecules of the present invention comprise a variant Fc Domain that has decreased affinity for FcγRIIB and decreased affinity for FcγRIIIA and/or FcγRIIA, relative to a comparable molecule with a wild-type Fc Domain. In still another embodiment, the Tri-Specific Binding Molecules of the present invention comprise a variant Fc Domain, which has unchanged affinity for FcγRIIB and decreased (or increased) affinity for FcγRIIIA and/or FcγRIIA, relative to a comparable molecule with a wild-type Fc Domain.

In certain embodiments, the Tri-Specific Binding Molecules of the present invention comprise a variant Fc Domain having an altered affinity for FcγRIIIA and/or FcγRIIA such that the immunoglobulin has an enhanced effector function, e.g., antibody-dependent cell-mediated cytotoxicity. Non-limiting examples of effector cell functions include antibody-dependent cell-mediated cytotoxicity (ADCC), antibody-dependent phagocytosis, phagocytosis, opsonization, opsonophagocytosis, cell binding, rosetting, C1q binding, and complement dependent cell-mediated cytotoxicity.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Domain. In other embodiments of the invention, the variant Fc Domain immunospecifically binds one or more FcRs with at least 65%, preferably at least 70%, 75%, 80%, 85%, 90%, 95%, 100%, 125%, 150%, 175%, 200%, 225%, or 250% greater affinity relative to a molecule comprising a wild-type Fc Domain. Such measurements can be in vivo or in vitro assays, and in a preferred embodiment are in vitro assays such as ELISA or surface plasmon resonance assays.

In different embodiments, the Tri-Specific Binding Molecules of the present invention comprise a variant Fc Domain wherein said variant agonizes at least one activity of an FcγR receptor, or antagonizes at least one activity of an FcγR receptor. In a preferred embodiment, the molecules comprise a variant that antagonizes one or more activities of FcγRIIB, for example, B cell receptor-mediated signaling, activation of B cells, B cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the Tri-Specific Binding Molecules of the present invention comprise a variant that agonizes one or more activities of FcεRI, for example, mast cell activation, calcium mobilization, degranulation, cytokine production, or serotonin release.

In certain embodiments, the molecules comprise an Fc Domain comprising regions from two or more IgG isotypes (e.g., IgG1, IgG2, IgG3 and IgG4). The various IgG isotypes exhibit differing physical and functional properties including serum half-life, complement fixation, FcγR binding affinities and effector function activities (e.g., ADCC, CDC, etc.) due to differences in the amino acid sequences of their hinge and/or Fc Domains, for example as described in Flesch and Neppert (1999) J. Clin. Lab. Anal. 14:141-156; Chappel et al. (1993) J. Biol. Chem. 33:25124-25131; Chappel et al. (1991) Proc. Natl. Acad. Sci. (U.S.A.) 88:9036-9040; or Brüggemann et al. (1987) J. Exp. Med 166:1351-1361. This type of variant Fc Domain may be used alone, or in combination with an amino acid modification, to affect Fc-mediated effector function and/or binding activity. In combination, the amino acid modification and IgG hinge/Fc Domain may display similar functionality (e.g., increased affinity for FcγRIIA) and may act additively or, more preferably, synergistically to modify the effector functionality in the molecule of the invention, relative to a molecule of the invention comprising a wild-type Fc Domain. In other embodiments, the amino acid modification and IgG Fc Domain may display opposite functionality (e.g., increased and decreased affinity for FcγRIIA, respectively) and may act to selectively temper or reduce a specific functionality in the molecule of the invention, relative to a molecule of the invention not comprising an Fc Domain or comprising a wild-type Fc Domain of the same isotype.

In a preferred specific embodiment, the Tri-Specific Binding Molecules of the present invention comprise a variant Fc Domain, wherein said variant Fc Domain comprises at least one amino acid modification relative to a wild-type Fc Domain, such that said molecule has an altered affinity for an FcR, provided that said variant Fc Domain does not have a substitution at positions that make a direct contact with FcγR based on crystallographic and structural analysis of Fc-FcR interactions such as those disclosed by Sondermann et al. (2000) Nature 406:267-73. Examples of positions within the Fc Domain that make a direct contact with FcγR are amino acid residues 234-239 (hinge region), amino acid residues 265-269 (B/C loop), amino acid residues 297-299 (C'/E loop), and amino acid residues 327-332 (F/G loop). In some embodiments, the molecules of the invention comprise variant Fc Domains comprise modification of at least one residue that does not make a direct contact with an FcγR based on structural and crystallographic analysis, e.g., is not within the Fc-FcγR binding site.

Variant Fc Domains are well-known in the art, and any known Fc variant may be used in the present invention to confer or modify the effector function exhibited by a molecule of the invention comprising an Fc Domain (or portion thereof) as functionally assayed, e.g., in an NK dependent or macrophage dependent assay. For example, Fc Domain variants identified as altering effector function are disclosed in the Antibody Engineering Technology Art, and any suitable variant disclosed therein may be used in the present molecules.

In certain embodiments, the Tri-Specific Binding Molecules of the present invention comprise a variant Fc Domain, having one or more amino acid modifications in one or more sites, which modification(s) alter (relative to a wild-type Fc Domain) the Ratio of Affinities of the variant Fc Domain to an activating FcγR (such as FcγRIIA or FcγRIIIA) relative to an inhibiting FcγR (such as FcγRIIB):

Ratio of Affinities=

$$\frac{\text{Wild-Type to Variant Change in Affinity to } Fc\gamma R_{Activating}}{\text{Wild-Type to Variant Change in Affinity to } Fc\gamma R_{Inhibiting}}$$

Particularly preferred are Tri-Specific Binding Molecules of the present invention that possess a variant Fc Domain (relative to the wild-type Fc Domain) in which the Fc variant has a Ratio of Affinities greater than 1. Such molecules have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. In contrast, an Fc variant having a Ratio of Affinities less than 1 mediates decreased efficacy of effector cell function. Table 1 lists exemplary single, double, triple, quadruple and quintuple mutations by whether their Ratio of Affinities is greater than or less than 1.

TABLE 1

Exemplary Single and Multiple Mutations Listed by Ratio of Affinities

| Single | Double | Triple | Quadruple | Quintuple |
|---|---|---|---|---|
| \multicolumn{5}{c}{Ratio of Affinities > 1} | | | | |
| F243L | F243L & R292P | F243L, P247L & N421K | L234F, F243L, R292P & Y300L | L235V, F243L, R292P, Y300L & P396L |
| D270E | F243L & Y300L | F243L, R292P & Y300L | L235I, F243L, R292P & Y300L | |
| R292G | F243L & P396L | F243L, R292P & V305I | L235P, F243L, R292P & Y300L | L235P, F243L, R292P, Y300L & P396L |
| R292P | | | L235Q, F243L, R292P & Y300L | |
| | D270E & P396L | F243L, R292P & P396L | F243L, P247L, R292P, V305I, Y300L | |
| | R292P & Y300L | F243L, Y300L & P396L | D270E & N421K | F243L, R255L & P396L |
| | R292P & V305I | P247L, D270E & N421K | F243L, D270E, G316D & R416G | |
| | R292P & P396L | R255L, D270E & P396L | F243L, D270E, K392T & P396L | |
| | Y300L & P396L | D270E, G316D & R416G | F243L, D270E, P396L & Q419H | |
| | P396L & Q419H | D270E, K392T & P396L | F243L, R292P, Y300L, & P396L | |
| | | D270E, P396L & Q419H | F243L, R292P, V305I & P396L | |
| | | V284M, R292L & K370N | P247L, D270E, Y300L & N421K | |
| | | R292P, Y300L & P396L | R255L, D270E, R292G & P396L | |
| | | | R255L, D270E, Y300L & P396L | |
| | | | D270E, G316D, P396L & R416G | |
| \multicolumn{5}{c}{Ratio of Affinities < 1} | | | | |
| Y300L | F243L & P396L | F243L, R292P & V305I | | |
| P396L | P247L & N421K | | | |
| | R255L & P396L | | | |
| | R292P & V305I | | | |
| | K392T & P396L | | | |

TABLE 1-continued

Exemplary Single and Multiple Mutations Listed by Ratio of Affinities

| Single | Double | Triple | Quadruple | Quintuple |
|---|---|---|---|---|
| \multicolumn{5}{c}{Ratio of Affinities > 1} | | | | |
| | P396L & Q419H | | | |

In a specific embodiment, in variant Fc Domains, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Domains, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a preferred embodiment, in variant Fc Domains that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Domain has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc Domains that bind an FcγR (via its Fc Domain) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439.

In a different embodiment, in variant Fc Domains that bind an FcγR (via its Fc Domain) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398 or 430. In a different embodiment, in variant Fc Domains that binds FcγRIIA with an enhanced affinity, any of the following residues: A255, A256, A258, A267, A268, N268, A272, Q272, A276, A280, A283, A285, A286, D286, Q286, S286, A290, S290, M301, E320, M320, Q320, R320, E322, A326, D326, E326, S326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |

| | |
|---|---|
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from Groups 1-105:

| Group | Variant | Group | Variant |
|---|---|---|---|
| 1 | A330L/I332E | 54 | S239D/D265L/N297D/I332E |
| 2 | D265F/N297E/I332E | 55 | S239D/D265T/N297D/I332E |
| 3 | D265Y/N297D/I332E | 56 | S239D/D265V/N297D/I332E |
| 4 | D265Y/N297D/T299L/I332E | 57 | S239D/D265Y/N297D/I332E |
| 5 | F241E/F243Q/V262T/V264F | 58 | S239D/I332D |
| 6 | F241E/F243Q/V262T/V264E/I332E | 59 | S239D/I332E |
| 7 | F241E/F243R/V262E/V264R | 60 | S239D/I332E/A330I |
| 8 | F241E/F243R/V262E/V264R/I332E | 61 | S239D/I332N |
| 9 | F241E/F243Y/V262T/V264R | 62 | S239D/I332Q |
| 10 | F241E/F243Y/V262T/V264R/I332E | 63 | S239D/N297D/I332E |
| 11 | F241L/F243L/V262I/V264I | 64 | S239D/N297D/I332E/A330Y |
| 12 | F241L/V262I | 65 | S239D/N297D/I332E/A330Y/F241S/F243H/V262T/V264T |
| 13 | F241R/F243Q/V262T/V264R | 66 | S239D/N297D/I332E/K326E |
| 14 | F241R/F243Q/V262T/V264R/I332E | 67 | S239D/N297D/I332E/L235D |
| 15 | F241W/F243W/V262A/V264A | 68 | S239D/S298A/I332E |
| 16 | F241Y/F243Y/V262T/V264T | 69 | S239D/V264I/A330L/I332E |
| 17 | F241Y/F243Y/V262T/V264T/N297D/I332E | 70 | S239D/V264I/I332E |
| 18 | F243L/V262I/V264W | 71 | S239D/V264I/S298A/I332E |
| 19 | P243L/V264I | 72 | S239E/D265N |
| 20 | L328D/I332E | 73 | S239E/D265Q |
| 21 | L328E/I332E | 74 | S239E/I332D |
| 22 | L328H/I332E | 75 | S239E/I332E |
| 23 | L328I/I332E | 76 | S239E/I332N |
| 24 | L328M/I332E | 77 | S239E/I332Q |
| 25 | L328N/I332E | 78 | S239E/N297D/I332E |
| 26 | L328Q/I332E | 79 | S239E/V264I/A330Y/I332E |
| 27 | L328T/I332E | 80 | S239E/V264I/I332E |
| 28 | L328V/I332E | 81 | S239E/V264I/S298A/A330Y/I332E |
| 29 | N297D/A330Y/I332E | 82 | S239N/A330L/I332E |
| 30 | N297D/I332E | 83 | S239N/A330Y/I332E |
| 31 | N297D/I332E/S239D/A330L | 84 | S239N/I332D |
| 32 | N297D/S298A/A330Y/I332E | 85 | S239N/I332E |
| 33 | N297D/T299L/I332E | 86 | S239N/I332N |
| 34 | N297D/T299F/I332E/N297D/T299H/I332E | 87 | S239N/I332Q |
| 35 | N297D/T299I/I332E | 88 | S239N1S298A/I332E |
| 36 | N297D/T299L/I332E | 89 | S239Q/I332D |
| 37 | N297D/T299V/I332E | 90 | S239Q/I332E |
| 38 | N297E/I332E | 91 | S239Q/I332N |
| 39 | N297S/I332E | 92 | S239Q/I332Q |
| 40 | P230A/E233D/I332E | 93 | S239Q/V264I/I332E |
| 41 | P244H/P245A/P247V | 94 | S298A/I332E |
| 42 | S239D/A330L/I332E | 95 | V264E/N297D/I332E |
| 43 | S239D/A330Y/I332E | 96 | V264I/A330L/I332E |
| 44 | S239D/A330Y/I332E/K326E | 97 | V264I/A330Y/I332E |
| 45 | S239D/A330Y/I332E/K326T | 98 | V264I/I332E |
| 46 | S239D/A330Y/I332E/L234I | 99 | V264I/S298A/I332E |
| 47 | S239D/A330Y/I332E/L235D | 100 | Y296D/N297D/I332E |
| 48 | S239D/A330Y/I332E/V240I | 101 | Y296E/N297D/I332E |
| 49 | S239D/A330Y/I332E/V264T | 102 | Y296H/N297D/I332E |
| 50 | S239D/A330Y/I332E/V266I | 103 | Y296N/N297D/I332E |
| 51 | S239D/D265F/N297D/I332E | 104 | Y296Q/N297I/I332E |
| 52 | S239D/D265H/N297D/I332E | 105 | Y296T/N297D/I332E. |
| 53 | S239D/D265I/N297D/I332E | | |

In one embodiment, a multivalent DR5 binding molecule of the invention will comprise a variant Fc Domain having at least one modification in the Fc Domain. In certain embodiments, the variant Fc Domain comprises at least one substitution selected from the group consisting of L235V, F243L, R292P, Y300L, V305I, and P396L, wherein said numbering is that of the EU index as in Kabat.

In a specific embodiment, the variant Fc Domain comprises:

(A) at least one substitution selected from the group consisting of F243L, R292P, Y300L, V305I, and P396L;

(B) at least two substitutions selected from the group consisting of:

(1) F243L and P396L;

(2) F243L and R292P; and (3) R292P and V305I;

(C) at least three substitutions selected from the group consisting of:

(1) F243L, R292P and Y300L;

(2) F243L, R292P and V305I;

(3) F243L, R292P and P396L; and (4) R292P, V305I and P396L;

(D) at least four substitutions selected from the group consisting of:

(1) F243L, R292P, Y300L and P396L; and (2) F243L, R292P, V305I and P396L; or (E) at least the five substitutions selected from the group consisting of:
(1) F243L, R292P, Y300L, V305I and P396L; and
(2) L235V, F243L, R292P, Y300L and P396L.

In another specific embodiment, the variant Fc Domain comprises substitutions of:
(A) F243L, R292P, and Y300L;
(B) L235V, F243L, R292P, Y300L, and P396L; or
(C) F243L, R292P, Y300L, V305I, and P396L.

In other embodiments, the invention encompasses the use of any Fc variant known in the art, such as those disclosed in Jefferis, B. J. et al. (2002) "*Interaction Sites On Human IgG-Fc For FcgammaR: Current Models*," Immunol. Lett. 82:57-65; Presta, L. G. et al. (2002) "*Engineering Therapeutic Antibodies For Improved Function*," Biochem. Soc. Trans. 30:487-90; Idusogie, E. E. et al. (2001) "*Engineered Antibodies With Increased Activity To Recruit Complement*," J. Immunol. 166:2571-75; Shields, R. L. et al. (2001) "*High Resolution Mapping Of The Binding Site On Human IgG1 For Fc Gamma RI, Fc Gamma RII, Fc Gamma RIg And FcRn And Design Of IgG1 Variants With Improved Binding To The Fc gamma R*," J. Biol. Chem. 276:6591-6604; Idusogie, E. E. et al. (2000) "*Mapping Of The C1q Binding Site On Rituxan, A Chimeric Antibody With A Human IgG Fc*," J. Immunol. 164:4178-84; Reddy, M. P. et al. (2000) "*Elimination Of Fc Receptor-Dependent Effector Functions Of A Modified IgG4 Monoclonal Antibody To Human CD4*," J. Immunol. 164:1925-1933; Xu, D. et al. (2000) "*In Vitro Characterization of Five Humanized OKT3 Effector Function Variant Antibodies*," Cell. Immunol. 200:16-26; Armour, K. L. et al. (1999) "*Recombinant human IgG Molecules Lacking Fcgamma Receptor I Binding And Monocyte Triggering Activities*," Eur. J. Immunol. 29:2613-24; Jefferis, R. et al. (1996) "*Modulation Of Fc(Gamma)R And Human Complement Activation By IgG3-Core Oligosaccharide Interactions*," Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969; Hutchins et al. (1995) "*Improved Biodistribution, Tumor Targeting, And Reduced Immunogenicity In Mice With A Gamma 4 Variant Of Campath-1H*," Proc. Natl. Acad. Sci. (U.S.A.) 92:11980-84; Jefferis, R. et al. (1995) "*Recognition Sites On Human IgG For Fc Gamma Receptors: The Role Of Glycosylation*," Immunol. Lett. 44:111-17; Lund, J. et al. (1995) "*Oligosaccharide-Protein Interactions In IgG Can Modulate Recognition By Fc Gamma Receptors*," FASEB J. 9:115-19; Alegre, M. L. et al. (1994) "*A Non-Activating "Humanized" Anti-CD3 Monoclonal Antibody Retains Immunosuppressive Properties In Vivo*," Transplantation 57:1537-1543; Lund et al. (1992) "*Multiple Binding Sites On The CH2 Domain Of IgG For Mouse Fc Gamma R11*," Mol. Immunol. 29:53-59; Lund et al. (1991) "*Human Fc Gamma RI And Fc Gamma RII Interact With Distinct But Overlapping Sites On Human IgG*," J. Immunol. 147:2657-2662; Duncan, A. R. et al. (1988) "*Localization Of The Binding Site For The Human High-Affinity Fc Receptor On IgG*," Nature 332:563-564; U.S. Pat. Nos. 5,624,821; 5,885,573; 6,194,551; 7,276,586; and 7,317,091; and PCT Publications WO 00/42072 and PCT WO 99/58572.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc Domain confer or have an enhanced antibody-mediated effector function, e.g., enhanced ADCC activity, compared to a parent antibody. In some embodiments, the invention further comprises molecules comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well-known in the art to which this invention pertains (see for example, IN VITRO MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies (and molecules comprising antibody domains) are well-known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc Domain of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc Domain, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced antitumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc Domains and may thereby have enhanced complement lysis and ADCC capabilities (Stevenson, G. T. et al. (1989) "*A Chimeric Antibody With Dual Fc Domains (bisFabFc) Prepared By Manipulations At The IgG Hinge*," Anti-Cancer Drug Design 3:219-230).

III. Exemplary Trispecific Binding Molecules

F. gpA33 mAb 1×CD3 mAb 2×DR5 mAb 1

An exemplary Tri-Specific Binding Molecule composed of four polypeptide chains was constructed. The Tri-Specific Binding Molecule comprises the VL and VH domains of gpA33 mAb 1, the VL and VH domains of antibody CD3 mAb 2 and the VL and VH domains of DR5 mAb 1, and was accordingly designated "gpA33 mAb 1×CD3 mAb 2×DR5 mAb 1." The amino acid sequence of the first polypeptide chain of this Tri-Specific Binding Molecule is (SEQ ID NO:212):

```
DIQLTQSPSF LSASVGDRVT ITCSARSSIS FMYWYQQKPG
KAPKLLIYDT SNLASGVPSR FSGSGSGTEF TLTISSLEAE
DAATYYCQQW SSYPLTFGQG TKLEIKGGGS GGGGEVQLVE
SGGGLVQPGG SLRLSCAASG FTFSTYAMNW VRQAPGKGLE
WVGRIRSKYN NYATYYADSV KGRFTISRDD SKNSLYLQMN
SLKTEDTAVY YCVRHGNFGN SYVSWFAYWG QGTLVTVSSG
GCGGGEVAAL EKEVAALEKE VAALEKEVAA LEKGGGDKTH
TCPPCPAPEA AGGPSVFLFP PKPKDTLMIS RTPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

In SEQ ID NO:212, amino acid residues 1-106 correspond to the amino acid sequence of the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:212 is SEQ ID NO:213:

```
gacattcagc tgactcagtc cccctctttt ctgtccgcat
ccgtcggaga tcgagtgact attacttgct ctgctaggtc
ctcaatcagc ttcatgtact ggtatcagca gaagcccggc
aaagcaccta agctgctgat ctacgacaca agcaacctgg
cctccggggt gccatctcgg ttctctggca gtgggtcagg
aactgagttt accctgacaa ttagctccct ggaggctgaa
gatgccgcta cctactattg ccagcagtgg agcagctatc
ctctgacctt cggacagggg actaaactgg aaatcaaggg
tggaggatcc ggcggcggag gcgaggtgca gctggtggag
tctggggggag gcttggtcca gcctggaggg tccctgagac
tctcctgtgc agcctctgga ttcaccttca gcacatacgc
tatgaattgg gtccgccagg ctccagggaa ggggctggag
tgggttggaa ggatcaggtc caagtacaac aattatgcaa
cctactatgc cgactctgtg aagggtagat tcaccatctc
aagagatgat tcaaagaact cactgtatct gcaaatgaac
agcctgaaaa ccgaggacac ggccgtgtat tactgtgtga
gacacggtaa cttcggcaat tcttacgtgt cttggtttgc
ttattgggga caggggacac tggtgactgt gtcttccgga
ggatgtgcg gtggagaagt ggccgcactg gagaaagagg
ttgctgcttt ggagaaggag gtcgctgcac ttgaaaagga
ggtcgcagcc ctggagaaag gcggcgggga caaaactcac
acatgcccac cgtgcccagc acctgaagcc gcgggggac
cgtcagtctt cctcttcccc ccaaaaccca aggacaccct
catgatctcc cggacccctg aggtcacatg cgtggtggtg
gacgtgagcc acgaagaccc tgaggtcaag ttcaactggt
acgtggacgg cgtggaggtg cataatgcca agacaaagcc
gcgggaggag cagtacaaca gcacgtaccg tgtggtcagc
gtcctcaccg tcctgcacca ggactggctg aatggcaagg
agtacaagtg caaggtctcc aacaaagccc tcccagcccc
catcgagaaa accatctcca aagccaaagg gcagcccga
gaaccacagg tgtacaccct gcccccatcc cgggaggaga
tgaccaagaa ccaggtcagc ctgtggtgcc tggtcaaagg
cttctatccc agcgacatcg ccgtggagtg ggagagcaat
gggcagccgg agaacaacta caagaccacg cctcccgtgc
tggactccga cggctccttc ttcctctaca gcaagctcac
```

The amino acid sequence of the second polypeptide chain of gpA33 mAb 1×CD3 mAb 2×DR5 mAb 1 is (SEQ ID NO:214):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLVQSGAEVK KPGASVKVSC KASGYTFTGS WMNWVRQAPG
QGLEWIGRIY PGDGETNYNG KFKDRVTITA DKSTSTAYME
LSSLRSEDTA VYYCARIYGN NVYFDVWGQG TTVTVSSGGC
GGGKVAALKE KVAALKEKVA ALKEKVAALK E
```

In SEQ ID NO:214, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-243 correspond to the linker GGCGGG (SEQ ID NO:34), and residues 244-271 are a K-coil Domain (SEQ ID NO:40).

A polynucleotide that encodes SEQ ID NO:214 is (SEQ ID NO:215):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc ggggtggca caaaactgac
tgtgctggga ggggtggat ccggcggagg tggacaggtc
cagctggtcc agagcgggc cgaagtcaaa aaacccgag
caagcgtgaa ggtctcctgc aaagcatcag gctatacatt
tacaggcagc tggatgaact gggtgaggca ggctccagga
cagggactgg agtggatcgg gcgcatctac cctggagacg
gcgaaactaa ctataatgga aagttcaaag accgagtgac
catcacagcc gataagtcta ctagtaccgc ctacatggag
ctgagctccc tgcggtctga agataccgcc gtctactatt
gcgctagaat ttacggaaac aatgtctatt ttgacgtgtg
ggggcaggga acaactgtga ctgtctcctc cggaggatgt
ggcggtggaa aagtggccgc actgaaggag aaagttgctg
ctttgaaaga gaaggtcgcc gcacttaagg aaaaggtcgc
agccctgaaa gag
```

The amino acid sequence of the third polypeptide chain of gpA33 mAb 1×CD3 mAb 2×DR5 mAb 1 is (SEQ ID NO:216):

```
EVKFLESGGG LVQPGGSLKL SCVASGFDFS RYWMSWVRQA
PGKGLEWIGE INPDSNTINY TPSLKDKFII SRDNAKNTLY
LQMTKVRSED TALYYCTRRA YYGNPAWFAY WGQGTLVTVS
SASTKGPSVF PLAPSSKSTS GGTAALGCLV KDYFPEPVTV
SWNSGALTSG VHTFPAVLQS SGLYSLSSVV TVPSSSLGTQ
TYICNVNHKP SNTKVDKRVE PKSCDKTHTC PPCPAPEAAG
GPSVFLFPPK PKDTLMISRT PEVTCVVVDV SHEDPEVKFN
WYVDGVEVHN AKTKPREEQY NSTYRVVSVL TVLHQDWLNG
KEYKCKVSNK ALPAPIEKTI SKAKGQPREP QVYTLPPSRE
EMTKNQVSLS CAVKGFYPSD IAVEWESNGQ PENNYKTTPP
VLDSDGSFFL VSKLTVDKSR WQQGNVFSCS VMHEALHNRY
TQKSLSLSPG K
```

In SEQ ID NO:216, amino acid residues 1-121 correspond to the amino acid sequence of the VH Domain of DR5 mAb 1 (SEQ ID NO:8), residues 122-219 correspond to a modified CH1 Domain (SEQ ID NO:208), residues 220-234 correspond to a linker (SEQ ID NO:209), and residues 235-451 correspond to the "hole-bearing" CH2-CH3 Domain (SEQ ID NO:53).

A polynucleotide that encodes SEQ ID NO:216 is (SEQ ID NO:217):

```
gaggtgaagt tctctgagtc tggaggtggc ctggtgcagc
ctggaggatc cctgaaactc tcctgtgtag cctcaggatt
cgatttagt agatactgga tgagttgggt ccggcaggct
ccagggaaag ggctagaatg gattggagaa attaatccag
atagcaatac gataaactat acgccatctc taaaggataa
attcatcatc tccagagaca acgccaaaaa tacgctgtat
ctgcaaatga ccaaagtgag atctgaggac acagcccttt
attattgtac aagaagggcc tactatggta acccggcctg
gtttgcttac tggggccaag ggactctggt cactgtctct
tccgcctcca ccaagggccc atcggtcttc cccctggcac
cctcctccaa gagcacctct gggggcacag cggccctggg
ctgcctggtc aaggactact ccccgaacc ggtgacggtg
tcgtggaact caggcgccct gaccagcggc gtgcacacct
tcccggctgt cctacagtcc tcaggactct actccctcag
cagcgtggtg accgtgccct ccagcagctt gggcacccag
acctacatct gcaacgtgaa tcacaagccc agcaacacca
aggtggacaa gagagttgag cccaaatctt gtgacaaaac
```

-continued

```
tcacacatgc ccaccgtgcc cagcacctga agccgcgggg ggaccgtcag tcttcctctt cccccaaaa cccaaggaca ccctcatgat ctcccggacc cctgaggtca catgcgtggt ggtggacgtg agccacgaag accctgaggt caagttcaac tggtacgtgg acggcgtgga ggtgcataat gccaagacaa agccgcggga ggagcagtac aacagcacgt accgtgtggt cagcgtcctc accgtcctgc accaggactg gctgaatggc aaggagtaca agtgcaaggt ctccaacaaa gccctcccag cccccatcga gaaaaccatc tccaaagcca aagggcagcc ccgagaacca caggtgtaca ccctgccccc atcccgggag gagatgacca agaaccaggt cagcctgagt gcgcagtca aaggcttcta tcccagcgac atcgccgtgg agtgggagag caatgggcag ccggagaaca actacaagac cacgcctccc gtgctggact ccgacggctc cttcttcctc gtcagcaagc tcaccgtgga caagagcagg tggcagcagg ggaacgtctt ctcatgctcc gtgatgcatg aggctctgca caaccgctac acgcagaaga gcctctccct gtctccgggt aaa
```

The amino acid sequence of the fourth polypeptide chain of gpA33 mAb 1×CD3 mAb 2×DR5 mAb 1 is (SEQ ID NO:218):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

In SEQ ID NO:218, amino acid residues 1-111 correspond to the amino acid sequence of the VL Domain of DR5 mAb 1 (SEQ ID NO:3), and residues 112-218 correspond to the CL Kappa Domain (SEQ ID NO:210).

A polynucleotide that encodes SEQ ID NO:218 is (SEQ ID NO:219):

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaacgtacgg tggctgcacc atcggtcttc atcttcccgc catctgatga gcagttgaaa tctggaactg cctctgttgt gtgcctgctg aataacttct atcccagaga ggccaaagta cagtggaagg tggataacgc cctccaatcg ggtaactccc aggagagtgt cacagagcag gacagcaagg acagcaccta cagcctcagc agcaccctga cgctgagcaa agcagactac gagaaacaca agtctacgc ctgcgaagtc acccatcagg gcctgagctc gcccgtcaca aagagcttca acaggggaga gtgt
```

G. gpA33 mAb 1×CD3 mAb 2×DR5 mAb 2

A second exemplary Tri-Specific Binding Molecule composed of four polypeptide chains was constructed. The Tri-Specific Binding Molecule comprises the VL and VH domains of gpA33 mAb 1, the VL and VH domains of antibody CD3 mAb 2 and the VL and VH domains of DR5 mAb 2, and was accordingly designated "gpA33 mAb 1×CD3 mAb 2×DR5 mAb 2." The amino acid sequence of the first polypeptide chain of this Tri-Specific Binding Molecule is (SEQ ID NO:220):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

In SEQ ID NO:220, amino acid residues 1-106 correspond to the amino acid sequence of the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:220 is (SEQ ID NO:221):

```
gacattcagc tgactcagtc ccoctctttt ctgtccgcat
ccgtcggaga tcgagtgact attacttgct ctgctaggtc
ctcaatcagc ttcatgtact ggtatcagca gaagcccggc
aaagcaccta agctgctgat ctacgacaca agcaacctgg
cctccggggt gccatctcgg ttctctggca gtgggtcagg
aactgagttt accctgacaa ttagctccct ggaggctgaa
gatgccgcta cctactattg ccagcagtgg agcagctatc
ctctgacctt cggacagggg actaaactgg aaatcaaggg
tggaggatcc ggcggcgag gcgaggtgca gctggtggag
tctgggggag gcttggtcca gcctggaggg tccctgagac
tctcctgtgc agcctctgga ttcaccttca gcacatacgc
tatgaattgg gtccgccagg ctccagggaa ggggctggag
tgggttggaa ggatcaggtc caagtacaac aattatgcaa
cctactatgc cgactctgtg aagggtagat caccatctc
aagagatgat tcaaagaact cactgtatct gcaaatgaac
agcctgaaaa ccgaggacac ggccgtgtat tactgtgtga
gacacggtaa cttcggcaat tcttacgtgt cttggtttgc
ttattgggga caggggacac tggtgactgt gtcttccgga
ggatgtggcg gtggagaagt ggccgcactg gagaagagg
ttgctgcttt ggagaaggag gtcgctgcac ttgaaaagga
ggtcgcagcc ctggagaaag gcggcgggga caaaactcac
acatgcccac cgtgcccagc acctgaagcc gcggggggac
cgtcagtctt cctcttcccc ccaaaaccca aggacaccct
catgatctcc cggacccctg aggtcacatg cgtggtggtg
gacgtgagcc acgaagaccc tgaggtcaag ttcaactggt
acgtggacgg cgtggaggtg cataatgcca agacaaagcc
gcgggaggag cagtacaaca gcacgtaccg tgtggtcagc
gtcctcaccg tcctgcacca ggactggctg aatggcaagg
agtacaagtg caaggtctcc aacaaagccc tcccagcccc
catcgagaaa accatctcca aagccaaagg cagcccga
gaaccacagg tgtacaccct gcccccatcc cggaggaga
tgaccaagaa ccaggtcagc ctgtggtgcc tggtcaaagg
cttctatccc agcgacatcg ccgtggagtg ggagagcaat
gggcagccgg agaacaacta caagaccacg cctcccgtgc
tggactccga cggctccttc ttcctctaca gcaagctcac
cgtggacaag agcaggtggc agcaggggaa cgtcttctca
tgctccgtga tgcatgaggc tctgcacaac cactacacgc
agaagagcct ctccctgtct ccgggtaaa
```

The amino acid sequence of the second polypeptide chain of gpA33 mAb 1×CD3 mAb 2×DR5 mAb 2 is (SEQ ID NO:222):

```
QAVVTQEPSL TVSPGGTVTL TCRSSTGAVT TSNYANWVQQ
KPGQAPRGLI GGINKRAPWT PARFSGSLLG GKAALTITGA
QAEDEADYYC ALWYSNLWVF GGGTKLTVLG GGGSGGGGQV
QLVQSGAEVK KPGASVKVSC KASGYTFTGS WMNWVRQAPG
QGLEWIGRIY PGDGETNYNG KFKDRVTITA DKSTSTAYME
LSSLRSEDTA VYYCARIYGN NVYFDVWGQG TTVTVSSGGC
GGGKVAALKE KVAALKEKVA ALKEKVAALK E
```

In SEQ ID NO:222, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-243 correspond to the linker GGCGGG (SEQ ID NO:34), and residues 244-271 are a K-coil Domain (SEQ ID NO:40).

A polynucleotide that encodes SEQ ID NO:222 is (SEQ ID NO:223):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga gggggtggat ccggcggagg tggacaggtc
cagctggtcc agagcggggc cgaagtcaaa aacccggag
caagcgtgaa ggtctcctgc aaagcatcag gctatacatt
tacaggcagc tggatgaact gggtgaggca ggctccagga
cagggactgg agtggatcgg cgcatctac cctggagacg
gcgaaactaa ctataatgga aagttcaaag accgagtgac
catcacagcc gataagtcta ctagtaccgc ctacatggag
ctgagctccc tgcggtctga agataccgcc gtctactatt
gcgctagaat ttacggaaac aatgtctatt ttgacgtgtg
ggggcaggga acaactgtga ctgtctcctc cggaggatgt
ggcggtggaa aagtggccgc actgaaggag aaagttgctg
ctttgaaaga gaaggtcgcc gcacttaagg aaaaggtcgc
agccctgaaa gag
```

The amino acid sequence of the third polypeptide chain of gpA33 mAb 1×CD3 mAb 2×DR5 mAb 2 is (SEQ ID NO:224):

```
KVQLQQSGAE LVKPGASVKL SCKASGYTFT EYILHWVKQK

SGQGLEWIGW FYPGNNNIKY NEKFKDKATL TADKSSSTVY

MELSRLTSED SAVYFCARHE QGPGYFDYWG QGTTLTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

In SEQ ID NO:224, amino acid residues 1-119 correspond to the amino acid sequence of the VH Domain of DR5 mAb 2 (SEQ ID NO:18), residues 120-217 correspond to a modified CH1 Domain (SEQ ID NO:208), residues 218-232 correspond to a linker (SEQ ID NO:209), and residues 233-449 correspond to the "hole-bearing" CH2-CH3 Domain (SEQ ID NO:53).

A polynucleotide that encodes SEQ ID NO:224 is (SEQ ID NO:225):

```
aaggtccagc tgcagcagtc tggagctgaa ctggtgaaac ccggggcatc agtgaagctg tcctgcaagg cttctgggta caccttcact gagtatattt tacactgggt aaagcagaag tctggacagg gtcttgagtg gattgggtgg ttttatcctg gaaataataa tataaagtac aatgagaaat tcaaggacaa ggccacactg actgcggaca atcctccag cacagtctat atggaactta gtagattgac atctgaagac tctgcggtct atttctgtgc aagacacgaa caaggaccag gttactttga ctactgggg c caaggcacca ctctcacagt ctcctccgcc tccaccaagg gcccatcggt cttcccctg gcaccctcct ccaagagcac ctctggggc acagcggcc tgggctgcct ggtcaaggac tacttcccg aaccggtgac ggtgtcgtgg aactcaggcg ccctgaccag cggcgtgcac accttcccgg ctgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaagccgc gggggaccg tcagtcttcc tcttcccccc aaaacccaag gacaccctca tgatctcccg gacccctgag gtcacatgcg tggtggtgga cgtgagccac gaagaccctg aggtcaagtt caactggtac gtggacggcg tggaggtgca taatgccaag acaaagccgc
```

```
gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaaagggc agccccgaga accacaggtg tacaccctgc ccccatcccg ggaggagatg accaagaacc aggtcagcct gacctgcgca gtcaaaggct tctatcccag cgacatcgcc gtggagtggg agagcaatgg gcagccggag aacaactaca agaccacgcc tcccgtgctg gactccgacg gctccttctt cctcgtcagc aagctcaccg tggacaagag caggtggcag caggggaacg tcttctcatg ctccgtgatg catgaggctc tgcacaaccg ctacacgcag aagagcctct ccctgtctcc gggtaaa
```

The amino acid sequence of the fourth polypeptide chain of gpA33 mAb 1×CD3 mAb 2×DR5 mAb 2 is (SEQ ID NO:226):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

In SEQ ID NO:226, amino acid residues 1-107 correspond to the amino acid sequence of the VL Domain of DR5 mAb 2 (SEQ ID NO:13), and residues 108-214 correspond to the CL Kappa Domain (SEQ ID NO:210).

A polynucleotide that encodes SEQ ID NO:226 is (SEQ ID NO:227):

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa acgtacggtg gctgcaccat cggtcttcat cttcccgcca tctgatgagc agttgaaatc tggaactgcc tctgttgtgt gcctgctgaa taacttctat cccagagagg ccaaagtaca gtggaaggtg gataacgccc tccaatcggg taactcccag gagagtgtca cagagcagga cagcaaggac agcacctaca gcctcagcag caccctgacg ctgagcaaag cagactacga
```

-continued

```
gaaacacaaa gtctacgcct gcgaagtcac ccatcagggc ctgagctcgc ccgtcacaaa gagcttcaac aggggagagt gt
```

H. EphA2 mAb 1×CD3 mAb 2×DR5 mAb 1

A further exemplary Tri-Specific Binding Molecule composed of four polypeptide chains was constructed. The Tri-Specific Binding Molecule comprises the VL and VH domains of EphA2 mAb 1, the VL and VH domains of antibody CD3 mAb 2 and the VL and VH domains of DR5 mAb 1, and was accordingly designated "EphA2 mAb 1×CD3 mAb 2×DR5 mAb 1." The amino acid sequence of the first polypeptide chain of this Tri-Specific Binding Molecule is (SEQ ID NO:228):

```
DIQMTQTTSS LSASLGDRIT ISCRASQDIS NYLNWYQQKP
DGTVKLLIYY TSRLHSGVPS RFSGSGSGTD YSLTISNLEQ
EDIATYFCQQ GYTLYTFGGG TKLEIKGGGS GGGGEVQLVE
SGGGLVQPGG SLRLSCAASG FTFSTYAMNW VRQAPGKGLE
WVGRIRSKYN NYATYYADSV KGRFTISRDD SKNSLYLQMN
SLKTEDTAVY YCVRHGNFGN SYVSWFAYWG QGTLVTVSSG
GCGGGEVAAL EKEVAALEKE VAALEKEVAA LEKGGGDKTH
TCPPCPAPEA AGGPSVFLFP PKPKDTLMIS RTPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

In SEQ ID NO:228, amino acid residues 1-106 correspond to the amino acid sequence of the VL Domain of EphA2 mAb 1 (SEQ ID NO:153), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:228 is (SEQ ID NO:229):

```
gatatccaga tgacacagac tacatcctcc ctgtctgcct ctctgggaga cagaatcacc atcagttgca gggcaagtca ggacattagc aattatttaa actggtatca gcagaaacca gatggaactg ttaaactcct gatctactac acatcaagat tacactcagg agtcccatca aggttcagtg gcagtgggtc tggaacagat tattctctca ccattagcaa cctggagcaa gaagatattg ccacttactt ttgccaacag ggttatacgc tgtacacgtt cggagggggg accaagctgg aaataaaagg tggaggatcc ggcggcggag gcgaggtgca gctggtggag tctgggggag gcttggtcca gcctggaggg tccctgagac tctcctgtgc agcctctgga ttcaccttca gcacatacgc tatgaattgg gtccgccagg ctccagggaa ggggctggag tgggttggaa ggatcaggtc caagtacaac aattatgcaa cctactatgc cgactctgtg aagggtagat tcaccatctc aagagatgat tcaaagaact cactgtatct gcaaatgaac agcctgaaaa ccgaggacac ggccgtgtat tactgtgtga gacacggtaa cttcggcaat tcttacgtgt cttggtttgc ttattgggga caggggacac tggtgactgt gtcttccgga ggatgtggcg gtggagaagt ggccgcactg gagaagagg ttgctgcttt ggagaaggag gtcgctgcac ttgaaaagga ggtcgcagcc ctggagaaag gcggcgggga caaaactcac acatgcccac cgtgcccagc acctgaagcc gcgggggac cgtcagtctt cctcttccccc ccaaaaccca aggacaccct catgatctcc cggacccctg aggtcacatg cgtggtggtg gacgtgagcc acgaagaccc tgaggtcaag ttcaactggt acgtggacgg cgtggaggtg cataatgcca agacaaagcc gcgggaggag cagtacaaca gcacgtaccg tgtggtcagc gtcctcaccg tcctgcacca ggactggctg aatggcaagg agtacaagtg caaggtctcc aacaaagccc tcccagcccc catcgagaaa accatctcca aagccaaagg gcagccccga gaaccacagg tgtacaccct gcccccatcc cgggaggaga tgaccaagaa ccaggtcagc ctgtggtgcc tggtcaaagg cttctatccc agcgacatcg ccgtggagtg ggagagcaat gggcagccgg agaacaacta caagaccacg cctcccgtgc tggactccga cggctccttc ttcctctaca gcaagctcac cgtggacaag agcaggtggc agcaggggaa cgtcttctca tgctccgtga tgcatgaggc tctgcacaac cactacacgc agaagagcct ctccctgtct ccgggtaa
```

The amino acid sequence of the second polypeptide chain of EphA2 mAb 1×CD3 mAb 2×DR5 mAb 1 is (SEQ ID NO:230):

```
QAVVTQEPSL TVSPGGTVTL TCRSSTGAVT TSNYANWVQQ
KPGQAPRGLI GGINKRAPWT PARFSGSLLG GKAALTITGA
QAEDEADYYC ALWYSNLWVF GGGTKLTVLG GGGSGGGGQV
QLKESGPGLV APSQSLSITC TVSGFSLSRY SVHWVRQPPG
KGLEWLGMIW GGGSTDYNSA LKSRLSISKD NSKSQVFLKM
```

```
NSLQTDDTAM YYCARKHGNY YTMDYWGQGT SVTVSSGGCG

GGKVAALKEK VAALKEKVAA LKEKVAALKE
```

In SEQ ID NO:230, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 1 (SEQ ID NO:158), residues 237-242 correspond to the linker GGCGGG (SEQ ID NO:34), and residues 243-270 are a K-coil Domain (SEQ ID NO:40).

A polynucleotide that encodes SEQ ID NO:230 is (SEQ ID NO:231):

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaaggccg ctctgactat taccggggca caggccgagg acgaagccga ttactattgt gctctgtggt atagcaatct gtgggtgttc gggggtggca caaaactgac tgtgctggga gggggtggat ccggcggagg tggacaggtg cagctgaagg agtcaggacc tggcctggtg gcaccctcac agagcctgtc catcacatgc actgtctctg ggttctcatt atccagatat agtgtacact gggttcgcca gcctccagga aagggtctgg agtggctggg aatgatatgg ggtggtggaa gcacagacta taattcagct ctcaaatcca gactgagtat cagcaaggac aactccaaga gccaagtttt cttaaaaatg aacagtctgc aaactgatga cacagccatg tactactgtg ccagaaaaca tggtaactac tatactatgg actactgggg tcaaggaacc tcagtcaccg tctcctccgg aggatgtggc ggtggaaaag tggccgcact gaaggagaaa gttgctgctt tgaaagagaa ggtcgccgca cttaaggaaa aggtcgcagc cctgaaagag
```

The amino acid sequence of the third polypeptide chain of EphA2 mAb 1×CD3 mAb 2×DR5 mAb 1 is (SEQ ID NO:232):

```
EVKFLESGGG LVQPGGSLKL SCVASGFDFS RYWMSWVRQA

PGKGLEWIGE INPDSNTINY TPSLKDKFII SRDNAKNTLY

LQMTKVRSED TALYYCTRRA YYGNPAWFAY WGQGTLVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPEAAG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRE

EMTKNQVSLS CAVKGFYPSD IAVEWESNGQ PENNYKTTPP

VLDSDGSFFL VSKLTVDKSR WQQGNVFSCS VMHEALHNRY

TQKSLSLSPG K
```

In SEQ ID NO:232, amino acid residues 1-121 correspond to the amino acid sequence of the VH Domain of DR5 mAb 1 (SEQ ID NO:8), residues 122-219 correspond to a modified CH1 Domain (SEQ ID NO:208), residues 220-234 correspond to a linker (SEQ ID NO:209), and residues 235-451 correspond to the "hole-bearing" CH2-CH3 Domain (SEQ ID NO:53).

A polynucleotide that encodes SEQ ID NO:232 is (SEQ ID NO:233):

```
gaggtgaagt ttctcgagtc tggaggtggc ctggtgcagc ctggaggatc cctgaaactc tcctgtgtag cctcaggatt cgattttagt agatactgga tgagttgggt ccggcaggct ccaggaaaag ggctagaatg gattggagaa attaatccag atagcaatac gataaactat acgccatctc taaaggataa attcatcatc tccagagaca acgccaaaaa tacgctgtat ctgcaaatga ccaaagtgag atctgaggac acagcccttt attattgtac aagaagggcc tactatggta acccggcctg gtttgcttac tggggccaag ggactctggt cactgtctct tccgcctcca caagggccc atcggtcttc ccctggcac cctcctccaa gagcacctct gggggcacag cggccctggg ctgcctggtc aaggactact ccccgaacc ggtgacggtg tcgtggaact caggcgcccct gaccagcggc gtgcacacct tcccggctgt cctacagtcc tcaggactct actccctcag cagcgtggtg accgtgccct ccagcagctt gggcacccag acctacatct gcaacgtgaa tcacaagccc agcaacacca aggtggacaa gagagttgag cccaaatctt gtgacaaaac tcacacatgc ccaccgtgcc cagcacctga gccgcgggg ggaccgtcag tcttcctctt ccccccaaaa cccaaggaca ccctcatgat ctcccggacc cctgaggtca catgcgtggt ggtggacgtg agccacgaag accctgaggt caagttcaac tggtacgtgg acggcgtgga ggtgcataat gccaagacaa agccgcggga ggagcagtac aacagcacgt accgtgtggt cagcgtcctc accgtcctgc accaggactg gctgaatggc aaggagtaca gtgcaaggt ctccaacaaa gccctcccag cccccatcga gaaaaccatc tccaaagcca aagggcagcc ccgagaacca caggtgtaca cctgcccccc atcccgggag gagatgacca agaaccaggt cagcctgagt tgcgcagtca
```

```
aaggcttcta tcccagcgac atcgccgtgg agtgggagag caatgggcag ccggagaaca actacaagac cacgcctccc gtgctggact ccgacggctc cttcttcctc gtcagcaagc tcaccgtgga caagagcagg tggcagcagg ggaacgtctt ctcatgctcc gtgatgcatg aggctctgca caaccgctac acgcagaaga gcctctccct gtctccgggt aaa
```

The amino acid sequence of the fourth polypeptide chain of EphA2 mAb 1×CD3 mAb 2×DR5 mAb 1 is (SEQ ID NO:234):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

In SEQ ID NO:234, amino acid residues 1-111 correspond to the amino acid sequence of the VL Domain of DR5 mAb 1 (SEQ ID NO:3), and residues 112-218 correspond to the CL Kappa Domain (SEQ ID NO:210).

A polynucleotide that encodes SEQ ID NO:234 is (SEQ ID NO:235):

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaacgtacgg tggctgcacc atcggtcttc atcttccgc catctgatga gcagttgaaa tctggaactg cctctgttgt gtgcctgctg aataacttct atcccagaga ggccaaagta cagtggaagg tggataacgc cctccaatcg ggtaactccc aggagagtgt cacagagcag gacagcaagg acagcaccta cagcctcagc agcaccctga cgctgagcaa agcagactac gagaaacaca agtctacgc ctgcgaagtc acccatcagg gcctgagctc gcccgtcaca aagagcttca acaggggaga gtgt
```

I. EphA2 mAb 2×CD3 mAb 2×DR5 mAb 1

A further exemplary Tri-Specific Binding Molecule composed of four polypeptide chains was constructed. The Tri-Specific Binding Molecule comprises the VL and VH domains of EphA2 mAb 2, the VL and VH domains of antibody CD3 mAb 2 and the VL and VH domains of DR5 mAb 1, and was accordingly designated "EphA2 mAb 2×CD3 mAb 2×DR5 mAb 1." The amino acid sequence of the first polypeptide chain of this Tri-Specific Binding Molecule is (SEQ ID NO:236):

```
DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI KGGGSGGGGE

VQLVESGGGL VQPGGSLRLS CAASGFTFST YAMNWVRQAP

GKGLEWVGRI RSKYNNYATY YADSVKGRFT ISRDDSKNSL

YLQMNSLKTE DTAVYYCVRH GNFGNSYVSW FAYWGQGTLV

TVSSGGCGGG EVAALEKEVA ALEKEVAALE KEVAALEKGG

GDKTHTCPPC PAPEAAGPS VFLFPPKPKD TLMISRTPEV

TCVVVDVSHE DPEVKFNWYV DGVEVHNAKT KPREEQYNST

YRVVSVLTVL HQDWLNGKEY KCKVSNKALP APIEKTISKA

KGQPREPQVY TLPPSREEMT KNQVSLWCLV KGFYPSDIAV

EWESNGQPEN NYKTTPPVLD SDGSFFLYSK LTVDKSRWQQ

GNVFSCSVMH EALHNHYTQK SLSLSPGK
```

In SEQ ID NO:236, amino acid residues 1-111 correspond to the amino acid sequence of the VL Domain of EphA2 mAb 2 (SEQ ID NO:163), residues 112-119 correspond to the intervening spacer peptide GGGSGGGG (Linker 1) (SEQ ID NO:33), residues 120-244 correspond to the amino acid sequence of the VH Domain of CD3 mAb 2 having the D65G substitution (SEQ ID NO:112), residues 245-250 correspond to the GGCGGG linker (SEQ ID NO:34), residues 251-278 correspond to an E-coil Domain (SEQ ID NO:39), residues 279-281 are the linker GGG, residues 282-291 are the linker DKTHTCPPCP (SEQ ID NO:48), and residues 292-508 are the "knob-bearing" CH2-CH3 Domain (SEQ ID NO:52).

A polynucleotide that encodes SEQ ID NO:236 is (SEQ ID NO:237):

```
gatgttgtga tgacccaaac tccactctcc ctgcctgtca gtcttggaga tcaagcctcc atctcttgca gatctagtca gagccttgta cacagtagtg gaaacaccta tttacattgg tacctgcaga agccaggcca gtctccaaag ctcctgatct acaaagtttc caaccgattt tctggggtcc cagacaggtt cagtggcagt ggatcaggga cagatttcac actcaagatc agcagagtgg aggctgagga tctgggagtt tatttctgct ctcaaagtac acatgttccc acgttcggct cggggacaaa gttggaaata aaaggtggag gatccggcgg cggaggcgag gtgcagctgg tggagtctgg gggaggcttg gtccagcctg gagggtccct gagactctcc tgtgcagcct ctggattcac cttcagcaca tacgctatga attgggtccg ccaggctcca gggaaggggc tggagtgggt tggaaggatc aggtccaagt
```

```
acaacaatta tgcaacctac tatgccgact ctgtgaaggg tagattcacc atctcaagag atgattcaaa gaactcactg tatctgcaaa tgaacagcct gaaaaccgag gacacggccg tgtattactg tgtgagacac ggtaacttcg gcaattctta cgtgtcttgg tttgcttatt ggggacaggg gacactggtg actgtgtctt ccggaggatg tggcggtgga gaagtggccg cactggagaa agaggttgct gctttggaga aggaggtcgc tgcacttgaa aaggaggtcg cagccctgga gaaggcggc ggggacaaaa ctcacacatg cccaccgtgc ccagcacctg aagccgcggg gggaccgtca gtcttcctct tccccccaaa acccaaggac accctcatga tctcccggac ccctgaggtc acatgcgtgg tggtggacgt gagccacgaa gaccctgagg tcaagttcaa ctggtacgtg gacggcgtgg aggtgcataa tgccaagaca aagccgcggg aggagcagta caacagcacg taccgtgtgg tcagcgtcct caccgtcctg caccaggact ggctgaatgg caaggagtac aagtgcaagg tctccaacaa agccctccca gccccatcg agaaaaccat ctccaaagcc aaagggcagc cccgagaacc acaggtgtac accctgcccc catcccggga ggagatgacc aagaaccagg tcagcctgtg gtgcctggtc aaaggcttct atcccagcga catcgccgtg gagtgggaga gcaatgggca gccggagaac aactacaaga ccacgcctcc cgtgctggac tccgacggct ccttcttcct ctacagcaag ctcaccgtgg acaagagcag gtggcagcag gggaacgtct tctcatgctc cgtgatgcat gaggctctgc acaaccacta cacgcagaag agcctctccc tgtctccggg taaa
```

The amino acid sequence of the second polypeptide chain of EphA2 mAb 2×CD3 mAb 2×DR5 mAb 1 is (SEQ ID NO:238):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQI
QLVQSGPELK KPGETVKISC KASGFTFTNY GMNWVKQAPG
KGLKWMGWIN TYIGEPTYAD DFKGRFVFSL ETSASTAYLQ
INNLKNEDMA TYFCARELGP YYFDYWGQGT TLTVSSGGCG
GGKVAALKEK VAALKEKVAA LKEKVAALKE
```

In SEQ ID NO:238, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 2 (SEQ ID NO:167), residues 237-242 correspond to the linker GGCGGG (SEQ ID NO:34), and residues 243-270 are a K-coil Domain (SEQ ID NO:40).

A polynucleotide that encodes SEQ ID NO:238 is (SEQ ID NO:239):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gggcctgatc gggggtacaa
acaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga gggggtggat ccggcggagg tggacagatc
cagttggtgc agtctggacc tgagctgaag aagcctggag
agacagtcaa gatctcctgc aaggcttctg gtttaccttc
cacaaactat ggaatgaact gggtgaagca ggctccagga
aagggtttaa agtggatggg ctggataaac acctatattg
gagagccgac atatgctgat gacttcaagg gacggtttgt
cttctctttg gaaacctctg ccagcactgc ctatttgcag
atcaacaacc tcaaaatga ggacatggcc acatatttct
gtgcaagaga actgggacca tactactttg actactgggg
ccaaggcacc actctcacag tctcctccgg aggatgtggc
ggtggaaaag tggccgcact gaaggagaaa gttgctgctt
tgaaagagaa ggtcgccgca cttaaggaaa aggtcgcagc
cctgaaagag
```

The amino acid sequence of the third polypeptide chain of EphA2 mAb 2×CD3 mAb 2×DR5 mAb 1 is (SEQ ID NO:240):

```
EVKFLESGGG LVQPGGSLKL SCVASGFDFS RYWMSWVRQA
PGKGLEWIGE INPDSNTINY TPSLKDKFII SRDNAKNTLY
LQMTKVRSED TALYYCTRRA YYGNPAWFAY WGQGTLVTVS
SASTKGPSVF PLAPSSKSTS GGTAALGCLV KDYFPEPVTV
SWNSGALTSG VHTFPAVLQS SGLYSLSSVV TVPSSSLGTQ
TYICNVNHKP SNTKVDKRVE PKSCDKTHTC PPCPAPEAAG
GPSVFLFPPK PKDTLMISRT PEVTCVVVDV SHEDPEVKFN
WYVDGVEVHN AKTKPREEQY NSTYRVVSVL TVLHQDWLNG
KEYKCKVSNK ALPAPIEKTI SKAKGQPREP QVYTLPPSRE
EMTKNQVSLS CAVKGFYPSD IAVEWESNGQ PENNYKTTPP
VLDSDGSFFL VSKLTVDKSR WQQGNVFSCS VMHEALHNRY
TQKSLSLSPG K
```

In SEQ ID NO:240, amino acid residues 1-121 correspond to the amino acid sequence of the VH Domain of DR5 mAb 1 (SEQ ID NO:8), residues 122-219 correspond to a modified CH1 Domain (SEQ ID NO:208), residues 220-234 correspond to a linker (SEQ ID NO:209), and residues 235-451 correspond to the "hole-bearing" CH2-CH3 Domain (SEQ ID NO:53).

A polynucleotide that encodes SEQ ID NO:240 is (SEQ ID NO:241):

```
gaggtgaagt tctctcgagtc tggaggtggc ctggtgcagc
ctggaggatc cctgaaactc tcctgtgtag cctcaggatt
cgattttagt agatactgga tgagttgggt ccggcaggct
ccagggaaag gctagaatg gattggagaa attaatccag
atagcaatac gataaactat acgccatctc taaaggataa
attcatcatc tccagagaca acgccaaaaa tacgctgtat
ctgcaaatga ccaaagtgag atctgaggac acagccttt
attattgtac aagaaggggcc tactatggta acccggcctg
gtttgcttac tggggccaag ggactctggt cactgtctct
tccgcctcca ccaagggccc atcggtcttc cccctggcac
cctcctccaa gagcacctct gggggcacag cggccctggg
ctgcctggtc aaggactact tccccgaacc ggtgacggtg
tcgtggaact caggcgccct gaccagcggc gtgcacacct
tcccggctgt cctacagtcc tcaggactct actccctcag
cagcgtggtg accgtgccct ccagcagctt gggcacccag
acctacatct gcaacgtgaa tcacaagccc agcaacacca
aggtggacaa gagagttgag cccaaatctt gtgacaaaac
tcacacatgc ccaccgtgcc cagcacctga gccgcgggg
ggaccgtcag tcttcctctt cccccaaaa cccaaggaca
ccctcatgat ctcccggacc cctgaggtca catgcgtggt
ggtggacgtg agccacgaag accctgaggt caagttcaac
```

```
tggtacgtgg acggcgtgga ggtgcataat gccaagacaa
agccgcggga ggagcagtac aacagcacgt accgtgtggt
cagcgtcctc accgtcctgc accaggactg gctgaatggc
aaggagtaca agtgcaaggt ctccaacaaa gccctcccag
cccccatcga gaaaaccatc tccaaagcca agggcagcc
ccgagaacca caggtgtaca ccctgccccc atcccgggag
gagatgacca agaaccaggt cagcctgagt tgcgcagtca
aaggcttcta tcccagcgac atcgccgtgg agtgggagag
caatgggcag ccggagaaca actacaagac cacgcctccc
gtgctggact ccgacggctc cttcttcctc gtcagcaagc
tcaccgtgga caagagcagg tggcagcagg ggaacgtctt
ctcatgctcc gtgatgcatg aggctctgca caaccgctac
acgcagaaga gcctctccct gtctccgggt aaa
```

The amino acid sequence of the fourth polypeptide chain of EphA2 mAb 2×CD3 mAb 2×DR5 mAb 1 is (SEQ ID NO:242):

```
DIVLTQSPAS LAVSLGQRAT ISCRASKSVS SSGYSYMHWY
QQKPGQPPKV LIFLSSNLDS GVPARFSGSG SGTDFTLNIH
PVEDGDAATY YCQHSRDLPP TFGGGTKLEI KRTVAAPSVF
IFPPSDEQLK SGTASVVCLL NNFYPREAKV QWKVDNALQS
GNSQESVTEQ DSKDSTYSLS STLTLSKADY EKHKVYACEV
THQGLSSPVT KSFNRGEC
```

In SEQ ID NO:242, amino acid residues 1-111 correspond to the amino acid sequence of the VL Domain of DR5 mAb 1 (SEQ ID NO:3), and residues 112-218 correspond to the CL Kappa Domain (SEQ ID NO:210).

A polynucleotide that encodes SEQ ID NO:242 is (SEQ ID NO:243):

```
gacattgtgc tgacacagtc tcctgcttcc ttagctgtat ctctcgggca
gagggccacc atctcatgca gggccagcaa aagtgtcagt tcctctggct
atagttatat gcactggtac caacagaaac caggacagcc acccaaagtc
ctcatctttc tttcatccaa cctagattct ggggtccctg ccaggttcag
tggcagtggg tctgggacag acttcaccct caacatccat cctgtggagg
atggggatgc tgcaacctat tactgtcagc acagtaggga tcttcctccg
acgttcggtg gaggcaccaa gctggaaatc aaacgtacgg tggctgcacc
atcggtcttc atcttcccgc catctgatga gcagttgaaa tctggaactg
cctctgttgt gtgcctgctg aataacttct atcccagaga ggccaaagta
cagtggaagg tggataacgc cctccaatcg gtaactccc aggagagtgt
cacagagcag gacagcaagg acagcaccta cagcctcagc agcaccctga
cgctgagcaa agcagactac gagaaacaca agtctacgc ctgcgaagtc
acccatcagg gcctgagctc gcccgtcaca aagagcttca cagggggaga
gtgt
```

J. EphA2 mAb 3×CD3 mAb 2×DR5 mAb 1

A further exemplary Tri-Specific Binding Molecule composed of four polypeptide chains was constructed. The Tri-Specific Binding Molecule comprises the VL and VH domains of EphA2 mAb 3, the VL and VH domains of antibody CD3 mAb 2 and the VL and VH domains of DR5 mAb 1, and was accordingly designated "EphA2 mAb 3×CD3 mAb 2×DR5 mAb 1." The amino acid sequence of the first polypeptide chain of this Tri-Specific Binding Molecule is (SEQ ID NO:244):

```
DIVLTQSHRS   MSTSVGDRVN   ITCKASQDVT   TAVAWYQQKP   GQSPKLLIFW
ASTRHAGVPD   RFTGSGSGTD   FTLTISSVQA   GDLALYYCQQ   HYSTPYTFGG
GTKLEIKGGG   SGGGGEVQLV   ESGGGLVQPG   GSLRLSCAAS   GFTFSTYAMN
WVRQAPGKGL   EWVGRIRSKY   NNYATYYADS   VKGRFTISRD   DSKNSLYLQM
NSLKTEDTAV   YYCVRHGNFG   NSYVSWFAYW   GQGTLVTVSS   GGCGGGEVAA
LEKEVAALEK   EVAALEKEVA   ALEKGGGDKT   HTCPPCPAPE   AAGGPSVFLF
PPKPKDTLMI   SRIPEVICVV   VDVSHEDPEV   KFNWYVDGVE   VHNAKTKPRE
EQYNSTYRVV   SVLTVLHQDW   LNGKEYKCKV   SNKALPAPIE   KTISKAKGQP
REPQVYTLPP   SREEMTKNQV   SLWCLVKGFY   PSDIAVEWES   NGQPENNYKT
TPPVLDSDGS   FFLYSKLTVD   KSRWQQGNVF   SCSVMHEALH   NHYTQKSLSL
SPGK
```

In SEQ ID NO:244, amino acid residues 1-107 correspond to the amino acid sequence of the VL Domain of EphA2 mAb 3 (SEQ ID NO:172), residues 108-115 correspond to the intervening spacer peptide GGGSGGGG (Linker 1) (SEQ ID NO:33), residues 116-240 correspond to the amino acid sequence of the VH Domain of CD3 mAb 2 having the D65G substitution (SEQ ID NO:112), residues 241-246 correspond to the GGCGGG linker (SEQ ID NO:34), residues 247-274 correspond to an E-coil Domain (SEQ ID NO:39), residues 275-277 are the linker GGG, residues 278-287 are the linker DKTHTCPPCP (SEQ ID NO:48), and residues 288-504 are the "knob-bearing" CH2-CH3 Domain (SEQ ID NO:52).

A polynucleotide that encodes SEQ ID NO:244 is (SEQ ID NO:245):

```
gacattgtgc   tgacccagtc   tcacagatcc   atgtccacat   cagtaggaga
cagggtcaac   atcacctgca   aggccagtca   ggatgtgact   actgctgtag
cctggtatca   acaaaaacca   gggcaatctc   ctaaattact   gattttctgg
gcatccaccc   ggcacgctgg   agtccctgat   cgcttcacag   gcagtggatc
tgggacagat   tttactctca   ccatcagcag   tgtgcaggct   ggagacctgg
cactttatta   ctgtcaacaa   cattatagca   caccgtacac   attcggaggg
gggaccaagc   tggaaataaa   aggtggagga   tccggcggcg   gaggcgaggt
gcagctggtg   gagtctgggg   gaggcttggt   ccagcctgga   gggtccctga
gactctcctg   tgcagcctct   ggattcacct   tcagcacata   cgctatgaat
tgggtccgcc   aggctccagg   gaaggggctg   gagtgggttg   gaaggatcag
gtccaagtac   aacaattatg   caacctacta   tgccgactct   gtgaagggta
gattcaccat   ctcaagagat   gattcaaaga   actcactgta   tctgcaaatg
aacagcctga   aaaccgagga   cacggccgtg   tattactgtg   tgagacacgg
taacttcggc   aattcttacg   tgtcttggtt   tgcttattgg   ggacagggga
cactggtgac   tgtgtcttcc   ggaggatgtg   gcggtggaga   agtggccgca
ctggagaaag   aggttgctgc   tttggagaag   gaggtcgctg   cacttgaaaa
```

-continued

```
ggaggtcgca    gccctggaga    aaggcggcgg    ggacaaaact    cacacatgcc
caccgtgccc    agcacctgaa    gccgcggggg    gaccgtcagt    cttcctcttc
cccccaaaac    ccaaggacac    cctcatgatc    tcccggaccc    ctgaggtcac
atgcgtggtg    gtggacgtga    gccacgaaga    ccctgaggtc    aagttcaact
ggtacgtgga    cggcgtggag    gtgcataatg    ccaagacaaa    gccgcgggag
gagcagtaca    acagcacgta    ccgtgtggtc    agcgtcctca    ccgtcctgca
ccaggactgg    ctgaatggca    aggagtacaa    gtgcaaggtc    tccaacaaag
ccctcccagc    ccccatcgag    aaaaccatct    ccaaagccaa    agggcagccc
cgagaaccac    aggtgtacac    cctgccccca    tcccgggagg    agatgaccaa
gaaccaggtc    agcctgtggt    gcctggtcaa    aggcttctat    cccagcgaca
tcgccgtgga    gtgggagagc    aatgggcagc    cggagaacaa    ctacaagacc
acgcctcccg    tgctggactc    cgacggctcc    ttcttcctct    acagcaagct
caccgtggac    aagagcaggt    ggcagcaggg    gaacgtcttc    tcatgctccg
tgatgcatga    ggctctgcac    aaccactaca    cgcagaagag    cctctccctg
tctccgggta    aa
```

The amino acid sequence of the second polypeptide chain of EphA2 mAb 3×CD3 mAb 2×DR5 mAb 1 is (SEQ ID NO:246):

```
QAVVTQEPSL    TVSPGGTVTL    TCRSSTGAVT    TSNYANWVQQ    KPGQAPRGLI
GGINKRAPWT    PARFSGSLLG    GKAALTITGA    QAEDEADYYC    ALWYSNLWVF
GGGTKLTVLG    GGGSGGGGEV    QLVESGGGSV    KPGGSLKLSC    AASGFTFTDH
YMYWVRQTPE    KRLEWVATIS    DGGSFTSYPD    SVKGRFTISR    DIAKNNLYLQ
MSSLKSEDTA    MYYCTRDESD    RPFPYWGQGT    LVTVSSGGCG    GGKVAALKEK
VAALKEKVAA    LKEKVAALKE
```

In SEQ ID NO:246, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 3 (SEQ ID NO:177), residues 237-242 correspond to the linker GGCGGG (SEQ ID NO:34), and residues 243-270 are a K-coil Domain (SEQ ID NO:40).

A polynucleotide that encodes SEQ ID NO:246 is (SEQ ID NO:247):

```
caggctgtgg    tgactcagga    gccttcactg    accgtgtccc    caggcggaac
tgtgaccctg    acatgcagat    ccagcacagg    cgcagtgacc    acatctaact
acgccaattg    ggtgcagcag    aagccaggac    aggcaccaag    gggcctgatc
ggggtacaa    acaaagggc    tccctggacc    cctgcacggt    tttctggaag
tctgctgggc    ggaaaggccg    ctctgactat    taccggggca    caggccgagg
acgaagccga    ttactattgt    gctctgtggt    atagcaatct    gtgggtgttc
ggggtggca    caaaactgac    tgtgctggga    ggggtggat    ccggcggagg
tggagaagtg    cagctggtgg    agtctggggg    aggctcagtg    aagcctggag
ggtccctgaa    actctcctgt    gcagcctctg    gattcacttt    cactgaccat
tacatgtatt    gggttcgcca    gactccggaa    aagaggctgg    agtgggtcgc
aaccattagt    gatggcggta    gtttcacctc    ctatccagac    agtgtgaagg
```

```
ggcgattcac    catctccaga    gacattgcca    agaacaacct    gtacctccaa atgagcagtc    tgaagtctga    ggacacagcc    atgtattact    gtacaagaga tgagagcgat    aggccgtttc    cttactgggg    ccaagggact    ctggtcactg tctcctccgg    aggatgtggc    ggtggaaaag    tggccgcact    gaaggagaaa gttgctgctt    tgaaagagaa    ggtcgccgca    cttaaggaaa    aggtcgcagc cctgaaagag
```

The amino acid sequence of the third polypeptide chain of EphA2 mAb 3×CD3 mAb 2×DR5 mAb 1 is (SEQ ID NO:248):

```
EVKFLESGGG    LVQPGGSLKL    SCVASGFDFS    RYWMSWVRQA    PGKGLEWIGE

INPDSNTINY    TPSLKDKFII    SRDNAKNTLY    LQMTKVRSED    TALYYCTRRA

YYGNPAWFAY    WGQGTLVTVS    SASTKGPSVF    PLAPSSKSTS    GGTAALGCLV

KDYFPEPVTV    SWNSGALTSG    VHTFPAVLQS    SGLYSLSSVV    TVPSSSLGTQ

TYICNVNHKP    SNTKVDKRVE    PKSCDKTHTC    PPCPAPEAAG    GPSVFLFPPK

PKDTLMISRT    PEVTCVVVDV    SHEDPEVKFN    WYVDGVEVHN    AKTKPREEQY

NSTYRVVSVL    TVLHQDWLNG    KEYKCKVSNK    ALPAPIEKTI    SKAKGQPREP

QVYTLPPSRE    EMTKNQVSLS    CAVKGFYPSD    IAVEWESNGQ    PENNYKTTPP

VLDSDGSFFL    VSKLTVDKSR    WQQGNVFSCS    VMHEALHNRY    TQKSLSLSPG

K
```

In SEQ ID NO:248, amino acid residues 1-121 correspond to the amino acid sequence of the VH Domain of DR5 mAb 1 (SEQ ID NO:8), residues 122-219 correspond to a modified CH1 Domain (SEQ ID NO:208), residues 220-234 correspond to a linker (SEQ ID NO:209), and residues 235-451 correspond to the "hole-bearing" CH2-CH3 Domain (SEQ ID NO:53).

A polynucleotide that encodes SEQ ID NO:248 is (SEQ ID NO:249):

```
gaggtgaagt    ttctcgagtc    tggaggtggc    ctggtgcagc    ctggaggatc cctgaaactc    tcctgtgtag    cctcaggatt    cgattttagt    agatactgga tgagttgggt    ccggcaggct    ccagggaaag    ggctagaatg    gattggagaa attaatccag    atagcaatac    gataaactat    acgccatctc    taaaggataa attcatcatc    tccagagaca    acgccaaaaa    tacgctgtat    ctgcaaatga ccaaagtgag    atctgaggac    acagcccttt    attattgtac    aagaagggcc tactatggta    acccggcctg    gtttgcttac    tggggccaag    ggactctggt cactgtctct    tccgcctcca    ccaagggccc    atcggtcttc    ccctggcac cctcctccaa    gagcacctct    gggggcacag    cggccctggg    ctgcctggtc aaggactact    tccccgaacc    ggtgacggtg    tcgtggaact    caggcgccct gaccagcggc    gtgcacacct    tcccggctgt    cctacagtcc    tcaggactct actccctcag    cagcgtggtg    accgtgccct    ccagcagctt    gggcacccag acctacatct    gcaacgtgaa    tcacaagccc    agcaacacca    aggtggacaa gagagttgag    cccaaatctt    gtgacaaaac    tcacacatgc    ccaccgtgcc cagcacctga    agccgcgggg    ggaccgtcag    tcttcctctt    ccccccaaaa cccaaggaca    ccctcatgat    ctcccggacc    cctgaggtca    catgcgtggt
```

```
ggtggacgtg   agccacgaag   accctgaggt   caagttcaac   tggtacgtgg
acggcgtgga   ggtgcataat   gccaagacaa   agccgcggga   ggagcagtac
aacagcacgt   accgtgtggt   cagcgtcctc   accgtcctgc   accaggactg
gctgaatggc   aaggagtaca   agtgcaaggt   ctccaacaaa   gccctcccag
cccccatcga   gaaaaccatc   tccaaagcca   aagggcagcc   ccgagaacca
caggtgtaca   ccctgccccc   atcccgggag   gagatgacca   agaaccaggt
cagcctgagt   tgcgcagtca   aaggcttcta   tcccagcgac   atcgccgtgg
agtgggagag   caatgggcag   ccggagaaca   actacaagac   cacgcctccc
gtgctggact   ccgacggctc   cttcttcctc   gtcagcaagc   tcaccgtgga
caagagcagg   tggcagcagg   ggaacgtctt   ctcatgctcc   gtgatgcatg
aggctctgca   caaccgctac   acgcagaaga   gcctctccct   gtctccgggt
aaa
```

The amino acid sequence of the fourth polypeptide chain of EphA2 mAb 3×CD3 mAb 2×DR5 mAb 1 is (SEQ ID NO:250):

```
DIVLTQSPAS   LAVSLGQRAT   ISCRASKSVS   SSGYSYMHWY   QQKPGQPPKV
LIFLSSNLDS   GVPARFSGSG   SGTDFTLNIH   PVEDGDAATY   YCQHSRDLPP
TFGGGTKLEI   KRTVAAPSVF   IFPPSDEQLK   SGTASVVCLL   NNFYPREAKV
QWKVDNALQS   GNSQESVTEQ   DSKDSTYSLS   STLTLSKADY   EKHKVYACEV
THQGLSSPVT   KSFNRGEC
```

In SEQ ID NO:250, amino acid residues 1-111 correspond to the amino acid sequence of the VL Domain of DR5 mAb 1 (SEQ ID NO:3), and residues 112-218 correspond to the CL Kappa Domain (SEQ ID NO:210).

A polynucleotide that encodes SEQ ID NO:250 is (SEQ ID NO:251):

```
gacattgtgc   tgacacagtc   tcctgcttcc   ttagctgtat   ctctcgggca
gagggccacc   atctcatgca   gggccagcaa   aagtgtcagt   tcctctggct
atagttatat   gcactggtac   caacagaaac   caggacagcc   acccaaagtc
ctcatctttc   tttcatccaa   cctagattct   ggggtccctg   ccaggttcag
tggcagtggg   tctgggacag   acttcaccct   caacatccat   cctgtggagg
atggggatgc   tgcaacctat   tactgtcagc   acagtaggga   tcttcctccg
acgttcggtg   gaggcaccaa   gctggaaatc   aaacgtacgg   tggctgcacc
atcggtcttc   atcttcccgc   catctgatga   gcagttgaaa   tctggaactg
cctctgttgt   gtgcctgctg   aataacttct   atcccagaga   ggccaaagta
cagtggaagg   tggataacgc   cctccaatcg   ggtaactccc   aggagagtgt
cacagagcag   gacagcaagg   acagcaccta   cagcctcagc   agcaccctga
cgctgagcaa   agcagactac   gagaaacaca   aagtctacgc   ctgcgaagtc
acccatcagg   gcctgagctc   gcccgtcaca   aagagcttca   cagggggaga
gtgt
```

Although the exemplary Tri-Specific Binding Molecules described above comprise three Light Chain (VL) CDRs and three Heavy Chain (VH) CDRs for each binding domain, it will be recognized that the invention also includes Tri-Specific Binding Molecules that possess:
(1) at least one of the CDRs of the VL Domain of any such binding domain;
(2) at least two of the CDRs of the VL Domain of any such binding domain;

(3) the three CDRs of the VL Domain of any such binding domain;
(4) at least one of the CDRs of the VH Domain of any such binding domain;
(5) at least two of the CDRs of the VH Domain of any such binding domain;
(6) the three CDRs of the VH Domain of any such binding domain;
(7) at least one of the CDRs of the VL Domain of any such binding domain and at least one of the CDRs of the VH Domain of that binding domain;
(8) at least two of the CDRs of the VL Domain of any such binding domain and at least two of the CDRs of the VH Domain of that binding domain;
(9) the three CDRs of the VL Domain of any such binding domain and the three CDRs of the VH Domain of that binding domain;
(10) the VL Domain of any such binding domain;
(11) the VH Domain of any such binding domain; or
(12) the VL and VH Domains of any such binding domain.

K. gpA33 mAb 1×CD3 mAb 2×EphA2 mAb 1

A Tri-Specific Binding Molecule composed of four polypeptide chains was constructed that comprises the VL and VH domains of gpA33 mAb 1, the VL and VH domains of antibody CD3 mAb 2 and the VL and VH domains of EphA2 mAb 1. The Tri-Specific Binding Molecule was accordingly designated "gpA33 mAb 1×CD3 mAb 2×EphA2 mAb 1." The amino acid sequence of the first polypeptide chain of this Tri-Specific Binding Molecule is (SEQ ID NO:252):

| | | | | |
|---|---|---|---|---|
| DIQLTQSPSF | LSASVGDRVT | ITCSARSSIS | FMYWYQQKPG | KAPKLLIYDT |
| SNLASGVPSR | FSGSGSGTEF | TLTISSLEAE | DAATYYCQQW | SSYPLTFGQG |
| TKLEIKGGGS | GGGGEVQLVE | SGGGLVQPGG | SLRLSCAASG | FTFSTYAMNW |
| VRQAPGKGLE | WVGRIRSKYN | NYATYYADSV | KGRFTISRDD | SKNSLYLQMN |
| SLKTEDTAVY | YCVRHGNFGN | SYVSWFAYWG | QGTLVTVSSG | GCGGGEVAAL |
| EKEVAALEKE | VAALEKEVAA | LEKGGGDKTH | TCPPCPAPEA | AGGPSVFLFP |
| PKPKDTLMIS | RTPEVTCVVV | DVSHEDPEVK | FNWYVDGVEV | HNAKTKPREE |
| QYNSTYRVVS | VLTVLHQDWL | NGKEYKCKVS | NKALPAPIEK | TISKAKGQPR |
| EPQVYTLPPS | REEMTKNQVS | LWCLVKGFYP | SDIAVEWESN | GQPENNYKTT |
| PPVLDSDGSF | FLYSKLTVDK | SRWQQGNVFS | CSVMHEALHN | HYTQKSLSLS |
| PGK | | | | |

In SEQ ID NO:252, amino acid residues 1-106 correspond to the amino acid sequence of the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:252 is (SEQ ID NO:253):

| | | | | |
|---|---|---|---|---|
| gacattcagc | tgactcagtc | cccctctttt | ctgtccgcat | ccgtcggaga |
| tcgagtgact | attacttgct | ctgctaggtc | ctcaatcagc | ttcatgtact |
| ggtatcagca | gaagcccggc | aaagcaccta | agctgctgat | ctacgacaca |
| agcaacctgg | cctccggggt | gccatctcgg | ttctctggca | gtgggtcagg |
| aactgagttt | accctgacaa | ttagctccct | ggaggctgaa | gatgccgcta |
| cctactattg | ccagcagtgg | agcagctatc | ctctgacctt | cggacagggg |
| actaaactgg | aaatcaaggg | tggaggatcc | ggcggcggag | gcgaggtgca |
| gctggtggag | tctggggag | gcttggtcca | gcctggaggg | tccctgagac |

```
tctcctgtgc  agcctctgga  ttcaccttca  gcacatacgc  tatgaattgg gtccgccagg  ctccagggaa  ggggctggag  tgggttggaa  ggatcaggtc caagtacaac  aattatgcaa  cctactatgc  cgactctgtg  aagggtagat tcaccatctc  aagagatgat  tcaaagaact  cactgtatct  gcaaatgaac agcctgaaaa  ccgaggacac  ggccgtgtat  tactgtgtga  gacacggtaa cttcggcaat  tcttacgtgt  cttggtttgc  ttattgggga  caggggacac tggtgactgt  gtcttccgga  ggatgtggcg  gtggagaagt  ggccgcactg gagaaagagg  ttgctgcttt  ggagaaggag  gtcgctgcac  ttgaaaagga ggtcgcagcc  ctggagaaag  gcggcgggga  caaaactcac  acatgcccac cgtgcccagc  acctgaagcc  gcgggggac   cgtcagtctt  cctcttcccc ccaaaaccca  aggacaccct  catgatctcc  cggacccctg  aggtcacatg cgtggtggtg  gacgtgagcc  acgaagaccc  tgaggtcaag  ttcaactggt acgtggacgg  cgtggaggtg  cataatgcca  agacaaagcc  gcgggaggag cagtacaaca  gcacgtaccg  tgtggtcagc  gtcctcaccg  tcctgcacca ggactggctg  aatggcaagg  agtacaagtg  caaggtctcc  aacaaagccc tcccagcccc  catcgagaaa  accatctcca  aagccaaagg  gcagcccga gaaccacagg  tgtacaccct  gcccccatcc  cgggaggaga  tgaccaagaa ccaggtcagc  ctgtggtgcc  tggtcaaagg  cttctatccc  agcgacatcg ccgtggagtg  ggagagcaat  gggcagccgg  agaacaacta  caagaccacg cctcccgtgc  tggactccga  cggctccttc  ttcctctaca  gcaagctcac cgtggacaag  agcaggtggc  agcaggggaa  cgtcttctca  tgctccgtga tgcatgaggc  tctgcacaac  cactacacgc  agaagagcct  ctccctgtct ccgggtaaa
```

The amino acid sequence of the second polypeptide chain of gpA33 mAb 1×CD3 mAb 2×EphA2 mAb 1 is (SEQ ID NO:254):

```
QAVVTQEPSL  TVSPGGTVTL  TCRSSTGAVT  TSNYANWVQQ  KPGQAPRGLI

GGTNKRAPWT  PARFSGSLLG  GKAALTITGA  QAEDEADYYC  ALWYSNLWVF

GGGTKLTVLG  GGGSGGGGQV  QLVQSGAEVK  KPGASVKVSC  KASGYTFTGS

WMNWVRQAPG  QGLEWIGRIY  PGDGETNYNG  KFKDRVTITA  DKSTSTAYME

LSSLRSEDTA  VYYCARIYGN  NVYFDVWGQG  TTVTVSSGGC  GGGKVAALKE

KVAALKEKVA  ALKEKVAALK  E
```

In SEQ ID NO:254, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-243 correspond to the linker GGCGGG (SEQ ID NO:34), and residues 244-271 are a K-coil Domain (SEQ ID NO:40).

A polynucleotide that encodes SEQ ID NO:254 is (SEQ ID NO:255):

```
caggctgtgg  tgactcagga  gccttcactg  accgtgtccc  caggcggaac tgtgaccctg  acatgcagat  ccagcacagg  cgcagtgacc  acatctaact acgccaattg  ggtgcagcag  aagccaggac  aggcaccaag  gggcctgatc
```

-continued

```
gggggtacaa   acaaaagggc   tccctggacc   cctgcacggt   tttctggaag
tctgctgggc   ggaaaggccg   ctctgactat   taccggggca   caggccgagg
acgaagccga   ttactattgt   gctctgtggt   atagcaatct   gtgggtgttc
ggggggtggca  caaaactgac   tgtgctggga   ggggggtggat ccggcggagg
tggacaggtc   cagctggtcc   agagcggggc   cgaagtcaaa   aaacccggag
caagcgtgaa   ggtctcctgc   aaagcatcag   gctatacatt   tacaggcagc
tggatgaact   gggtgaggca   ggctccagga   cagggactgg   agtggatcgg
gcgcatctac   cctggagacg   gcgaaactaa   ctataatgga   aagttcaaag
accgagtgac   catcacagcc   gataagtcta   ctagtaccgc   ctacatggag
ctgagctccc   tgcggtctga   agataccgcc   gtctactatt   gcgctagaat
ttacggaaac   aatgtctatt   ttgacgtgtg   ggggcaggga   acaactgtga
ctgtctcctc   cggaggatgt   ggcggtggaa   aagtggccgc   actgaaggag
aaagttgctg   ctttgaaaga   gaaggtcgcc   gcacttaagg   aaaaggtcgc
agccctgaaa  gag
```

The amino acid sequence of the third polypeptide chain of gpA33 mAb 1×CD3 mAb 2×EphA2 mAb 1 is (SEQ ID NO:256):

```
QVQLKESGPG   LVAPSQSLSI   TCTVSGFSLS   RYSVHWVRQP   PGKGLEWLGM
IWGGGSTDYN   SALKSRLSIS   KDNSKSQVFL   KMNSLQTDDT   AMYYCARKHG
NYYTMDYWGQ   GTSVTVSSAS   TKGPSVFPLA   PSSKSTSGGT   AALGCLVKDY
FPEPVTVSWN   SGALTSGVHT   FPAVLQSSGL   YSLSSVVTVP   SSSLGTQTYI
CNVNHKPSNT   KVDKRVEPKS   CDKTHTCPPC   PAPEAAGGPS   VFLFPPKPKD
TLMISRTPEV   TCVVVDVSHE   DPEVKFNWYV   DGVEVHNAKT   KPREEQYNST
YRVVSVLTVL   HQDWLNGKEY   KCKVSNKALP   APIEKTISKA   KGQPREPQVY
TLPPSREEMT   KNQVSLSCAV   KGFYPSDIAV   EWESNGQPEN   NYKTTPPVLD
SDGSFFLVSK   LTVDKSRWQQ   GNVFSCSVMH   EALHNRYTQK   SLSLSPGK
```

In SEQ ID NO:256, amino acid residues 1-118 correspond to the amino acid sequence of the VH Domain of EphA2 mAb 1 (SEQ ID NO:158), residues 119-216 correspond to a modified CH1 Domain (SEQ ID NO:208), residues 217-231 correspond to a linker (SEQ ID NO:209), and residues 232-448 correspond to the "hole-bearing" CH2-CH3 Domain (SEQ ID NO:53).

A polynucleotide that encodes SEQ ID NO:256 is (SEQ ID NO:257):

```
caggtgcagc   tgaaggagtc   aggacctggc   ctggtggcac   cctcacagag
cctgtccatc   acatgcactg   tctctgggtt   ctcattatcc   agatatagtg
tacactgggt   tcgccagcct   ccaggaaagg   gtctggagtg   gctgggaatg
atatggggtg   gtggaagcac   agactataat   tcagctctca   aatccagact
gagtatcagc   aaggacaact   ccaagagcca   agttttctta   aaaatgaaca
gtctgcaaac   tgatgacaca   gccatgtact   actgtgccag   aaaacatggt
aactactata   ctatggacta   ctggggtcaa   ggaacctcag   tcaccgtctc
ctccgcctcc   accaagggcc   catcggtctt   cccctggca   ccctcctcca
agagcacctc   tggggggcaca   gcggccctgg   gctgcctggt   caaggactac
ttccccgaac   cggtgacggt   gtcgtggaac   tcaggcgccc   tgaccagcgg
```

```
cgtgcacacc  ttcccggctg  tcctacagtc  ctcaggactc  tactccctca
gcagcgtggt  gaccgtgccc  tccagcagct  tgggcaccca  gacctacatc
tgcaacgtga  atcacaagcc  cagcaacacc  aaggtggaca  agagagttga
gcccaaatct  tgtgacaaaa  ctcacacatg  cccaccgtgc  ccagcacctg
aagccgcggg  gggaccgtca  gtcttcctct  tcccccaaa   acccaaggac
accctcatga  tctcccggac  ccctgaggtc  acatgcgtgg  tggtggacgt
gagccacgaa  gaccctgagg  tcaagttcaa  ctggtacgtg  gacggcgtgg
aggtgcataa  tgccaagaca  aagccgcggg  aggagcagta  caacagcacg
taccgtgtgg  tcagcgtcct  caccgtcctg  caccaggact  ggctgaatgg
caaggagtac  aagtgcaagg  tctccaacaa  agccctccca  gcccccatcg
agaaaccat   ctccaaagcc  aaagggcagc  cccgagaacc  acaggtgtac
accctgcccc  catcccggga  ggagatgacc  aagaaccagg  tcagcctgag
ttgcgcagtc  aaaggcttct  atcccagcga  catcgccgtg  gagtgggaga
gcaatgggca  gccggagaac  aactacaaga  ccacgcctcc  cgtgctggac
tccgacggct  ccttcttcct  cgtcagcaag  ctcaccgtgg  acaagagcag
gtggcagcag  gggaacgtct  tctcatgctc  cgtgatgcat  gaggctctgc
acaaccgcta  cacgcagaag  agcctctccc  tgtctccggg  taaa
```

The amino acid sequence of the fourth polypeptide chain of gpA33 mAb 1×CD3 mAb 2×EphA2 mAb 1 is (SEQ ID NO:258):

```
DIQMTQTTSS LSASLGDRIT ISCRASQDIS NYLNWYQQKP
DGTVKLLIYY TSRLHSGVPS RFSGSGSGTD YSLTISNLEQ
EDIATYFCQQ GYTLYTFGGG TKLEIKRTVA APSVFIFPPS
DEQLKSGTAS VVCLLNNFYP REAKVQWKVD NALQSGNSQE
SVTEQDSKDS TYSLSSTLTL SKADYEKHKV YACEVTHQGL
SSPVTKSFNR GEC
```

In SEQ ID NO:258, amino acid residues 1-106 correspond to the amino acid sequence of the VL Domain of EphA2 mAb 1 (SEQ ID NO:153), and residues 107-213 correspond to the CL Kappa Domain (SEQ ID NO:210).

A polynucleotide that encodes SEQ ID NO:258 is (SEQ ID NO:259):

```
gatatccaga tgacacagac tacatcctcc ctgtctgcct
ctctgggaga cagaatcacc atcagttgca gggcaagtca
ggacattagc aattatttaa actggtatca gcagaaacca
gatggaactg ttaaactcct gatctactac acatcaagat
tacactcagg agtcccatca aggttcagtg gcagtgggtc
tggaacagat tattctctca ccattagcaa cctggagcaa
gaagatattg ccacttactt ttgccaacag ggttatacgc
tgtacacgtt cggaggggg accaagctgg aaataaaacg
tacggtggct gcaccatcgg tcttcatctt cccgccatct
gatgagcagt tgaaatctgg aactgcctct gttgtgtgcc
tgctgaataa cttctatccc agagaggcca agtacagtg
gaaggtggat aacgccctcc aatcgggtaa ctcccaggag
agtgtcacag agcaggacag caaggacagc acctacagcc
tcagcagcac cctgacgctg agcaaagcag actacgagaa
acacaaagtc tacgcctgcg aagtcaccca tcagggcctg
agctcgcccg tcacaaagag cttcaacagg ggagagtgt
```

L. gpA33 mAb 1×CD3 mAb 2×EphA2 mAb 2

A Tri-Specific Binding Molecule composed of four polypeptide chains was constructed that comprises the VL and VH domains of gpA33 mAb 1, the VL and VH domains of antibody CD3 mAb 2 and the VL and VH domains of EphA2 mAb 2. The Tri-Specific Binding Molecule was accordingly designated "gpA33 mAb 1×CD3 mAb 2×EphA2 mAb 2." The amino acid sequence of the first polypeptide chain of this Tri-Specific Binding Molecule is (SEQ ID NO:260):

```
DIQLTQSPSF LSASVGDRVT ITCSARSSIS FMYWYQQKPG
KAPKLLIYDT SNLASGVPSR FSGSGSGTEF TLTISSLEAE
DAATYYCQQW SSYPLTFGQG TKLEIKGGGS GGGGEVQLVE
SGGGLVQPGG SLRLSCAASG FTFSTYAMNW VRQAPGKGLE
WVGRIRSKYN NYATYYADSV KGRFTISRDD SKNSLYLQMN
SLKTEDTAVY YCVRHGNFGN SYVSWFAYWG QGTLVTVSSG
GCGGGEVAAL EKEVAALEKE VAALEKEVAA LEKGGGDKTH
```

```
TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

In SEQ ID NO:260, amino acid residues 1-106 correspond to the amino acid sequence of the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:260 is (SEQ ID NO:261):

```
gacattcagc tgactcagtc ccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca agcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacagggg actaaactgg aaatcaaggg tggaggatcc ggcggcgag gcgaggtgca gctggtggag tctggggag gcttggtcca gcctggaggg tccctgagac tctcctgtgc agcctctgga ttcaccttca gcacatacgc tatgaattgg gtccgccagg ctccagggaa ggggctggag tgggttggaa ggatcaggtc caagtacaac aattatgcaa cctactatgc cgactctgtg aagggtagat tcaccatctc aagagatgat tcaaagaact cactgtatct gcaaatgaac agcctgaaaa ccgaggacac ggccgtgtat tactgtgtga gacacggtaa cttcgcaat tcttacgtgt cttggttgc ttattgggga caggggacac tggtgactgt gtcttccgga ggatgtggcg gtggagaagt ggccgcactg gagaagagg ttgctgcttt ggagaaggag gtcgctgcac ttgaaaagga ggtcgcagcc ctggagaaag gcggcgggga caaaactcac acatgcccac cgtgcccagc acctgaagcc gcggggggac cgtcagtctt cctcttcccc ccaaaaccca aggacaccct catgatctcc cggacccctg aggtcacatg cgtggtggtg
```

```
gacgtgagcc acgaagaccc tgaggtcaag ttcaactggt acgtggacgg cgtggaggtg cataatgcca agacaaagcc gcgggaggag cagtacaaca gcacgtaccg tgtggtcagc gtcctcaccg tcctgcacca ggactggctg aatggcaagg agtacaagtg caaggtctcc aacaaagccc tcccagcccc catcgagaaa accatctcca aagccaaagg gcagcccga gaaccacagg tgtacaccct gcccccatcc cgggaggaga tgaccaagaa ccaggtcagc ctgtggtgcc tggtcaaagg cttctatccc agcgacatcg ccgtggagtg ggagagcaat gggcagccgg agaacaacta caagaccacg cctcccgtgc tggactccga cggctccttc ttcctctaca gcaagctcac cgtggacaag agcaggtggc agcaggggaa cgtcttctca tgctccgtga tgcatgaggc tctgcacaac cactacacgc agaagagcct ctccctgtct ccgggtaaa
```

The amino acid sequence of the second polypeptide chain of gpA33 mAb 1×CD3 mAb 2×EphA2 mAb 2 is (SEQ ID NO:262):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTGS WMNWVRQAPG

QGLEWIGRIY PGDGETNYNG KFKDRVTITA DKSTSTAYME

LSSLRSEDTA VYYCARIYGN NVYFDVWGQG TTVTVSSGGC

GGGKVAALKE KVAALKEKVA ALKEKVAALK E
```

In SEQ ID NO:262, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-243 correspond to the linker GGCGGG (SEQ ID NO:34), and residues 244-271 are a K-coil Domain (SEQ ID NO:40).

A polynucleotide that encodes SEQ ID NO:262 is (SEQ ID NO:263):

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaggccg ctctgactat taccggggca caggccgagg acgaagccga ttactattgt gctctgtggt atagcaatct gtgggtgttc gggggtggca caaaactgac
```

-continued

```
tgtgctggga gggggtggat ccggcggagg tggacaggtc cagctggtcc agagcggggc cgaagtcaaa aaacccggag caagcgtgaa ggtctcctgc aaagcatcag gctatacatt tacaggcagc tggatgaact gggtgaggca ggctccagga cagggactgg agtggatcgg gcgcatctac cctggagacg gcgaaactaa ctataatgga aagttcaaag accgagtgac catcacagcc gataagtcta ctagtaccgc ctacatggag ctgagctccc tgcggtctga agataccgcc gtctactatt gcgctagaat ttacggaaac aatgtctatt ttgacgtgtg ggggcaggga caactgtga ctgtctcctc cggaggatgt ggcggtggaa aagtggccgc actgaaggag aaagttgctg cttttgaaaga gaaggtcgcc gcacttaagg aaaaggtcgc agccctgaaa gag
```

The amino acid sequence of the third polypeptide chain of gpA33 mAb 1×CD3 mAb 2×EphA2 mAb 2 is (SEQ ID NO:264):

```
QIQLVQSGPE LKKPGETVKI SCKASGFTFT NYGMNWVKQA
PGKGLKWMGW INTYIGEPTY ADDFKGRFVF SLETSASTAY
LQINNLKNED MATYFCAREL GPYYFDYWGQ GTTLTVSSAS
TKGPSVFPLA PSSKSTSGGT AALGCLVKDY FPEPVTVSWN
SGALTSGVHT FPAVLQSSGL YSLSSVVTVP SSSLGTQTYI
CNVNHKPSNT KVDKRVEPKS CDKTHTCPPC PAPEAAGGPS
VFLFPPKPKD TLMISRTPEV TCVVVDVSHE DPEVKFNWYV
DGVEVHNAKT KPREEQYNST YRVVSVLTVL HQDWLNGKEY
KCKVSNKALP APIEKTISKA KGQPREPQVY TLPPSREEMT
KNQVSLSCAV KGFYPSDIAV EWESNGQPEN NYKTTPPVLD
SDGSFFLVSK LTVDKSRWQQ GNVFSCSVMH EALHNRYTQK
SLSLSPGK
```

In SEQ ID NO:264, amino acid residues 1-118 correspond to the amino acid sequence of the VH Domain of EphA2 mAb 2 (SEQ ID NO:167), residues 119-216 correspond to a modified CH1 Domain (SEQ ID NO:208), residues 217-231 correspond to a linker (SEQ ID NO:209), and residues 232-448 correspond to the "hole-bearing" CH2-CH3 Domain (SEQ ID NO:53).

A polynucleotide that encodes SEQ ID NO:264 is (SEQ ID NO:265):

```
cagatccagt tggtgcagtc tggacctgag ctgaagaagc ctggagagac agtcaagatc tcctgcaagg cttctggktt taccttcaca aactatggaa tgaactgggt gaagcaggct ccaggaaagg gtttaaagtg gatgggctgg ataaacacct atattggaga gccgacatat gctgatgact caagggacg gtttgtcttc tctttggaaa cctctgccag cactgcctat ttgcagatca acaacctcaa aaatgaggac atggccacat atttctgtgc aagagaactg ggaccatact actttgacta ctggggccaa ggcaccactc tcacagtctc ctccgcctcc accaagggcc catcggtctt cccctggca ccctcctcca agagcacctc tgggggcaca gcggccctgg gctgcctggt caaggactac ttccccgaac cggtgacggt gtcgtggaac tcaggcgccc tgaccagcgg cgtgcacacc ttcccggctg tcctacagtc ctcaggactc tactccctca gcagcgtggt gaccgtgccc tccagcagct gggcaccca gacctacatc tgcaacgtga atcacaagcc cagcaacacc aaggtggaca agagagttga gcccaaatct tgtgacaaaa ctcacacatg cccaccgtgc ccagcacctg aagccgcggg gggaccgtca gtcttcctct tccccccaaa acccaaggac accctcatga tctcccggac ccctgaggtc acatgcgtgg tggtggacgt gagccacgaa gaccctgagg tcaagttcaa ctggtacgtg gacggcgtgg aggtgcataa tgccaagaca aagccgcggg aggagcagta caacagcacg taccgtgtgg tcagcgtcct caccgtcctg caccaggact ggctgaatgg caaggagtac aagtgcaagg tctccaacaa agccctccca gccccatcg agaaaaccat ctccaaagcc aaagggcagc cccgagaacc acaggtgtac accctgcccc catcccggga ggagatgacc aagaaccagg tcagcctgag ttgcgcagtc aaaggcttct atcccagcga catcgccgtg gagtgggaga gcaatgggca gccggagaac aactacaaga ccacgcctcc cgtgctggac tccgacggct ccttcttcct cgtcagcaag ctcaccgtgg acaagagcag gtggcagcag gggaacgtct tctcatgctc cgtgatgcat gaggctctgc acaaccgcta cacgcagaag agcctctccc tgtctccggg taaa
```

The amino acid sequence of the fourth polypeptide chain of gpA33 mAb 1×CD3 mAb 2×EphA2 mAb 2 is (SEQ ID NO:266):

```
DVVMTQTPLS LPVSLGDQAS ISCRSSQSLV HSSGNTYLHW
YLQKPGQSPK LLIYKVSNRF SGVPDRFSGS GSGTDFTLKI
SRVEAEDLGV YFCSQSTHVP TFGSGTKLEI KRTVAAPSVF
IFPPSDEQLK SGTASVVCLL NNFYPREAKV QWKVDNALQS
GNSQESVTEQ DSKDSTYSLS STLTLSKADY EKHKVYACEV
THQGLSSPVT KSFNRGEC
```

In SEQ ID NO:266, amino acid residues 1-111 correspond to the amino acid sequence of the VL Domain of EphA2 mAb 1 (SEQ ID NO:163), and residues 112-218 correspond to the CL Kappa Domain (SEQ ID NO:210).

A polynucleotide that encodes SEQ ID NO:266 is (SEQ ID NO:267):

```
gatgttgtga tgacccaaac tccactctcc ctgcctgtca gtcttggaga tcaagcctcc atctcttgca gatctagtca gagccttgta cacagtagtg gaaacaccta tttacattgg tacctgcaga agccaggcca gtctccaaag ctcctgatct acaaagtttc caaccgattt tctggggtcc cagacaggtt cagtggcagt ggatcaggga cagatttcac actcaagatc agcagagtgg aggctgagga tctgggagtt tatttctgct ctcaaagtac acatgttccc acgttcggct cggggacaaa gttggaaata aaacgtacgg tggctgcacc atcggtcttc atcttcccgc catctgatga gcagttgaaa tctggaactg cctctgttgt gtgcctgctg aataacttct atcccagaga ggccaaagta cagtggaagg tggataacgc cctccaatcg ggtaactccc aggagagtgt cacagagcag gacagcaagg acagcaccta cagcctcagc agcaccctga cgctgagcaa agcagactac gagaaacaca agtctacgc ctgcgaagtc acccatcagg gcctgagctc gcccgtcaca aagagcttca acaggggaga gtgt
```

M. gpA33 mAb 1×CD3 mAb 2×EphA2 mAb 3

A Tri-Specific Binding Molecule composed of four polypeptide chains was constructed that comprises the VL and VH domains of gpA33 mAb 1, the VL and VH domains of antibody CD3 mAb 2 and the VL and VH domains of EphA2 mAb 3. The Tri-Specific Binding Molecule was accordingly designated "gpA33 mAb 1×CD3 mAb 2×EphA2 mAb 3." The amino acid sequence of the first polypeptide chain of this Tri-Specific Binding Molecule is (SEQ ID NO:268):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

In SEQ ID NO:268, amino acid residues 1-106 correspond to the amino acid sequence of the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:268 is (SEQ ID NO:269):

```
gacattcagc tgactcagtc cccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca agcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacaggg actaaactgg aaatcaaggg tggaggatcc ggcggcggag gcgaggtgca gctggtggag tctgggggag gcttggtcca gcctggaggg tccctgagac tctcctgtgc agcctctgga ttcaccttca gcacatacgc tatgaattgg gtccgccagg ctccagggaa ggggctggag tgggttggaa ggatcaggtc caagtacaac aattatgcaa cctactatgc cgactctgtg aagggtagat tcaccatctc aagagatgat tcaaagaact cactgtatct gcaaatgaac agcctgaaaa ccgaggacac ggccgtgtat tactgtgtga gacacggtaa cttcggcaat tcttacgtgt cttggtttgc ttattgggga caggggacac tggtgactgt gtcttccgga ggatgtggcg gtggagaagt ggccgcactg gagaaagagg ttgctgcttt ggagaaggag gtcgctgcac ttgaaaagga ggtcgcagcc ctggagaaag gcggcgggga caaaactcac acatgcccac cgtgcccagc acctgaagcc gcggggggac cgtcagtctt cctcttcccc ccaaaaccca aggacaccct catgatctcc cggacccctg aggtcacatg cgtggtggtg gacgtgagcc acgaagaccc tgaggtcaag ttcaactggt acgtggacgg cgtggaggtg cataatgcca agacaaagcc gcgggaggag cagtacaaca gcacgtaccg tgtggtcagc gtcctcaccg tcctgcacca ggactggctg aatggcaagg agtacaagtg caaggtctcc aacaaagccc tcccagcccc catcgagaaa accatctcca agccaaagg gcagccccga gaaccacagg tgtacaccct gcccccatcc cgggaggaga tgaccaagaa ccaggtcagc ctgtggtgcc tggtcaaagg cttctatccc agcgacatcg ccgtggagtg ggagagcaat gggcagccgg agaacaacta caagaccacg cctcccgtgc
```

```
tggactccga cggctccttc ttcctctaca gcaagctcac cgtggacaag agcaggtggc agcaggggaa cgtcttctca tgctccgtga tgcatgaggc tctgcacaac cactacacgc agaagagcct ctccctgtct ccgggtaaa
```

The amino acid sequence of the second polypeptide chain of gpA33 mAb 1×CD3 mAb 2×EphA2 mAb 3 is (SEQ ID NO:270):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTGS WMNWVRQAPG

QGLEWIGRIY PGDGETNYNG KFKDRVTITA DKSTSTAYME

LSSLRSEDTA VYYCARIYGN NVYFDVWGQG TTVTVSSGGC

GGGKVAALKE KVAALKEKVA ALKEKVAALK E
```

In SEQ ID NO:270, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-243 correspond to the linker GGCGGG (SEQ ID NO:34), and residues 244-271 are a K-coil Domain (SEQ ID NO:40).

A polynucleotide that encodes SEQ ID NO:270 is (SEQ ID NO:271):

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaaggc tccctggacc cctgcacggt tttctggaag tctgctgggc ggaaaggccg ctctgactat taccggggca caggccgagg acgaagccga ttactattgt gctctgtggt atagcaatct gtgggtgttc ggggtggca caaaactgac tgtgctggga gggggtggat ccggcggagg tggacaggtc cagctggtcc agagcgggc cgaagtcaaa aaacccggag caagcgtgaa ggtctcctgc aaagcatcag gctatacatt tacaggcagc tggatgaact gggtgaggca ggctccagga cagggactgg agtggatcgg cgcatctac cctggagacg gcgaaactaa ctataatgga aagttcaaag accgagtgac catcacagcc gataagtcta ctagtaccgc ctacatggag ctgagctccc tgcggtctga agataccgcc gtctactatt gcgctagaat ttacggaaac aatgtctatt ttgacgtgtg ggggcaggga acaactgtga ctgtctcctc cggaggatgt
```

```
ggcggtggaa aagtggccgc actgaaggag aaagttgctg cttttgaaaga gaaggtcgcc gcacttaagg aaaaggtcgc agccctgaaa gag
```

The amino acid sequence of the third polypeptide chain of gpA33 mAb 1×CD3 mAb 2×EphA2 mAb 3 is (SEQ ID NO:272):

```
EVQLVESGGG SVKPGGSLKL SCAASGFTFT DHYMYWVRQT

PEKRLEWVAT ISDGGSFTSY PDSVKGRFTI SRDIAKNNLY

LQMSSLKSED TAMYYCTRDE SDRPFPYWGQ GTLVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

In SEQ ID NO:272, amino acid residues 1-118 correspond to the amino acid sequence of the VH Domain of EphA2 mAb 3 (SEQ ID NO:177), residues 119-216 correspond to a modified CH1 Domain (SEQ ID NO:208), residues 217-231 correspond to a linker (SEQ ID NO:209), and residues 232-448 correspond to the "hole-bearing" CH2-CH3 Domain (SEQ ID NO:53).

A polynucleotide that encodes SEQ ID NO:272 is (SEQ ID NO:273):

```
gaagtgcagc tggtggagtc tgggggaggc tcagtgaagc ctggagggtc cctgaaactc tcctgtgcag cctctggatt cactttcact gaccattaca tgtattgggt tcgccagact ccggaaaaga ggctggagtg ggtcgcaacc attagtgatg gcggtagttt cacctcctat ccagacagtg tgaaggggcg attcaccatc tccagagaca ttgccaagaa caacctgtac ctccaaatga gcagtctgaa gtctgaggac acagccatgt attactgtac aagagatgag agcgataggc cgtttccttat ctggggccaa gggactctgg tcactgtctc ctccgcctcc accaagggcc catcggtctt ccccctggca ccctcctcca agagcacctc tgggggcaca gcggccctgg gctgcctggt caaggactac ttccccgaac cggtgacggt gtcgtggaac tcaggcgccc tgaccagcgg cgtgcacacc ttcccggctg tcctacagtc ctcaggactc tactccctca gcagcgtggt gaccgtgccc tccagcagct gggcaccca gacctacatc tgcaacgtga atcacaagcc cagcaacacc aaggtggaca
```

```
agagagttga gcccaaatct tgtgacaaaa ctcacacatg cccaccgtgc ccagcacctg aagccgcggg gggaccgtca gtcttcctct tccccccaaa acccaaggac accctcatga tctcccggac ccctgaggtc acatgcgtgg tggtggacgt gagccacgaa gaccctgagg tcaagttcaa ctggtacgtg gacggcgtgg aggtgcataa tgccaagaca aagccgcggg aggagcagta caacagcacg taccgtgtgg tcagcgtcct caccgtcctg caccaggact ggctgaatgg caaggagtac aagtgcaagg tctccaacaa agcccccca gccccatcg agaaaaccat ctccaaagcc aaagggcagc cccgagaacc acaggtgtac accctgcccc catcccggga ggagatgacc aagaaccagg tcagcctgag ttgcgcagtc aaaggcttct atcccagcga catcgccgtg gagtgggaga gcaatgggca gccggagaac aactacaaga ccacgcctcc cgtgctggac tccgacggct ccttcttcct cgtcagcaag ctcaccgtgg acaagagcag gtggcagcag gggaacgtct tctcatgctc cgtgatgcat gaggctctgc acaaccgcta cacgcagaag agcctctccc tgtctccggg taaa
```

The amino acid sequence of the fourth polypeptide chain of gpA33 mAb 1×CD3 mAb 2×EphA2 mAb 3 is (SEQ ID NO:274):

```
DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

In SEQ ID NO:274, amino acid residues 1-107 correspond to the amino acid sequence of the VL Domain of EphA2 mAb 3 (SEQ ID NO:172), and residues 108-214 correspond to the CL Kappa Domain (SEQ ID NO:210).

A polynucleotide that encodes SEQ ID NO:274 is (SEQ ID NO:275):

```
gacattgtgc tgacccagtc tcacagatcc atgtccacat cagtaggaga cagggtcaac atcacctgca aggccagtca ggatgtgact actgctgtag cctggtatca acaaaaacca gggcaatctc ctaaattact gattttctgg gcatccaccc ggcacgctgg agtccctgat cgcttcacag gcagtggatc tgggacagat tttactctca ccatcagcag tgtgcaggct ggagacctgg cactttatta ctgtcaacaa cattatagca caccgtacac attcggaggg gggaccaagc tggaaataaa acgtacggtg gctgcaccat cggtcttcat cttcccgcca tctgatgagc agttgaaatc tggaactgcc tctgttgtgt gcctgctgaa taacttctat cccagagagg ccaaagtaca gtggaaggtg gataacgccc tccaatcggg taactcccag gagagtgtca cagagcagga cagcaaggac agcacctaca gcctcagcag cacctgacg ctgagcaaag cagactacga gaaacacaaa gtctacgcct gcgaagtcac ccatcagggc ctgagctcgc ccgtcacaaa gagcttcaac aggggagagt gt
```

N. EphA2 mAb 1×CD3 mAb 2×gpA33 mAb 1

An alternative EphA2/CD3/gpA33 Tri-Specific Binding Molecule was constructed. The molecule was composed of four polypeptide chains and comprises the VL and VH domains of EphA2 mAb 1, the VL and VH domains of antibody CD3 mAb 2 and the VL and VH domains of gpA33 mAb 1. The molecule was designated "EphA2 mAb 1×CD3 mAb 2×gpA33 mAb 1." The amino acid sequence of the first polypeptide chain of this Tri-Specific Binding Molecule is (SEQ ID NO:276):

```
DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

In SEQ ID NO:276, amino acid residues 1-106 correspond to the amino acid sequence of the VL Domain of EphA2 mAb 1 (SEQ ID NO:153), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-245 correspond to the GGCGGG linker (SEQ ID NO:34), residues 246-273 correspond to an E-coil Domain (SEQ ID NO:39), residues 274-276 are the linker GGG, residues 277-286 are the linker DKTHTCPPCP (SEQ ID NO:48), and residues 287-503 are the "knob-bearing" CH2-CH3 Domain (SEQ ID NO:52).

A polynucleotide that encodes SEQ ID NO:276 is (SEQ ID NO:277):

```
gatatccaga tgacacagac tacatcctcc ctgtctgcct
ctctgggaga cagaatcacc atcagttgca gggcaagtca
ggacattagc aattatttaa actggtatca gcagaaacca
gatggaactg ttaaactcct gatctactac acatcaagat
tacactcagg agtccatca aggttcagtg gcagtgggtc
tggaacagat tattctctca ccattagcaa cctggagcaa
gaagatattg ccacttactt ttgccaacag ggttatacgc
tgtacacgtt cggagggggg accaagctgg aaataaaagg
tggaggatcc ggcggcgag gcgaggtgca gctggtggag
tctgggggag gcttggtcca gcctggaggg tccctgagac
tctcctgtgc agcctctgga ttcaccttca gcacatacgc
tatgaattgg gtccgccagg ctccagggaa ggggctggag
tgggttggaa ggatcaggtc caagtacaac aattatgcaa
cctactatgc cgactctgtg aagggtagat caccatctc
aagagatgat tcaaagaact cactgtatct gcaaatgaac
agcctgaaaa ccgaggacac ggccgtgtat tactgtgtga
gacacggtaa cttcggcaat tcttacgtgt cttggtttgc
ttattgggga caggggacac tggtgactgt gtcttccgga
ggatgtggcg gtggagaagt ggccgcactg gagaagagg
ttgctgcttt ggagaaggag gtcgctgcac ttgaaaagga
ggtcgcagcc ctggagaaag gcggcggga caaaactcac
acatgcccac cgtgcccagc acctgaagcc gcggggggac
cgtcagtctt cctcttcccc ccaaaaccca aggacaccct
catgatctcc cggacccctg aggtcacatg cgtggtggtg
gacgtgagcc acgaagaccc tgaggtcaag ttcaactggt
acgtggacgg cgtggaggtg cataatgcca agacaaagcc
gcgggaggag cagtacaaca gcacgtaccg tgtggtcagc
gtcctcaccg tcctgcacca ggactggctg aatggcaagg
agtacaagtg caaggtctcc aacaaagccc tcccagcccc
catcgagaaa accatctcca aagccaaagg gcagcccga
gaaccacagg tgtacaccct gcccccatcc cgggaggaga
tgaccaagaa ccaggtcagc ctgtggtgcc tggtcaaagg
cttctatccc agcgacatcg ccgtggagtg ggagagcaat
gggcagccgg agaacaacta caagaccacg cctcccgtgc
tggactccga cggctccttc ttcctctaca gcaagctcac
cgtggacaag agcaggtggc agcaggggaa cgtcttctca
tgctccgtga tgcatgaggc tctgcacaac cactacacgc
agaagagcct ctccctgtct ccgggtaaa
```

The amino acid sequence of the second polypeptide chain of EphA2 mAb 1×CD3 mAb 2×gpA33 mAb 1 is (SEQ ID NO:278):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLKESGPGLV APSQSLSITC TVSGFSLSRY SVHWVRQPPG
KGLEWLGMIW GGGSTDYNSA LKSRLSISKD NSKSQVFLKM
NSLQTDDTAM YYCARKHGNY YTMDYWGQGT SVTVSSGGCG
GGKVAALKEK VAALKEKVAA LKEKVAALKE
```

In SEQ ID NO:278, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 1 (SEQ ID NO:158), residues 237-242 correspond to the linker GGCGGG (SEQ ID NO:34), and residues 243-270 are a K-coil Domain (SEQ ID NO:40).

A polynucleotide that encodes SEQ ID NO:278 is (SEQ ID NO:279):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gggcctgatc gggggtacaa
acaaaagggc tccctggacc cctgcacggt tttctggaag
tctgctgggc ggaaaggccg ctctgactat taccgggca
caggccgagg acgaagccga ttactattgt gctctgtggt
atagcaatct gtgggtgttc gggggtggca caaaactgac
tgtgctggga gggggtggat ccggcggagg tggacaggtg
cagctgaagg agtcaggacc tggcctggtg gcaccctcac
agagcctgtc catcacatgc actgtctctg ggttctcatt
atccagatat agtgtacact gggttcgcca gcctccagga
aagggtctgg agtggctggg aatgatatgg ggtggtggaa
gcacagacta taattcagct ctcaaatcca gactgagtat
cagcaaggac aactccaaga gccaagtttt cttaaaaatg
aacagtctgc aaactgatga cacagccatg tactactgtg
ccagaaaaca tggtaactac tatactatgg actactgggg
tcaaggaacc tcagtcaccg tctcctccgg aggatgtggc
ggtggaaaag tggccgcact gaaggagaaa gttgctgctt
tgaaagagaa ggtcgccgca cttaaggaaa aggtcgcagc
cctgaaagag
```

The amino acid sequence of the third polypeptide chain of EphA2 mAb 1×CD3 mAb 2×gpA33 mAb 1 is (SEQ ID NO:280):

QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK

In SEQ ID NO:280, amino acid residues 1-119 correspond to the amino acid sequence of the VH Domain of gpA33 mAb 1 (SEQ ID NO:186), residues 120-217 correspond to a modified CH1 Domain (SEQ ID NO:208), residues 218-232 correspond to a linker (SEQ ID NO:209), and residues 233-449 correspond to the "hole-bearing" CH2-CH3 Domain (SEQ ID NO:53).

A polynucleotide that encodes SEQ ID NO:280 is (SEQ ID NO:281):

```
caggtccagc tggtccagag cggggccgaa gtcaaaaaac ccggagcaag cgtgaaggtc tcctgcaaag catcaggcta tacatttaca ggcagctgga tgaactgggt gaggcaggct ccaggacagg gactggagtg gatcgggcgc atctaccctg gagacggcga aactaactat aatggaaagt tcaaagaccg agtgaccatc acagccgata gtctactag taccgcctac atggagctga gctccctgcg gtctgaagat accgccgtct actattgcgc tagaatttac ggaaacaatg tctattttga cgtgtggggg cagggaacaa ctgtgactgt ctcctccgcc tccaccaagg gcccatcggt cttccccctg gcaccctcct ccaagagcac ctctgggggc acagcggccc tgggctgcct ggtcaaggac tacttccccg aaccggtgac ggtgtcgtgg aactcaggcg ccctgaccag cggcgtgcac accttcccgg ctgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaagccgc ggggggaccg tcagtcttcc tcttcccccc aaaacccaag gacaccctca tgatctcccg gacccctgag gtcacatgcg tggtggtgga cgtgagccac gaagaccctg aggtcaagtt caactggtac gtgacggcg tggaggtgca taatgccaag acaaagccgc
```

```
gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaaagggc agccccgaga accacaggtg tacaccctgc ccccatcccg ggaggagatg accaagaacc aggtcagcct gagttgcgca gtcaaaggct tctatcccag cgacatcgcc gtggagtggg agagcaatgg gcagccggag aacaactaca agaccacgcc tcccgtgctg gactccgacg gctccttctt cctcgtcagc aagctcaccg tggacaagag caggtggcag caggggaacg tcttctcatg ctccgtgatg catgaggctc tgcacaaccg ctacacgcag aagagcctct ccctgtctcc gggtaaa
```

The amino acid sequence of the fourth polypeptide chain of EphA2 mAb 1×CD3 mAb 2×gpA33 mAb 1 is (SEQ ID NO:282):

DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC

In SEQ ID NO:282, amino acid residues 1-106 correspond to the amino acid sequence of the VL Domain of gpA33 mAb 1 (SEQ ID NO:181), and residues 107-213 correspond to the CL Kappa Domain (SEQ ID NO:210).

A polynucleotide that encodes SEQ ID NO:282 is (SEQ ID NO:283):

```
gacattcagc tgactcagtc cccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca agcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacagggg actaaactgg aaatcaagcg tacggtggct gcaccatcgg tcttcatctt cccgccatct gatgagcagt tgaaatctgg aactgcctct gttgtgtgcc tgctgaataa cttctatccc agagaggcca agtacagtg gaaggtggat aacgccctcc aatcgggtaa ctcccaggag agtgtcacag agcaggacag caaggacagc acctacagcc tcagcagcac cctgacgctg agcaaagcag actacgagaa
```

-continued

```
acacaaagtc tacgcctgcg aagtcaccca tcagggcctg agctcgcccg tcacaaagag cttcaacagg ggagagtgt
```

O. EphA2 mAb 2×CD3 mAb 2×gpA33 mAb 1

A second alternative EphA2/CD3/gpA33 Tri-Specific Binding Molecule was constructed. The molecule was composed of four polypeptide chains and comprises the VL and VH domains of EphA2 mAb 2, the VL and VH domains of antibody CD3 mAb 2 and the VL and VH domains of gpA33 mAb 1. The molecule was designated "EphA2 mAb 2×CD3 mAb 2×gpA33 mAb 1." The amino acid sequence of the first polypeptide chain of this Tri-Specific Binding Molecule is (SEQ ID NO:284):

```
DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI KGGGSGGGGE

VQLVESGGGL VQPGGSLRLS CAASGFTFST YAMNWVRQAP

GKGLEWVGRI RSKYNNYATY YADSVKGRFT ISRDDSKNSL

YLQMNSLKTE DTAVYYCVRH GNFGNSYVSW FAYWGQGTLV

TVSSGGCGGG EVAALEKEVA ALEKEVAALE KEVAALEKGG

GDKTHTCPPC PAPEAAGGPS VFLFPPKPKD TLMISRTPEV

TCVVVDVSHE DPEVKFNWYV DGVEVHNAKT KPREEQYNST

YRVVSVLTVL HQDWLNGKEY KCKVSNKALP APIEKTISKA

KGQPREPQVY TLPPSREEMT KNQVSLWCLV KGFYPSDIAV

EWESNGQPEN NYKTTPPVLD SDGSFFLYSK LTVDKSRWQQ

GNVFSCSVMH EALHNHYTQK SLSLSPGK
```

In SEQ ID NO:284, amino acid residues 1-111 correspond to the amino acid sequence of the VL Domain of EphA2 mAb 2 (SEQ ID NO:163), residues 112-119 correspond to the intervening spacer peptide GGGSGGGG (Linker 1) (SEQ ID NO:33), residues 120-244 correspond to the amino acid sequence of the VH Domain of CD3 mAb 2 having the D65G substitution (SEQ ID NO:112), residues 245-250 correspond to the GGCGGG linker (SEQ ID NO:34), residues 251-278 correspond to an E-coil Domain (SEQ ID NO:39), residues 279-281 are the linker GGG, residues 282-291 are the linker DKTHTCPPCP (SEQ ID NO:48), and residues 292-508 are the "knob-bearing" CH2-CH3 Domain (SEQ ID NO:52).

A polynucleotide that encodes SEQ ID NO:284 is (SEQ ID NO:285):

```
gatgttgtga tgacccaaac tccactctcc ctgcctgtca gtcttggaga tcaagcctcc atctcttgca gatctagtca gagccttgta cacagtagtg gaaacaccta tttacattgg tacctgcaga agccaggcca gtctccaaag ctcctgatct acaaagtttc caaccgattt tctggggtcc cagacaggtt cagtggcagt ggatcaggga cagatttcac actcaagatc agcagagtgg aggctgagga tctgggagtt tatttctgct ctcaaagtac acatgttccc acgttcggct cggggacaaa gttggaaata aaaggtggag gatccggcgg cggaggcgag gtgcagctgg tggagtctgg gggaggcttg gtccagcctg gagggtccct gagactctcc tgtgcagcct ctggattcac cttcagcaca tacgctatga attgggtccg ccaggctcca gggaaggggc tggagtgggt tggaaggatc aggtccaagt acaacaatta tgcaacctac tatgccgact ctgtgaaggg tagattcacc atctcaagag atgattcaaa gaactcactg tatctgcaaa tgaacagcct gaaaaccgag gacacggccg tgtattactg tgtgagacac ggtaacttcg gcaattctta cgtgtcttgg tttgcttatt ggggacaggg gacactggtg actgtgtctt ccggaggatg tggcggtgga gaagtggccg cactggagaa agaggttgct gctttggaga aggaggtcgc tgcacttgaa aaggaggtcg cagccctgga gaaaggcggc ggggacaaaa ctcacacatg cccaccgtgc ccagcacctg aagccgcggg gggaccgtca gtcttcctct tccccccaaa acccaaggac accctcatga tctcccggac ccctgaggtc acatgcgtgg tggtggacgt gagccacgaa gaccctgagg tcaagttcaa ctggtacgtg gacggcgtgg aggtgcataa tgccaagaca aagccgcggg aggagcagta caacagcacg taccgtgtgg tcagcgtcct caccgtcctg caccaggact ggctgaatgg caaggagtac aagtgcaagg tctccaacaa agccctccca gcccccatcg agaaaaccat ctccaaagcc aaagggcagc ccgagaacc acaggtgtac accctgcccc catcccggga ggagatgacc aagaaccagg tcagcctgtg gtgcctggtc aaaggcttct atcccagcga catcgccgtg gagtgggaga gcaatgggca gccggagaac aactacaaga ccacgcctcc cgtgctggac tccgacggct ccttcttcct ctacagcaag ctcaccgtgg acaagagcag gtggcagcag gggaacgtct tctcatgctc cgtgatgcat gaggctctgc acaaccacta cacgcagaag agcctctccc tgtctccggg taaa
```

The amino acid sequence of the second polypeptide chain of EphA2 mAb 2×CD3 mAb 2×gpA33 mAb 1 is (SEQ ID NO:286):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQI

QLVQSGPELK KPGETVKISC KASGFTFTNY GMNWVKQAPG

KGLKWMGWIN TYIGEPTYAD DFKGRFVFSL ETSASTAYLQ
```

```
INNLKNEDMA TYFCARELGP YYFDYWGQGT TLTVSSGGCG

GGKVAALKEK VAALKEKVAA LKEKVAALKE
```

In SEQ ID NO:286, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 2 (SEQ ID NO:167), residues 237-242 correspond to the linker GGCGGG (SEQ ID NO:34), and residues 243-270 are a K-coil Domain (SEQ ID NO:40).

A polynucleotide that encodes SEQ ID NO:286 is (SEQ ID NO:287):

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaaggccg ctctgactat taccggggca caggccgagg acgaagccga ttactattgt gctctgtggt atagcaatct gtgggtgttc ggggggtggca caaaactgac tgtgctggga ggggggtggat ccggcggagg tggacagatc cagttggtgc agtctggacc tgagctgaag aagcctggag agacagtcaa gatctcctgc aaggcttctg ggtttacctt cacaaactat ggaatgaact gggtgaagca ggctccagga aagggtttaa agtggatggg ctggataaac acctatattg gagagccgac atatgctgat gacttcaagg acggtttgt cttctctttg gaaacctctg ccagcactgc ctatttgcag atcaacaacc tcaaaaatga ggacatggcc acatatttct gtgcaagaga actgggacca tactactttg actactgggg ccaaggcacc actctcacag tctcctccgg aggatgtggc ggtggaaaag tggccgcact gaaggagaaa gttgctgctt tgaaagagaa ggtcgccgca cttaaggaaa aggtcgcagc cctgaaagag
```

The amino acid sequence of the third polypeptide chain of EphA2 mAb 2×CD3 mAb 2×gpA33 mAb 1 is (SEQ ID NO:288):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

In SEQ ID NO:288, amino acid residues 1-119 correspond to the amino acid sequence of the VH Domain of gpA33 mAb 1 (SEQ ID NO:186), residues 120-217 correspond to a modified CH1 Domain (SEQ ID NO:208), residues 218-232 correspond to a linker (SEQ ID NO:209), and residues 233-449 correspond to the "hole-bearing" CH2-CH3 Domain (SEQ ID NO:53).

A polynucleotide that encodes SEQ ID NO:288 is (SEQ ID NO:289):

```
caggtccagc tggtccagag cggggccgaa gtcaaaaaac ccggagcaag cgtgaaggtc tcctgcaaag catcaggcta tacatttaca ggcagctgga tgaactgggt gaggcaggct ccaggacagg gactggagtg gatcgggcgc atctaccctg gagacggcga aactaactat aatggaaagt tcaaagaccg agtgaccatc acagccgata gtctactagt accgcctac atggagctga gctccctgcg gtctgaagat accgccgtct actattgcgc tagaatttac ggaaacaatg tctattttga cgtgtggggg cagggaacaa ctgtgactgt ctcctccgcc tccaccaagg gcccatcggt cttcccctg caccctcct ccaagagcac ctctgggggc acagcggcc tgggctgcct ggtcaaggac tacttccccg aaccggtgac ggtgtcgtgg aactcaggcg ccctgaccag cggcgtgcac accttcccgg ctgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaagccgc ggggggaccg tcagtcttcc tcttccccc aaaacccaag gacaccctca tgatctcccg gacccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaaaggc agccccgaga accacaggtg tacaccctgc cccatcccg ggaggagatg accaagaacc aggtcagcct gagttgcgca gtcaaaggct
```

-continued
```
tctatcccag cgacatcgcc gtggagtggg agagcaatgg gcagccggag aacaactaca agaccacgcc tcccgtgctg gactccgacg gctccttctt cctcgtcagc aagctcaccg tggacaagag caggtggcag caggggaacg tcttctcatg ctccgtgatg catgaggctc tgcacaaccg ctacacgcag aagagcctct ccctgtctcc gggtaaa
```

The amino acid sequence of the fourth polypeptide chain of EphA2 mAb 2×CD3 mAb 2×gpA33 mAb 1 is (SEQ ID NO:290):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

In SEQ ID NO:290, amino acid residues 1-106 correspond to the amino acid sequence of the VL Domain of gpA33 mAb 1 (SEQ ID NO:181), and residues 107-213 correspond to the CL Kappa Domain (SEQ ID NO:210).

A polynucleotide that encodes SEQ ID NO:290 is (SEQ ID NO:291):

```
gacattcagc tgactcagtc cccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca gcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacagggg actaaactgg aaatcaagcg tacggtggct gcaccatcgg tcttcatctt cccgccatct gatgagcagt tgaaatctgg aactgcctct gttgtgtgcc tgctgaataa cttctatccc agagaggcca aagtacagtg gaaggtggat aacgccctcc aatcgggtaa ctcccaggag agtgtcacag agcaggacag caaggacagc acctacagcc tcagcagcac cctgacgctg agcaaagcag actacgagaa acacaaagtc tacgcctgcg aagtcaccca tcagggcctg agctcgcccg tcacaaagag cttcaacagg ggagagtgt
```

P. EphA2 mAb 3×CD3 mAb 2×gpA33 mAb 1

A third alternative EphA2/CD3/gpA33 Tri-Specific Binding Molecule was constructed. The molecule was composed of four polypeptide chains and comprises the VL and VH domains of EphA2 mAb 3, the VL and VH domains of antibody CD3 mAb 2 and the VL and VH domains of gpA33 mAb 1. The molecule was designated "EphA2 mAb 3×CD3 mAb 2×gpA33 mAb 1." The amino acid sequence of the first polypeptide chain of this Tri-Specific Binding Molecule is (SEQ ID NO:292):

```
DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLWCLVKGFY PSDIAVEWES

NGQPENNYKT TPPVLDSDGS FFLYSKLTVD KSRWQQGNVF

SCSVMHEALH NHYTQKSLSL SPGK
```

In SEQ ID NO:292, amino acid residues 1-107 correspond to the amino acid sequence of the VL Domain of EphA2 mAb 3 (SEQ ID NO:172), residues 108-115 correspond to the intervening spacer peptide GGGSGGGG (Linker 1) (SEQ ID NO:33), residues 116-240 correspond to the amino acid sequence of the VH Domain of CD3 mAb 2 having the D65G substitution (SEQ ID NO:112), residues 241-246 correspond to the GGCGGG linker (SEQ ID NO:34), residues 247-274 correspond to an E-coil Domain (SEQ ID NO:39), residues 275-277 are the linker GGG, residues 278-287 are the linker DKTHTCPPCP (SEQ ID NO:48), and residues 288-504 are the "knob-bearing" CH2-CH3 Domain (SEQ ID NO:52).

A polynucleotide that encodes SEQ ID NO:292 is (SEQ ID NO:293):

```
gacattgtgc tgacccagtc tcacagatcc atgtccacat cagtaggaga cagggtcaac atcacctgca aggccagtca ggatgtgact actgctgtag cctggtatca acaaaaacca gggcaatctc ctaaattact gattttctgg gcatccaccc ggcacgctgg agtccctgat cgcttcacag gcagtggatc tgggacagat tttactctca ccatcagcag tgtgcaggct ggagacctgg cactttatta ctgtcaacaa cattatagca caccgtacac attcggaggg gggaccaagc tggaaataaa aggtggagga tccggcggcg gaggcgaggt gcagctggtg gagtctgggg gaggcttggt ccagcctgga gggtccctga gactctcctg tgcagcctct ggattcacct tcagcacata cgctatgaat tgggtccgcc aggctccagg gaagggggctg gagtggggttg gaaggatcag gtccaagtac aacaattatg caacctacta tgccgactct gtgaagggta gattcaccat
```

```
ctcaagagat gattcaaaga actcactgta tctgcaaatg aacagcctga aaaccgagga cacggccgtg tattactgtg tgagacacgg taacttcggc aattcttacg tgtcttggtt tgcttattgg ggacagggga cactggtgac tgtgtcttcc ggaggatgtg gcggtggaga agtggccgca ctggagaaag aggttgctgc tttggagaag gaggtcgctg cacttgaaaa ggaggtcgca gccctggaga aaggcggcgg ggacaaaact cacacatgcc caccgtgccc agcacctgaa gccgcggggg gaccgtcagt cttcctcttc cccccaaaac ccaaggacac cctcatgatc tcccgcaccc ctgaggtcac atgcgtggtg gtggacgtga gccacgaaga ccctgaggtc aagttcaact ggtacgtgga cggcgtggag gtgcataatg ccaagacaaa gccgcgggag gagcagtaca acagcacgta ccgtgtggtc agcgtcctca ccgtcctgca ccaggactgg ctgaatggca aggagtacaa gtgcaaggtc tccaacaaag ccctcccagc ccccatcgag aaaaccatct ccaaagccaa agggcagccc cgagaaccac aggtgtacac cctgccccca tcccgggagg agatgaccaa gaaccaggtc agcctgtggt gcctggtcaa aggcttctat cccagcgaca tcgccgtgga gtgggagagc aatgggcagc cggagaacaa ctacaagacc acgcctcccg tgctggactc cgacggctcc ttcttcctct acagcaagct caccgtggac aagagcaggt ggcagcaggg gaacgtcttc tcatgctccg tgatgcatga ggctctgcac aaccactaca cgcagaagag cctctccctg tctccgggta aa
```

The amino acid sequence of the second polypeptide chain of EphA2 mAb 3×CD3 mAb 2×gpA33 mAb 1 is (SEQ ID NO:294):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVESGGGSV KPGGSLKLSC AASGFTFTDH YMYWVRQTPE

KRLEWVATIS DGGSFTSYPD SVKGRFTISR DIAKNNLYLQ

MSSLKSEDTA MYYCTRDESD RPFPYWGQGT LVTVSSGGCG

GGKVAALKEK VAALKEKVAA LKEKVAALKE
```

In SEQ ID NO:294, amino acid residues 1-110 correspond to the amino acid sequence of the VL Domain of CD3 mAb 3 (SEQ ID NO:104), residues 111-118 correspond to the intervening spacer peptide GGGSGGGG (Linker 1) (SEQ ID NO:33), residues 119-236 correspond to the amino acid sequence of the VH Domain of EphA2 mAb 3 (SEQ ID NO:177), residues 237-242 correspond to the linker GGCGGG (SEQ ID NO:34), and residues 243-270 are a K-coil Domain (SEQ ID NO:40).

A polynucleotide that encodes SEQ ID NO:294 is (SEQ ID NO:295):

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaaggccg ctctgactat taccggggca caggccgagg acgaagccga ttactattgt gctctgtggt atagcaatct gtgggtgttc gggggtggca caaaactgac tgtgctggga gggggtggat ccggcggagg tggagaagtg cagctggtgg agtctggggg aggctcagtg aagcctggag ggtccctgaa actctcctgt gcagcctctg gattcacttt cactgaccat tacatgtatt gggttcgcca gactccggaa aagaggctgg agtgggtcgc aaccattagt gatggcggta gtttcacctc ctatccagac agtgtgaagg ggcgattcac catctccaga gacattgcca agaacaacct gtacctccaa atgagcagtc tgaagtctga ggacacagcc atgtattact gtacaagaga tgagagcgat aggccgtttc cttactgggg ccaagggact ctggtcactg tctcctccgg aggatgtggc ggtggaaaag tggccgcact gaaggagaaa gttgctgctt tgaaagagaa ggtcgccgca cttaaggaaa aggtcgcagc cctgaaagag
```

The amino acid sequence of the third polypeptide chain of EphA2 mAb 3×CD3 mAb 2×gpA33 mAb 1 is (SEQ ID NO:296):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

In SEQ ID NO:296, amino acid residues 1-119 correspond to the amino acid sequence of the VH Domain of gpA33 mAb 1 (SEQ ID NO:186), residues 120-217 correspond to a modified CH1 Domain (SEQ ID NO:208), residues 218-232 correspond to a linker (SEQ ID NO:209), and residues 233-449 correspond to the "hole-bearing" CH2-CH3 Domain (SEQ ID NO:53).

A polynucleotide that encodes SEQ ID NO:296 is (SEQ ID NO:297):

```
caggtccagc tggtccagag cggggccgaa gtcaaaaaac ccggagcaag cgtgaaggtc tcctgcaaag catcaggcta tacatttaca ggcagctgga tgaactgggt gaggcaggct ccaggacagg gactggagtg gatcgggcgc atctaccctg gagacggcga aactaactat aatggaaagt tcaaagaccg agtgaccatc acagccgata agtctactag taccgcctac atggagctga gctccctgcg gtctgaagat accgccgtct actattgcgc tagaatttac ggaaacaatg tctattttga cgtgtggggg cagggaacaa ctgtgactgt ctcctccgcc tccaccaagg gcccatcggt cttccccctg gcaccctcct ccaagagcac ctctgggggc acagcggccc tgggctgcct ggtcaaggac tacttccccg aaccggtgac ggtgtcgtgg aactcaggcg ccctgaccag cggcgtgcac accttccgg ctgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaagccgc ggggggaccg tcagtcttcc tcttcccccc aaaacccaag gacaccctca tgatctcccg gacccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaagggc agccccgaga accacaggtg tacaccctgc ccccatcccg ggaggagatg accaagaacc aggtcagcct gagttgcgca gtcaaaggct tctatcccag cgacatcgcc gtggagtggg agagcaatgg gcagccggag aacaactaca agaccacgcc tcccgtgctg gactccgacg gctccttctt cctcgtcagc aagctcaccg tggacaagag caggtggcag caggggaacg tcttctcatg ctccgtgatg catgaggctc tgcacaaccg ctacacgcag aagagcctct ccctgtctcc gggtaaa
```

The amino acid sequence of the fourth polypeptide chain of EphA2 mAb 3×CD3 mAb 2×gpA33 mAb 1 is (SEQ ID NO:298):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

In SEQ ID NO:298, amino acid residues 1-106 correspond to the amino acid sequence of the VL Domain of gpA33 mAb 1 (SEQ ID NO:181), and residues 107-213 correspond to the CL Kappa Domain (SEQ ID NO:210).

A polynucleotide that encodes SEQ ID NO:298 is (SEQ ID NO:299):

```
gacattcagc tgactcagtc cccctctttt ctgtccgcat ccgtcggaga tcgagtgact attacttgct ctgctaggtc ctcaatcagc ttcatgtact ggtatcagca gaagcccggc aaagcaccta agctgctgat ctacgacaca agcaacctgg cctccggggt gccatctcgg ttctctggca gtgggtcagg aactgagttt accctgacaa ttagctccct ggaggctgaa gatgccgcta cctactattg ccagcagtgg agcagctatc ctctgacctt cggacagggg actaaactgg aaatcaagcg tacggtggct gcaccatcgg tcttcatctt cccgccatct gatgagcagt tgaaatctgg aactgcctct gttgtgtgcc tgctgaataa cttctatccc agagaggcca agtacagtg gaaggtggat aacgccctcc aatcgggtaa ctcccaggag agtgtcacag agcaggacag caaggacagc acctacagcc tcagcagcac cctgacgctg agcaaagcag actacgagaa acacaaagtc tacgcctgcg aagtcaccca tcagggcctg agctcgcccg tcacaaagag cttcaacagg ggagagtgt
```

IV. Reference Antibodies and Diabodies

In order to assist in the characterization of the Tri-Specific Binding Molecules of the present invention, the following reference diabodies were constructed.

Q. DR5 mAb 1×CD3 mAb 2 Diabody

An exemplary bi-specific diabody composed of two polypeptide chains was constructed having the VL and VH domains of anti-human DR5 antibody DR5 mAb 1 and the VL and VH domains of CD3 mAb 2. The diabody was designated "DR5 mAb 1×CD3 mAb 2 diabody." The amino acid sequence of the first polypeptide chain of this diabody is (SEQ ID NO:140):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KGGGSGGGGE
```

```
VQLVESGGGL VQPGGSLRLS CAASGFTFST YAMNWVRQAP

GKGLEWVGRI RSKYNNYATY YADSVKGRFT ISRDDSKNSL

YLQMNSLKTE DTAVYYCVRH GNFGNSYVSW FAYWGQGTLV

TVSSASTKGE VAACEKEVAA LEKEVAALEK EVAALEK
```

In SEQ ID NO:140, amino acid residues 1-111 correspond to the amino acid sequence of the VL Domain of DR5 mAb 1 (SEQ ID NO:3), residues 112-119 correspond to the intervening spacer peptide GGGSGGGG (Linker 1) (SEQ ID NO:33), residues 120-244 correspond to the amino acid sequence of the VH Domain of CD3 mAb 2 having the D65G substitution (SEQ ID NO:112), residues 245-249 correspond to the ASTKG linker (SEQ ID NO:47) and residues 250-277 correspond to a cysteine-containing E-coil Domain (SEQ ID NO:41). A polynucleotide that encodes SEQ ID NO:140 is SEQ ID NO:141:

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaaggaggcg gatccgcgg cggaggcgag gtgcagctgg tggagtctgg gggaggcttg gtccagcctg gagggtccct gagactctcc tgtgcagcct ctggattcac cttcagcaca tacgctatga attgggtccg ccaggctcca gggaaggggc tggagtgggt tggaaggatc aggtccaagt acaacaatta tgcaacctac tatgccgact ctgtgaaggg tagattcacc atctcaagag atgattcaaa gaactcactg tatctgcaaa tgaacagcct gaaaaccgag gacacggccg tgtattactg tgtgagacac ggtaacttcg gcaattctta cgtgtcttgg tttgcttatt ggggacaggg gacactggtg actgtgtctt ccgcctccac caagggcgaa gtggccgcat gtgagaaaga ggttgctgct ttggagaagg aggtcgctgc acttgaaaag gaggtcgcag ccctggagaa a
```

The amino acid sequence of the second polypeptide chain of the DR5 mAb 1×CD3 mAb 2 diabody is (SEQ ID NO:142):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

KFLESGGGLV QPGGSLKLSC VASGFDFSRY WMSWVRQAPG

KGLEWIGEIN PDSNTINYTP SLKDKFIISR DNAKNTLYLQ

MTKVRSEDTA LYYCTRRAYY GNPAWFAYWG QGTLVTVSAA

STKGKVAACK EKVAALKEKV AALKEKVAAL KE
```

In SEQ ID NO:142, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-239 correspond to the amino acid sequence of the VH Domain of DR5 mAb 1 (SEQ ID NO:8), except that the C-terminal serine residue of SEQ ID NO:8 has been replaced with an alanine residue), residues 240-244 correspond to an ASTKG linker (SEQ ID NO:47), and residues 245-272 correspond to a cysteine-containing K-coil Domain (SEQ ID NO:42). A polynucleotide that encodes SEQ ID NO:142 is SEQ ID NO:143:

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaaggccg ctctgactat taccgggca caggccgagg acgaagccga ttactattgt gctctgtggt atagcaatct gtgggtgttc gggggtggca caaaactgac tgtgctggga ggtggtggat ccggcggcgg aggcgaggtg aagtttctcg agtctggagg tggcctggtg cagcctggag gatccctgaa actctcctgt gtagcctcag gattcgattt tagtagatac tggatgagtt gggtccggca ggctccaggg aaagggctag aatggattgg agaaattaat ccagatagca atacgataaa ctatacgcca tctctaaagg ataaattcat catctccaga gacaacgcca aaaatacgct gtatctgcaa atgaccaaag tgagatctga ggacacagcc ctttattatt gtacaagaag ggcctactat ggtaacccgg cctggtttgc ttactggggc caagggactc tggtcactgt ctctgcagcc tccaccaagg gcaaagtggc cgcatgtaag gagaaagttg ctgctttgaa agagaaggtc gccgcactta aggaaaaggt cgcagccctg aaagag
```

R. DR5 mAb 2×CD3 mAb 2 Diabody

An exemplary bi-specific diabody composed of two polypeptide chains was constructed having the VL and VH domains of anti-human DR5 antibody DR5 mAb 2 and the VL and VH domains of CD3 mAb 2. The diabody was designated "DR5 mAb 2×CD3 mAb 2 diabody." The amino acid sequence of the first polypeptide chain of this diabody is (SEQ ID NO:144):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

ASTKGEVAAC EKEVAALEKE VAALEKEVAA LEK
```

In SEQ ID NO:144, amino acid residues 1-107 correspond to the amino acid sequence of the VL Domain of DR5 mAb 2 (SEQ ID NO:13), residues 108-115 correspond to intervening spacer peptide (Linker 1) (SEQ ID NO:33), residues 116-240 correspond to the amino acid sequence of the VH Domain of CD3 mAb 2 having the D65G substitution (SEQ ID NO:112), residues 241-245 correspond to an ASTKG linker (SEQ ID NO:47) and residues 246-273 correspond to a cysteine-containing E-coil Domain (SEQ ID NO:41). A polynucleotide that encodes SEQ ID NO:144 is SEQ ID NO:145:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcgaggt gcagctggtg gagtctgggg gaggcttggt ccagcctgga gggtccctga gactctcctg tgcagcctct ggattcacct tcagcacata cgctatgaat tgggtccgcc aggctccagg aaggggctg gagtgggttg gaaggatcag gtccaagtac aacaattatg caacctacta tgccgactct gtgaagggta gattcaccat ctcaagagat gattcaaaga actcactgta tctgcaaatg aacagcctga aaaccgagga cacggccgtg tattactgtg tgagacacgg taacttcggc aattcttacg tgtcttggtt tgcttattgg ggacagggga cactggtgac tgtgtcttcc gcctccacca agggcgaagt ggccgcatgt gagaagagg ttgctgcttt ggagaaggag gtcgctgcac ttgaaaagga ggtcgcagcc ctggagaaa
```

The amino acid sequence of the second polypeptide chain of the DR5 mAb 2×CD3 mAb 2 diabody is (SEQ ID NO:146):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGKV

QLQQSGAELV KPGASVKLSC KASGYTFTEY ILHWVKQKSG

QGLEWIGWFY PGNNNIKYNE KFKDKATLTA DKSSSTVYME

LSRLTSEDSA VYFCARHEQG PGYFDYWGQG TTLTVSSAST

KGKVAACKEK VAALKEKVAA LKEKVAALKE
```

In SEQ ID NO:146, amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of DR5 mAb 2 (SEQ ID NO:18), residues 238-242 correspond to an ASTKG linker (SEQ ID NO:47), and residues 243-270 correspond to a cysteine-containing K-coil Domain (SEQ ID NO:42). A polynucleotide that encodes SEQ ID NO:146 is SEQ ID NO:147:

```
caggctgtgg tgactcagga gccttcactg accgtgtccc caggcggaac tgtgaccctg acatgcagat ccagcacagg cgcagtgacc acatctaact acgccaattg ggtgcagcag aagccaggac aggcaccaag gggcctgatc gggggtacaa acaaaagggc tccctggacc cctgcacggt tttctggaag tctgctgggc ggaaaggccg ctctgactat taccggggca caggccgagg acgaagccga ttactattgt gctctgtggt atagcaatct gtgggtgttc gggggtggca caaaactgac tgtgctggga gggggtggat ccggcggcgg aggcaaggtc cagctgcagc agtctggagc tgaactggtg aaacccgggg catcagtgaa gctgtcctgc aaggcttctg ggtacaccct cactgagtat attttacact gggtaaagca gaagtctgga cagggtcttg agtggattgg gtggttttat cctggaaata ataatataaa gtacaatgag aaattcaagg acaaggccac actgactgcg gacaaatcct ccagcacagt ctatatggaa cttagtagat tgacatctga agactctgcg gtctatttct gtgcaagaca cgaacaagga ccaggttact ttgactactg gggccaaggc accactctca cagtctcctc cgcctccacc aagggcaaag tggccgcatg taaggagaaa gttgctgctt tgaaagagaa ggtcgccgca cttaaggaaa aggtcgcagc cctgaaagag
```

S. DR5 mAb 3×CD3 mAb 2 Diabody

An exemplary bi-specific diabody composed of two polypeptide chains was constructed having the VL and VH domains of anti-human DR5 antibody DR5 mAb 3 and the VL and VH domains of CD3 mAb 2. The amino acid sequence of the first polypeptide chain of the diabody had the sequence (SEQ ID NO:148) (CDR residues are shown underlined):

```
SELTQDPAVS VALGQTVRIT CSGDSLRSYY ASWYQQKPGQ

APVLVIYGAN NRPSGIPDRF SGSSSGNTAS LTITGAQAED

EADYYCNSAD SSGNHVVFGG GTKLTVLGGG GSGGGGEVQL

VESGGGLVQP GGSLRLSCAA SGFTFSTYAM NWVRQAPGKG

LEWVGRIRSK YNNYATYYAD SVKGRFTISR DDSKNSLYLQ

MNSLKTEDTA VYYCVRHGNF GNSYVSWFAY WGQGTLVTVS

SASTKGEVAA CEKEVAALEK EVAALEKEVA ALEK
```

In SEQ ID NO:148, amino acid residues 1-108 correspond to the VL Domain of DR5 mAb 3 (SEQ ID NO:54), residues 109-116 correspond to the intervening spacer peptide GGGSGGGG (Linker 1) (SEQ ID NO:33), residues 117-241 correspond to the amino acid sequence of the VH Domain of CD3 mAb 2 having the D65G substitution (SEQ ID NO:112), residues 242-246 correspond to an ASTKG linker (SEQ ID NO:47), and residues 247-275 correspond to a cysteine-containing K-coil Domain (SEQ ID NO:42).

The amino acid sequence of the second polypeptide chain of the diabody had the sequence (SEQ ID NO:149) (CDR residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVQSGGGVE RPGGSLRLSC AASGFTFDDY AMSWVRQAPG

KGLEWVSGIN WQGGSTGYAD SVKGRVTISR DNAKNSLYLQ

MNSLRAEDTA VYYCAKILGA GRGWYFDYWG KGTTVTVSSA

STKGKVAACK EKVAALKEKV AALKEKVAAL KE
```

In SEQ ID NO:149, amino acid residues 1-110 correspond to the VL Domain of CD3 mAb 2 (SEQ ID NO:104), residues 111-118 correspond to the intervening spacer peptide GGGSGGGG (Linker 1) (SEQ ID NO:33), residues 119-239 correspond to the amino acid sequence of the VH Domain of DR5 mAb 3 (SEQ ID NO:58), residues 240-244 correspond to an ASTKG linker (SEQ ID NO:47), and residues 245-272 correspond to a cysteine-containing K-coil Domain (SEQ ID NO:42).

T. DR5 mAb 4×CD3 mAb 2 Diabody

An exemplary bi-specific diabody composed of two polypeptide chains was constructed having the VL and VH domains of anti-human DR5 antibody DR5 mAb 4 and the VL and VH domains of CD3 mAb 2. The amino acid sequence of the first polypeptide chain of the diabody had the sequence (SEQ ID NO:150) (CDR residues are shown underlined):

```
EIVLTQSPGT LSLSPGERAT LSCRASQGIS RSYLAWYQQK

PGQAPSLLIY GASSRATGIP DRFSGSGSGT DFTLTISRLE

PEDFAVYYCQ QFGSSPWTFG QGTKVEIKGG GSGGGGEVQL

VESGGGLVQP GGSLRLSCAA SGFTFSTYAM NWVRQAPGKG

LEWVGRIRSK YNNYATYYAD SVKGRFTISR DDSKNSLYLQ

MNSLKTEDTA VYYCVRHGNF GNSYVSWFAY WGQGTLVTVS

SASTKGEVAA CEKEVAALEK EVAALEKEVA ALEK
```

In SEQ ID NO:150, amino acid residues 1-108 correspond to the VL Domain of DR5 mAb 4 (SEQ ID NO:62), residues 109-116 correspond to the intervening spacer peptide GGGSGGGG (Linker 1) (SEQ ID NO:33), residues 117-241 correspond to the amino acid sequence of the VH Domain of CD3 mAb 2 having the D65G substitution (SEQ ID NO:112), residues 242-246 correspond to an ASTKG linker (SEQ ID NO:47), and residues 247-275 correspond to a cysteine-containing E-coil Domain (SEQ ID NO:41).

The amino acid sequence of the second polypeptide chain of the diabody had the sequence (SEQ ID NO:151) (CDR residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLQESGPGLV KPSQTLSLTC TVSGGSISSG DYFWSWIRQL

PGKGLEWIGH IHNSGTTYYN PSLKSRVTIS VDTSKKQFSL

RLSSVTAADT AVYYCARDRG GDYYGMDVW GQGTTVTVSS

ASTKGKVAAC KEKVAALKEK VAALKEKVAA LKE
```

In SEQ ID NO:151, amino acid residues 1-110 correspond to the VL Domain of CD3 mAb 2 (SEQ ID NO:104), residues 111-118 correspond to the intervening spacer peptide GGGSGGGG (Linker 1) (SEQ ID NO:33), residues 119-240 correspond to the amino acid sequence of the VH Domain of DR5 mAb 4 (SEQ ID NO:66), residues 241-245 correspond to an ASTKG linker (SEQ ID NO:47), and residues 246-273 correspond to a cysteine-containing K-coil Domain (SEQ ID NO:42).

U. Reference gpA33×CD3 mAb 2 Diabody

To further exemplify the bi-specific Tri-Specific Binding Molecules of the present invention, a diabody composed of two polypeptide chains was constructed using the VL and VH domains of gpA33 mAb 1 and CD3 mAb 2. The amino acid sequence of the first polypeptide chain of the diabody had the sequence (SEQ ID NO:316) (CDR residues are shown underlined):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSA

STKGEVAACE KEVAALEKEV AALEKEVAAL EK
```

In SEQ ID NO:316, amino acid residues 1-106 correspond to the VL Domain of gpA33 mAb 1 (SEQ ID NO:181), residues 107-114 correspond to the intervening spacer peptide GGGSGGGG (Linker 1) (SEQ ID NO:33), residues 115-239 correspond to the amino acid sequence of the VH Domain of CD3 mAb 2 having the D65G substitution (SEQ ID NO:112), residues 240-244 correspond to an ASTKG linker (SEQ ID NO:47), and residues 245-272 correspond to a cysteine-containing E-coil Domain (SEQ ID NO:41).

The amino acid sequence of the second polypeptide chain of the diabody had the sequence (SEQ ID NO:317) (CDR residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTGS WMNWVRQAPG

QGLEWIGRIY PGDGETNYNG KFKDRVTITA DKSTSTAYME

LSSLRSEDTA VYYCARIYGN NVYFDVWGQG TTVTVSSAST

KGKVAACKEK VAALKEKVAA LKEKVAALKE
```

In SEQ ID NO:317, amino acid residues 1-110 correspond to the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of gpA33 mAb 1 (SEQ ID NO:186), residues 238-242 correspond to an ASTKG linker (SEQ ID NO:47), and residues 243-270 correspond to a cysteine-containing K-coil Domain (SEQ ID NO:42).

V. Reference Anti-Fluorescein Antibody

The anti-fluorescein antibody 4-4-20 (Gruber, M. et al. (1994) "Efficient Tumor Cell Lysis Mediated By A Bi-specific Single Chain Antibody Expressed In *Escherichia coli*," J. Immunol. 152(11):5368-5374; Bedzyk, W. D. et al. (1989) "Comparison Of Variable Region Primary Structures Within An Anti-Fluorescein Idiotype Family," J. Biol. Chem. 264(3): 1565-1569) was used in control diabodies. The amino acid sequences of the variable light and variable heavy Domains of anti-fluorescein antibody 4-4-20 are as follows:

Amino Acid Sequence Of The Variable Light Chain Domain Of Anti-Fluorescein Antibody 4-4-20 (SEQ ID NO:138) (CDR residues are underlined):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGIKLE IK
```

Amino Acid Sequence Of The Variable Heavy Chain Domain Of Anti-Fluorescein Antibody 4-4-20 (SEQ ID NO:139) (CDR residues are underlined):

```
EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSS
```

V. Methods of Production

The Tri-Specific Binding Molecules of the present invention can be created from the polynucleotides and/or sequences of antibodies that are immunospecific for DR5, a desired Cancer Antigen, and a desired Effector Cell by methods known in the art, for example, synthetically or recombinantly. One method of producing such peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well-known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "General Method For The Rapid Solid-Phase Synthesis Of Large Numbers Of Peptides: Specificity Of Antigen Antibody Interaction At The Level Of Individual Amino Acids," Proc. Natl. Acad. Sci. (U.S.A.) 82(15):5131-5135; Ganesan, A. (2006) "Solid-Phase Synthesis In The Twenty-First Century," Mini Rev. Med. Chem. 6(1):3-10).

In yet another alternative, suitable antibodies having one or more of the CDRs of a desired anti-DR5 antibody, anti-Cancer Antigen antibody or anti-Effector Cell antibody may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and HUMAB-MOUSE® and TC MOUSE™ (both from Medarex, Inc., Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "Production Of Antibodies And Antibody Fragments In Plants," Vaccine 19:2756; Lonberg, N. et al. (1995) "Human Antibodies From Transgenic Mice," Int. Rev. Immunol 13:65-93; and Pollock et al. (1999) "Transgenic Milk As A Method For The Production Of Recombinant Antibodies," J. Immunol Methods 231:147-157). Suitable methods for making derivatives of antibodies, e.g., humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "Making Antibodies By Phage Display Technology," Annu. Rev. Immunol. 12.433-455).

The antibodies or protein of interest may be subjected to sequencing by Edman degradation, which is well-known to those of skill in the art. The peptide information generated from mass spectrometry or Edman degradation can be used to design probes or primers that are used to clone the protein of interest.

An alternative method of cloning the protein of interest is by "panning" using purified DR5, and/or a desired Cancer Antigen, and/or a molecule expressed on the surface of a desired Effector Cell (or portions of any such molecules), for cells expressing an antibody or protein of interest that possesses one or more CDRs so as to be capable of binding to DR5, or such desired Cancer Antigen or Effector Cell molecule. The "panning" procedure may be conducted by obtaining a cDNA library from tissues or cells that express DR5, overexpressing the cDNAs in a second cell type, and screening the transfected cells of the second cell type for a specific binding to DR5 in the presence or absence of a known antibody that is capable of binding to such molecule (e.g., DR5 mAb 1 or DR5 mAb 2 in the case of panning for new anti-DR5 antibodies, etc.). Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854).

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to DR5 is effected by an immunoassay or FACS. A cell overexpressing the antibody or protein of interest can be identified.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-DR5 polypeptide could be produced by an automated polypeptide synthesizer employing the solid phase method.

The invention includes modifications to any such antibodies (or to any of their polypeptide fragments that bind to DR5, the Cancer Antigen or the effector cell, as the case may be) and the agonists, antagonists, and modulators of such molecules, including functionally equivalent antibodies and fusion polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the polypeptides of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a light chain variable region and a heavy chain variable region of an antibody produced from a publicly-deposited hybridoma. For purposes of this invention, an antibody fusion protein contains one or more polypeptide domains that specifically bind to DR5, a Cancer Antigen, or an effector cell (as the case may be) and another amino acid sequence to which it is not attached in the native molecule, for example, a heterologous sequence or a homologous sequence from another region.

VI. Uses of the Trispecific Binding Molecules of the Present Invention

The Tri-Specific Binding Molecules of the present invention provide a general therapy for cancer. The cancers that may be treated by such molecules include cancers characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer. The Tri-Specific Binding Molecules of the present invention may be used in the treatment of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer.

The Tri-Specific Binding Molecules of the present invention augment the cancer therapy provided by an antibody directed to a Cancer Antigen that is characteristic of cells of a target tumor by being additionally able to bind to DR5 molecules arrayed on the surface of such tumor cells. The utility of the invention is particularly seen in circumstances in which the density of the Cancer Antigen is low, or when the binding kinetics of the anti-Cancer Antigen antibody is suboptimal (or insufficient) to promote a clinically sufficient therapeutic response. In such cases, the ability of the molecules of the present invention to bind both the Cancer Antigen and DR5 of the tumor cells provides enhanced binding (via avidity) that is sufficient to promote a clinically sufficient therapeutic response. Additionally, by also possessing a Binding Domain capable of binding to a molecule on the surface of an immune system effector cell, the Tri-Specific Binding Molecules of the present invention permit the co-localization of such immune system cells to the tumor cells, thereby promoting a cytotoxic response against the tumor cells via redirected killing.

As shown in Table 2, Tri-Specific Binding Molecules of the present invention that possess particular combinations of Cancer Antigen-Binding Domains have preferred utility in the treatment of specific cancers.

TABLE 2

| Cancer Antigen-Binding Domains | | Preferred Utility |
|---|---|---|
| gpA33 | DR5 | Treatment Of Colorectal Cancer |
| gpA33 | EphA2 | |
| gpA33 | B7-H3 | |
| gpA33 | BST2 | |
| 5T4 | EphA2 | Broadly Applicable To Treatment Of Many Types Of Cancers |
| 5T4 | CEACAM5 | |
| 5T4 | B7-H3 | |
| 5T4 | DR5 | |
| B7-H3 | CEACAM5 | |
| B7-H3 | CEACAM6 | |
| B7-H3 | IL1Rα2 | Glioblastoma, Melanoma |
| EphA2 | IL1Rα2 | |
| EphA2 | DR5 | Broadly Applicable To Treatment Of Many Types Of Cancers |
| EphA2 | CEACAM5 | |
| EphA2 | CEACAM6 | |
| ITGB6 | B7-H3 | |
| ITGB6 | DR5 | |
| ITGB6 | BST2 | |

TABLE 2-continued

| Cancer Antigen-Binding Domains | | Preferred Utility |
|---|---|---|
| BST2 | CEACAM5 | |
| BST2 | EGFR | |

In addition to their utility in therapy, the Tri-Specific Binding Molecules of the present invention may be detectably labeled and used in the diagnosis of cancer or in the imaging of tumors and tumor cells.

VII. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the Tri-Specific Binding Molecules of the present invention, or a combination of such agents and a pharmaceutically acceptable carrier. Preferably, compositions of the invention comprise a prophylactically or therapeutically effective amount of the Tri-Specific Binding Molecules of the present invention and a pharmaceutically acceptable carrier. The invention particularly encompasses such pharmaceutical compositions in which the Tri-Specific Binding Molecule has a DR5-Binding Domain of:
(1) a DR5 mAb 1 antibody;
(2) a DR5 mAb 2 antibody;
(3) a DR5 mAb 3 antibody;
(4) a DR5 mAb 4 antibody;
(5) a DR5 mAb 5 antibody;
(6) a DR5 mAb 6 antibody;
(7) a DR5 mAb 7 antibody; or
(8) a DR5 mAb 8 antibody
(or a humanized derivative of any such antibodies).

The invention further particularly encompasses such pharmaceutical compositions in which the Tri-Specific Binding Molecule has a Cancer Antigen-Binding Domain that:
(A) binds to an epitope of EphA2, especially wherein the Tri-Specific Binding Molecule has a Cancer Antigen-Binding Domain of EphA2 mAb 1, EphA2 mAb 2 or EphA2 mAb 3, or a humanized or chimeric variant thereof; or
(B) binds to an epitope of gpA33, especially wherein the Tri-Specific Binding Molecule has a Cancer Antigen-Binding Domain of gpA33 mAb 1, or a humanized or chimeric variant thereof or
(C) binds to an epitope of Her2, especially wherein the Tri-Specific Binding Molecule has a Cancer Antigen-Binding Domain of Her2 mAb 1 or trastuzumab, or a humanized or chimeric variant thereof or
(D) binds to an epitope of B7-H3, especially wherein the Tri-Specific Binding Molecule has a Cancer Antigen-Binding Domain of B7-H3 mAb 1, B7-H3 mAb 2, or B7-H3 mAb 3, or a humanized or chimeric variant thereof.

The invention further particularly encompasses such pharmaceutical compositions in which the Tri-Specific Binding Molecule has an Effector Cell-Binding Domain that binds to CD2, CD3, CD17, CD20, CD22, CD32B, CD64, BCR/CD79, the T cell Receptor or the NKG2D Receptor. The invention further particularly encompasses such pharmaceutical compositions in which the Tri-Specific Binding Molecule has an Effector Cell-Binding Domain of antibody: Lo-CD2a, CD3 mAb 2, OKT3, 3G8, A9, HD37, rituximab, epratuzumab, CD32B mAb 1, CD64 mAb 1, CD79 mAb 1, BMA 031, KYK-1.0, or KYK-2.0.

The invention specifically contemplates Tri-Specific Binding Molecules, pharmaceutical compositions that comprise such binding molecule and uses of such Tri-Specific Binding Molecules, in which:
(1) the DR5 Binding Domain is a DR5 binding domain of any anti-DR5 antibody;
(2) the Cancer Binding Domain is any of the Cancer Antigens disclosed herein;
and
(3) the Effector Cell-Binding Domains binds to any of CD2, CD3, CD17, CD20, CD22, CD32B, CD64, BCR/CD79, the T cell Receptor or the NKG2D Receptor.

The invention further specifically contemplates Tri-Specific Binding Molecules, pharmaceutical compositions that comprise such binding molecule and uses of such Tri-Specific Binding Molecules, in which:
(1) the DR5 Binding Domain is a DR5 binding domain of any anti-DR5 antibody;
(2) the Cancer Binding Domain is any of: EphA1, gpA33, Her2, or B7-H3;
and
(3) the Effector Cell-Binding Domains binds to any of CD2, CD3, CD17, CD20, CD22, CD32B, CD64, BCR/CD79, the T cell Receptor or the NKG2D Receptor.

The invention particularly contemplates each of the Tri-Specific Binding Molecules, as well as pharmaceutical compositions that comprise such binding molecule and uses of such Tri-Specific Binding Molecules, in which:
(1) the DR5 Binding Domain is a DR5 binding domain of any of: a DR5 mAb 1 antibody, a DR5 mAb 2 antibody, a DR5 mAb 3 antibody, a DR5 mAb 4 antibody, a DR5 mAb 5 antibody, a DR5 mAb 6 antibody, a DR5 mAb 7 antibody, or a DR5 mAb 8 antibody;
(2) the Cancer Antigen-Binding Domain is a binding domain of any of: EphA2 mAb 1, EphA2 mAb 2, EphA2 mAb 3, gpA33 mAb 1, Her2 mAb 1, trastuzumab, B7-H3 mAb 1, B7-H3 mAb 2, or B7-H3 mAb 3;
and
(3) the Effector Cell-Binding Domain is a binding domain of any of: Lo-CD2a, CD3 mAb 2, OKT3, 3G8, A9, HD37, rituximab, epratuzumab, CD32B mAb 1, CD64 mAb 1, CD79 mAb 1, BMA 031, KYK-1.0, or KYK-2.0.

As 8 anti-DR5 Binding Domain antibodies, 9 anti-Cancer Antigen-Binding Domain antibodies and 14 anti-Effector Cell-Binding Domain antibodies are listed, such specific contemplation encompasses all (8×9×14=) 1,008 combinations of such binding domains.

The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with a Tri-Specific Binding Molecule of the present invention (and more preferably, any of the specific binding molecules discussed or exemplified above). Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the Tri-Specific Binding Molecules of the present invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

VIII. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the Tri-Specific Binding Molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the Tri-Specific Binding Molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the Tri-Specific Binding Molecules of the present invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized Tri-Specific Binding Molecules of the present invention should be stored at between 2 and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such Tri-Specific Binding Molecules when provided in liquid form are supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For the Tri-Specific Binding Molecules monovalent diabodies encompassed by the invention, the dosage administered to a patient is preferably determined based upon the body weight (kg) of the recipient subject. The dosage administered is typically from at least about 0.3 ng/kg per day to about 0.9 ng/kg per day, from at least about 1 ng/kg per day to about 3 ng/kg per day, from at least about 3 ng/kg per day to about 9 ng/kg per day, from at least about 10 ng/kg per day to about 30 ng/kg per day, from at least about 30 ng/kg per day to about 90 ng/kg per day, from at least about 100 ng/kg per day to about 300 ng/kg per day, from at least about 200 ng/kg per day to about 600 ng/kg per day, from at least about 300 ng/kg per day to about 900 ng/kg per day, from at least about 400 ng/kg per day to about 800 ng/kg per day, from at least about 500 ng/kg per day to about 1000 ng/kg per day, from at least about 600 ng/kg per day to about 1000 ng/kg per day, from at least about 700 ng/kg per day to about 1000 ng/kg per day, from at least about 800 ng/kg per day to about 1000 ng/kg per day, from at least about 900 ng/kg per day to about 1000 ng/kg per day, or at least about 1,000 ng/kg per day.

In another embodiment, the patient is administered a treatment regimen comprising one or more doses of such prophylactically or therapeutically effective amount of a Tri-Specific Binding Molecule of the present invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the Tri-Specific Binding Molecules of the present invention (for example, administering a dose on day 1, day 2, day 3 and day 4 of a given week and not administering doses of the prophylactically or therapeutically effective amount of the Tri-Specific Binding Molecule Especially encompassed is the administration of such Tri-Specific Binding Molecules that comprise any of the specific combinations of DR5 Binding Domains, Cancer Antigen-Binding Domains and Effector Cell-Binding Domains discussed above, on day 5, day 6 and day 7 of the same week). Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the Tri-Specific Binding Molecule is achieved. Table 3 provides 5 examples of different dosing regimens described above for a typical course of treatment.

TABLE 3

| Regimen | Day | Diabody Dosage (ng diabody per kg subject weight per day) | | | | |
|---|---|---|---|---|---|---|
| 1 | 1, 2, 3, 4 | 100 | 100 | 100 | 100 | 100 |
|   | 5, 6, 7 | none | none | none | none | none |
| 2 | 1, 2, 3, 4 | 300 | 500 | 700 | 900 | 1,000 |
|   | 5, 6, 7 | none | none | none | none | none |
| 3 | 1, 2, 3, 4 | 300 | 500 | 700 | 900 | 1,000 |
|   | 5, 6, 7 | none | none | none | none | none |
| 4 | 1, 2, 3, 4 | 300 | 500 | 700 | 900 | 1,000 |
|   | 5, 6, 7 | none | none | none | none | none |

The dosage and frequency of administration of a Tri-Specific Binding Molecule of the present invention may be reduced or altered by enhancing uptake and tissue penetration of the molecule by modifications such as, for example, lipidation.

The dosage of a Tri-Specific Binding Molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327).

The compositions of the invention can be delivered in a controlled-release or sustained-release system. Any technique known to one of skill in the art can be used to produce sustained-release formulations comprising one or more of the Tri-Specific Binding Molecule(s) of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228: 190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion Induced Memory Deficits*," J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained-release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled-release systems are discussed in the review by Langer (1990, "*New Methods Of Drug Delivery*," Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

Where the composition of the invention is a nucleic acid encoding a Tri-Specific Binding Molecule of the present invention, the nucleic acid can be administered in vivo to promote expression of its encoded Tri-Specific Binding Molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a Tri-Specific Binding Molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

EXAMPLES

Having now generally described the invention, the same will be more readily understood through reference to the following examples, which are provided by way of illustration and are not intended to be limiting of the present invention unless specified. It will be apparent to those skilled in the art that many modifications, both to materials and methods, can be practiced without departing from the scope of the present disclosure.

W. Example 1: Characterization of Anti-Human DR5 Monoclonal Antibodies DR5 mAb 1 and DR5 mAb 2

Two monoclonal antibodies were isolated as being capable of immunospecifically binding to human DR5, and accorded the designations "DR5 mAb 1" and "DR5 mAb 2". As discussed above, the CDRs of these antibodies were found to differ. In order to determine whether the antibodies bound to different DR5 epitopes, a human DR5-Fc fusion protein was prepared and was coated to an immobilized surface. DR5 mAb 1 (1 μg/mL) was biotinylated and incubated with either a control IgG or with DR5 mAb 2 (10 μg/mL), and the ability of the IgG or DR5 mAb 2 antibody to compete for binding (to human DR5-Fc fusion protein) with DR5 mAb 1 was assessed by measuring the amount of immobilized biotinylated antibody. Additionally, the ability of the IgG or DR5 mAb 1 antibody to compete for binding with biotinylated DR5 mAb 2 was assessed. The results of this experiment are shown in Table 4.

TABLE 4

| 1 μg/mL DR5-Fc Fusion coat | | 10 μg/mL Competitor mAb | | |
|---|---|---|---|---|
| | | mIgG | DR5 mAb 1 | DR5 mAb 2 |
| 1 μg/mL biotinylated DR5 mAb | DR5 mAb 1 | 2.162 | self | 0.826 |
| | DR5 mAb 2 | 2.102 | 2.377 | self |

The results of this experiment indicate that the biotinylated antibody was capable of binding to the DR5 protein even in the presence of excess amounts of the non-biotinylated antibody. Thus, the results show that DR5 mAb 1 and DR5 mAb 2 bind to different epitopes of DR5.

In order to further characterize the DR5 mAb 1 and DR mAb 2 antibodies, their ability to block binding between DR5 and the TRAIL ligand as assessed. Thus, biotinylated DR5 mAb 1, biotinylated DR5 mAb 2 or biotinylated DR5-Fc fusion (each at 2 μg/mL) were separately incubated with immobilized DR5-Fc fusion (1 μg/mL) in the presence of either buffer or histidine tagged TRAIL (20 μg/mL). The amount of immobilized biotinylated antibody was assessed. The results of this experiment are shown in Table 5.

TABLE 5

| 2 μg/mL Biotinylated DR5 mAb | 1 μg/mL DR5-Fc fusion coat | | 1 μg/mL TRAIL-His coat |
|---|---|---|---|
| | 20 μg/mL TRAIL-His | Buffer | |
| DR5 mAb 1 | 1.939 | 2.118 | 0.007 |
| DR5 mAb 2 | 2.052 | 2.052 | 0.008 |
| DR5-Fc fusion | — | — | 0.288 |

The results show that the amount of DR5 mAb 1 or DR5 mAb 2 bound to the immobilized DR5-Fc was not affected by the presence of the histidine tagged TRAIL, thus indicating that neither DR5 mAb 1 nor DR5 mAb 2 block the TRAIL ligand binding site of DR5. Additionally, neither antibody was capable of binding to the histidine tagged TRAIL ligand.

X. Example 2: Species Specificity of Anti-Human DR5 Monoclonal Antibodies DR5 mAb 1 and DR5 mAb 2

Figure 6:
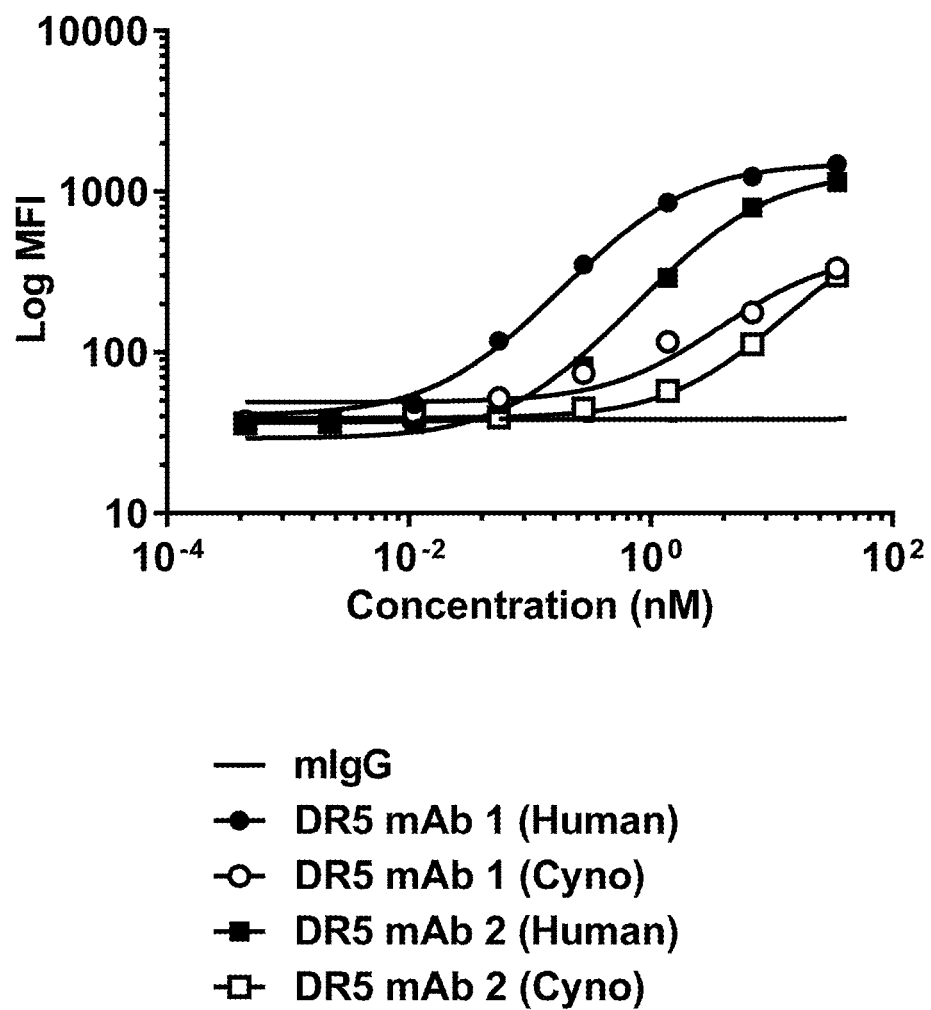
FIG. 6 shows the ability of anti-human DR5 monoclonal antibodies DR5 mAb 1 and DR5 mAb 2 to bind to human DR5 and to the DR5 of cynomolgus monkey.

In order to assess the species specificity of anti-human DR5 monoclonal antibodies DR5 mAb 1 and DR5 mAb 2, the ability of the antibodies to bind to human DR5 was compared with their ability to bind cynomolgus monkey (*Macaca fascicularis*) DR5. The results of this experiment are shown in FIG. 6. The results show that both antibodies are capable of binding to cynomolgus monkey DR5, but that they each exhibit higher binding affinity for human DR5.

Figure 7:
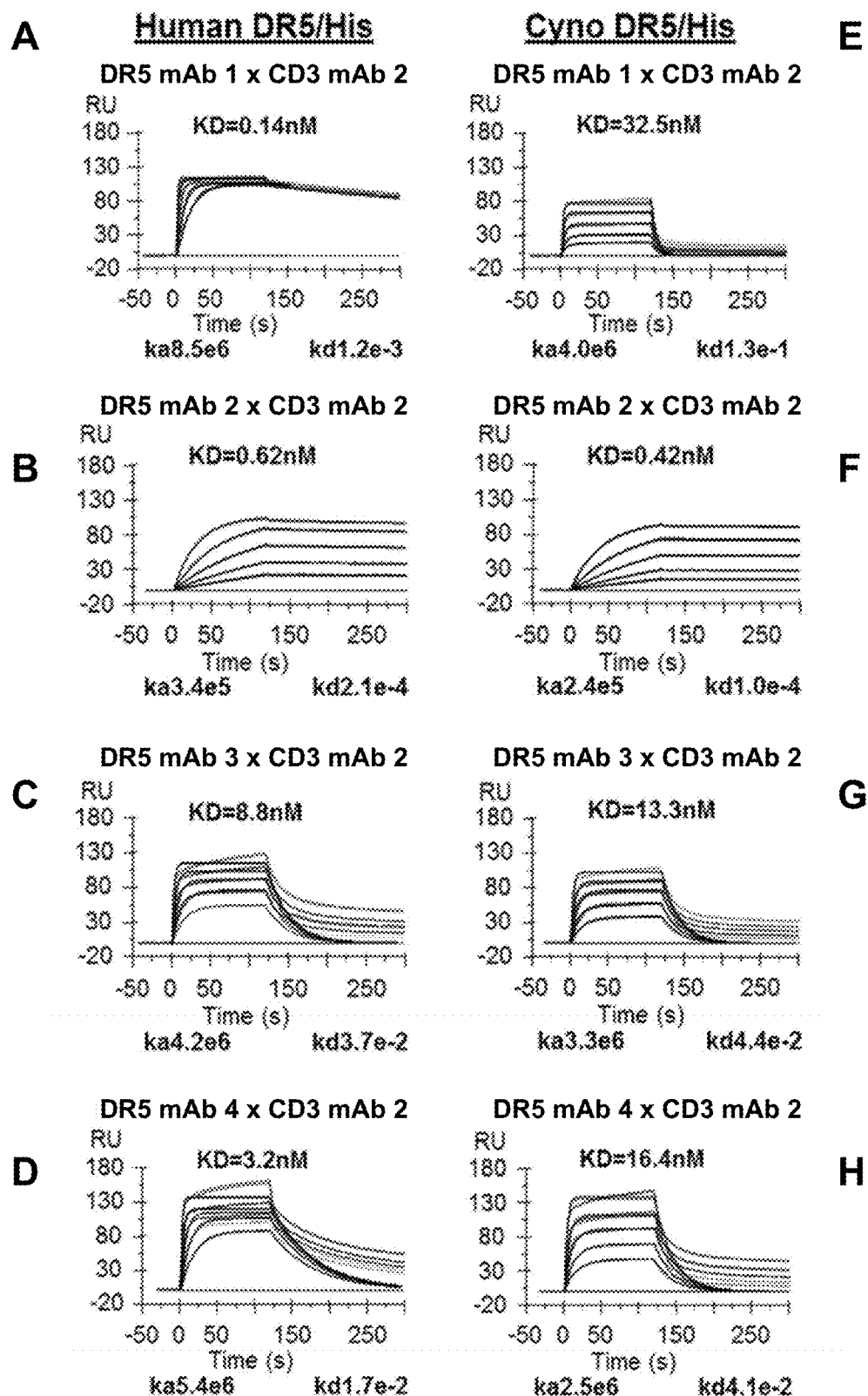
FIG. 7, Panels A-H, show the kinetics of binding of DR5 mAb 1 (Panels A and E), DR5 mAb 2 (Panels B and F), DR5 mAb 3 (Panels C and G) and DR5 mAb 4 (Panels D and H) for human DR 5 (Panels A-D) and for cynomolgus monkey DR5 (Panels E-H).

The kinetics of binding was investigated using Biacore Analysis, as shown in FIG. 7. Bi-specific DR5×CD3 diabodies were incubated with His-tagged DR5 and the kinetics of binding was determined via Biacore analysis. The diabodies employed were DR5 mAb 1×CD3 mAb 2 (FIG. 7, Panels A and E), DR5 mAb 2×CD3 mAb 2 (FIG. 7, Panels B and F), DR5 mAb 3×CD3 mAb 2 (FIG. 7, Panels C and G), and DR5 mAb 4×CD3 mAb 2 (FIG. 7, Panels D and H). FIG. 7, Panels A-D show the results for human DR5. FIG. 7, Panels E-H show the results for cynomolgus monkey DR5. The calculated ka, kd and KD are presented in Table 6.

TABLE 6

| Anti-DR Antibody | Human | | | Cynomolgus Monkey | | |
|---|---|---|---|---|---|---|
| | ka | kd | KD (nM) | ka | kd | KD (nM) |
| DR mAb 1 | $8.5 \times 10^6$ | $1.2 \times 10^{-3}$ | 0.14 | $4.0 \times 10^6$ | $1.3 \times 10^{-1}$ | 32.5 |
| DR mAb 2 | $3.4 \times 10^5$ | $2.1 \times 10^{-4}$ | 0.62 | $2.4 \times 10^5$ | $1.0 \times 10^{-4}$ | 0.42 |
| DR mAb 3 | $4.2 \times 10^6$ | $3.7 \times 10^{-2}$ | 8.8 | $3.3 \times 10^6$ | $4.4 \times 10^{-2}$ | 13.3 |
| DR mAb 4 | $5.4 \times 10^6$ | $1.7 \times 10^{-2}$ | 3.2 | $2.5 \times 10^6$ | $4.1 \times 10^{-2}$ | 16.4 |

The results demonstrate that DR5 mAb 1 and DR5 mAb 2 exhibit altered kinetics of binding relative to reference antibodies DR5 mAb 3 and DR5 mAb 4.

Y. Example 3: Unexpected Superiority of DR5 mAb 1 and DR5 mAb 2

The ability of DR5-binding molecules DR5 mAb 1 and DR5 mAb 2 of the present invention to mediate cytotoxicity was compared with that of the reference anti-DR5 antibodies: DR5 mAb 3 and DR5 mAb 4. In order to make such a comparison, a bi-specific DR5×CD3 diabody containing the VL and VH Domains of these antibodies and the VL and VH Domains of CD3 mAb 2 were prepared. The prepared diabodies were: DR5 mAb 1×CD3 mAb 2; DR5 mAb 2×CD3 mAb 2; DR5 mAb 3×CD3 mAb 2; and DR5 mAb 4×CD3 mAb 2.

The employed control diabody contained the VL and VH domains of anti-fluorescein antibody 4-4-20 (respectively, SEQ ID NOs:138 and 139) and the VL and VH domains of CD3 mAb 2 (respectively, SEQ ID NOs:102 and 108), and was designated as the anti-fluorescein×anti-CD3 control diabody "4-4-20×CD3 mAb 2." The diabody was composed of two polypeptide chains. The first polypeptide chain of the diabody had the amino acid sequence (SEQ ID NO:300) (CDRs are shown in underline):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

EVQLVESGGG LVQPGGSLRL SCAASGFTFN TYAMNWVRQA

PGKGLEWVAR IRSKYNNYAT YYADSVKDRF TISRDDSKNS

LYLQMNSLKT EDTAVYYCVR HGNFGNSYVS WFAYWGQGTL

VTVSSGGCGG GEVAALEKEV AALEKEVAAL EKEVAALEK
```

In SEQ ID NO:300, amino acid residues 1-112 correspond to the VL Domain of anti-fluorescein antibody 4-4-20 (SEQ ID NO:138), residues 113-120 correspond to the intervening spacer peptide GGGSGGGG (Linker 1) (SEQ ID NO:33), residues 121-245 correspond to the VH Domain of CD3 mAb 2 (SEQ ID NO:108), residues 246-251 are a cysteine-containing spacer peptide (GGCGGG) (SEQ ID NO:34), and residues 252-280 correspond to an E-coil Domain (SEQ ID NO:39).

The second polypeptide chain of the diabody had the amino acid sequence (SEQ ID NO:301) (CDRs are shown in underline):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

KLDETGGGLV QPGRPMKLSC VASGFTFSDY WMNWVRQSPE

KGLEWVAQIR NKPYNYETYY SDSVKGRFTI SRDDSKSSVY

LQMNNLRVED MGIYYCTGSY YGMDYWGQGT SVTVSSGGCG

GGKVAALKEK VAALKEKVAA LKEKVAALKE
```

In SEQ ID NO:301, amino acid residues 1-110 correspond to the VL Domain of CD3 mAb 2 (SEQ ID NO:104), residues 111-118 correspond to the intervening spacer peptide GGGSGGGG (Linker 1) (SEQ ID NO:33), residues 119-236 correspond to the VH Domain of anti-fluorescein antibody 4-4-20 (SEQ ID NO:139), residues 237-242 are a cysteine-containing spacer peptide (GGCGGG) (SEQ ID NO:34), and residues 243-270 correspond to a K-coil Domain (SEQ ID NO:40).

Target tumor cells were incubated with one of these diabodies or with the control diabody (4-4-20×CD3 mAb 2) in the presence of peripheral blood mononuclear cells (PBMC) and A549 adenocarcinomic human alveolar basal epithelial cells for 24 hours at an effector to target cell ratio of 20:1. The percentage cytotoxicity was determined by measuring the release of lactate dehydrogenase (LDH) into the media by damaged cells.

Figure 8:
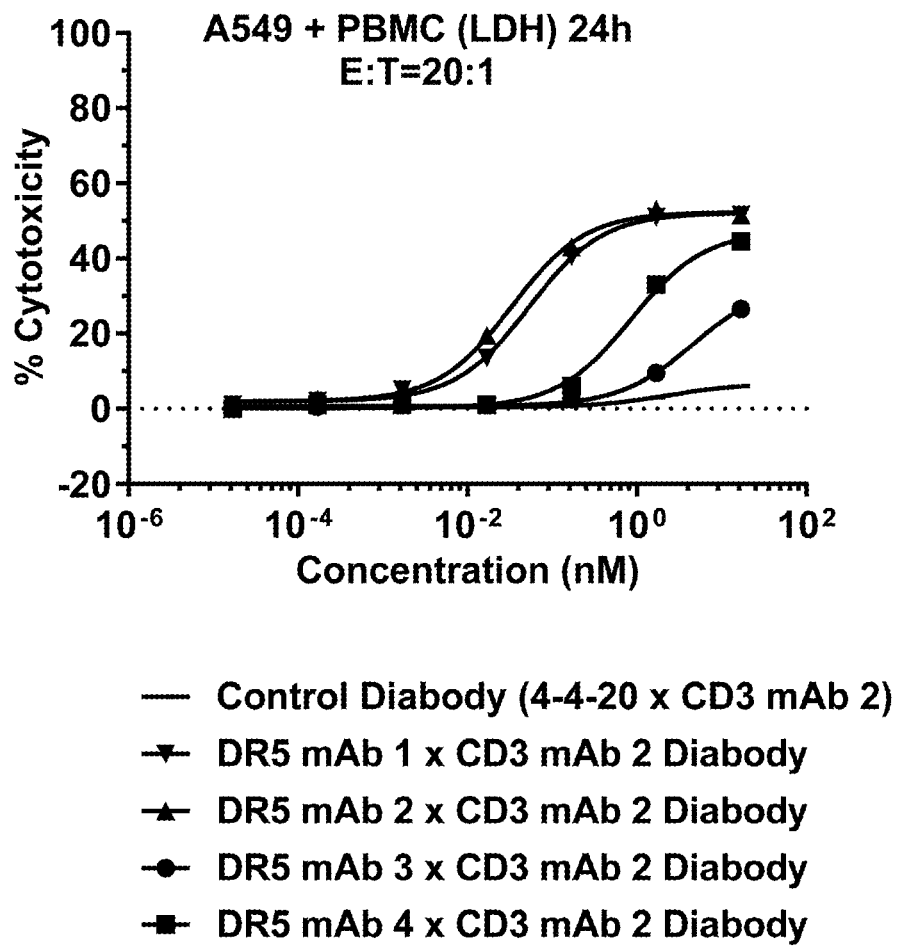
FIG. 8 shows the unexpected superiority of DR5 mAb 1 and DR5 mAb 2. Superiority was assessed by comparing the ability of DR5×CD3 diabodies having the VL and VH Domains of DR5 mAb 1, DR5 mAb 2, DR5 mAb 3, or DR5 mAb 4, to mediate the cytotoxicity of A549 adenocarcinomic human alveolar basal epithelial tumor cells.

The results of this investigation are shown in FIG. 8. Similar results were obtained using SKMES human lung cancer cells, DU145 human prostate cancer cells, A375 human malignant melanoma cells, SKBR3 human HER2-overexpressing breast carcinoma cells, and JIMT human breast carcinoma cells. The results indicate that the VL and VH domains of DR5 mAb 1 and DR5 mAb 2 are significantly and unexpectedly more potent in inducing cytotoxicity than those of the reference DR5 mAbs.

Figure 9A:
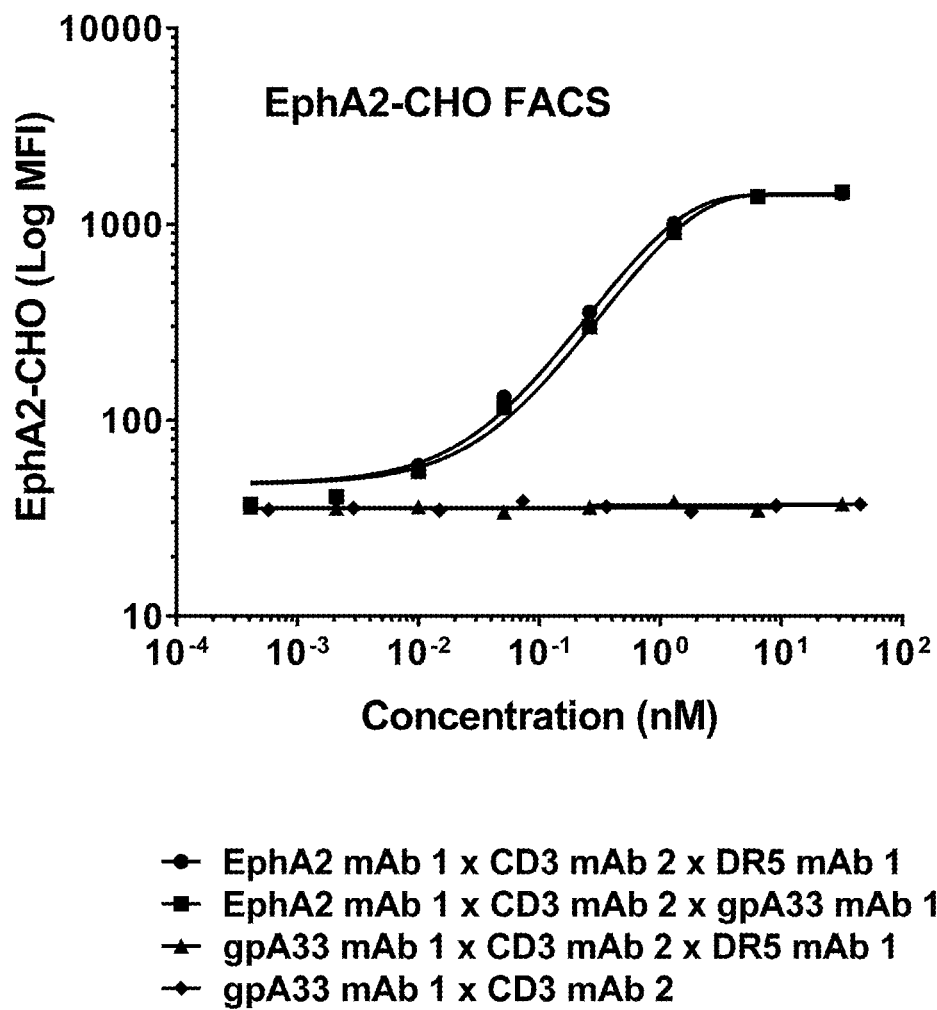
FIGS. 9A-9C demonstrate the synergistic enhancement in target cell binding that is attained when both of the two Cancer Antigen-Binding Domains of a Tri-Specific Binding Molecule of the present invention are able to bind to a target cell.
Figure 9B:
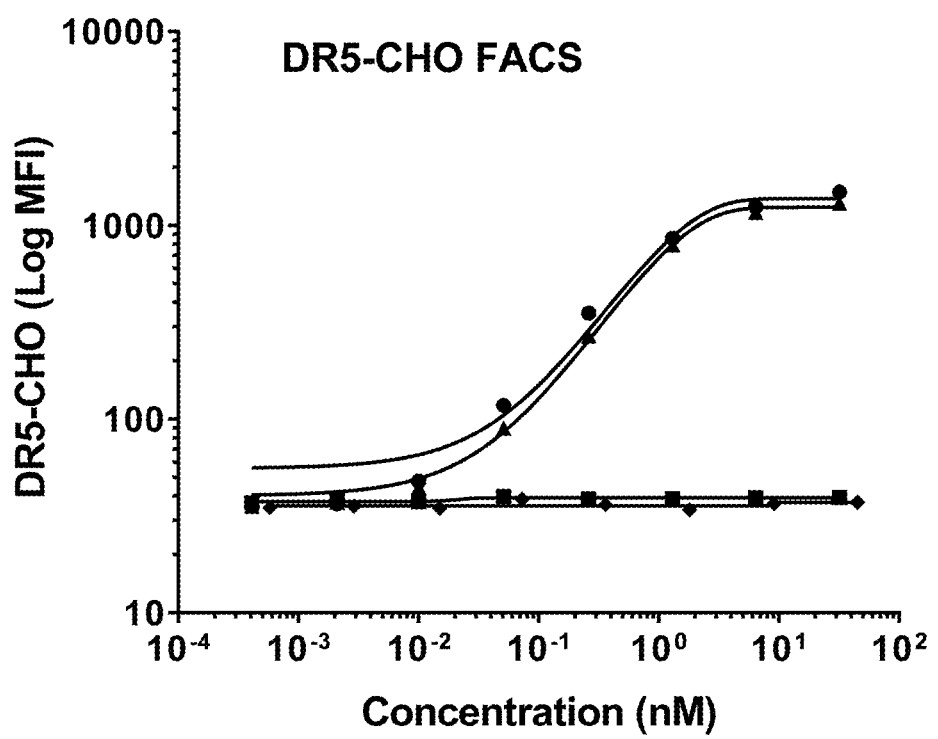
Figure 9C:
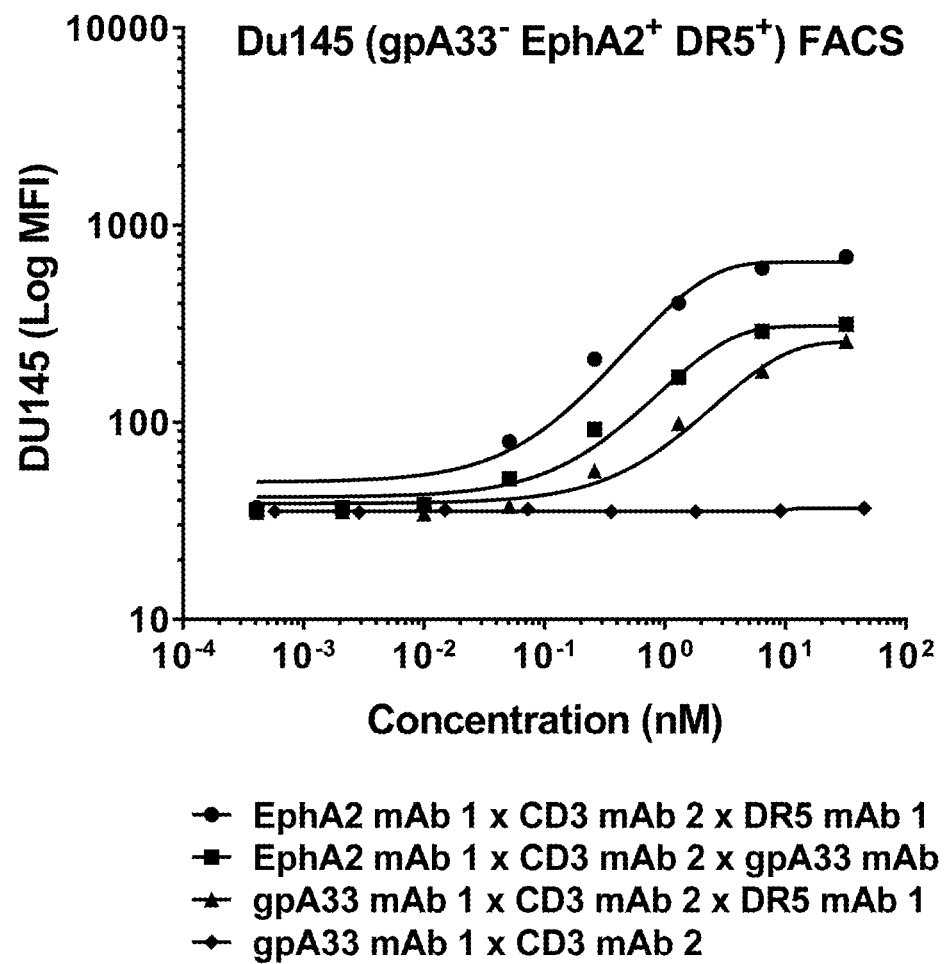

Z. Example 4: The Trispecific Binding Molecules Mediate Coordinated and Simultaneous Binding to Target Cells The ability of Tri-Specific Binding Molecules of the present invention to bind to target cells was investigated. The employed trispecific molecules were: EphA2 mAb 1×CD3 mAb 2×DR5 mAb 1; EphA2 mAb 1×CD3 mAb 2×gpA33 mAb 1; and gpA33 mAb 1×CD3 mAb 2×DR5 mAb 1. As shown in FIG. 9A, those Tri-Specific Binding Molecules that comprise an EphA2 Cancer Antigen-Binding Domain were found to be capable of binding to EphA2-expressing CHO target cells. As shown in FIG. 9B, those Tri-Specific Binding Molecules that comprise a DR5 Cancer Antigen-Binding Domain were found to be capable of binding to DR5-expressing CHO target cells. As shown in FIG. 9C, those Tri-Specific Binding Molecules that comprise an EphA2 Cancer Antigen-Binding or a DR5 Cancer Binding Domain were found to be capable of binding to DU145 cells. DU145 cells are a human prostate cell line that express both EphA2 and DR5, but not gpA33. The above-described reference gpA33 mAb 1×CD3 mAb 2 diabody was used as a control.

Significantly, the data show that when both of the two Cancer Antigen-Binding Domains of a Tri-Specific Binding Molecule of the present invention are able to bind to a target cell, such dual binding is associated with a synergistic (e.g., a 5-25 fold) enhancement in target binding.

AA. Example 5: The Trispecific Binding Molecules Mediate Cytotoxicity of Bound Target Cells The ability of Tri-Specific Binding Molecules of the present invention to mediate the cytotoxicity of bound target cells in the presence of cytotoxic lymphocytes was investigated. The employed trispecific molecules were: EphA2 mAb 1×CD3 mAb 2×DR5 mAb 1; EphA2 mAb 1×CD3 mAb 2×gpA33 mAb 1; and gpA33 mAb 1×CD3 mAb 2×DR5 mAb 1. The above-described reference gpA33 mAb 1×CD3 mAb 2 diabody and the 4-4-20×CD3 mAb 2 diabody were used as controls.

Figure 10A:
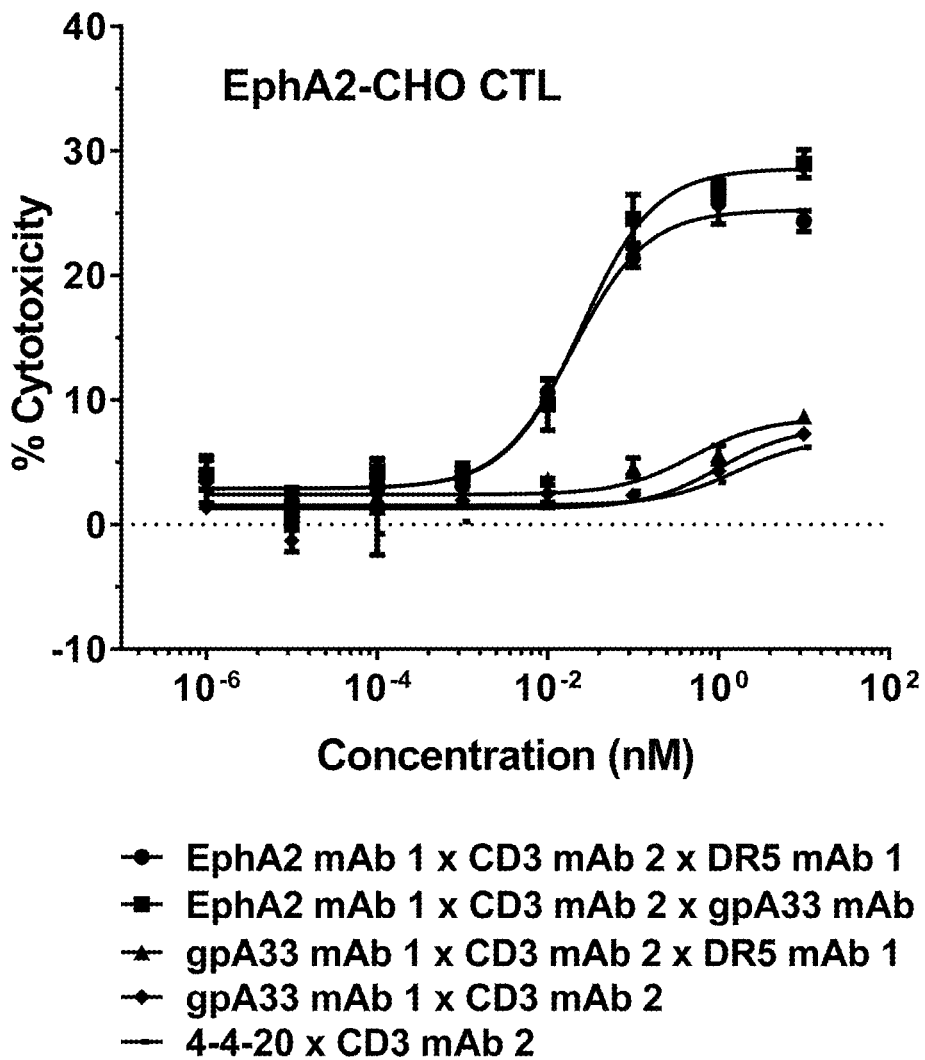
FIGS. 10A-10C demonstrate the synergistic enhancement in target cell cytotoxicity that is attained when both of the two Cancer Antigen-Binding Domains of a Tri-Specific Binding Molecule of the present invention are able to bind to a target cell.
Figure 10B:
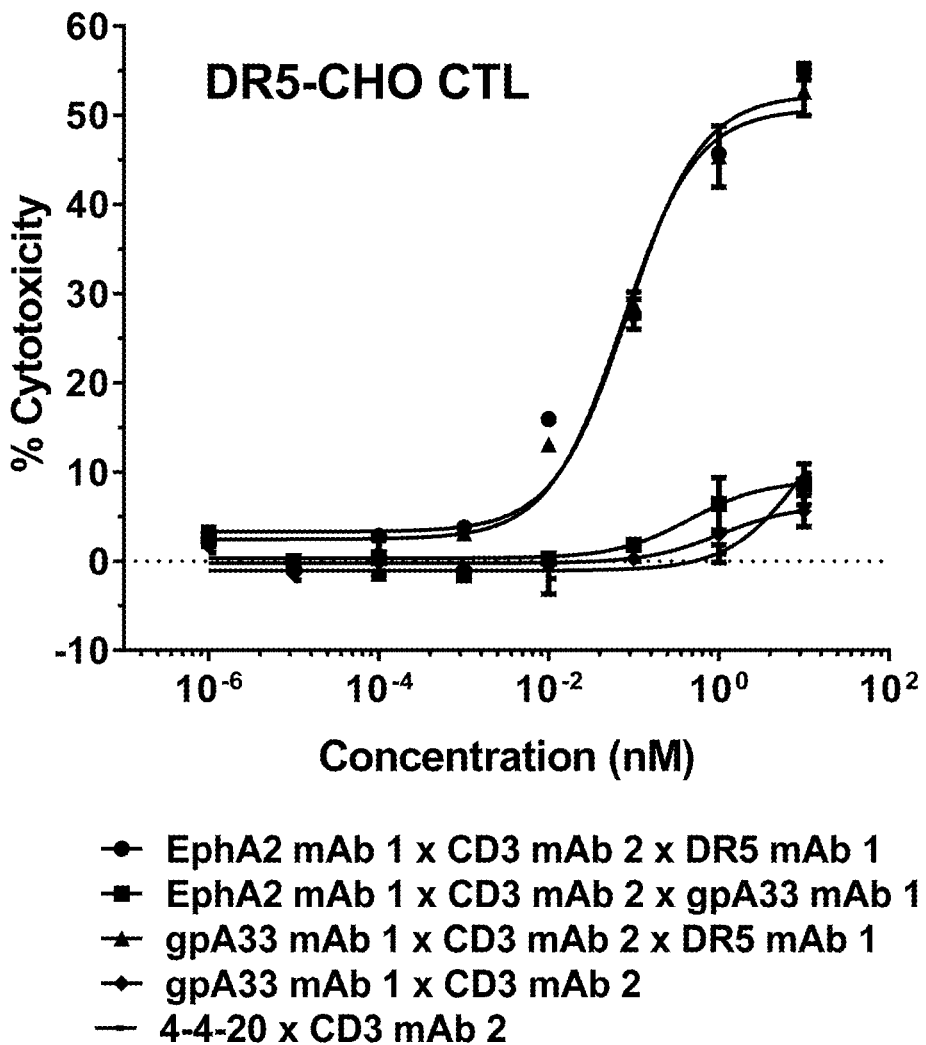

As shown in FIG. 10A, those Tri-Specific Binding Molecules that comprise an EphA2 Cancer Antigen-Binding Domain, and thus were able to bind to bind to EphA2-expressing CHO cells, were able to mediate the cytotoxicity of such cells in the presence of the cytotoxic lymphocytes. As shown in FIG. 10B, those Tri-Specific Binding Molecules that comprise a DR5 Cancer Antigen-Binding Domain, and thus were able to bind to bind to DR5-expressing CHO cells, were found to be capable of mediating cytotoxicity of DR5-expressing CHO target cells in the presence of the cytotoxic lymphocytes.

Figure 10C:
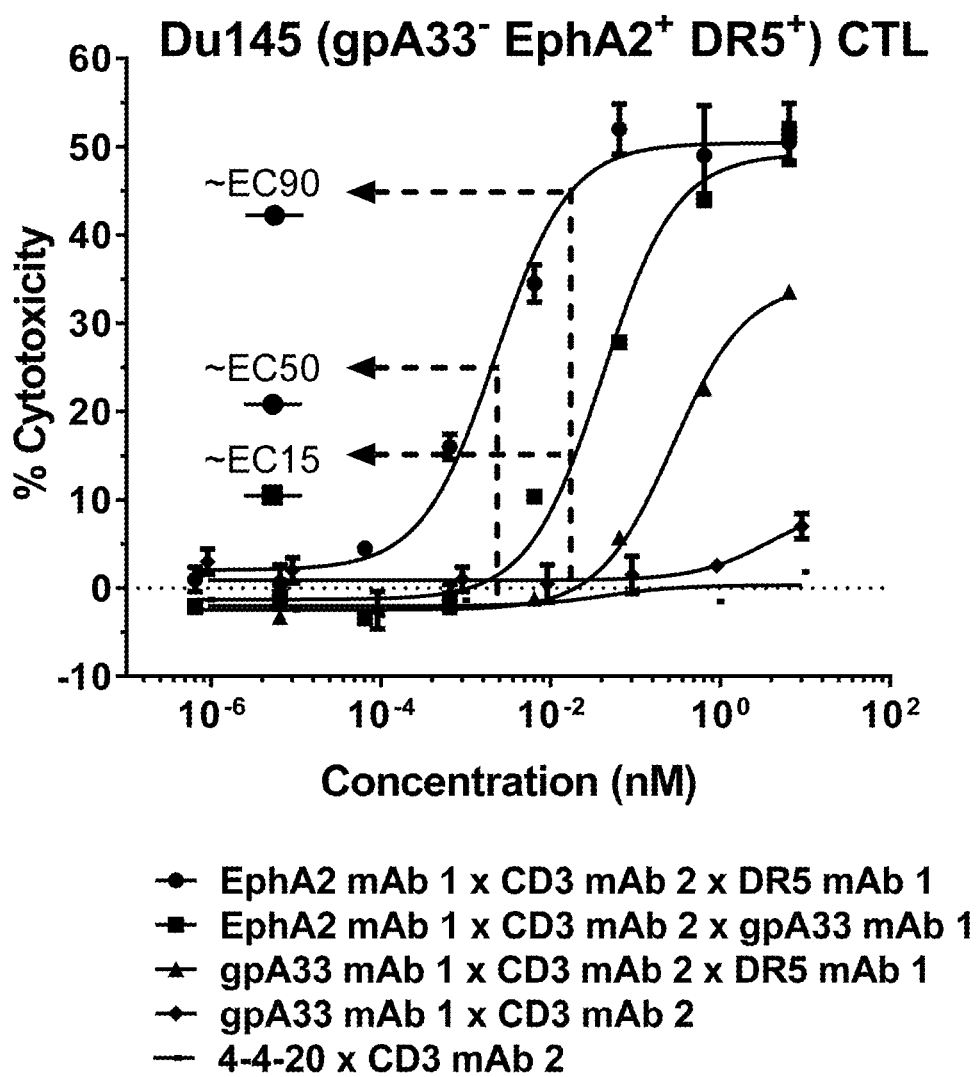

As shown in FIG. 10C, those Tri-Specific Binding Molecules that comprise an EphA2 Cancer Antigen-Binding or a DR5 Cancer Binding Domain, and thus are capable of binding to DU145 cells, were able to mediate the cytotoxicity of such cells in the presence of the cytotoxic lymphocytes. Significantly, the data show that when both of the two Cancer Antigen-Binding Domains of a Tri-Specific Binding Molecule of the present invention are able to bind to a target cell, such dual binding is associated with a synergistic enhancement in target binding. Thus, EphA2 mAb 1×CD3 mAb 2×DR5 mAb 1, which is capable of binding to both EphA2 and DR5, mediated substantially greater cytotoxicity than EphA2 mAb 1×CD3 mAb 2×gpA33 mAb 1 or gpA33 mAb 1×CD3 mAb 2×DR5 mAb 1, which were capable of binding to only EphA2 or DR5 molecules of the DU146 cells (since such cells lack gpA33).

In this regard, at approximately the EC50 of EphA2 mAb 1×CD3 mAb 2×DR5 mAb 1, no cytotoxic lymphocyte response is seen for either EphA2 mAb 1×CD3 mAb 2×gpA33 mAb 1 or gpA33 mAb 1×CD3 mAb 2×DR5 mAb 1. At approximately the EC90 of EphA2 mAb 1×CD3 mAb 2×DR5 mAb 1, EphA2 mAb 1×CD3 mAb 2×gpA33 mAb 1 shows only an EC15, and gpA33 mAb 1×CD3 mAb 2×DR5 mAb 1 shows no cytotoxic lymphocyte response at all.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

---

What is claimed is:

1. A multi-chain polypeptide-containing Tri-Specific Binding Molecule that immunospecifically binds to three different epitopes, comprising:
   (I) three different polypeptide chains covalently complexed together;
   (II) an Antigen-Binding Domain I that immunospecifically binds to an Epitope I present on a first antigen, an Antigen-Binding Domain II that immunospecifically binds to an Epitope II present on a second antigen, and an Antigen-Binding Domain III that immunospecifically binds to an Epitope III present on a third antigen; and
   (III) a Fc Domain; wherein:
   (A) one of Epitope I, Epitope II or Epitope III is an epitope of an Effector Cell Antigen, a second of Epitope I, Epitope II or Epitope III is an epitope of a first Cancer Antigen, and a third of Epitope I, Epitope II or Epitope III is an epitope of a second Cancer Antigen;
   (B) a first polypeptide chain comprises, in the N-terminus to C-terminus direction:
   ($VL_I$ Domain)-(Linker 1)-($VH_{II}$ Domain)-(Linker 2)-(Heterodimer-Promoting Domain)-(Linker 3)-(CH2-CH3 Domain); or
   (Cysteine-Containing Domain)-(CH2-CH3 Domain)-(Linker 4)-($VL_I$ Domain)-(Linker 1)-($VH_{II}$ Domain)-(Linker 2)-(Heterodimer-Promoting Domain);
   (C) a second polypeptide chain comprises, in the N-terminus to C-terminus direction:
   ($VL_{II}$ Domain)-(Linker 1)-($VH_I$ Domain)-(Linker 2)-(Heterodimer-Promoting Domain);
   (D) a third polypeptide chain comprises, in the N-terminus to C-terminus direction:
   ($VL_{III}$ Domain)-(Flexible Linker)-($VH_{III}$ Domain)-(Cysteine-Containing Domain)-(CH2-CH3 Domain); or
   (CL Domain)-($VL_{III}$ Domain)-(Flexible Linker)-($VH_{III}$ Domain)-(CH1 Domain)-(Cysteine-Containing Domain)-(CH2-CH3 Domain);
   (E) the $VL_I$ Domain is a Light Chain Variable Domain of an immunoglobulin that binds to Epitope I, the $VH_I$ Domain is a Heavy Chain Variable Domain of an immunoglobulin that binds to Epitope I, the $VL_{II}$ Domain is a Light Chain Variable Domain of an immunoglobulin that binds to Epitope II, the $VH_{II}$ Domain is a Heavy Chain Variable Domain of an immunoglobulin that binds to Epitope II, the $VL_{III}$ Domain is a Light Chain Variable Domain of an immunoglobulin that binds to Epitope III, and the $VH_{III}$ Domain is a Heavy Chain Variable Domain of an immunoglobulin that binds to Epitope III;
   (F) the $VL_I$ Domain and the $VH_I$ Domain associate to form the Antigen-Binding Domain I, the $VL_{II}$ Domain and the $VH_{II}$ Domain associate to form the Antigen-Binding Domain II, the $VL_{III}$ Domain and the $VH_{III}$ Domain associate to form the Antigen-Binding Domain III, and the CH2-CH3 Domain of the first polypeptide chain and the CH2-CH3 Domain of the third polypeptide chain associate to form the Fc Domain; and
   (G) the Linker 1 comprises the sequence of SEQ ID NO: 33;
   the Linker 2 comprises the sequence of SEQ ID NO: 34 or 47;
   the Linker 3 comprises the sequence of SEQ ID NO: 46, 47, 48, 49, 50, 51, 152, or GCG or GGG;
   the Linker 4 comprises the sequence of SEQ ID NO: 50 or 152;
   the Heterodimer-Promoting Domain on the first polypeptide chain is an E-coil Domain and the Heterodimer-Promoting Domain on the second polypeptide chain is a K-coil Domain, or the Heterodimer-Promoting Domain on the first polypeptide chain is a K-coil Domain and the Heterodimer-Promoting Domain on the second polypeptide chain is an E-coil Domain, the E-coil Domain independently comprises the sequence of SEQ ID NO: 39 or 41, and the K-coil Domain independently comprises the sequence of SEQ ID NO: 40 or 42;
   the Cysteine-Containing Domain independently comprises the sequence of SEQ ID NO: 34, 36, 38, 48, 210 or 211;
   the CH1 Domain comprises the sequence of SEQ ID NO: 207 or 208; and
   the CL Domain comprises the sequence of SEQ ID NO: 210 or 211.

2. The Tri-Specific Binding Molecule of claim 1, wherein:
   the CH2-CH3 Domain of the first polypeptide chain is a knob-bearing CH2-CH3 Domain and the CH2-CH3 Domain of the third polypeptide chain is a hole-bearing CH2-CH3 Domain; or
   the CH2-CH3 Domain of the third polypeptide chain is a knob-bearing CH2-CH3 Domain and the CH2-CH3 Domain of the first polypeptide chain is a hole-bearing CH2-CH3 Domain.

3. The Tri-Specific Binding Molecule of claim 2, wherein:
the knob-bearing CH2-CH3 Domain comprises the sequence of SEQ ID NO: 52, and
the hole-bearing CH2-CH3 Domain comprises the sequence of SEQ ID NO: 53.

4. The Tri-Specific Binding Molecule of claim 1, wherein the CH2-CH3 Domain of the first polypeptide chain and the third polypeptide chain comprise at least one amino acid substitution, relative to the sequence of SEQ ID NO:1, and the Fc Domain formed from their association exhibits altered FcγR-mediated effector function.

5. The Tri-Specific Binding Molecule of claim 4, wherein the CH2-CH3 Domain of the first polypeptide chain and the third polypeptide chain comprise:
  (A) one substitution selected from the group consisting of: F243L, R292P, Y300L, V305I, and P396L;
  (B) two substitutions selected from the group consisting of:
    (1) F243L and P396L;
    (2) F243L and R292P; and
    (3) R292P and V305I;
  (C) three substitutions selected from the group consisting of:
    (1) F243L, R292P and Y300L;
    (2) F243L, R292P and V305I;
    (3) F243L, R292P and P396L; and
    (4) R292P, V305I and P396L;
  (D) four substitutions selected from the group consisting of:
    (1) F243L, R292P, Y300L and P396L; and
    (2) F243L, R292P, V305I and P396L; or
  (E) five substitutions selected from the group consisting of:
    (1) F243L, R292P, Y300L, V305I and P396L; and
    (2) L235V, F243L, R292P, Y300L and P396L.

6. The Tri-Specific Binding Molecule of claim 1, wherein:
the Linker 2 comprises a cysteine residue,
the E-coil Domain and the K-coil Domain adjacent to the Linker 2 each comprises a cysteine residue, or
the Linker 2 comprises a cysteine residue and the E-coil Domain or the K-coil Domain adjacent to the Linker 2 comprises a cysteine residue.

7. The Tri-Specific Binding Molecule of claim 6, wherein:
the E-coil Domain of SEQ ID NO: 41 or the K-coil Domain of SEQ ID NO: 42 is adjacent to the Linker 2 when the Linker 2 comprises the sequence of SEQ ID NO: 47;
the E-coil Domain of SEQ ID NO: 39 or the K-coil Domain of SEQ ID NO: 40 is adjacent to the Linker 2 when the Linker 2 comprises the sequence of SEQ ID NO: 34; or
the E-coil Domain of SEQ ID NO: 41 or the K-coil Domain of SEQ ID NO: 42 is adjacent to the Linker 2 when the Linker 2 comprises the sequence of SEQ ID NO: 34.

8. The Tri-Specific Binding Molecule of claim 1, wherein:
  (A) the Epitope I, Epitope II and Epitope III are, respectively, an epitope of the first Cancer Antigen, an epitope of the second Cancer Antigen and an epitope of the Effector Cell Antigen;
  (B) the Epitope I, Epitope II and Epitope III are, respectively, an epitope of the first Cancer Antigen, an epitope of the Effector Cell Antigen and an epitope of the second Cancer Antigen;
  (C) the Epitope I, Epitope II and Epitope III are, respectively, an epitope of second Cancer Antigen, an epitope of the first Cancer Antigen, and an epitope of the Effector Cell Antigen;
  (D) the Epitope I, Epitope II and Epitope III are, respectively, an epitope of the second Cancer Antigen, an epitope of the Effector Cell Antigen and an epitope of the first Cancer Antigen;
  (E) the Epitope I, Epitope II and Epitope III are, respectively, an epitope of the Effector Cell Antigen, an epitope of the first Cancer Antigen, and an epitope of the second Cancer Antigen; or
  (F) the Epitope I, Epitope II and Epitope III are, respectively, an epitope of the Effector Cell Antigen, an epitope of second Cancer Antigen, and an epitope of the first Cancer Antigen.

9. The Tri-Specific Binding Molecule of claim 1, wherein the Effector Cell Antigen is CD2, CD3, CD16, CD19, CD20, CD22, CD32B, CD64, B cell Receptor (BCR), T cell Receptor (TCR), or NKG2D Receptor.

10. The Tri-Specific Binding Molecule of any of claim 9, wherein:
  (A) the epitope of an Effector Cell Antigen is a CD2 epitope recognized by antibody Lo-CD2a;
  (B) the epitope of an Effector Cell Antigen is a CD3 epitope recognized by antibody OKT3, M291, YTH12.5, Anti-CD3 mAb 1 or Anti-CD3 mAb 2;
  (C) the epitope of an Effector Cell Antigen is a CD16 epitope recognized by antibody 3G8 or A9;
  (D) the epitope of an Effector Cell Antigen is a CD19 epitope recognized by antibody MD1342, MEDI-551, blinatumomab or HD37;
  (E) the epitope of an Effector Cell Antigen is a CD20 epitope recognized by antibody rituximab, ibritumomab, ofatumumab, and tositumomab;
  (F) the epitope of an Effector Cell Antigen is a CD22 epitope recognized by antibody epratuzumab;
  (G) the epitope of an Effector Cell Antigen is a CD32B epitope recognized by antibody CD32B mAb 1;
  (H) the epitope of an Effector Cell Antigen is a CD64 epitope recognized by antibody CD64 mAb 1;
  (I) the epitope of an Effector Cell Antigen is a BCR/CD79 epitope recognized by antibody CD79 mAb 1;
  (J) the epitope of an Effector Cell Antigen is a TCR epitope recognized by antibody BMA 031;
  (K) the epitope of an Effector Cell Antigen is a NKG2D Receptor epitope recognized by antibody KYK-2.0; or
  (L) one of Epitope I, Epitope II or Epitope III is an epitope of an Effector Cell Antigen and the Antigen-Binding Domain that immunospecifically binds to the epitope comprises:
  the six CDRs of SEQ ID NO:102 and 103; 104 and 108; 104 and 112; 114 and 115; 116 and 117; 118 and 119; 120 and 121; 122 and 123; 124 and 125; 126 and 127; 128 and 129; 130 and 131; 132 and 133; 134 and 135; or 136 and 137; or
  the Light Chain Variable Domain of SEQ ID NO:102 and the Heavy Chain Variable Domain of SEQ ID NO:103; the Light Chain Variable Domain of SEQ ID NO:104 and the Heavy Chain Variable Domain of SEQ ID NO:108; the Light Chain Variable Domain of SEQ ID NO:104 and the Heavy Chain Variable Domain of SEQ ID NO:112; the Light Chain Variable Domain of SEQ ID NO:114 and the Heavy Chain Variable Domain of SEQ ID NO:115; the Light Chain Variable Domain of SEQ ID NO:116 and the Heavy Chain Variable Domain of SEQ ID NO:117; the Light Chain Variable Domain of SEQ ID NO:118 and the Heavy Chain Variable Domain of SEQ ID NO:119; the Light Chain Variable Domain of SEQ ID NO:120 and the Heavy Chain Variable Domain of SEQ ID NO:121; the Light Chain Variable Domain of SEQ ID NO:122 and the Heavy Chain Variable Domain of SEQ ID NO:123; the Light Chain Variable Domain of SEQ ID NO:124 and the Heavy Chain Variable Domain of SEQ ID NO:125; the Light Chain Variable Domain of SEQ ID NO:126 and the Heavy Chain Variable Domain of SEQ ID NO:127; the Light Chain Variable Domain of SEQ ID NO:128 and the Heavy Chain Variable Domain of SEQ ID NO:129; the Light Chain Variable Domain of SEQ ID NO:130 and the Heavy Chain Variable Domain of SEQ ID NO:131; the Light Chain Variable Domain of SEQ ID NO:132 and the Heavy Chain Variable Domain of SEQ ID NO:133; the Light Chain Variable Domain of SEQ ID NO:134 and the Heavy Chain Variable Domain of SEQ ID NO:135; or the Light Chain Variable Domain of SEQ ID NO:136 and the Heavy Chain Variable Domain of SEQ ID NO:137.

11. The Tri-Specific Binding Molecule of claim 8, wherein the first Cancer Antigen and the second Cancer Antigen are independently selected from: colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7-H3; beta-catenin; blood group $ALe^b/Le^y$; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD28; CD30; CD33; CD36; CD45; CD46; CD52; CD79a/CD79b; CD103; CD317; CDK4; carcinoembryonic antigen (CEA); CEACAM5; CEACAM6; C017-1A; CO-43 (blood group $Le^b$); CO-514 (blood group $Le^a$); CTA-1; CTLA4; Cytokeratin 8; antigen D1.1; antigen $D_156$-22; DR5; $E_1$ series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; $G_{D2}$; $G_{D3}$; GICA 19-9; GM2; gp100; human leukemia T cell antigen Gp37; melanoma antigen gp75; gpA33; HER2 antigen ($p185^{HER2}$); human milk fat globule antigen (HMFG); human papillomavirus-E6/human papillomavirus-E7; high molecular weight melanoma antigen (HMW-MAA); I antigen (differentiation antigen) I(Ma); Integrin Alpha-V-Beta-6 Integrinβ6 (ITGB6); Interleukin-13; Receptor α2 (IL13Rα2); JAM-3; KID3; KID31; KS 1/4 pan-carcinoma antigen; human lung carcinoma antigens L6 and L20; LEA; LUCA-2; M1:22:25:8; M18; M39; MAGE-1; MAGE-3; MART; MUC-1; MUM-1; Myl; N-acetylglucosam inyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; $R_{24}$, ROR1; sphingolipids; SSEA-1; SSEA-3; SSEA-4; sTn; T cell receptor derived peptide; $T_5A_7$; TAG-72; TL5 (blood group A); TNF-α receptor; TNF-β receptor; TNF-γ receptor; TRA-1-85 (blood group H); Transferrin Receptor; tumor-specific transplantation antigen (TSTA), oncofetal antigen-alpha-fetoprotein (AFP); VEGF, VEGFR; VEP8; VEP9; VIM-D5; and Y hapten, $Le^y$.

12. The Tri-Specific Binding Molecule of claim 11, wherein one of Epitope I, Epitope II or Epitope III is an epitope of a Cancer Antigen and the Antigen-Binding Domain that immunospecifically binds to the epitope comprises:

the six CDRs of SEQ ID NO: 3 and 8; 13 and 18; 23 and 31; 25 and 31; 27 and 31; 29 and 31; 54 and 58; 62 and 66; 70 and 74; 78 and 82; 86 and 90; 94 and 98; 153 and 158; 163 and 167; 172 and 177; 181 and 186; 191 and 192; 193 and 194; 195 and 196; 197 and 198; 199 and 200; 201 and 202; 203 and 204; 205 and 206; 302 and 303; 304 and 305; 306 and 307; 308 and 309; 310 and 311; 312 and 313; 314 and 315; or 321 and 322; or the Light Chain Variable Domain of SEQ ID NO:3 and the Heavy Chain Variable Domain of SEQ ID NO:8; the Light Chain Variable Domain of SEQ ID NO:13 and the Heavy Chain Variable Domain of SEQ ID NO:18; the Light Chain Variable Domain of SEQ ID NO:23 and the Heavy Chain Variable Domain of SEQ ID NO:31; the Light Chain Variable Domain of SEQ ID NO:25 and the Heavy Chain Variable Domain of SEQ ID NO:31; the Light Chain Variable Domain of SEQ ID NO:27 and the Heavy Chain Variable Domain of SEQ ID NO:31; the Light Chain Variable Domain of SEQ ID NO:29 and the Heavy Chain Variable Domain of SEQ ID NO:31; the Light Chain Variable Domain of SEQ ID NO:54 and the Heavy Chain Variable Domain of SEQ ID NO:58; the Light Chain Variable Domain of SEQ ID NO:62 and the Heavy Chain Variable Domain of SEQ ID NO:66; the Light Chain Variable Domain of SEQ ID NO:70 and the Heavy Chain Variable Domain of SEQ ID NO:74; the Light Chain Variable Domain of SEQ ID NO:78 and the Heavy Chain Variable Domain of SEQ ID NO:82; the Light Chain Variable Domain of SEQ ID NO:86 and the Heavy Chain Variable Domain of SEQ ID NO:90; the Light Chain Variable Domain of SEQ ID NO:94 and the Heavy Chain Variable Domain of SEQ ID NO:98; the Light Chain Variable Domain of SEQ ID NO:153 and the Heavy Chain Variable Domain of SEQ ID NO:158; the Light Chain Variable Domain of SEQ ID NO:163 and the Heavy Chain Variable Domain of SEQ ID NO:167; the Light Chain Variable Domain of SEQ ID NO:172 and the Heavy Chain Variable Domain of SEQ ID NO:177; the Light Chain Variable Domain of SEQ ID NO:181 and the Heavy Chain Variable Domain of SEQ ID NO:186; the Light Chain Variable Domain of SEQ ID NO:191 and the Heavy Chain Variable Domain of SEQ ID NO:192; the Light Chain Variable Domain of SEQ ID NO:193 and the Heavy Chain Variable Domain of SEQ ID NO:194; the Light Chain Variable Domain of SEQ ID NO:195 and the Heavy Chain Variable Domain of SEQ ID NO:196; the Light Chain Variable Domain of SEQ ID NO:197 and the Heavy Chain Variable Domain of SEQ ID NO:198; the Light Chain Variable Domain of SEQ ID NO:199 and the Heavy Chain Variable Domain of SEQ ID NO:200; the Light Chain Variable Domain of SEQ ID NO:201 and the Heavy Chain Variable Domain of SEQ ID NO:202; the Light Chain Variable Domain of SEQ ID NO:203 and the Heavy Chain Variable Domain of SEQ ID NO:204; the Light Chain Variable Domain of SEQ ID NO:205 and the Heavy Chain Variable Domain of SEQ ID NO:206; the Light Chain Variable Domain of SEQ ID NO:302 and the Heavy Chain Variable Domain of SEQ ID NO:303; the Light Chain Variable Domain of SEQ ID NO:304 and the Heavy Chain Variable Domain of SEQ ID NO:305; the Light Chain Variable Domain of SEQ ID NO:306 and the Heavy Chain Variable Domain of SEQ ID NO:307; the Light Chain Variable Domain of SEQ ID NO:308 and the Heavy Chain Variable Domain of SEQ ID NO:309; the Light Chain Variable Domain of SEQ ID NO:310 and the Heavy Chain Variable Domain of SEQ ID NO:311; the Light Chain Variable Domain of SEQ ID NO:312 and the Heavy Chain Variable Domain of SEQ ID NO:313; the Light Chain Variable Domain of SEQ ID NO:314 and the Heavy Chain Variable Domain of SEQ ID NO:315; or the Light Chain Variable Domain of SEQ ID NO:321 and the Heavy Chain Variable Domain of SEQ ID NO:322.

13. A pharmaceutical composition comprising the Tri-Specific Binding Molecule of claim 1, and a pharmaceutically acceptable carrier, excipient or diluent.

* * * * *